(12) United States Patent
Franciskovich et al.

(10) Patent No.: US 7,615,568 B2
(45) Date of Patent: Nov. 10, 2009

(54) ANTITHROMBOTIC ETHERS

(75) Inventors: Jeffry Bernard Franciskovich, Zionsville, IN (US); David Kent Herron, Indianapolis, IN (US); Jared Harris Linebarger, Indianapolis, IN (US); Angela Lynn Marquart, Greenwood, IN (US); John Joseph Masters, Fishers, IN (US); David Mendel, Indianapolis, IN (US); Leander Merritt, Indianapolis, IN (US); Andrew Michael Ratz, Zionsville, IN (US); Gerald Floyd Smith, Greenwood, IN (US); Leland Otto Weigel, Indianpolis, IN (US); Michael Robert Wiley, Zionsville, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 572 days.

(21) Appl. No.: 10/556,313

(22) PCT Filed: Apr. 13, 2004

(86) PCT No.: PCT/US2004/009282

§ 371 (c)(1),
(2), (4) Date: Nov. 10, 2005

(87) PCT Pub. No.: WO2004/108677

PCT Pub. Date: Dec. 10, 2004

(65) Prior Publication Data

US 2008/0108594 A1 May 8, 2008

Related U.S. Application Data

(60) Provisional application No. 60/474,689, filed on May 30, 2003.

(51) Int. Cl.
*A61K 31/4427* (2006.01)
*C07D 417/12* (2006.01)

(52) U.S. Cl. .................................. 514/352; 546/270.7
(58) Field of Classification Search ................ 514/352; 546/270.7
See application file for complete search history.

(56) References Cited

U.S. PATENT DOCUMENTS

| | | | |
|---|---|---|---|
| 6,140,351 A | 10/2000 | Arnaiz et al. |
| 6,313,122 B1 | 11/2001 | Beight et al. |
| 6,313,151 B1 | 11/2001 | Beight et al. |
| 6,372,759 B1 | 4/2002 | Beight et al. |
| 6,417,200 B1 | 7/2002 | Beight et al. |
| 6,610,704 B1 | 8/2003 | Beight et al. |
| 6,635,657 B1 | 10/2003 | Beight et al. |
| 6,689,780 B1 | 2/2004 | Beight et al. |
| 2004/0058959 A1 | 3/2004 | Herron et al. |
| 2004/0097491 A1 | 5/2004 | Herron et al. |
| 2004/0242581 A1 | 12/2004 | Herron et al. |

FOREIGN PATENT DOCUMENTS

| | | |
|---|---|---|
| WO | WO 02/10154 | 2/2002 |
| WO | WO 02/064567 | 8/2002 |
| WO | WO 2005/049604 | 6/2005 |

OTHER PUBLICATIONS

Zhu, et al.: "Factor Xa Inhibitors: Recent Advances in Anticoagulant Agents" Annual Reports in Medicinal Chemistry, (2000), 35, 83-102.

*Primary Examiner*—Taofiq A Solola
(74) *Attorney, Agent, or Firm*—Thomas E. Jackson

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa and/or thrombin, as well as a process for its preparation and intermediates therefor (I).

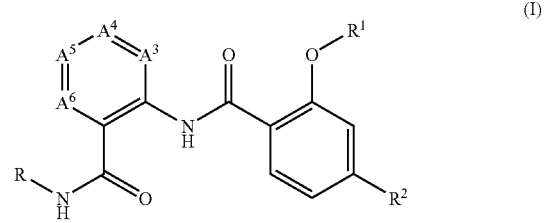

16 Claims, No Drawings

ANTITHROMBOTIC ETHERS

This application claims the benefit of U.S. Provisional Application No. 60/474,689, filed May 30, 2003, which is incorporated by reference herein in its entirety.

This invention relates to antithrombotic ethers which demonstrate activity as inhibitors of thrombin and/or factor Xa and, accordingly, which are useful antithrombotics in mammals. In particular it relates to antithrombotic ethers having high anticoagulant activity, good oral exposure and antithrombotic activity. Thus, this invention relates to new antithrombotic ethers which are inhibitors of thrombin and/or factor Xa, pharmaceutical compositions containing the antithrombotic ethers as active ingredients, and the use of the antithrombotic ethers as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic ethers are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, for example, B. Y. Zhu and R. M. Scarborough, *Annual Reports in Medicinal Chemistry*, (2000), 35, 83-102, Factor Xa Inhibitors: Recent Advances in Anticoagulant Agents.

Although the heparins and coumarins are effective anticoagulants, there still exists a need for anticoagulants which act selectively on factor Xa and/or thrombin, and which, independent of antithrombin III, exert inhibitory action shortly after administration, preferably by an oral route, and do not interfere with lysis of blood clots, as required to maintain hemostasis.

The present invention is directed to the discovery that the antithrombotic ethers of the present invention, as defined below, are potent inhibitors of thrombin and/or factor Xa which may have high bioavailability following oral administration.

According to the invention there is provided a compound of formula I

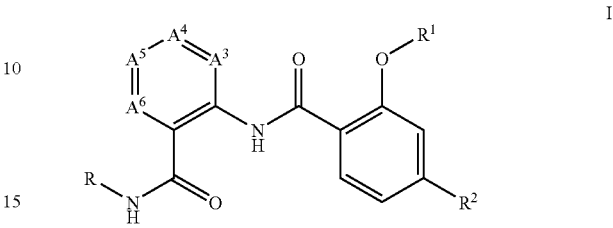

or a pharmaceutically acceptable salt thereof, wherein:

$A^3$, $A^4$, $A^5$ and $A^6$, together with the two carbons to which they are attached, complete a substituted pyridine ring in which (a) $A^3$ is N, and each of the others is $CR^4$, $CR^5$ or $CR^6$, respectively; wherein $R^4$ is hydrogen, carboxy, aminocarbonyl or methylaminocarbonyl; $R^5$ is hydrogen, fluoro, chloro, or methyl; and $R^6$ is hydrogen; or wherein each of $R^3$, $R^4$ and $R^6$ is hydrogen and $R^5$ is acetyl or cyano;

(b) $A^4$ is N, and each of the others is $CR^3$, $CR^5$ or $CR^6$, respectively; wherein each of $R^3$ and $R^6$ is hydrogen and $R^5$ is hydrogen, methyl, acetyl or cyano;

(c) $A^5$ is N, and each of the others is $CR^3$, $CR^4$ or $CR^6$, respectively; wherein each of $R^3$ and $R^6$ is hydrogen and $R^4$ is hydrogen, carboxy, aminocarbonyl or methylamino-carbonyl;

(d) $A^6$ is N, and each of the others is $CR^3$, $CR^4$ or $CR^5$, respectively; wherein $R^3$ is hydrogen; $R^4$ is hydrogen, carboxy, aminocarbonyl or methylaminocarbonyl; and $R^5$ is hydrogen or methyl;

R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);

$R^1$ is —$(CH_2)_i$-Q-$(CH_2)_j$—$NR^aR^b$ in which a) Q is a single bond; the sum of i and j is 2 or 3; and each of $R^a$ and $R^b$ is hydrogen, or each of $R^a$ and $R^b$ is independently (1-3C) normal alkyl, or $R^a$ is hydrogen and $R^b$ is (1-3C)alkyl or formyl, or $NR^aR^b$ is 1-pyrrolidinyl or 4-morpholinyl;

b) Q is —$CH(CH_3)$—, —$C(CH_3)_2$—, or —$CH(OR^c)$—; each of and j is 1; $R^a$ is hydrogen; and $R^b$ is hydrogen or methyl; and $R^c$ is hydrogen, methyl or benzyl;

c) Q is cis- or trans-cyclohexane-1,4-diyl; each of and j is 0; $R^a$ is hydrogen; and $R^b$ is hydrogen or methyl;

d) Q is —$CHR^d$—; i is 0; j is 1; $R^a$ is hydrogen or methyl; and $R^b$ and $R^d$ together are —$(CH_2)_k$— wherein k is 2 or 3;

e) Q is —$CHR^d$—; i is 1; j is 1; $R^a$ is hydrogen or methyl; and $R^b$ and $R^d$ together are —$(CH_2)_k$— wherein k is 1, 2 or 3; or f) Q is —CHR$^d$—; i is 0 or 1; j is 2; R$^a$ is hydrogen or methyl; and R$^b$ and R$^d$ together are —(CH$_2$)$_k$— wherein k is 2; and R$^2$ is —(CH$_2$)$_m$—S(O)$_n$—R$^e$ in which m is 0 or 1, n is 0, 1 or 2, and R$^e$ is (1-3C)alkyl or 2-fluoroethyl; and wherein (1-3C) normal alkyl is methyl, ethyl or propyl; and (1-3C)alkyl is methyl, ethyl, propyl, or isopropyl.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin and/or factor Xa, it being well known in the art how to prepare or isolate particular forms and how to determine inhibitory properties against thrombin and/or factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

One particular compound of formula I is one wherein one of A$^3$, A$^4$, A$^5$ and A$^6$ is N, and each of the others is CR$^3$, CR$^4$, CR$^5$ or CR$^6$, respectively; wherein each of R$^3$, R$^4$ and R$^6$ is hydrogen and R$^5$ is hydrogen or methyl;

R is 2-pyridinyl, which bears a methyl, fluoro or chloro substituent at the 5-position.

A more particular compound, or salt thereof, as described above is one wherein

A$^6$ is N;

each of R$^3$ and R$^4$ is hydrogen; and

R$^5$ is hydrogen or methyl;

R is 5-chloropyridin-2-yl or 5-methylpyridin-2-yl;

R$^1$ is 2-aminoethyl, 2-(dimethylamino)ethyl, 3-amino-propyl, 3-(formylamino)propyl, 3-(1-pyrrolidinyl)propyl, 3-(4-morpholinyl)propyl, 3-amino-2-methylpropyl, 3-amino-2,2-dimethylpropyl, 3-amino-2-hydroxypropyl, 3-amino-2-methoxypropyl, 3-amino-2-benzyloxypropyl, cis-4-aminocyclohexyl, cis-4-(methylamino)cyclohexyl, trans-4-aminocyclohexyl, 3-pyrrolidinyl, 3-piperidinyl, 3-azetidinylmethyl, 3-pyrrolidinylmethyl, 3-piperidinylmethyl, 4-piperidinyl, 4-piperidinylmethyl or 1-methyl-piperidin-4-yl; and R$^2$ is methylthio, methylsulfinyl, methylsulfonyl, ethylthio, ethylsulfinyl, ethylsulfonyl, isopropylthio, propylsulfonyl or methylsulfonylmethyl.

A further particular compound, or salt thereof, as described above is one wherein R is 5-chloropyridin-2-yl;

R$^1$ is 3-aminopropyl, 3-amino-2-methylpropyl, 3-amino-2,2-dimethylpropyl, 3-amino-2-methoxypropyl, 3-amino-2-benzyloxypropyl, cis-4-aminocyclohexyl, cis-4-(methylamino)-cyclohexyl, 3-pyrrolidinyl, 3-piperidinyl, 3-azetidinyl-methyl, 3-pyrrolidinylmethyl, 3-piperidinylmethyl, 4-piperidinyl, 4-piperidinylmethyl or 1-methyl-piperidin-4-yl; and R$^2$ is methylsulfinyl, ethylsulfinyl, methylsulfonyl, ethylsulfonyl or propylsulfonyl;

and, more particularly, the compound or salt wherein

R$^1$ is 3-aminopropyl, 3-amino-2-methylpropyl (as the racemate or as either isomer), 3-amino-2,2-dimethylpropyl; (2S)-3-amino-2-methoxypropyl; (2S)-3-amino-2-benzyloxy-propyl; cis-4-aminocyclohexyl, cis-4-(methylamino)-cyclohexyl, (3S)-3-pyrrolidinyl, 3-piperidinyl (as the racemate or as either isomer), 3-azetidinylmethyl, 3-pyrrolidinylmethyl (as the racemate or as either isomer), 4-piperidinyl, or 1-methylpiperidin-4-yl; and R$^2$ is methylsulfonyl, ethylsulfonyl or propylsulfonyl.

A specific compound, or pharmaceutically acceptable salt thereof, is any one of those provided in the Examples, particularly in one of Examples 3, 5, 6, 14, 17, 20-22, 25, 27-28, 34, 37-39, 41-42, 50, 53, 50-65, 67, 69-70 and 72; and, especially, is 3-[2-(cis-4-aminocyclohexyloxy)-4-methylsulfo-nylbenzoylamino]-N-(5-chloropyridin-2-yl)-pyridine-2-carboxamide, or a pharmaceutically acceptable salt thereof.

A pharmaceutically acceptable salt of a compound of the instant invention is one which is the acid addition salt of a basic compound of formula I with an inorganic or organic acid which affords a physiologically acceptable anion or which is the salt formed by an acidic compound of formula I with a base which affords a physiologically acceptable cation and provides a particular aspect of the invention. A particular pharmaceutically acceptable salt of any of the above compounds is an acid-addition salt made from a basic compound of formula I and an acid which provides a pharmaceutically acceptable anion.

As an additional aspect of the invention there is provided a pharmaceutical composition comprising in association with a pharmaceutically acceptable carrier, diluent or excipient, a compound of formula I, or a pharmaceutically acceptable salt thereof, as provided in any of the descriptions herein.

Further, there is provided a pharmaceutical composition for treating a thromboembolic disorder containing as an active ingredient a compound of formula I, or a pharmaceutically acceptable salt thereof, as provided in any of the descriptions herein.

In addition, there is provided the use of a compound of formula I, or a pharmaceutically acceptable salt thereof, as described herein as an active ingredient in the manufacture of a medicament for use in producing an anticoagulant or antithrombotic effect.

The present invention also provides a method of inhibiting coagulation in a mammal, particularly a human, comprising administering to a mammal in need of treatment, a coagulation inhibiting dose of a compound of formula I, or a pharmaceutically acceptable salt thereof, having any of the definitions herein.

The present invention further provides a method of inhibiting thrombin and/or factor Xa comprising administering to a mammal, particularly a human, in need of treatment, a thrombin and/or factor Xa inhibiting dose of compound of formula I having any of the definitions herein.

Further, the present invention provides a method of treating a thromboembolic disorder comprising administering to a mammal, particularly a human, in need of treatment, an effective dose of a compound of formula I, or a pharmaceutically acceptable salt thereof, having any of the definitions herein.

Also, there is provided a compound of formula I, or a pharmaceutically acceptable salt thereof, having any of the definitions herein for use as an antithrombotic agent.

In addition, there is provided the use of a compound of formula I, or a pharmaceutically acceptable salt thereof, having any of the definitions herein for the manufacture of a medicament for treatment of a thromboembolic disorder.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, comprising the step selected from (A) acylating an amine of formula II,

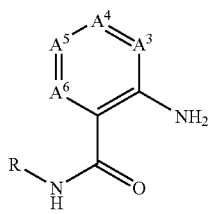

using an acid of formula III (in which $R^a$ as hydrogen may be replaced by a nitrogen protecting group $R^p$),

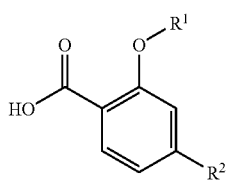

or an activated derivative thereof;

(B) for a compound of formula I in which n is 1, oxidizing the corresponding compound of formula I (in which $R^a$ as hydrogen may be replaced by a nitrogen protecting group $R^p$) in which n is 0;

(C) for a compound of formula I in which n is 2, oxidizing the corresponding compound of formula I (in which $R^a$ as hydrogen may be replaced by a nitrogen protecting group $R^p$) in which n is 1;

(D) for a compound of formula I in which each of $R^a$ and $R^b$ is (1-3C) normal alkyl, or $R^a$ is hydrogen and $R^b$ is methyl or (1-3C)alkyl, or $NR^aR^b$ is 1-pyrrolidinyl or 4-morpholinyl, alkylating a corresponding compound of formula I in which each of $R^a$ and $R^b$ is hydrogen;

(E) for a compound of formula I in which $R^a$ is methyl or (1-3C) normal alkyl, alkylating a corresponding compound of formula I in which $R^a$ is hydrogen;

(F) for a compound of formula I in which $R^b$ is formyl, formylating a corresponding compound of formula I in which $R^b$ is hydrogen;

(G) alkylating the phenolic oxygen of a compound of formula IV,

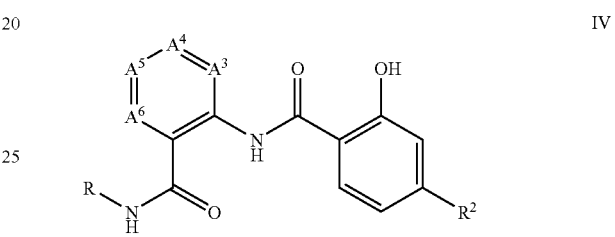

using a corresponding compound of formula V (in which $R^a$ as hydrogen may be replaced by a nitrogen protecting group $R^p$),

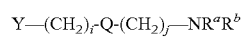

wherein Y is a conventional leaving group for nucleophilic substitution and wherein, for a compound of formula I in which i is 0, the stereochemistry of the carbon to which Y is attached is inverted from that of the product; and (H) acylating an amine of formula R—$NH_2$ using an acid of formula VI (in which $R^a$ as hydrogen may be replaced by a nitrogen protecting group $R^p$),

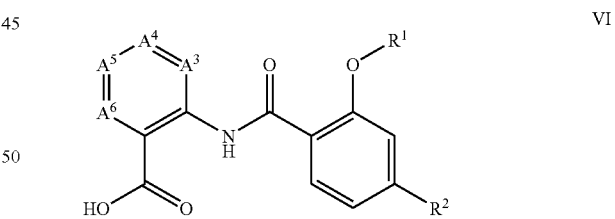

or an activated derivative thereof;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above in this section, $A^3$-$A^6$, R, $R^1$, $R^2$, Q, $R^a$-$R^e$, i, j, k, m and n have any of the values defined hereinabove.

For a carboxylic acid herein, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or anhydride derived from a coupling reagent).

Oxidizing a compound in which n is 0 to afford a compound in which n is 1 is conveniently carried out in a manner as described in Example 2-A or by using one equivalent of meta-choloroperbenzoic acid. Oxidizing a compound in which n is 1 to afford a compound in which n is 2 is conveniently carried out using at least one equivalent of meta-choloroperbenzoic acid. When a compound in which n is 2 is required, it is conveniently obtained from the compound in which n is 0 as described in Example 3-A, in which the intermediate compound in which n is 1 is not isolated but oxidized directly in situ into the compound in which n is 2.

A preferred method of formulating the nitrogen of a compound in which $R^b$ is hydrogen is the use of a formylating reagent such as formic acetic anhydride.

As used herein, a leaving group "Y" is a moiety which is displaced in a nucleophilic substitution reaction, for example a halo group (such as bromo or iodo), a sulfonate ester group (such as methylsulfonyloxy, p-toluoylsulfonyloxy or trifluoromethylsulfonyloxy), or the reactive species derived from treating an alcohol with triphenylphospine, diethyl azodicarboxylate and triethyl amine (in a Mitsunobu reaction). In addition, for the preparation of a compound in which Q is —CH(OH)—, the group Y—CH$_2$-Q- may represent an epoxy group. The substitution may be carried out, for example as described at Example 1-D or at Example 38-D.

If not commercially available, a necessary starting material for the preparation of a compound of formula I may be prepared by a novel process described herein or one analogous thereto or by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. A novel intermediate or starting material compound provides a further aspect of the invention.

Selective methods of substitution, protection and deprotection are well known in the art for preparation of a compound such as one of formulae II-VII.

Thus, one particular intermediate is an acid of formula III, or a salt thereof, or an activated derivative thereof, (in which $R^a$ as hydrogen may be replaced by a nitrogen protecting group $R^p$),

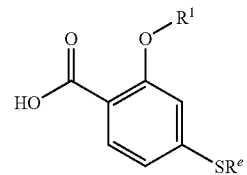

III wherein $R^1$ and $R^2$ have any of the values defined herein above. Conveniently, the salt of a carboxylic acid herein may be the sodium or potassium salt.

A particular acid, or salt thereof, or an activated derivative thereof, of formula III is the acid wherein m is 0 and n is 0 (in which $R^a$ as hydrogen may be replaced by a nitrogen protecting group $R^p$), denoted as an acid of formula VII,

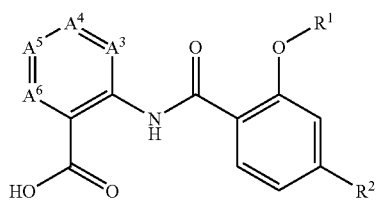

VII or a salt thereof, or an activated derivative thereof.

Another aspect is an acid of formula VI (in which $R^a$ as hydrogen may be replaced by a nitrogen protecting group $R^p$),

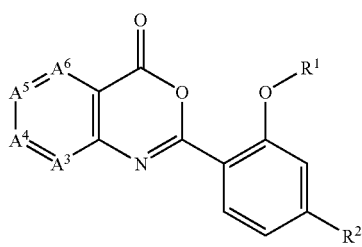

VI or an activated derivative thereof, wherein $A^3$-$A^6$, $R^1$ and $R^2$ have any of the values defined herein. In addition, for an acid of formula VI, a particular activated derivative is a compound of formula VIa,

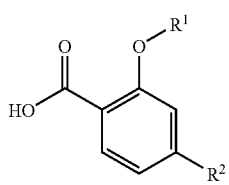

VIa or a salt of the active derivative, in which $A^3$-$A^6$, $R^1$ and $R^2$ have any of the values defined herein, or a derivative thereof in which a functional group other than the activated derivative of the carboxy group is protected using a protecting group.

Another aspect of the invention is a process for preparing an acid of formula VII, as described above, or a salt thereof,

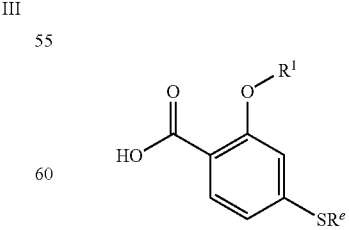

VII from 2,4-difluorobenzoic acid, or a salt thereof, comprising
(a) treating 2,4-difluorobenzoic acid, or the salt thereof, with an alkoxide of an alcohol of formula HO—$R^1$ (in which $R^a$ as hydrogen may be replaced by a nitrogen protecting group $R^p$) to form a corresponding ether of formula VIII, or salt thereof; and

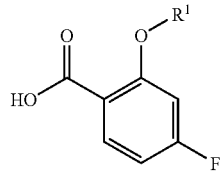

VIII (b) treating the ether of formula VIII (in which $R^a$ as hydrogen may be replaced by a nitrogen protecting group $R^p$), or salt thereof, with a thiolate of the thiol of formula HS—$R^e$ to form a corresponding compound of formula VII, or salt thereof;

whereafter, a nitrogen protecting group $R^p$ may be removed or converted into another nitrogen protecting group $R^p$;

and whereafter, a salt and/or protonated form of the acid may be converted into the protonated form or a salt form, as required, using a conventional method.

A further aspect is a process for preparing a compound of formula I, in which m is 0, or a pharmaceutically acceptable salt thereof, from 2,4-difluorobenzoic acid, or a salt thereof, comprising (a) treating 2,4-difluorobenzoic acid, or the salt thereof, with an alkoxide of an alcohol of formula HO—$R^1$ (in which $R^a$ as hydrogen may be replaced by a nitrogen protecting group $R^p$), to form a corresponding ether of formula VIII (in which $R^a$ as hydrogen may be replaced by a nitrogen protecting group $R^p$), or salt thereof;

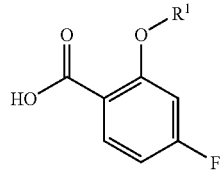

VIII (b) treating the ether of formula VIII (in which $R^a$ as hydrogen may be replaced by a nitrogen protecting group $R^p$), or salt thereof, with a thiolate of the thiol of formula HS—$R^e$ to form a compound of formula VII (in which $R^a$ as hydrogen may be replaced by a nitrogen protecting group $R^p$), or salt thereof;

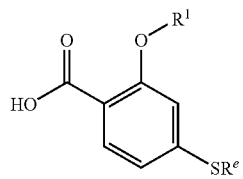

VII followed by converting the compound of formula VII (in which $R^a$ as hydrogen may be replaced by a nitrogen protecting group $R^p$), or salt thereof, into a compound of formula I in which m is 0;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above in this process, $A^3$-$A^6$, R, $R^1$, Q, $R^a$-$R^e$, i, j, k, and n have any of the values defined herein.

A further aspect is the above process, further comprising:

(c) for an acid of formula VII in which $R^a$ is hydrogen, converting the acid of formula VII into a corresponding acid of formula VII in which $R^a$ as hydrogen is replaced by a nitrogen protecting group $R^p$;

(d) acylating an amine of formula II,

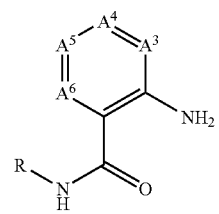

II using the acid of formula VII (in which $R^a$ is not hydrogen or $R^a$ as hydrogen is replaced by a nitrogen protecting group $R^p$) or an activated derivative thereof, to form a compound of formula IX (in which $R^a$ is not hydrogen or $R^a$ as hydrogen is replaced by a nitrogen protecting group $R^p$),

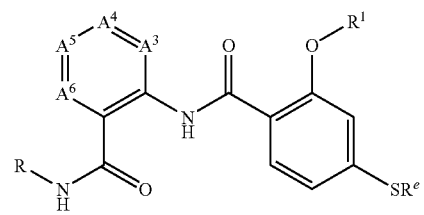

IX which is a compound of Formula I in which m is 0 and n is 0 in which $R^a$ is not hydrogen when $R^a$ is not hydrogen;

(e) for a compound of formula I in which n is 1, oxidizing the sulfur of the compound of formula IX (in which $R^a$ is not hydrogen or $R^a$ as hydrogen is replaced by a nitrogen protecting group $R^p$), followed by reducing any N-oxide formed for a compound in which $R^a$ is not hydrogen, to afford the corresponding sulfoxide of formula X (in which $R^a$ is not hydrogen or $R^a$ as hydrogen is replaced by a nitrogen protecting group $R^p$),

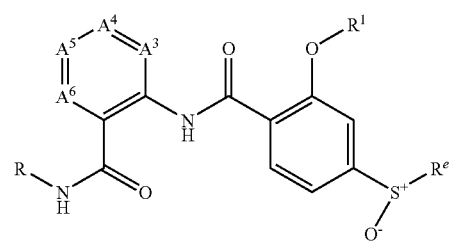

X which is a compound of Formula I in which m is 0 and n is 1 in which $R^a$ is not hydrogen when $R^a$ is not hydrogen;

(f) for a compound of formula I in which n is 2, oxidizing the corresponding sulfoxide of the compound of formula X (in which $R^a$ is not hydrogen or $R^a$ as hydrogen is replaced by a nitrogen protecting group $R^p$), followed by reducing any N-oxide formed for a compound in which $R^a$ is not hydrogen, to afford the corresponding sulfone of formula XI (in which $R^a$ is not hydrogen or $R^a$ as hydrogen is replaced by a nitrogen protecting group $R^p$),

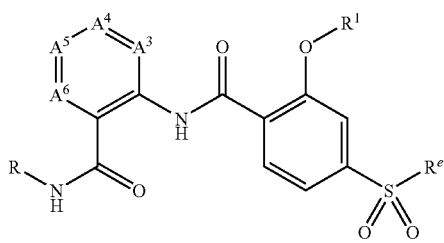

XI which is a compound of Formula I in which m is 0 and n is 2 in which $R^a$ is not hydrogen when $R^a$ is not hydrogen; or, optionally, combining steps (e) and (f) to directly provide the compound of formula XI from the compound of formula IX; and (g) when $R^a$ as hydrogen is replaced by a nitrogen protecting group $R^p$, removing the nitrogen protecting group $R^p$ from the product of step (d), (e) or (f), respectively, to provide a compound of formula I in which $R^a$ is hydrogen, m is 0, and n is 0, 1 or 2, respectively;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above in this claim, $A^3$-$A^6$, R, $R^1$, Q, $R^a$-$R^e$, i, j, k, and n have any of the values defined herein.

A particular process is the process above in which $R^1$ is 3-aminopropyl, 3-amino-2,2-dimethylpropyl; cis-4-aminocyclohexyl, 4-piperidinyl or 1-methylpiperidin-4-yl;

$R^e$ is methyl; and for steps (c) through (f), $R^p$ is t-butoxycarbonyl.

A further aspect is any one of the above processes in which $R^1$ is cis-4-aminocyclohexyl; and, more particularly, wherein the starting cis-4-aminocyclohexanol is prepared using a process comprising (i) dehydrogenating a substituted hydroxylamine derivative of formula $R^q$NHOH, in which $R^q$ is an electron withdrawing nitrogen protecting group, in the presence of 1,3-cyclohexadiene to afford a 2-substituted 2-aza-3-oxa-bicyclo[2.2.2]oct-5-ene compound of formula XII,

XII

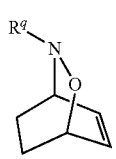

(ii) removing the protecting group $R^q$ to provide 3-aza-2-oxabicyclo[2.2.2]oct-5-ene, formula XIII;

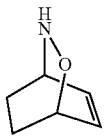

XIII optionally obtained as an acid addition salt; and (iii) hydrogenating and hydrogenolyzing the compound of formula XIII to provide cis-4-aminocyclohexanol, optionally obtained as an acid addition salt, and followed, when required, by formation of the free base by a conventional method.

For any of the above processes: The alkoxide of an alcohol of formula HO—$R^1$ (in which $R^a$ as hydrogen may be replaced by a nitrogen protecting group $R^p$) may be, for example, the sodium, potassium, lithium, cesium or magnesium alkoxide, as well as a copper species. In general, it will be necessary that the nitrogen protecting group $R^p$ (if present) be other than a urethane when the intramolecular formation of a (cyclic) urethane is favorable. It may be preferred to introduce or change the nitrogen protecting group $R^p$ during the process, for example as described in Example 27-G. The thiolate of the thiol of formula HS—$R^e$ may be, for example, the sodium, potassium, lithium, cesium or magnesium thiolate. An electron withdrawing nitrogen protecting group $R^q$ is, for example an acyl group (which forms an amide or urethane), such as a trifluoroacetyl, t-butoxycarbonyl or benzyloxycarbonyl group, or a sulfonyl or sulfinyl group.

A particular embodiment of any one of the above processes is one wherein the salt of 2,4-difluorobenzoic acid is the sodium or potassium salt, the alkoxide of an alcohol of formula HO—$R^1$ (in which $R^a$ as hydrogen may be replaced by a nitrogen protecting group $R^p$) is the sodium or potassium alkoxide; and the thiolate of the thiol of formula HS—$R^e$ is the sodium or potassium thiolate.

A further aspect of the invention is a process for the preparation of cis-4-aminocyclohexanol, or an acid addition salt thereof, comprising (i) dehydrogenating a substituted hydroxylamine derivative of formula $R^q$NHOH, in which $R^q$ is an electron withdrawing nitrogen protecting group, in the presence of 1,3-cyclohexadiene to afford a 2-substituted 2-aza-3-oxa-bicyclo[2.2.2]oct-5-ene compound of formula XII,

XII

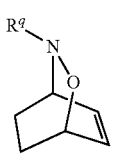

(ii) removing the protecting group $R^q$ to provide 3-aza-2-oxabicyclo[2.2.2]oct-5-ene, formula XIII;

XIII

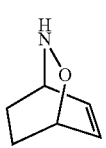

optionally obtained as an acid addition salt; and (iii) hydrogenating and hydrogenolyzing the compound of formula XIII to provide cis-4-aminocyclohexanol, optionally obtained as an acid addition salt, and followed, when required, by formation of the free base by a conventional method.

A particular embodiment of any one of the above processes is one wherein $R^q$ is t-butoxycarbonyl, the dehydrogenation reagent of step (i) is $NaIO_4$, trifluoroacetic acid is the reagent of step (ii) for removing the protecting group $R^q$ and is the acid with which the optional acid addition salts of steps (ii) and (iii) are formed, and Pd/C is the catalyst for the hydrogenation and hydrogenolysis of step (iii).

As a further aspect of the invention, there is provided the use of a compound (or activated and/or protected derivative thereof or salt of the compound or derivative) of formula III or VI as a starting material in the preparation of an inhibitor of thrombin and/or factor Xa.

As mentioned above, the invention includes a pharmaceutically acceptable salt of the thrombin and/or factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt.

Generally, a basic compound of the invention is isolated best in the form of an acid addition salt. A salt of a compound of formula I formed with an acid such as mentioned above is useful as a pharmaceutically acceptable salt for administration of the antithrombotic agent and for preparation of a pharmaceutical composition of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors.

The compounds of the invention are believed to selectively inhibit thrombin and/or factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin and/or factor Xa in a mammal comprising administering to a mammal in need of treatment an effective (thrombin and/or factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The thrombin and/or factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of thrombin and/or factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis.

Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., *Lung*, (1999), 177(4), 253-262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises a compound of formula I, or a pharmaceutically acceptable salt thereof, in association with a pharmaceutically acceptable carrier, diluent or excipient.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art.

The ability of a compound of the present invention to be an effective and orally active thrombin and/or factor Xa inhibitor may be evaluated in one or more of the following assays or in other standard assays known to those in the art.

The inhibition by a compound of the invention of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265-300. The inhibitor binding affinity is measured as apparent association constant Kass which is the hypothetical equilibrium constant for the reaction between enzyme and the test inhibitor compound (I).

Enzyme + I ⇌ Enzyme-I $$\text{Kass} = \frac{[\text{Enzyme} - I]}{([\text{Enzyme}] \times [I])}$$

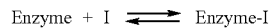

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: In each well is placed 50 μL buffer (0.06 M Tris, 0.3 M NaCl, pH 7.4), followed by 25 μL of inhibitor solution (in 100% methanol) and 25 μL enzyme solution (e.g., human factor Xa, 32 nM in 0.03 M Tris, 0.15 M NaCl, 1 mg/mL HAS); finally, within two minutes, 150 μL aqueous solution of chromogenic substrate (e.g., 0.3 mM BzIle-Glu-Gly-Arg-pNA) is added to start the enzymatic reaction. Final factor Xa concentration is 3.2 nM. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, human factor Xa is used to hydrolyze BzIle-Glu-Gly-Arg-pNA; 5.9 nM human thrombin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a compound of formula I of the instant invention, as exemplified hereinbelow in the examples, exhibits a Kass for factor Xa of $10-100\times10^6$ L/mole or greater and a Kass for thrombin (factor IIa) of $0.3-100\times10^6$ L/mole or greater.

The thrombin and/or factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1-11 (1980; and Smith, et al., *Biochemistry*, 11, 2958-2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958-2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1-11 (1980); and Smith, et al., *Biochemistry*, 11, 2958-2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research,* 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. Thus, the plasma concentrations are three times the assay concentrations. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention potently extended the prolongation times in the APTT and PT assays, for example in some cases, with assay concentrations necessary to double the APPT or PT of less than 1 $\mu M$.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2-3%, conveniently 2.5%, for surgery; 1.5-2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol,* 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu L$ is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.,* 60:269, 1990).

Ex vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, Organon Teknika) are incubated for 5 minutes (37° C.); and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nm ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acaia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes before the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthesized rabbit, for example an infusion rate of 6.8 mL/h was used for one compound infused in 5% PEG200 in water.

Statistics

Results are expressed as means +/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months-2 years; 12-13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66-74° F.; 45-50 percent relative humidity; and lighted from 0600-1800 hours.

Pharmacokinetic Model.

Test compound is formulated immediately prior to dosing by making a suspension in a "wet granulation" (povidone, 0.85 mg/mL; lactose, 15.0 mg/mL; and polysorbate 80, 65 µL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, $T_{max}$; maximum concentration of test compound of $T_{max}$, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is formulated immediately prior to dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate: 9 parts blood) is drawn before drug administration, at 60 min after administration, at 60 min after initiation of vessel injury and just prior to the end of the experiment. Whole blood cell counts, hemoglobin, and hematocrit values are determined on a 40-µL sample of the citrated whole blood with a hematology analyzer (Cell-Dyn 900, Sequoia-Turner, Mount View, Calif., U.S.A.). The remaining blood was centrifuged at 3,000 g for 5 min to prepare cell-free plasma. Plasma clotting times, prothrombin time (PT) and activated partial thromboplastin times (APTT) were performed using standard Dade reagents and the Coa-Screener coagulation device (American Labor, Largo, Fla.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of p<0.05. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587-599.

Compounds of the instant invention are potent anticoagulant and antithrombotic agents which exhibit particularly good plasma exposure following oral administration, as well as desirable volume of distribution and tissue selectivity properties, as evidenced by standard pharmacokinetic/pharmacodynamic and brain flux assays.

The following Examples are provided to further describe the invention and are not to be construed as limitations thereof.

The abbreviations, symbols and terms used in the examples have the following meanings.

Ac=acetyl
Analysis=elemental analysis
aq=aqueous
Boc=t-butyloxycarbonyl
Calcd=calculated
conc=concentrated
DME=1,2-dimethoxyethane
DMF=dimethylformamide
DMSO=dimethylsulfoxide
EtOAc=ethyl acetate
EtOH=ethanol
MeOH=methanol
HPLC=High Performance Liquid Chromatography
IR=Infrared Spectrum
APCI-MS=atmospheric pressure chemical ionization mass spectrum

EXAMPLE 1

Preparation of N-(5-Chloropyridin-2-yl)-3-[4-(methylthio)-2-(piperidin-4-yloxy)benzoylamino]pyridine-2-carboxamide

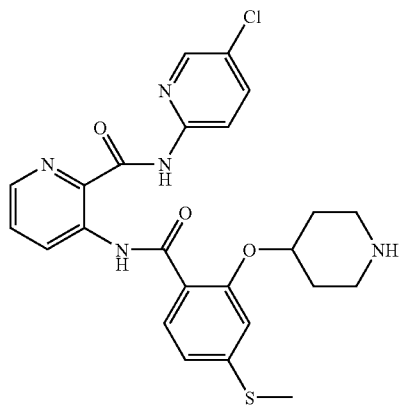

A. 2-Hydroxy-4-(methylthio)benzoic acid

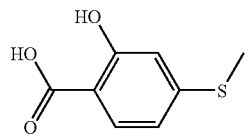

2-Methoxy-4-(methylthio)benzoic acid (1.002 g, 5.05 mmol) was dissolved in dichloromethane (18 mL). The solution was cooled to −65° C. in a dry ice/chloroform bath. Then a dichloromethane solution of boron tribromide (5.4 mL, 5.4 mmol) was added slowly. After 3 hours, the reaction was quenched with water (5 mL) and 1 N HCl (10 mL). After stirring for 10 minutes, the reaction was extracted with dichloromethane (100 mL). The organic layer was washed with 1 N HCl (10 mL) and then dried over magnesium sulfate, filtered, and concentrated to give the pure product as a pale yellow solid (866 mg, 4.70 mmol, 93%).

IR (CHCl$_3$): 1657, 1616, 1451, 1287, 1225, 918 cm$^{-1}$.
$^1$NMR (400 MHz, DMSO-d$_6$): δ 7.63(d, J=8.0 Hz, 1H); 6.75(m, 2H); 2.46(s, 3H).
IS-MS, m/e 185.2 (m+1).
Analysis for C$_8$H$_8$SO$_3$:

| | |
|---|---|
| Calcd: | C, 52.16; H, 4.38; |
| Found: | C, 52.26; H, 4.40. |

B. Methyl 2-hydroxy-4-(methylthio)benzoate

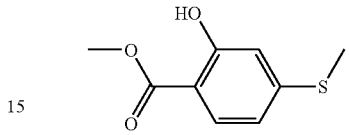

The 2-hydroxy-4-(methylthio)benzoic acid (836 mg, 4.54 mmol) was dissolved in MeOH (45 mL). Thionyl chloride (0.35 mL, 4.80 mmol) was added and the solution was heated to 65° C. and left overnight. TLC indicated that there was still starting material present; so more thionyl chloride (1.0 mL, 13.7 mmol) was added. After about 1.5 hour, TLC indicated formation of baseline material; so the reaction was concentrated in vacuo. The crude residue was purified using flash column chromatography (100% CH$_2$Cl$_2$) to give the desired compound as an off-white solid (567 mg, 2.86 mmol, 63%).

IR (CHCl$_3$): 1670, 1441, 1340, 1291, 1110, 910 cm$^{-1}$.
$^1$NMR (300 MHz, DMSO-d$_6$): δ 10.62(s, 1H); 7.63(d, J=9.0 Hz, 1H); 6.77(m, 2H); 3.83(s, 3H); 2.46 (s, 3H).
IS-MS, m/e 199.1 (m+1).
Analysis for C$_9$H$_{10}$O$_3$S:

| | |
|---|---|
| Calcd: | C, 54.53; H, 5.08; |
| Found: | C, 54.47; H, 4.95. |

C. 1-Boc-4-hydroxypiperidine

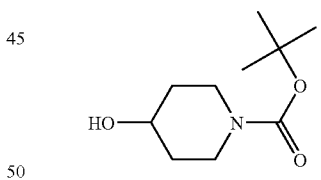

To a mixture of 4-hydroxypiperidine (60.69 g, 0.6 mol), 4-(dimethylamino)pyridine (74 mg, 0.6 mmol), CH$_2$Cl$_2$ (150 mL), and THF (150 mL) was added di-t-butyl dicarbonate [(Boc)$_2$O] (130.95 g, 0.6 mol). After stirring for 6 hours, the reaction was heated to 35° C. for 16 hours. More (Boc)$_2$O (13.09 g, 0.06 mol) in THF (20 mL) was added and the reaction was heated for 10 hours. After cooling, water and ether (1 L) were added and the mixture was stirred for 2 hours. The organic layer was partitioned, dried (MgSO$_4$), and concentrated in vacuo. The residue was crystallized from ether to give the desired product as a white solid (105 g, 87%).

$^1$NMR (300 MHz, DMSO-d$_6$): δ 3.85 (m, 3H), 3.04 (m, 2H), 1.88 (m, 2H), 1.56 (m, 2H), 1.25 (s, 9H).
IS-MS, m/e: 202.0 (m+1).

D. Methyl 2-(1-tert-butoxycarbonylpiperidin-4-yloxy)-4-(methylthio)benzoate

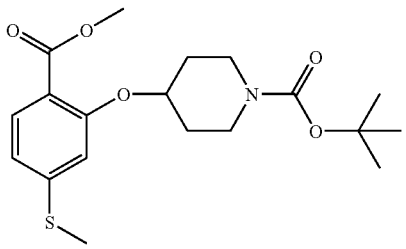

The methyl 2-hydroxy-4-(methylthio)benzoate (4.00 g, 20.2 mmol) was dissolved in THF (300 mL). The solution was cooled to 0° C. and the 1-Boc-4-hydroxypiperidine (4.07 g, 20.2 mmol) and triphenylphosphine (6.35 g, 24.2 mmol) were added, followed by diethyl azodicarboxylate (4.0 mL, 25.4 mmol). After 5 minutes, the reaction was allowed to warm to room temperature and left overnight. The reaction was concentrated in vacuo and the crude material was purified by flash column chromatography (about 500 g silica, 15% EtOAc/hexanes through 20% EtOAc/hexanes) to give the desired product (7.185 g, 18.83 mmol, 93%).

IR (CHCl$_3$): 1683, 1593, 1435, 1235 cm$^{-1}$.

$^1$NMR (400 MHz, DMSO-d$_6$): δ 7.60(d, J=8.0 Hz, 1H); 6.97(s, 1H); 6.85(d, J=8.0 Hz, 1H); 4.76(m, 1H); 3.72(s, 3H); 3.38(m, 4H); 2.48(s, 3H); 1.75(m, 2H); 1.60(m, 2H); 1.37(s, 9H).

IS-MS, m/e 382.4 (m+1).

Analysis for C$_{19}$H$_{27}$NO$_5$S:

| Calcd: | C, 59.82 ; H, 7.13 ; N, 3.67; |
|---|---|
| Found: | C, 59.58 ; H, 7.00 ; N, 3.73. |

E. 2-(1-tert-Butoxycarbonylpiperidin-4-yloxy)-4-(methylthio)benzoic acid

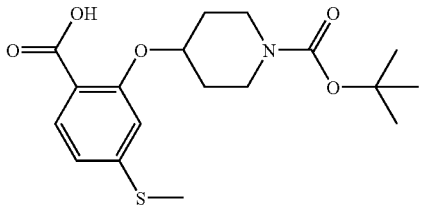

The methyl 2-(1-tert-butoxycarbonylpiperidin-4-yloxy)-4-(methylthio)benzoate (504 mg, 1.32 mmol) was dissolved in a mixture of 1 M aq LiOH (2 mL), MeOH (2 mL), and THF (6 mL) and left to stir overnight. The mixture was concentrated in vacuo to remove MeOH and THF. The residue was diluted with dichloromethane (50 mL), washed with saturated aqueous citric acid (2×5 mL) and water (2×5 mL), dried over sodium sulfate, filtered, and concentrated to give the desired product as a yellow solid (417 mg, 1.13 mmol, 86%).

$^1$NMR (300 MHz, DMSO-d$_6$): δ 7.58(d, J=8.1 Hz, 1H); 6.95(s, 1H); 6.83(d, J=8.1 Hz, 1H); 4.73(m, 1H); 3.48-3.32 (m, 4H); 1.87(s, 3H); 1.74(m, 2H); 1.58(m, 2H); 1.36(s, 9H).

IS-MS, m/e 368.1 (m+1).

Analysis for C$_{18}$H$_{25}$NO$_5$S:

| Calcd: | C, 58.84 ; H, 6.86 ; N, 3.81; |
|---|---|
| Found: | C, 58.80 ; H, 6.64 ; N, 4.00. |

F. N-(5-Chloropyridin-2-yl)-3-aminopyridine-2-carboxamide

A medium pressure reaction apparatus was charged with 3-amino-2-chloropyridine (500 mg, 3.89 mmol), 2-amino-5-chloropyridine (1.00 g, 7.78 mmol), palladium acetate (88 mg, 0.39 mmol), 1,3-bis(diphenylphosphino)propane (483 mg, 1.17 mmol) and triethylamine (590 mg, 5.84 mmol). The mixture was placed under a carbon monoxide atmosphere (4.1 bar) and heated at 100° C. After 72 h, the mixture was filtered, concentrated and the residue purified by column chromatography (SiO$_2$: 0 to 5% EtOAc in methylene chloride) affording 550 mg (57%) of the title compound.

$^1$NMR, IR

IS-MS, m/e 249 (m)

Analysis for C$_{11}$H$_9$ClN$_4$O:

| Calcd: | C, 53.13; H, 3.65; N, 22.53; |
|---|---|
| Found: | C, 53.40; H, 3.66; N, 22.45. |

An alternative preparation of N-(5-chloropyridin-2-yl)-3-aminopyridine-2-carboxamide (part F, above) is as follows:

i. N-(2-Chloropyridin-3-yl)trifluoroacetamide

To a solution of 3-amino-2-chloropyridine (10.0 g, 77.82 mmol) in 100 mL of dichloromethane was added trifluoroacetic anhydride (16.34 g, 77.82 mmol) over 20 min. The solution stirred for 1 h, and the reaction was quenched with 50 mL of saturated aqueous NaHCO$_3$. The phases were separated; and the organic layer was dried over Na$_2$SO$_4$, filtered and concentrated in vacuo to give the trifluoro-acetamide (15.9 g, 99%). The product was used without further purification.

ii. N-(5-Chloropyridin-2-yl)-3-(trifluoroacetyl)amino-pyridine-2-carboxamide

In a pressure reactor, N-(2-chloropyridin-3-yl)-trifluoroacetamide (5 g, 22 mmol, 1 equivalent), 2-amino-5-chloropyridine (4 g, 27 mmol, 1.2 eq.), Pd(OAc)$_2$ (50 mg, 0.22 mmol, 1 mol %), 1,3-bis(diphenylphosphino)propane (42 mg, 0.22 mmol, 1 mol %), and triethylamine (4.5 g, 45 mmol, 2 equivalents) were dissolved in acetonitrile (125 mL, 25 volumes). The reaction temperature was set at 100° C., and the reactor was pressurized with CO at 4.8 bar (70 psig). The reaction was monitored by observing the loss of starting material by NMR. Typically, the reaction was complete within 20 h. The reaction mixture was concentrated to a solid (about 12 g) and then slurried in 60 mL (5 vols) of MeOH. The mixture was filtered after stirring for 15 min at room temperature to afford the product, N-(5-chloropyridin-2-yl)-3-(trifluoroacetyl)aminopyridine-2-carboxamide (4.35 g, 57%), as the filter cake. (No product was observed in the mother liquor when it was concentrated to a solid). This reaction has been run a number of times, with yields in the 50% range, on a scale up to 20 g.

iii. N-(5-Chloropyridin-2-yl)-3-aminopyridine-2-carboxamide

To N-(5-chloropyridin-2-yl)-3-(trifluoroacetyl)amino-pyridine-2-carboxamide (1 g, 2.9 mmol) was added 5 mL of 2 M NH$_3$ in MeOH. The reaction vessel was capped and heated to 50° C. for 12 h. The reaction mixture was cooled to 0° C. for 30 min and filtered to provide N-(5-chloropyridin-2-yl)-3-aminopyridine-2-carboxamide (0.72 g, 100%).

G. 3-[2-(1-tert-Butoxycarbonylpiperidin-4-yloxy)-4-(methylthio)benzoylamino]-N-(5-chloropyridin-2-yl)pyridine-2-carboxamide

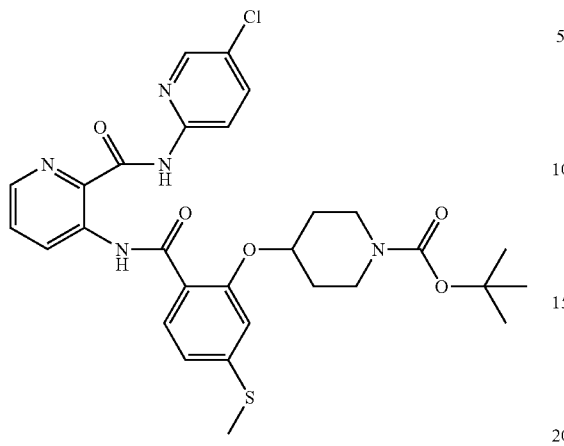

The 2-(1-tert-butoxycarbonylpiperidin-4-yloxy)-4-(methylthio)benzoic acid (201 mg, 0.55 mmol) was diluted with dichloromethane (5 mL), pyridine (52 µL, 0.64 mmol), and DMF (2 drops). Oxalyl chloride (52 µL, 0.60 mmol) was added and vigorous bubbling occurred. After about 30 minutes, the reaction was concentrated in vacuo. The residue was diluted with dichloromethane (5 mL) and the 3-amino-N-(5-chloropyridin-2-yl)pyridine-2-carboxamide (123 mg, 0.50 mmol) was added, followed by pyridine (72 µL, 0.64 mmol). The reaction was stirred overnight and then diluted with dichloromethane (50 mL) and washed with water (3×5 mL). The organic layer was dried over sodium sulfate, filtered, and concentrated. The crude residue was purified by flash column chromatography ($CH_2Cl_2$ through 5% $EtOAc/CH_2Cl_2$) to give the desired product as a pale yellow amorphous solid (214 mg, 0.36 mmol, 72%).

$^1$NMR (300 MHz, DMSO-$d_6$): δ 12.19(s, 1H); 10.78(s, 1H) 9.16(d, J=8.4 Hz, 1H); 8.43(m, 2H); 8.18(d, J=9.0 Hz, 1H); 7.96(m, 1H); 7.80(d, J=7.8 Hz, 1H); 7.73(m, 1H); 7.11 (s, 1H); 6.95(d, J=8.7 Hz, 1H); 4.86(m, 1H); 3.72(m, 2H); 3.04(m, 2H); 2.53(s, 3H); 1.86-1.76(m, 4H); 1.24(s, 9H).

IS-MS, m/e 598.3 (m+1).

H. N-(5-Chloropyridin-2-yl)-3-[4-(methylthio)-2-(piperidin-4-yloxy)benzoylamino]pyridine-2-carboxamide The 3-[2-(1-tert-butoxycarbonylpiperidin-4-yloxy)-4-(methylthio)benzoylamino]-N-(5-chloropyridin-2-yl)pyridine-2-carboxamide (184 mg, 0.31 mmol) was dissolved in TFA (4 mL). After 5 minutes, the reaction was concentrated in vacuo. The residue was diluted with dichloromethane (100 mL) and extracted with saturated aqueous sodium carbonate (2×10 mL). The organic layer was dried over sodium sulfate, filtered, and concentrated to give the desired product as a white solid (139 mg, 0.28 mmol, 90%).

mp 157-8° C.

$^1$NMR (300 MHz, DMSO-$d_6$): δ 12.20(s, 1H); 10.70(br s, 1H); 9.17(d, J=8.7 Hz, 1H); 8.43(m, 2H); 8.33(d, J=9.0 Hz, 1H); 7.99(dd, J=2.3, 8.9 Hz, 1H); 7.79(d, J=8.1 Hz, 1H); 7.72(m, 1H); 7.07(s, 1H); 6.93(d, J=8.1 Hz, 1H); 4.75(m, 1H); 2.85(d, J=12.9 Hz, 2H); 2.52(s, 3H); 2.51(m, 2H); 1.89 (m, 2H); 1.76(m, 2H).

IS-MS, m/e 498.2 (m+1).

EXAMPLE 2

Preparation of N-(5-Chloropyridin-2-yl)-3-[4-methylsulfinyl-2-(piperidin-4-yloxy)benzoylamino]pyridine-2-carboxamide

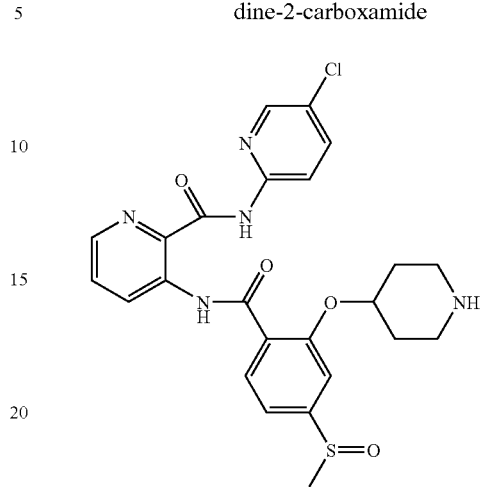

A. 3-[2-(1-tert-Butoxycarbonylpiperidin-4-yloxy)-4-methylsulfinylbenzoylamino]-N-(5-chloropyridin-2-yl)-pyridine-2-carboxamide

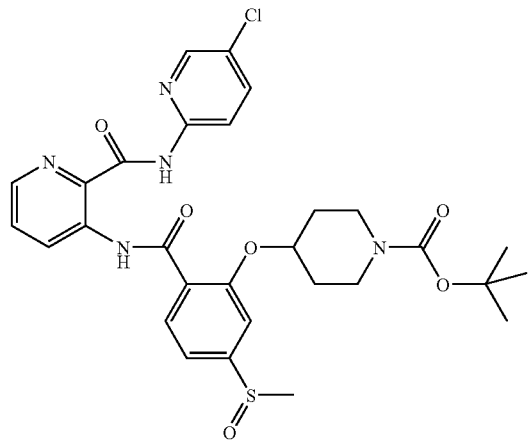

3-[2-(1-tert-Butoxycarbonylpiperidin-4-yloxy)-4-(methylthio)benzoylamino]-N-(5-chloropyridin-2-yl)pyridine-2-carboxamide (2.19 g, 3.66 mmol) was diluted with chloroform (20 mL). Camphorsulfonic acid (179 mg, 0.77 mmol) was added, followed by a solution of t-butyl hydroperoxide (0.75 mL, 7.50 mmol). After stirring overnight, the reaction was concentrated and purified by flash column chromatography (about 225 g silica, 10% $EtOAc/CH_2Cl_2$ through 10% $MeOH/CH_2Cl_2$) to give the desired product as a white solid (1.775 g, 2.89 mmol, 79%).

$^1$NMR (300 MHz, DMSO-$d_6$): δ 12.27(s, 1H); 10.79(s, 1H); 9.18(d, J=8.7 Hz, 1H); 8.44(m, 2H); 8.16(d, J=8.7 Hz, 1H); 7.99(d, J=8.1 Hz, 1H); 7.94(dd, J=2.4, 9.0 Hz, 1H); 7.75(dd, J=4.5, 8.7 Hz, 1H); 7.55(s, 1H); 7.38(d, J=8.1 Hz, 1H); 4.88(m, 1H); 3.72(m, 2H); 3.08(m, 2H); 2.81(s, 3H); 1.98(m, 2H); 1.81(m, 2H); 1.24(s, 9H).

IS-MS, m/e 614.2 (m+1).

Analysis for $C_{29}H_{32}ClN_5O_6S$:

| | |
|---|---|
| Calcd: | C, 56.72; H, 5.25; N, 11.40; |
| Found: | C, 56.99; H, 5.32; N, 11.43. |

B. N-(5-Chloropyridin-2-yl)-3-[4-methylsulfinyl-2-(piperidin-4-yloxy)benzoylamino]pyridine-2-carboxamide Using methods substantially equivalent to those described in example 1-H, N-(5-chloropyridin-2-yl)-3-[4-methylsulfinyl-2-(piperidin-4-yloxy)benzoylamino]pyridine-2-carboxamide (1.163 g, 2.26 mmol, 80%) was prepared from 3-[2-(1-tert-butoxycarbonylpiperidin-4-yloxy)-4-methylsulfinylbenzoylamino]-N-(5-chloropyridin-2-yl)-pyridine-2-carboxamide.

$^1$NMR (300 MHz, DMSO-$d_6$): δ 12.28(s, 1H); 9.19(d, J=8.4 Hz, 1H); 8.44(m, 2H); 8.30(d, J=8.7 Hz, 1H); 8.01(s, 1H); 7.99(d, J=8.4 Hz, 1H); 7.75(dd, J=4.5, 8.7 Hz, 1H); 7.52(s, 1H); 7.36(d, J=8.1 Hz, 1H); 4.76(m, 1H); 2.86(m, 2H); 2.80(s, 3H); 2.53(m, 2H); 1.93(m, 2H); 1.74(m, 2H).
IS-MS, m/e 514.4 (m+1).
Analysis for $C_{24}H_{24}ClN_5O_5S \cdot 0.25H_2O$:

| | |
|---|---|
| Calcd: | C, 55.59; H, 4.76; N, 13.51; |
| Found: | C, 55.41; H, 4.51; N, 13.35. |

EXAMPLE 3

Preparation of N-(5-Chloropyridin-2-yl)-3-[4-methylsulfonyl-2-(piperidin-4-yloxy)benzoylamino]pyridine-2-carboxamide

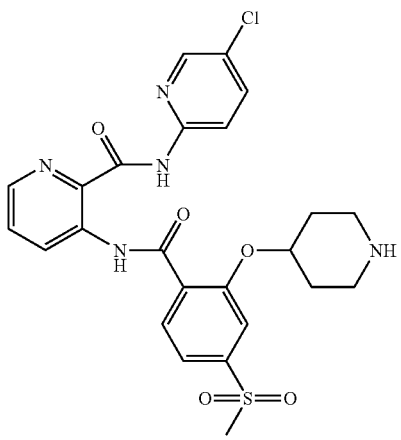

A. Methyl 2-(1-tert-butoxycarbonylpiperidin-4-yloxy)-4-(methylsulfonyl)benzoate

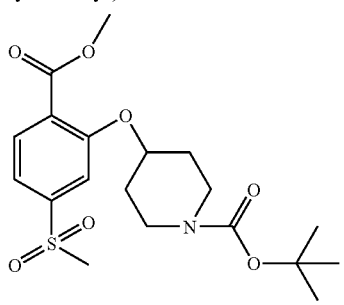

The methyl 2-(1-tert-butoxycarbonylpiperidin-4-yloxy)-4-(methylthio)benzoate (3.65 g, 9.56 mmol) was dissolved in chloroform (100 mL) and the solution was cooled to 0° C. Then 3-chloroperoxybenzoic acid (7.68 g, 25.81 mmol, 58% purity) was added in portions. After 30 minutes, the reaction was extracted with saturated aqueous sodium bicarbonate (2×50 mL). The organic layer was dried over sodium sulfate, filtered, and concentrated. The crude material was purified by flash column chromatography (5% EtOAc/CH$_2$Cl$_2$ through 10% EtOAc/CH$_2$Cl$_2$) to give the desired product (2.996 g, 7.25 mmol, 76%).

$^1$NMR (300 MHz, DMSO-$d_6$): δ 7.81(d, J=8.1 Hz, 1H); 7.63(s, 1H); 7.52(d, J=8.1 Hz, 1H); 4.88(m, 1H); 3.80(s, 3H); 3.33(m, 5H); 1.79(m, 2H); 1.62(m, 2H).
IS-MS, m/e 414.2 (m+1).

B. 2-(1-tert-Butoxycarbonylpiperidin-4-yloxy)-4-(methylsulfonyl)benzoic acid

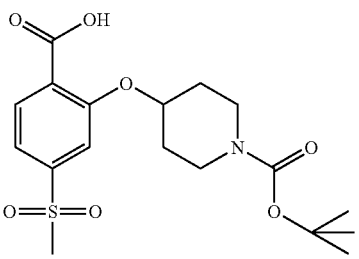

Using methods substantially equivalent to those described in Example 1-E, 2-(1-tert-butoxycarbonylpiperidin-4-yloxy)-4-(methylsulfonyl)benzoic acid (2.79 g, 6.98 mmol, 96%) was prepared from methyl 2-(1-tert-butoxycarbonylpiperidin-4-yloxy)-4-(methylsulfonyl)benzoate.

$^1$NMR (300 MHz, DMSO-$d_6$): δ 7.16(d, J=7.8 Hz, 1H); 7.60(s, 1H); 7.49(d, J=7.8 Hz, 1H); 5.72(m, 1H); 3.39-3.30 (m, 4H); 1.80(m, 2H); 1.62(s, 2H).
IS-MS, m/e 400.1 (m+1).
Analysis for $C_{18}H_{25}NO_7S$:

| | |
|---|---|
| Calcd: | C, 54.12; H, 6.31; N, 3.51; |
| Found: | C, 54.13; H, 6.29; N, 3.26. |

C. 3-[2-(1-tert-Butoxycarbonylpiperidin-4-yloxy)-4-methylsulfonylbenzoylamino]-N-(5-chloropyridin-2-yl)-pyridine-2-carboxamide

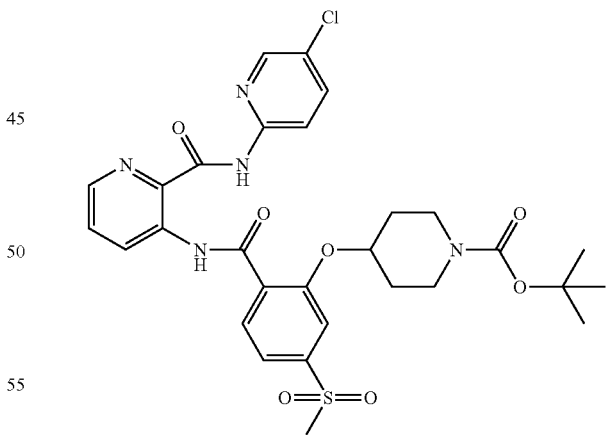

Using methods substantially equivalent to those described in Example 1-G, 3-[2-(1-tert-butoxycarbonyl-piperidin-4-yloxy)-4-methylsulfonylbenzoylamino]-N-(5-chloropyridin-2-yl)pyridine-2-carboxamide (103 mg, 0.16 mmol, 23%) was prepared from 2-(1-tert-butoxycarbonyl-piperidin-4-yloxy)-4-(methylsulfonyl)benzoic acid and 3-amino-N-(5-chloropyridin-2-yl)pyridine-2-carboxamide.

$^1$NMR (400 MHz, DMSO-$d_6$): δ 12.28(s, 1H); 10.80(s, 1H); 9.17(d, J=8.7 Hz, 1H); 8.46(m, 2H); 8.15(d, J=8.7 Hz,

1H); 8.03(d, J=7.8 Hz, 1H); 7.95(d, J=8.1 Hz, 1H); 7.76(m, 2H); 7.61(d, J=8.1 Hz, 1H); 4.96(m, 1H); 3.65(m, 2H); 3.31 (s, 3H); 3.11(m, 2H); 1.97(m, 2H); 1.80(m, 2H); 1.24(s, 9H).

IS-MS, m/e 630.2 (m+1).

Analysis for $C_{29}H_{32}ClN_5O_7S$:

| | |
|---|---|
| Calcd: | C, 55.28; H, 5.12; N, 11.11; |
| Found: | C, 55.32; H, 4.94; N, 11.04. |

D. N-(5-Chloropyridin-2-yl)-3-[4-methylsulfonyl-2-(piperidin-4-yloxy)benzoylamino]pyridine-2-carboxamide Using methods substantially equivalent to those described in Example 1-H, N-(5-chloropyridin-2-yl)-3-[4-methylsulfonyl-2-(piperidin-4-yloxy)benzoylamino]pyridine-2-carboxamide (87 mg, 0.14 mmol, 92%) was prepared from 3-[2-(1-tert-butoxycarbonylpiperidin-4-yloxy)-4-methylsulfonylbenzoylamino]-N-(5-chloropyridin-2-yl)-pyridine-2-carboxamide.

mp 148-9° C.

$^1$NMR (400 MHz, DMSO-d$_6$): δ 10.83(s, 1H); 9.15(d, J=9.2 Hz, 1H); 8.50(d, J=4.4 Hz, 1H); 8.46(d, J=2.8 Hz, 1H); 8.15(d, J=8.8 Hz, 1H); 7.99(d, J=8.8 Hz, 1H); 7.80(m, 1H); 7.76(s, 1H); 7.66(d, J=7.6 Hz, 1H); 5.04(m, 1H); 3.16(m, 4H); 2.02(m, 4H).

IS-MS, m/e 530.0 (m+1).

EXAMPLE 4

Preparation of 3-[2-(2-Aminoethoxy)-4-methylsulfonylbenzoyl-amino]-N-(5-chloropyridin-2-yl)pyridine-2-carboxamide Hydrochloride

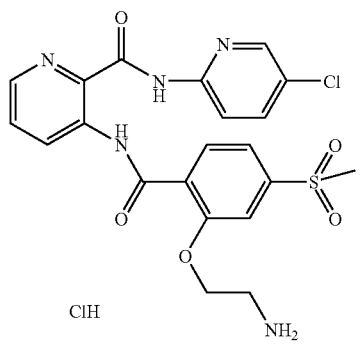

A. Methyl 2-(2-tert-butoxycarbonylaminoethoxy)-4-(methyl-thio)benzoate

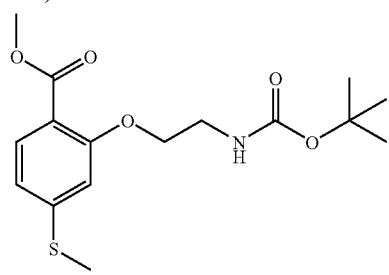

Methyl 2-(2-tert-butoxycarbonylaminoethoxy)-4-(methyl-thio)benzoate was prepared (12.6 g, 76%) as described in Example 1-D from methyl 2-hyroxy-4-(methylthio)benzoate and 2-tert-butoxycarbonylaminoethanol.

IR (CHCl$_3$): 1707, 1595, 1249, 1162 cm$^{-1}$.

$^1$NMR (300 MHz, DMSO-d$_6$) δ ppm: 7.78 (d, J=8.3 Hz, 1H), 7.26 (s, 1H), 6.83 (dd, J=1.5, 8.3 Hz, 1H), 6.78 (d, J=1.5 Hz, 1H), 4.11 (m, 2H), 3.89 (s, 3H), 3.57 (m, 2H), 2.49 (s, 3H), 1.45 (s, 9H).

IS-MS, m/e: 342.1 (m+1).

B. Methyl 2-(2-t-Butoxycarbonylaminoethoxy)-4-methylsulfonylbenzoate

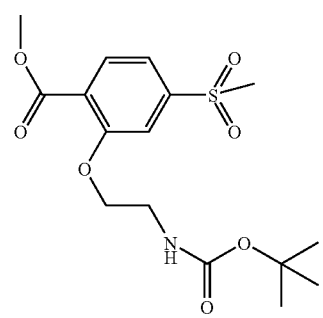

Using a procedure analogous to Example 3-A, methyl 2-(2-tert-butoxycarbonylaminoethoxy)-4-(methylthio)benzoate gave the desired product as a colorless oil (8.58 g, quant.).

$^1$NMR (300 MHz, DMSO-d$_6$) δ ppm: 7.79 (d, J=8.1 Hz, 1H), 7.57 (s, 1H), 7.52 (d, J=8.1 Hz, 1H), 4.10 (t, J=5.4 Hz, 1H), 3.80 (s, 3H), 3.29 (m, 2H), 3.25 (s, 3H), 1.34 (s, 9H).

IS-MS, m/e: 391.1 (m+NH$_4^+$).

C. 2-(2-t-Butoxycarbonylaminoethoxy)-4-methylsulfonylbenzoic acid

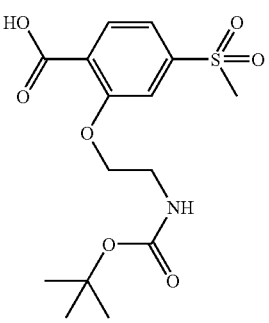

A mixture of methyl 2-(2-t-butoxycarbonylaminoethoxy)-4-methylsulfonylbenzoate (8.6 g, 23 mmol), EtOH (200 mL), and KOH (6.5 g, 115 mmol) in water (200 mL) was heated to 70° C. for 4 hours. The EtOH was removed in vacuo and the residue was diluted with CH$_2$Cl$_2$. The mixture was acidified with satd citric acid and partitioned. The organic layer was dried (Na$_2$SO$_4$) and concentrated to give the desired product as a solid (7.5 g, 91%).

$^1$NMR (300 MHz, DMSO-d$_6$) δ ppm: 7.90 (d, J=7.9 Hz, 1H), 7.59 (d, J=1.1 Hz, 1H), 7.54 (dd, J=1.1, 7.9 Hz, 1H), 6.87 (m, 1H), 4.15 (t, 6.0 Hz, 1H), 3.35 (m, 2H).

IS-MS, m/e: 358.2 (m−1).

D. 3-[2-(2-t-Butoxycarbonylaminoethoxy)-4-methylsulfonyl-benzoylamino]-N-(5-chloropyridin-2-yl)pyridine-2-carboxamide

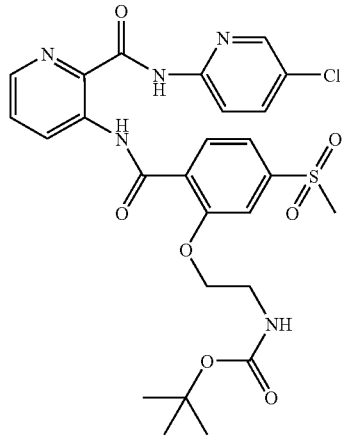

Using a procedure analogous to Example 1-G, 2-(2-t-butoxycarbonylaminoethoxy)-4-methylsulfonylbenzoic acid and 3-amino-N-(5-chloropyridin-2-yl)pyridine-2-carboxamide gave the desired product as a solid (4.0 g, 84%).

$^1$NMR (300 MHz, DMSO-$d_6$) δ ppm: 12.54 (s, 1H), 10.83 (s, 1H), 9.23 (dd, J=1.1, 8.7 Hz, 1H), 8.47 (m, 2H), 8.29 (d, J=8.7 Hz, 1H), 8.15 (d, J=7.9 Hz, 1H), 8.01 (dd, J=2.3, 8.7 Hz, 1H), 7.77 (m, 2H), 7.65 (dd, J=1.1, 7.9 Hz, 1H), 7.20 (m, 1H), 6.93 (m, 1H), 4.41 (t, J=5.6 Hz, 2H), 3.48 (m, 2H), 3.33 (s, 3H).

IS-MS, m/e: 590.4 (m+1).

E. 3-[2-(2-Aminoethoxy)-4-methylsulfonylbenzoylamino]-N-(5-chloropyridin-2-yl)pyridine-2-carboxamide

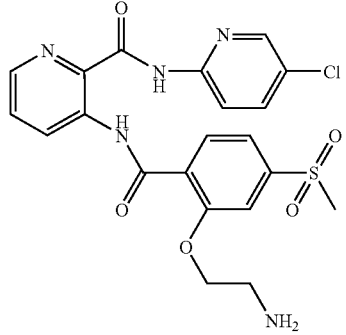

Using a procedure analogous to Example 1-H, 3-[2-(2-t-butoxycarbonylaminoethoxy)-4-methylsulfonylbenzoylamino]-N-(5-chloropyridin-2-yl)pyridine-2-carboxamide gave the desired product as a solid (3.2 g, 99%).

$^1$NMR

IS-MS, m/e: 490.2 (m+1).

Analysis for $C_{21}H_{20}ClN_5O_5S$:

| Calcd: | C, 51.48; H, 4.11; N, 14.29; |
| --- | --- |
| Found: | C, 51.73; H, 4.27; N, 14.18. |

F. 3-[2-(2-Aminoethoxy)-4-methylsulfonylbenzoylamino]-N-(5-chloropyridin-2-yl)pyridine-2-carboxamide hydrochloride To a mixture of 3-[2-(2-aminoethoxy)-4-methylsulfonyl-benzoylamino]-N-(5-chloropyridin-2-yl)pyridine-2-carboxamide (3.17 g, 6.5 mmol) and 10% MeOH/CH$_2$Cl$_2$ (250 mL) was added 5 N HCl. After stirring for 1 hour, the mixture was concentrated to give the desired product as a solid (3.25 g, 96%).

$^1$NMR (300 MHz, DMSO-$d_6$) δ ppm: 12.46 (s, 1H), 10.96 (S, 1H), 9.26 (dd, J=1.3, 8.5 Hz, 1H), 8.51 (m, 2H), 8.18 (m, 5H), 8.04 (dd, J=2.7, 8.7 Hz, 1H), 7.79 (m, 2H), 7.72 (dd, J=1.5, 8.5 Hz, 1H), 4.65 (t, J=4.7 Hz, 2H), 3.43 (m, 2H), 3.36 (s, 3H).

IS-MS, m/e: 490.2 (m+1).

Analysis for $C_{21}H_{20}ClN_5O_5S\cdot HCl$:

| Calcd: | C, 47.92; H, 4.02; N, 13.30; |
| --- | --- |
| Found: | C, 47.22; H, 4.22; N, 12.99. |

EXAMPLE 5

Preparation of N-(5-Chloropyridin-2-yl)-3-[2-(1-methyl-piperidin-4-yloxy)-4-methylsulfonylbenzoylamino]pyridine-2-carboxamide Hydrochloride

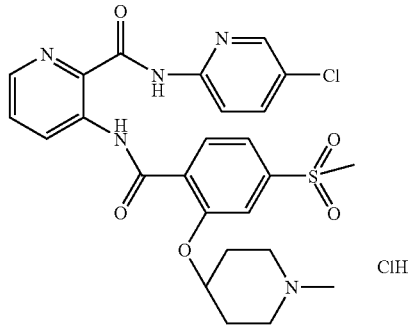

To a mixture of N-(5-chloropyridin-2-yl)-3-[4-methyl-sulfonyl-2-(piperidin-4-yloxy)benzoylamino]pyridine-2-carboxamide (400 mg, 0.75 mmol), paraformaldehyde (95 mg, 3.2 mmol), and MeOH (75 mL) was added a few drops of 1 N HCl and NaCNBH$_3$ (94 mg, 1.5 mmol). After stirring overnight, the reaction was acidified to pH 2 with 1 N HCl and stirred for 1 hour. The mixture was extracted with CH$_2$Cl$_2$. The organic layer was washed with satd Na$_2$CO$_3$, dried (Na$_2$SO$_4$), and concentrated. The residue was purified by HPLC on a Vydac C18 column [prep: gradient 5% CH$_3$CN/(0.01% HCl in H$_2$O) to 55% CH$_3$CN/(0.01% HCl in H$_2$O) over 6 h on a 5×25 cm column; analytical: 5% CH$_3$CN/(0.1% TFA in H$_2$O) to 70% CH$_3$CN/(0.1% TFA in H$_2$O); rt: 27.13 min] to give the title product as a white solid (210 mg, 48.3%).

mp>200° C.

$^1$NMR (300 MHz, DMSO-$d_6$) δ ppm: 12.20 (s, 0.5H), 12.09 (s, 0.5H), 10.86 (s, 0.5H), 10.81 (s, 0.5H), 10.40 (br s, 0.5H), 10.10 (br s, 0.5H), 9.13 (m, 1H), 8.48 (m, 2H), 8.17 (d, J=9.0 Hz, 0.5H), 8.09 (d, J=9.0 Hz, 0.5H), 8.00 (m, 2H), 7.80-7.63 (m, 3H), 5.13 (s, 0.5H), 4.90 (m, 0.5H), 3.42 (m, 2H), 3.30 (s, 3H), 3.04 (m, 2H), 2.68 (d, J=3.9 hz, 1.5H), 2.55 (d, J=3.9 hz, 1.5H), 2.24 (m, 4H).

IS-MS, m/e: 544.3 (m+1).

Analysis for $C_{25}H_{26}ClN_5O_5S\cdot HCl$:

| Calcd: | C, 51.73; H, 4.69; N, 12.06; |
| --- | --- |
| Found: | C, 51.36; H, 4.47; N, 11.61. |

EXAMPLE 6

Preparation of 3-[2-(3-Aminopropoxy)-4-methylsulfonyl-benzoylamino]-N-(5-chloropyridin-2-yl)pyridine-2-carboxamide Hydrochloride

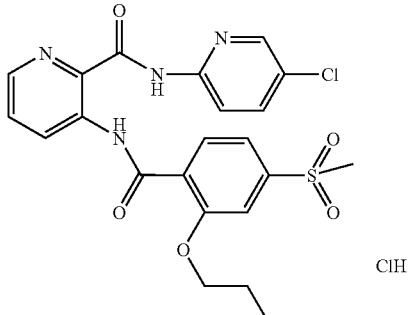

A. Methyl 2-(3-tert-Butoxycarbonylaminopropoxy)-4-(methylthio)benzoate

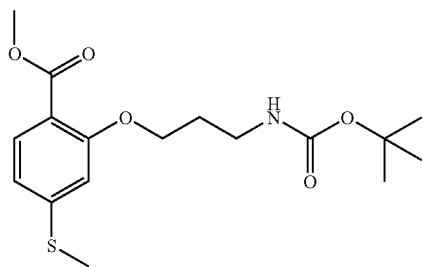

Methyl 2-(3-tert-butoxycarbonylaminopropoxy)-4-(methylthio)benzoate was prepared (7.0 g, 82%) as described in Example 1-D from methyl 2-hydroxy-4-(methylthio)benzoate and 3-tert-butoxycarbonylaminopropanol.

$^1$NMR (300 MHz, DMSO-$d_6$) δ ppm: 7.82 (d, J=8.3 Hz, 1H), 6.80 (m, 2H), 6.0 (s, 1H), 4.11 (t, 5.3 Hz, 2H), 3.88 (s, 3H), 3.42 (m, 2H), 2.50 (s, 3H), 2.05 (m, 2H), 1.44 (s, 9H).

IS-MS, m/e: 356.4 (m+1).

Analysis for $C_{17}H_{25}NO_5S$:

| | |
|---|---|
| Calcd: | C, 57.44; H, 7.09; N, 3.94; |
| Found: | C, 57.41; H, 7.04; N, 4.24. |

B. Methyl 2-(3-tert-Butoxycarbonylaminopropoxy)-4-methylsulfonylbenzoate

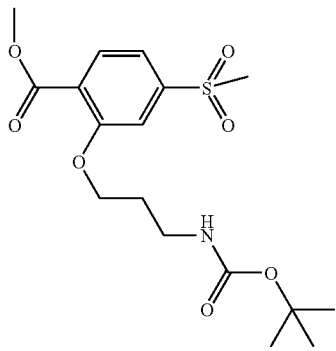

Using a procedure analogous to Example 3-A, methyl 2-(3-tert-butoxycarbonylaminopropoxy)-4-(methylthio)benzoate gave the desired product as a colorless oil (10.87 g, 100%).

$^1$NMR (300 MHz, DMSO-$d_6$) δ ppm: 7.81 (d, J=8.1 Hz, 1H), 7.54 (s, 1H), 7.51 (d, J=8.1 Hz, 1H), 6.85 (m, 1H), 4.12 (t, J=6.0 Hz, 1H), 3.81 (s, 3H), 3.29 (s, 3H), 3.08 (m, 2H), 1.82 (m, 2H), 1.33 (s, 9H).

IS-MS, m/e: 388.1 (m+1).

C. 2-(3-tert-Butoxycarbonylaminopropoxy)-4-methylsulfonyl-benzoic acid

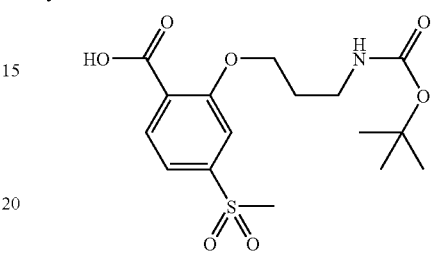

Using a procedure analogous to Example 4-C, methyl 2-(3-tert-butoxycarbonylaminopropoxy)-4-methylsulfonyl-benzoate gave the desired product as a solid (9.48 g, 91%).

$^1$NMR (300 MHz, DMSO-$d_6$) δ ppm: 13.13 (br s, 1H), 7.79 (d, J=7.5 Hz, 1H), 7.54 (m, 2H), 6.87 (m, 1H), 4.14 (t, J=6.4 Hz, 2H), 3.26 (s, 3H), 3.10 (m, 2H), 1.86 (m, 2H), 1.36 (s, 9H).

IS-MS, m/e: 374.1 (m+1).

D. 3-[2-(3-tert-Butoxycarbonylaminopropoxy)-4-methylsulfonylbenzoylamino]-N-(5-chloropyridin-2-yl)pyridine-2-carboxamide

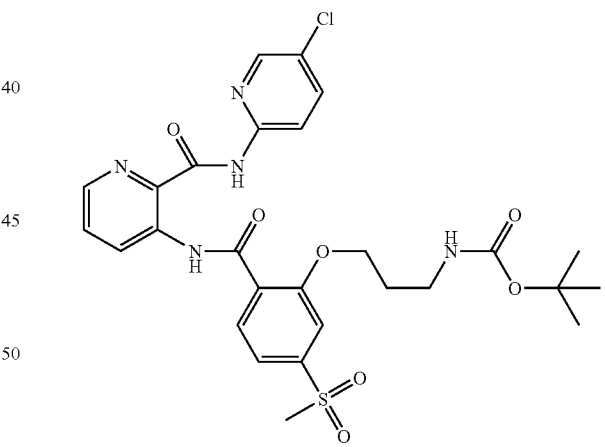

Using a procedure analogous to Example 1-G, 2-(3-tert-butoxycarbonylaminopropoxy)-4-methylsulfonylbenzoic acid and 3-amino-N-(5-chloropyridin-2-yl)pyridine-2-carboxamide gave the desired product as a solid (1.95 g, 40%).

$^1$NMR (300 MHz, DMSO-$d_6$) δ ppm: 12.44 (s, 1H), 10.82 (s, 1H), 9.22 (dd, J=1.1, 8.7 Hz, 1H), 8.48 (m, 2H), 8.23 (d, J=9 Hz, 1H), 8.11 (d, J=8.3 Hz, 1H), 8.02 (dd, J=2.6, 8.7 Hz, 2H), 7.79 (dd, J=4.5, 8.7 Hz, 1H), 7.72 (s, 1H), 7.65 (dd, J=1.1, 8.3 Hz, 1H), 6.79 (m, 1H), 4.40 (t, J=6.0 Hz, 2H), 3.32 (s, 3H), 3.04 (m, 2H), 1.97 (m, 2H), 1.26 (s, 9H).

IS-MS, m/e: 604.3 (m+1).

E. 3-[2-(3-Aminopropoxy)-4-methylsulfonylbenzoylamino]-N-(5-chloropyridin-2-yl)pyridine-2-carboxamide Hydrochloride Using a procedure analogous to Example 1-H, 3-[2-(3-tert-butoxycarbonylaminopropoxy)-4-methylsulfonylbenzoyl-amino]-N-(5-chloropyridin-2-yl)pyridine-2-carboxamide gave the desired product as a solid (1.5 g, 90%).

$^1$NMR (300 MHz, DMSO-$d_6$) δ ppm: 9.20 (dd, J=1.1, 8.4 Hz, 1H), 8.51 (m, 2H), 8.21 (d, J=8.8 Hz, 1H), 8.10 (d, J=8.0 Hz, 1H), 8.04 (dd, J=2.6, 8.8 Hz, 1H), 7.81 (dd, J=4.4, 8.4 Hz, 1H), 7.75 (d, J=1.1, Hz, 1H), 7.68 (dd, 1.5, 8.0 Hz, 1H), 4.50 (t, J=6.2 Hz, 2H), 3.34 (s, 3H), 2.89 (m, 2H), 2.11 (m, 2H).

IS-MS, m/e: 506.1 (m+1).

Analysis for $C_{22}H_{23}ClN_5O_5S$—HCl:

| Calcd: | C, 48.90; H, 4.29; N, 12.96; |
| Found: | C, 48.78; H, 4.34; N, 12.83. |

EXAMPLE 7

Preparation of 3-[2-(2-Aminoethoxy)-4-(methylthio)benzoyl-amino]-N-(5-chloropyridin-2-yl)pyridine-2-carboxamide

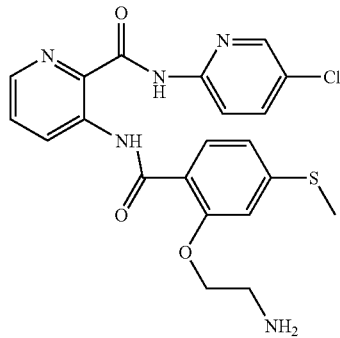

A. 2-(2-tert-Butoxycarbonylaminoethoxy)-4-(methylthio)-benzoic acid

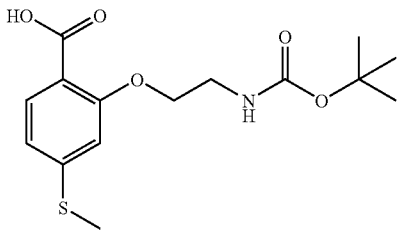

Methyl 2-(2-tert-butoxycarbonylaminoethoxy)-4-(methylthio)benzoate was added to a solution of KOH (9.05 g, 161.2 mmol) in EtOH (200 mL) and H$_2$O (200 mL). The reaction was heated to 70° C. for two hours. Ethanol was removed in vacuo and the remaining aqueous solution was diluted with CH$_2$Cl$_2$ (500 mL) and saturated citric acid (200 mL). The organic layer was partitioned, dried over Na$_2$SO$_4$, and concentrated to yield 2-(2-tert-butoxycarbonyl-aminoethoxy)-4-(methylthio)benzoic acid (9.1 g, 87%).

IR (CHCl$_3$): 1711, 1597, 1412, 1162 cm$^{-1}$.

$^1$NMR (300 MHz, DMSO-$d_6$) δ ppm: 8.05 (d, J=8.3 Hz, 1H), 7.26 (s, 1H), 6.93 (dd, J=1.5, 8.3 Hz, 1H), 6.84 (d, J=1.5 Hz, 1H), 5.05 (s, 1H), 4.28 (t, J=5.7 Hz, 2H), 3.62 (dt, J=5.7, 10.9 Hz, 2H), 2.52 (s, 3H), 1.45 (s, 9H).

IS-MS, m/e: 328.2 (m+1).

Analysis for $C_{15}H_{21}NO_5S$:

| Calcd: | C, 55.03; H, 6.47; N, 4.28; |
| Found: | C, 54.80; H, 6.21; N, 4.50. |

B. 3-[2-(2-tert-Butoxycarbonylaminoethoxy)-4-(methylthio)-benzoylamino]-N-(5-chloropyridin-2-yl)pyridine-2-carboxamide

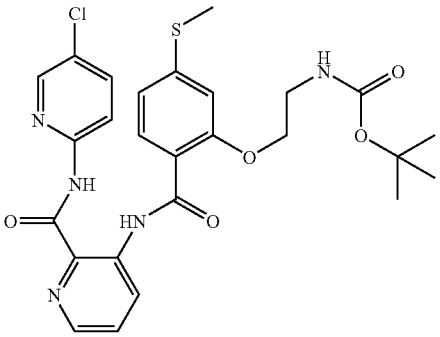

Using a procedure analogous to Example 1-G, 2-(2-tert-butoxycarbonylaminoethoxy)-4-(methylthio)benzoic acid and 3-amino-N-(5-chloropyridin-2-yl)pyridine-2-carboxamide gave the desired product as a solid (4.0 g, 79%).

$^1$NMR (300 MHz, DMSO-$d_6$) δ ppm: 12.45 (s, 1), 10.81 (s, 1H), 9.24 (d, J=8.4 Hz, 1H), 8.44 (m, 2H), 8.31 (d, J=8.8 Hz, 1H), 8.02 (dd, J=2.6, 8.8 Hz, 1H), 7.91 (d, J=8.0 Hz, 1H), 7.73 (dd, J=4.4, 8.4 Hz, 1H), 7.11 (s, 1H), 6.96 (m, 2H), 4.37 (t, J=5.5 Hz, 2H), 3.46 (m, 2H), 2.58 (s, 3H), 1.23 (s, 9H).

IS-MS, m/e: 558.1 (m+1).

Analysis for $C_{26}H_{28}ClN_5O_5S$:

| Calcd: | C, 55.96; H, 5.06; N, 12.55; |
| Found: | C, 55.64; H, 5.11; N, 12.18. |

C. 3-[2-(2-Aminoethoxy)-4-(methylthio)benzoylamino]-N-(5-chloropyridin-2-yl)pyridine-2-carboxamide Using a procedure analogous to Example 1-H, 3-[2-(2-tert-butoxycarbonylaminoethoxy)-4-(methylthio)benzoyl-amino]-N-(5-chloropyridin-2-yl)pyridine-2-carboxamide gave the desired product as a solid (300 mg, 16.6%).

mp 158-9° C.

$^1$NMR (300 MHz, DMSO-$d_6$) δ ppm: 9.18 (dd, J=1.1, 8.8 Hz, 1H), 8.46 (m, 2H), 8.24 (d, J=8.8 Hz, 1H), 8.04 (dd, J=2.6, 8.8 Hz, 1H), 7.88 (d, J=8.4 Hz, 1H), 7.74 (dd, J=4.4, 8.4 Hz, 1H), 7.09 (d, J=1.1 Hz, 1H), 6.98 (dd, J=1.4, 8.4 Hz, 1H), 4.31 (t, J=5.9 hz, 2H), 2.99 (t, J=5.9 Hz, 2H), 2.57 (s, 3H).

IS-MS, m/e: 458.4 (m+1).

Analysis for $C_{21}H_{20}ClN_5O_3S$:

| Calcd: | C, 55.08; H, 4.40; N, 15.29; |
| Found: | C, 55.21; H, 4.23; N, 14.90. |

EXAMPLE 8

Preparation of 3-[2-(2-Aminoethoxy)-4-methylsulfinylbenzoyl-amino]-N-(5-chloropyridin-2-yl)pyridine-2-carboxamide Hydrochloride

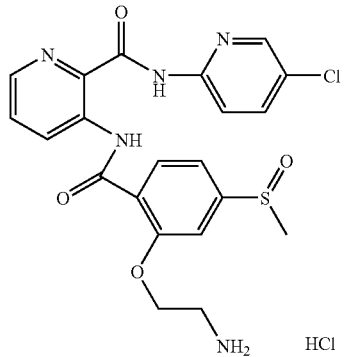

A. 3-[2-(2-t-Butoxycarbonylaminoethoxy)-4-methylsulfinyl-benzoylamino]-N-(5-chloropyridin-2-yl)pyridine-2-carboxamide

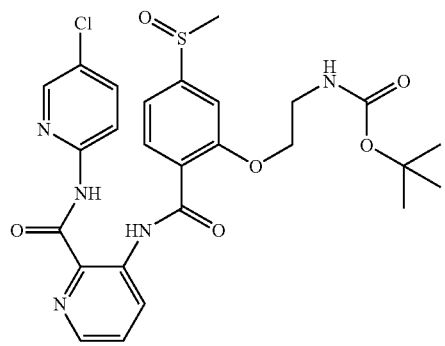

Using a procedure analogous to Example 2-A, 3-[2-(2-tert-butoxycarbonylaminoethoxy)-4-(methylthio)benzoylamino]-N-(5-chloropyridin-2-yl)pyridine-2-carboxamide gave the desired product as a solid (2.7 g, 75%).

$^1$NMR (300 MHz, DMSO-$d_6$) δ ppm: 12.51 (s, 1H), 10.83 (s, 1H), 9.23 (dd, J=1.1, 8.8 Hz, 1H), 8.46 (m, 2H), 8.30 (d, J=8.8 Hz, 1H), 8.12 (d, J=8.0 Hz, 1H), 8.01 (dd, J=2.6, 8.8 Hz, 1H), 7.76 (dd, J=4.4, 8.4 Hz, 1H), 7.55 (s, 1H), 7.43 (dd, J=0.7, 8.0 Hz, 1H), 6.91 (m, 1H), 4.38 (t, J=5.5 Hz, 2H), 3.48 (m, 2H), 2.84 (s, 3H), 1.20 (s, 9H).

IS-MS, m/e: 574 (m+1).

Analysis for $C_{26}H_{28}ClN_5O_6S$:

| Calcd: | C, 54.40; H, 4.92; N, 12.20; |
| Found: | C, 54.56; H, 4.94; N, 12.26. |

B. 3-[2-(2-Aminoethoxy)-4-methylsulfinylbenzoylamino]-N-(5-chloropyridin-2-yl)pyridine-2-carboxamide Using a procedure analogous to Example 1-H, 3-[2-(2-t-butoxycarbonylaminoethoxy)-4-methylsulfinylbenzoylamino]-N-(5-chloropyridin-2-yl)pyridine-2-carboxamide gave the desired product as a solid (2.2 g, 99%).

1NMR (300 MHz, DMSO-$d_6$) δ ppm: 9.20 (dd, J=1.1, 8.8 Hz, 1H), 8.48 (m, 2H), 8.23 (d, J=8.8 Hz, 1H), 8.05 (m, 2H), 7.78 (dd, J=4.4, 8.4 Hz, 1H), 7.56 (d, J=1.1, 1H), 7.41 (dd, J=1.1, 8.0 Hz, 1H), 4.32 (t, J=5.9 Hz, 2H), 2.99 (t, J=5.9 Hz, 1H), 2.84 (s, 3H).

IS-MS, m/e: 474.0 (m+1).

C. 3-[2-(2-Aminoethoxy)-4-methylsulfinylbenzoylamino]-N-(5-chloropyridin-2-yl)pyridine-2-carboxamide hydrochloride Using a procedure analogous to Example 4-F, 3-[2-(2-aminoethoxy)-4-methylsulfinylbenzoylamino]-N-(5-chloropyridin-2-yl)pyridine-2-carboxamide gave the desired product as a solid (2.37 g, quant.).

$^1$NMR (300 MHz, DMSO-$d_6$) δ ppm: 12.42 (s, 1H), 10.95 (s, 1H), 9.26 (dd, J=1.1, 8.8 Hz, 1H), 8.48 (m, 2H), 8.15 (m, 5H), 8.03 (dd, J=2.6, 8.8 Hz, 1H), 7.79 (dd, J=4.4, 8.4 Hz, 1H), 7.61 (s, 1H), 7.47 (dd, J=1.1, 8.4 Hz, 1H), 4.62 (t, J=5.1 Hz, 2H), 3.42 (m, 2H), 2.86 (s, 3H).

IS-MS, m/e: 474.0 (m+1).

Analysis for $C_{21}H_{20}ClN_5O_4S \cdot HCl$:

| Calcd: | C, 49.42; H, 4.15; N, 13.72; |
| Found: | C, 49.98; H, 4.15; N, 13.50. |

EXAMPLE 9

Preparation of N-(5-Chloropyridin-2-yl)-3-[2-(2-dimethyl-aminoethoxy)-4-methylsulfonylbenzoylamino]pyridine-2-carboxamide Hydrochloride

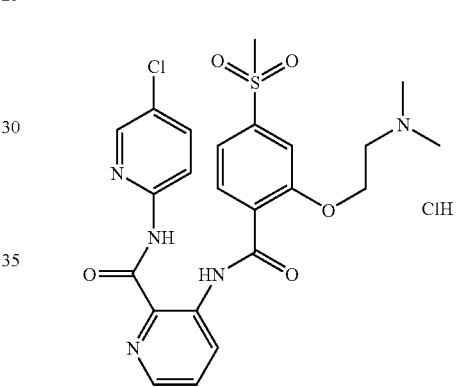

A. N-(5-Chloropyridin-2-yl)-3-[2-(2-dimethylaminoethoxy)-4-methylsulfonylbenzoylamino]pyridine-2-carboxamide using a procedure analogous to Example 5, 3-[2-(2-aminoethoxy)-4-methylsulfonylbenzoylamino]-N-(5-chloro-pyridin-2-yl)pyridine-2-carboxamide gave the desired product as a solid (590 mg, quant.).

$^1$NMR (300 MHz, DMSO-$d_6$) δ ppm: 12.39 (s, 1H), 10.85 (s, 1H), 9.18 (dd, J=1.1, 8.4 Hz, 1H), 8.48 (m, 2H), 8.24 (d, J=8.8 Hz, 1H), 8.09 (d, J=8.0 Hz, 1H), 8.03 (dd, J=2.6, 8.8 Hz, 1H), 7.77 (m, 2H), 7.65 (dd, J=1.5, 8.0 Hz, 1H), 4.46 (t, J=5.9 Hz, 2H), 3.33 (s, 3H), 2.72 (t, J=5.9 Hz, 2H), 2.09 (s, 6H).

IS-MS, m/e: 518.2 (m+1).

B. N-(5-Chloropyridin-2-yl)-3-[2-(2-dimethylaminoethoxy)-4-methylsulfonylbenzoylamino]pyridine-2-carboxamide hydrochloride N-(5-Chloropyridin-2-yl)-3-[2-(2-dimethylaminoethoxy)-4-methylsulfonylbenzoylamino]pyridine-2-carboxamide was purified by HPLC on a Vydac C18 column [prep: gradient 5% $CH_3CN$/(0.01% HCl in $H_2O$) to 55% $CH_3CN$/(0.01% HCl in $H_2O$) over 6 h on a 5×25 cm column; analytical: 5% $CH_3CN$/(0.1% TFA in $H_2O$) to 70% $CH_3CN$/(0.1% TFA in $H_2O$); rt: 20.69 min] to give the title product (316 mg, 59%).

mp>200° C.

¹NMR (300 MHz, DMSO-d₆) δ ppm: 12.30 (s, 1H), 10.90 (s, 1H), 9.85 (br s, 1H), 9.18 (d, J=8.7 Hz, 1H), 8.47 (m, 2H), 8.15 (d, J=9.0 Hz, 1H), 8.07 (d, J=8.1 Hz, 1H), 7.99 (dd, J=2.4, 8.7 Hz, 1H), 7.76 (m, 2H), 7.70 (d, J=8.1 Hz, 1H), 4.74 (m, 2H), 3.62 (m, 2H), 3.13 (s, 3H), 2.74 (s, 6H).

IS-MS, m/e: 518.2 (m+1).

Analysis for $C_{23}H_{24}ClN_5O_5S \cdot HCl$:

| Calcd: | C, 49.82; H, 4.54; N, 12.63; |
| Found: | C, 49.24; H, 4.33; N, 12.35. |

EXAMPLE 10

Preparation of 3-[2-(3-Aminopropoxy)-4-(methylthio)benzoyl-amino]-N-(5-chloropyridin-2-yl)pyridine-2-carboxamide

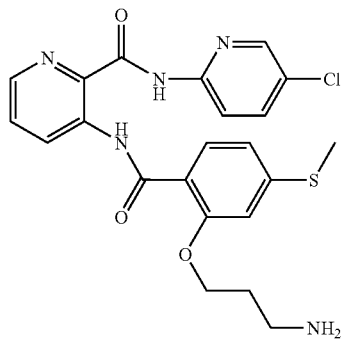

A. 2-(3-tert-Butoxycarbonylaminopropoxy)-4-(methylthio)-benzoic acid

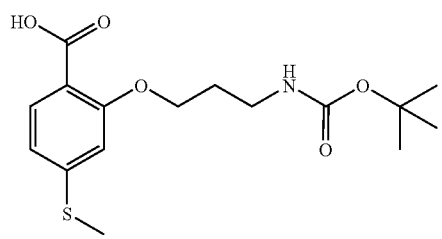

Using a procedure analogous to Example 4-C, methyl 2-(3-tert-butoxycarbonylaminopropoxy)-4-(methylthio)benzoate gave 2-(3-tert-butoxycarbonylaminopropoxy)-4-(methylthio)-benzoic acid (6.04 g, 93%).

¹NMR (300 MHz, DMSO-d₆) δ ppm: 8.03 (d, J=8.3 Hz, 1H), 6.92 (dd, J=1.5, 8.3 Hz, 1H), 6.83 (d, 1.5 Hz, 1H), 4.85 (m, 1H), 4.27 (t, J=6.4 Hz, 2H), 3.35 (m, 2H), 2.52 (s, 3H), 2.10 (m, 2H), 1.42 (s, 9H).

IS-MS, m/e: 342.1 (m+1).

Analysis for $C_{16}H_{23}NO_5S$:

| Calcd: | C, 56.29; H, 6.79; N, 4.10; |
| Found: | C, 56.33; H, 6.49; N, 4.38. |

B. 3-[2-(3-tert-Butoxycarbonylaminopropoxy)-4-(methylthio)benzoylamino]-N-(5-chloropyridin-2-yl)pyridine-2-carboxamide Using a procedure analogous to Example 1-G, 2-(3-tert-butoxycarbonylaminopropoxy)-4-(methylthio)benzoic acid and 3-amino-N-(5-chloropyridin-2-yl)pyridine-2-carboxamide gave the desired product as a solid which was purified by HPLC (2.2 g, 28%).

¹NMR (300 MHz, DMSO-d₆) δ ppm: 12.37 (s, 1H), 10.81 (s, 1H), 9.21 (dd, J=8.4 Hz, 1H), 8.46 (m, 2H), 8.26 (d, J=9.1 Hz, 1H), 8.03 (dd, J=2.2, 8.8 Hz, 1H), 7.89 (d, J=8.4 Hz, 1H), 7.74 (dd, J=4.4, 8.4 Hz, 1H), 7.05 (s, 1H), 6.99 (d, J=8.4 Hz, 1H), 6.78 (m, 1H), 4.37 (t, J=6.6 Hz, 2H), 3.04 (m, 2H), 2.57 (s, 3H), 1.98 (m, 2H), 1.7 (s, 9H).

IS-MS, m/e: 572.2 (m+1).

Analysis for $C_{27}H_{30}ClN_5O_5S$:

| Calcd: | C, 56.69; H, 5.29; N, 12.24; |
| Found: | C, 56.70; H, 5.03; N, 12.01. |

C. 3-[2-(3-Aminopropoxy)-4-(methylthio)benzoylamino]-N-(5-chloropyridin-2-yl)pyridine-2-carboxamide Using a procedure analogous to Example 1-H, 3-[2-(3-tert-butoxycarbonylaminopropoxy)-4-(methylthio)benzoyl-amino]-N-(5-chloropyridin-2-yl)pyridine-2-carboxamide gave the desired product as a solid (340 mg, quant.).

¹NMR (300 MHz, DMSO-d₆) δ ppm: 9.21 (dd, J=1.5, 8.8 Hz, 1H), 8.45 (m, 2H), 8.28 (d, J=8.8 Hz, 1H), 8.04 (dd, J=2.6, 8.8 Hz, 1H), 7.88 (d, J=8.1 Hz, 1H), 7.74 (dd, J=4.4, 8.4 Hz, 1H), 7.09 (d, J=1.5 Hz, 1H), 6.97 (dd, J=1.5, 8.4 Hz, 1H), 4.44 (t, J=6.6 Hz, 2H), 2.62 (t, J=6.6 Hz, 2H), 2.57 (s, 3H), 1.89 (m, 2H).

IS-MS, m/e: 472.2 (m+1).

EXAMPLE 11

Preparation of 3-[2-(3-Aminopropoxy)-4-methyl-sulfinyl-benzoylamino]-N-(5-chloropyridin-2-yl)pyridine-2-carboxamide

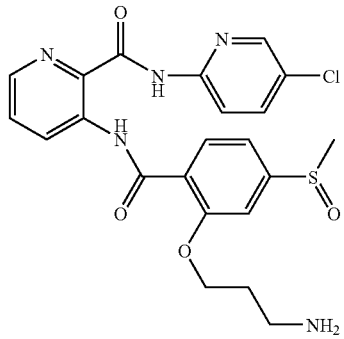

A. 3-[2-(3-t-Butoxycarbonylaminopropoxy)-4-methylsulfinyl-benzoylamino]-N-(5-chloropyridin-2-yl)pyridine-2-carboxamide Using a procedure analogous to Example 2-A, 3-[2-(3-t-butoxycarbonylaminopropoxy)-4-(methylthio)benzoyl-amino]-N-(5-chloropyridin-2-yl)pyridine-2-carboxamide gave the desired product as a solid (1.2 g, 69%).

¹NMR (300 MHz, DMSO-d₆) δ ppm: 12.44 (s, 1H), 10.82 (s, 1H), 9.22 (dd, J=1.1, 8.8 Hz, 1H), 8.46 (m, 2H), 8.25 (d, J=8.8 Hz, 1H), 8.08 (d, J=8.1 Hz, 1H), 8.02 (dd, J=2.6, 9.1 Hz, 1H), 7.77 (dd, J=4.4, 8.4 Hz, 1H), 7.98 (s, 1H), 7.41 (dd, J=1.1, 8.0 Hz, 1H), 6.79 (m, 1H), 4.38 (t, J=6.2 Hz, 2H), 3.05 (m, 2H), 2.84 (s, 3H), 1.98 (m, 2H), 1.26 (s, 9H).

IS-MS, m/e: 588.2 (m+1).

Analysis for $C_{27}H_{30}ClN_5O_6S$:

| Calcd: | C, 55.15; H, 5.14; N, 11.91; |
| Found: | C, 54.96; H, 5.13; N, 11.96. |

B. 3-[2-(3-Aminopropoxy)-4-methylsulfinylbenzoylamino]-N-(5-chloropyridin-2-yl)pyridine-2-carboxamide Using a procedure analogous to Example 1-H, 3-[2-(3-t-butoxycarbonylaminopropoxy)-4-methylsulfinylbenzoylamino]-N-(5-chloropyridin-2-yl)pyridine-2-carboxamide gave the desired product as a solid (940 mg, 94%).

$^1$NMR (300 MHz, DMSO-d$_6$) δ ppm: 9.21 (dd, J=1.1, 8.8 Hz, 1H), 8.46 (m, 2H), 8.25 (d, J=9.1 Hz, 1H), 8.07 (d, J=8.4 Hz, 1H), 8.03 (m, 2H), 7.77 (dd, J=4.4, 8.8 Hz, 1H), 7.56 (d, J=1.1 Hz, 1H), 7.40 (dd, J=1.1, 8.1 Hz, 1H), 4.45 (t, J=6.6 Hz, 2H), 2.84 (s, 3H), 2.63 (t, J=6.6 Hz, 2H), 1.91 (m, 2H).

IS-MS, m/e: 488.3 (m+1).

EXAMPLE 12

Preparation of 3-[2-(3-Aminopropoxy)-4-methylsulfinyl-benzoylamino]-N-(5-chloropyridin-2-yl)pyridine-2-carboxamide hydrochloride

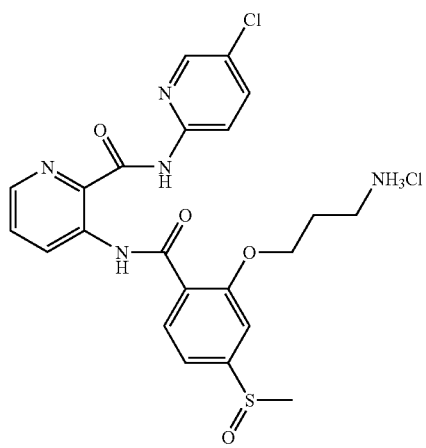

Using a procedure analogous to Example 4-F, 3-[2-(3-aminopropoxy)-4-methylsulfinylbenzoylamino]-N-(5-chloro-pyridin-2-yl)pyridine-2-carboxamide gave the title compound as a white solid (635 mg, 99%).

$^1$NMR (300 MHz, DMSO-d$_6$) δ 2.16 (m, 2H), 2.92 (m, 2H), 3.55 (s, 3H), 4.49 (t, J=5.9 Hz, 2H), 7.44 (dd, J=1.1, 8.1 Hz, 1H), 7.58 (s, 1H), 7.86 (m, 2H), 8.06 (m, 2H), 8.22 (d, J=8.8 Hz, 1H), 8.49 (m, 2H), 9.21 (dd, J=1.1, 8.4 Hz, 1H), 10.86 (s, 1H), 12.39 (s, 1H).

FIA-MS, m/e: 488.3 (m+1).
Analysis for C$_{22}$H$_{22}$ClN$_5$O$_4$S.HCl:

| | |
|---|---|
| Calcd: | C, 50.39; H, 4.42; N, 13.35; |
| Found: | C, 50.70; H, 4.40; N, 13.16. |

EXAMPLE 13

Preparation of N-(5-Chloropyridin-2-yl)-3-[4-methylsulfinyl-2-[3-(1-pyrrolidinyl)propoxy]benzoylamino]pyridine-2-carboxamide Hydrochloride

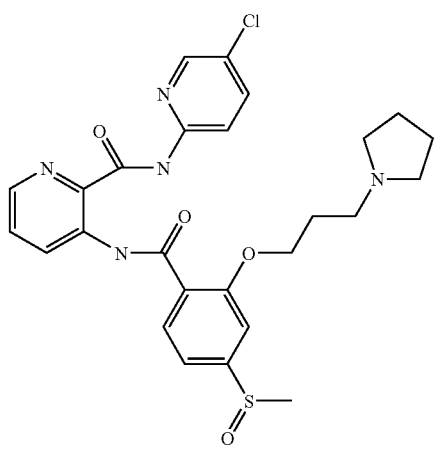

To a mixture of 3-[2-(3-aminopropoxy)-4-methylsulfinyl-benzoylamino]-N-(5-chloropyridin-2-yl)pyridine-2-carboxamide (650 mg, 1.33 mmol), DMF (10 mL) and K$_2$CO$_3$ (552 mg, 4.0 mmol) was added 1,4-dibromobutane (0.16 mL, 1.33 mmol) and the mixture was heated to 80° C. for 5 h. The reaction mixture was cooled, diluted with EtOAc and water, and partitioned. The organic layer was concentrated and chromatographed (250 g of SiO$_2$, CH$_2$Cl$_2$ to 5% of 2 M NH$_3$/MeOH in CH$_2$Cl$_2$) to give impure product. This material was HPLC on a Vydac C18 column [5% CH$_3$CN/(0.1% TFA in H$_2$O) to 70% CH$_3$CN/(0.1% TFA in H$_2$O); Rt: 26.1 m] to give the desired product as a white solid (279 mg, 36%).

$^1$NMR (300 MHz, DMSO-d$_6$) δ 1.81(m, 4H), 2.29(m, 2H), 2.82(m, 2H), 286(s, 3H), 323(m, 2H), 3.38(m, 2H), 4.50(t, J=6.2 Hz, 1H), 7.44(d, J=8.1 Hz, 1H), 7.58(s, 1H), 7.79(dd, J=4.4, 8.4 Hz, 1H), 8.07 (m, 2H), 8.22(d, J=8.8 Hz, 1H), 8.49(m, 2H), 9.21(d, J=8.4 Hz, 1H), 10.45(br s, 1H), 10.88(s, 1H), 12.36(s, 1H).

FIA-MS, m/e: 542.3 (m+1).
Analysis for C$_{26}$H$_{28}$ClN$_5$O$_4$S.HCl:

| | |
|---|---|
| Calcd: | C, 53.98; H, 5.05; N, 12.11; |
| Found: | C, 53.74; H, 4.95; N, 11.71. |

EXAMPLE 14

Preparation of 3-[2-(3-aminopropoxy)-4-methylsulfonyl-benzoylamino]-N-(5-chloropyridin-2-yl)pyridine-2-carboxamide

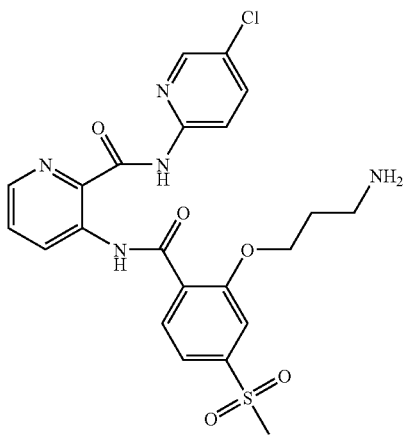

A. 3-[2-[3-(t-Butoxycarbonylamino)propoxy]-4-methyl-sulfonylbenzoylamino]-N-(5-chloropyridin-2-yl)pyridine-2-carboxamide Using a procedure analogous to Example 3-A, 3-[2-[3-(t-butoxycarbonylamino)propoxy]-4-methylthiobenzoylamino]-N-(5-chloropyridin-2-yl)pyridine-2-carboxamide gave the title compound as a solid (6.3 g, quantitative).

$^1$NMR (400 MHz, DMSO-$d_6$): δ 1.22(s, 9H), 1.94(m, 2H), 3.01(m, 2H), 3.29(s, 3H), 4.37(t, J=6.4 Hz, 2H), 6.78(m, 1H), 7.61(dd, J=1.6, 8.0 Hz, 1H), 7.68(s, 1H), 7.75(dd, J=3.6, 8.4 Hz, 1H), 7.99(dd, J=2.4, 8.8 Hz, 1H), 8.08(d, J=7.6 Hz, 1H), 8.20(d, J=8.8 Hz, 1H), 8.43(d, J=2.4 Hz, 1H), 8.46(dd, J=0.8, 3.6 Hz, 1H), 9.18(dd, J=0.8, 8.8 Hz, 1H), 10.80(s, 1H), 12.42 (s, 1H).

B. 3-[4-Methylsulfonyl-2-(3-aminopropoxy)benzoylamino]-N-(5-chloropyridin-2-yl)pyridine-2-carboxamide Using a procedure analogous to Example 1-H, 3-[2-[3-(t-butoxycarbonylamino)propoxy]-4-methylsulfonylbenzoylamino]-N-(5-chloropyridin-2-yl)pyridine-2-carboxamide gave the title compound as a white solid (4.66 g, 93%).

$^1$NMR (300 MHz, DMSO-$d_6$) δ 1.89 (m, 2H), 2.62 (t, J=6.6 Hz, 2H), 3.33 (s, 3H), 4.46 (t, J=6.6 Hz, 2H), 7.64 (dd, J=1.5, 8.1 Hz, 1H), 7.78 (m, 2H), 8.03 (dd, J=2.6, 8.8 Hz, 1H), 8.10 (d, J=8.1 Hz, 1H), 8.25 (d, J=9.1 Hz, 1H), 8.49 (m, 2H), 9.21 (dd, J=1.1, 8.8 Hz, 1H).

FIA-MS, m/e: 504.1 (m+1)

Analysis for $C_{22}H_{22}ClN_5O_5S$:

| | |
|---|---|
| Calcd: | C, 52.43; H, 4.40; N, 13.90; |
| Found: | C, 52.45; H, 4.22; N, 12.93. |

EXAMPLE 15

Preparation of (S)-N-(5-Chloropyridin-2-yl)-3-[4-methylthio-2-(3-pyrrolidinyloxy)benzoylamino]pyridine-2-carboxamide

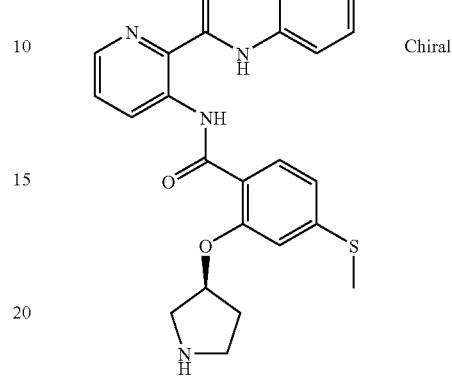

A. Methyl (S)-2-(1-t-butoxycarbonylpyrrolidin-3-yloxy)-4-methylthiobenzoate

Using a procedure analogous to Example 1-D, methyl 2-hydroxy-4-methylthiobenzoate and (R)-2-(1-t-butoxy-carbonylpyrrolidin-3-ol gave the desired product as a solid (15.5 g, 79%).

$^1$NMR (300 MHz, DMSO-$d_6$): δ 1.40 (s, 9H), 2.06 (m, 2H), 2.52 (s, 3H), 3.41 (m, 4H), 3.73 (s, 3H), 5.16 (m, 1H), 6.91 (dd, J=1.5, 8.4 Hz, 1H), 6.99 (s, 1H), 7.63 (d, J=8.4 Hz, 1H).

FIA-MS, m/e: 368.1 (m+1)

Analysis for $C_{18}H_{25}NO_5S$:

| | |
|---|---|
| Calcd: | C, 58.84; H, 6.86; N, 3.81; |
| Found: | C, 58.64; H, 6.84; N, 4.03. |

B. (S)-2-(1-t-Butoxycarbonylpyrrolidin-3-yloxy)-4-methylthiobenzoic acid

Using a procedure analogous to Example 1-E, methyl (S)-2-(1-t-butoxycarbonylpyrrolidin-3-yloxy)-4-methylthiobenzoate gave the desired product as a solid (14.9 g, quantitative).

1NMR (300 MHz, DMSO-$d_6$): δ 1.39 (s, 9H), 2.05 (m, 2H), 2.52 (s, 3H), 3.31 (m, 1H), 3.41 (m, 2H), 3.51 (m, 1H), 5.12 (m, 1H), 6.89 (dd, J=1.5, 8.1 Hz, 1H), 6.94 (s, 1H), 7.62 (d, J=8.1 Hz, 1H), 12.40 (s, 1H).

FIA-MS, m/e: 354 (m+1)

Analysis for $C_{17}H_{23}NO_5S$:

| | |
|---|---|
| Calcd: | C, 57.77; H, 6.56; N, 3.96; |
| Found: | C, 60.62; H, 7.00; N, 4.40. |

C. (S)-2-(1-t-Butoxycarbonylpyrrolidin-3-yloxy)-4-methylthiobenzoylamino]-N-(5-chloropyridin-2-yl)pyridine-2-carboxamide Using a procedure analogous to Example 1-G, (S)-2-(1-t-butoxycarbonylpyrrolidin-3-yloxy)-4-methylthio-benzoic acid gave the desired product as a solid (1.2 g, 30%).

$^1$NMR (300 MHz, DMSO-$d_6$) δ ppm: 1.14 (s, 9H), 2.18 (m, 2H), 2.57 (s, 3H), 3.30 (m, 2H), 3.64 (m, 2H), 5.40 (s, 1H), 7.02 (dd, J=1.1, 8.4 Hz, 1H), 7.14 (s, 1H), 7.75 (dd, J=4.4, 8.4

Hz, 1H), 7.82 (d, J=8.4 Hz, 1H), 8.01 (J=2.6, 8.8 Hz, 1H), 8.23 (d, J=8.4 Hz, 1H), 8.46 (m, 2H), 9.15 (d, J=8.8 Hz, 1H), 10.81 (m, 1H), 12.22 (s, 1H).

FIA-MS, m/e: 584.0 (m+1)

Analysis for $C_{28}H_{30}ClN_5O_5S$:

| Calcd: | C, 57.58; H, 5.18; N, 11.99; |
|---|---|
| Found: | C, 57.96; H, 5.32; N, 12.02. |

D. (S)-N-(5-Chloropyridin-2-yl)-3-[4-methylthio-2-(3-pyrrolidinyloxy)benzoylamino]pyridine-2-carboxamide Using a procedure analogous to Example 1-H, (S)-2-(1-t-butoxycarbonylpyrrolidin-3-yloxy)-4-methylthio-benzoylamino]-N-(5-chloropyridin-2-yl)pyridine-2-carboxamide gave the desired product as a solid (100 mg, 64%).

$^1$NMR (300 MHz, DMSO-$d_6$): δ 1.96 (m, 1H), 2.11 (m, 1H), 2.62 (s, 3H), 2.73 (m, 1H), 2.85 (m, 1H), 3.10 (m, 2H), 5.20 (m, 1H), 7.00 (m, 2H), 7.75 (dd, J=4.4, 8.8 Hz, 1H), 7.81 (d, J=8.4 Hz, 1H), 8.04 (dd, J=2.6, 8.8 Hz, 1H), 8.19 (d, J=8.8 Hz, 1H), 8.46 (m, 2H), 9.14 (dd, J=1.1, 8.8 Hz, 1H).

FIA-MS, m/e: 484.4 (m+1)

Analysis for $C_{23}H_{22}ClN_5O_3S$:

| Calcd: | C, 57.08; H, 4.58; N, 14.47; |
|---|---|
| Found: | C, 56.16; H, 4.20; N, 13.94. |

EXAMPLE 16

Preparation of N-(5-Chloropyridin-2-yl)-3-[4-methylsulfinyl-2-[(3S)-pyrrolidin-3-yloxy]benzoylamino]pyridine-2-carboxamide

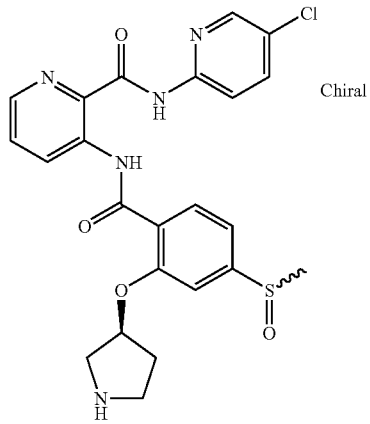

A. 2-[(3S)-1-t-Butoxycarbonylpyrrolidin-3-yloxy]-4-methylsulfinylbenzoylamino]-N-(5-chloropyridin-2-yl)-pyridine-2-carboxamide Using a procedure analogous to Example 2-A, (S)-2-(1-t-butoxycarbonylpyrrolidin-3-yloxy)-4-methylthio-benzoylamino]-N-(5-chloropyridin-2-yl)pyridine-2-carboxamide gave the desired product as a solid (500 mg, 97%).

$^1$NMR (300 MHz, DMSO-$d_6$) δ ppm: 1.15 (s, 9H), 2.20 (m, 2H), 2.85 (s, 3H), 3.31 (m, 2H), 3.63 (m, 2H), 5.39 (m, 1H), 7.45 (d, J=8.4 Hz, 1H), 7.60 (s, 1H), 7.78 (dd, J=4.4, 8.4 Hz, 1H), 8.01 (m, 2H), 8.21 (d, J=8.4 Hz, 1H), 8.47 (m, 2H), 9.18 (d, J=8.4 Hz, 1H), 10.82 (m, 1H), 12.29 (s, 1H).

FIA-MS, m/e: 600.2 (m+1)

Analysis for $C_{28}H_{30}ClN_5O_6S$:

| Calcd: | C, 56.04; H, 5.04; N, 11.67 |
|---|---|
| Found: | C, 55.57; H, 4.82; N, 11.85 |

B. N-(5-Chloropyridin-2-yl)-3-[4-methylsulfinyl-2-[(3S)-pyrrolidin-3-yloxy]benzoylamino]pyridine-2-carboxamide Using a procedure analogous to Example 1-H, (S)-2-(1-t-butoxycarbonylpyrrolidin-3-yloxy)-4-methyl-sulfinylbenzoylamino]-N-(5-chloropyridin-2-yl)pyridine-2-carboxamide gave the desired product as a solid (300 mg, 72%).

$^1$NMR (300 MHz, DMSO-$d_6$) δ ppm: 1.93 (m, 1H), 2.12 (m, 1H), 2.71 (m, 1H), 2.84 (s, 3H), 2.89 (m, 1H), 3.06 (m, 2H), 5.18 (m, 1H), 7.40 (d, J=8.1 Hz, 1H), 7.49 (s, 1H), 7.77 (dd, J=4.4, 8.4 Hz, 1H), 8.02 (m, 2H), 8.19 (d, J=8.8 Hz, 1H), 8.47 (m, 2H), 9.17 (d, J=8.8 Hz, 1H).

FIA-MS, m/e: 498.2 (m−1)

Analysis for $C_{23}H_{22}ClN_5O_4S$:

| Calcd: | C, 55.25; H, 4.44; N, 14.01; |
|---|---|
| Found: | C, 49.59; H, 3.84; N, 12.39. |

EXAMPLE 17

Preparation of (S)-N-(5-Chloropyridin-2-yl)-3-[4-methyl-sulfonyl-2-(3-pyrrolidinyloxy)benzoylamino]pyridine-2-carboxamide

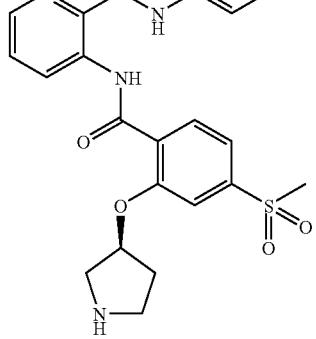

A. (S)-2-(1-t-Butoxycarbonylpyrrolidin-3-yloxy)-4-methyl-sulfonylbenzoylamino]-N-(5-chloropyridin-2-yl)pyridine-2-carboxamide

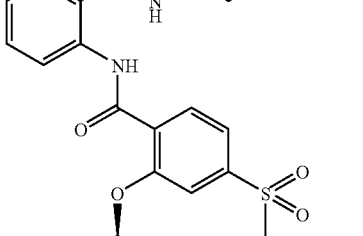

Using a procedure analogous to Example 3-A, (S)-2-(1-t-butoxycarbonylpyrrolidin-3-yloxy)-4-methylthiobenzoylamino]-N-(5-chloropyridin-2-yl)pyridine-2-carboxamide gave the desired product as a solid (500 mg, 95%).

$^1$NMR (300 MHz, DMSO-$d_6$) δ ppm: 1.14 (s, 9H), 2.21 (m, 2H), 3.26 (M, 2H), 3.35 (s, 3H), 3.67 (m, 2H), 5.47 (m, 1H), 7.68 (d, J=8.1 Hz, 1H), 7.80 (m, 2H), 8.00 (dd, J=2.6, 8.8 Hz, 1H), 8.06 (d, J=8.1 Hz, 1H), 8.20 (d, J=8.8 Hz, 1H), 8.46 (m, 2H), 9.17 (d, J=8.4 Hz, 1H), 10.82 (d, J=7.0 Hz, 1H), 12.32 (s, 1H).

FIA-MS, m/e: 614.1 (m−1)

Analysis for $C_{28}H_{30}ClN_5O_6S$:

| Calcd: | C, 54.59; H, 4.91; N, 11.37; |
|---|---|
| Found: | C, 54.32; H, 4.76; N, 11.30. |

B. (S)-N-(5-Chloropyridin-2-yl)-3-[4-methylsulfonyl-2-(3-pyrrolidinyloxy)benzoylamino]pyridine-2-carboxamide Using a procedure analogous to Example 1-H, (S)-2-(1-t-butoxycarbonylpyrrolidin-3-yloxy)-4-methyl-sulfonylbenzoylamino]-N-(5-chloropyridin-2-yl)pyridine-2-carboxamide gave the desired product as a solid (3.6 g, 90%).

$^1$NMR (300 MHz, DMSO-$d_6$) δ ppm: 1.94 (s, 9H), 2.12 (m, 1H), 2.73 m, 1H), 2.89 (m, 1H), 3.07 (d, J=3.7 Hz, 2H), 3.33 (s, 3H), 5.25 (m, 1H), 7.66 (m, 2H), 7.79 (dd, J=4.4, 8.6 Hz, 1H), 8.04 (m, 2H), 8.18 (d, J=8.8 Hz, 1H), 8.48 (m, 2H), 9.17 (dd, J=1.1, 8.6 Hz, 1H).

FIA-MS, m/e: 516.1 (m+1)

Analysis for $C_{23}H_{22}ClN_5O_5S$:

| Calcd: | C, 53.54; H, 4.30; N, 13.57; |
|---|---|
| Found: | C, 53.42; H, 4.24; N, 13.39. |

EXAMPLE 18

Preparation of (S)-N-(5-Chloropyridin-2-yl)-3-[4-methyl-sulfonyl-2-(3-pyrrolidinyloxy)benzoylamino]pyridine-2-carboxamide Hydrochloride

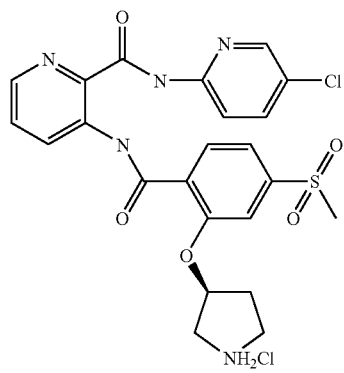

Using a procedure analogous to Example 4-F, (S)-N-(5-chloropyridin-2-yl)-3-[4-methylsulfonyl-2-(3-pyrrolidinyloxy)benzoylamino]pyridine-2-carboxamide gave the title compound as a white solid (407 mg, 95%).

$^1$NMR (300 MHz, DMSO-$d_6$) δ 2.35(m, 2H), 3.29(m, 2H), 3.36(s, 3H), 3.61(m, 2H), 5.62(m, 1H), 7.71(dd, J=1.5, 8.1 Hz, 1H), 7.75(s, 1H), 7.80(dd, J=4.4, 8.8 Hz, 1H), 8.06(m, 2H), 8.11(d, J=8.1 Hz, 1H), 8.52(m, 2H), 9.19(dd, J=1.1, 8.4 Hz, 1H), 9.40(br s, 1H), 11.03(s, 1H), 12.25(s, 1H).

FIA-MS, m/e: 516.1 (m+1).

Analysis for $C_{30}H_{34}ClN_5O_6S \cdot HCl \cdot 0.5H_2O$:

| Calcd: | C, 49.20; H, 4.31; N, 12.47; |
|---|---|
| Found: | C, 48.84; H, 4.06; N, 12.34. |

EXAMPLE 19

Preparation of (R)—N-(5-Chloropyridin-2-yl)-3-[4-methyl-sulfonyl-2-(3-pyrrolidinyloxy)benzoylamino]pyridine-2-carboxamide Hydrochloride

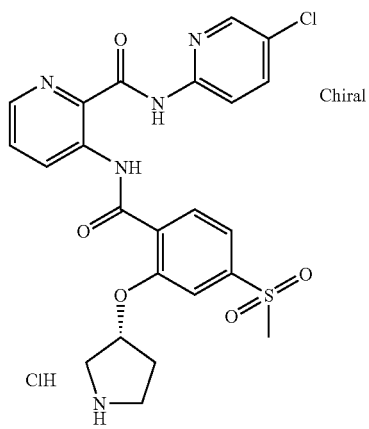

A. (S)-1-t-Butoxycarbonyl-3-hydroxypyrrolidine

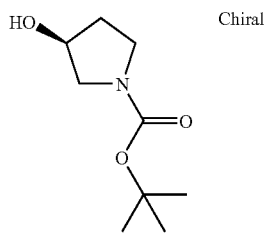

Using a procedure analogous to Example 1-C, (S)-3-hydroxypyrrolidine gave the title compound as a white solid (15.7 g, 73%).

$^1$NMR (300 MHz, DMSO-$d_6$): δ 1.39 (s, 9H), 1.73 (m, 1H), 1.83 (m, 1H), 3.09 (m, 1H), 3.26 (m, 3H), 4.20 (m, 1H), 4.86 (d, J=3.3 Hz, 1H).

FIA-MS, m/e: 187.4 (m+)

Analysis for $C_9H_{17}NO_3$:

| Calcd: | C, 57.73; H, 9.15; N, 7.48; |
|---|---|
| Found: | C, 57.93; H, 9.17; N, 7.51. |

B. (R)-2-(1-t-Butoxycarbonylpyrrolidin-3-yloxy)-4-methylthiobenzoylamino]-N-(5-chloropyridin-2-yl)pyridine-2-carboxamide

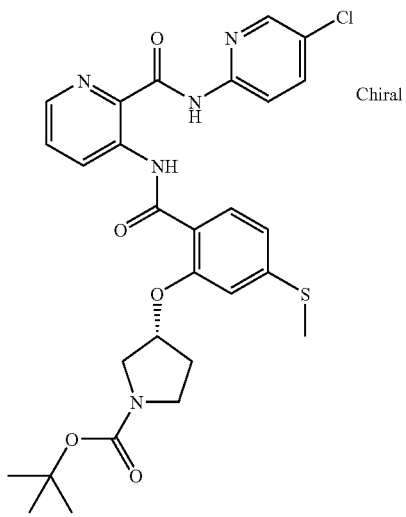

Using a procedure analogous to Example 1-D, (S)-1-t-butoxycarbonyl-3-hydroxypyrrolidine gave the title compound as a white solid (2.2 g).

¹NMR (300 MHz, DMSO-d₆) δ ppm: 1.14 (s, 9H), 2.18 (m, 2H), 2.51 (s, 3H), 3.29 (m, 2H), 3.64 (m, 2H), 5.43 (m, 1H), 7.02 (dd, J=1.5, 8.4 Hz, 1H), 7.15 (s, 1H), 7.75 (dd, J=4.4, 8.8 Hz, 1H), 7.83 (d, J=8.4 Hz, 1H), 8.01 (dd, J=2.6, 8.8 Hz, 1H), 8.21 (d, J=0.7 Hz, 1H), 8.46 (m, 2H), 9.15 (dd, J=0.7, 8.4 Hz, 1H), 10.79 (d, J=12.7 Hz, 1H), 12.22 (s, 1H).

FIA-MS, m/e: 582.2 (m−1).

Analysis for $C_{28}H_{30}ClN_5O_5S$:

| | |
|---|---|
| Calcd: | C, 57.57; H, 5.18; N, 11.99; |
| Found: | C, 56.25; H, 4.99; N, 11.30. |

C. (R)—N-(5-Chloropyridin-2-yl)-3-[4-methylsulfonyl-2-(3-pyrrolidinyloxy)benzoylamino]pyridine-2-carboxamide Using a procedure analogous to Example 3-A, (R)-2-(1-t-butoxycarbonylpyrrolidin-3-yloxy)-4-methylthiobenzoylamino]-N-(5-chloropyridin-2-yl)pyridine-2-carboxamide gave the title compound as a white solid (1.24 g).

¹NMR (300 MHz, DMSO-d₆): δ 1.13 (s, 9H), 2.17 (m, 2H), 3.26 (m, 2H), 3.30 (s, 3H), 3.58 (m, 2H), 5.43 (m, 1H), 7.65 (dd, J=1.5, 7.8 Hz, 1H), 7.76 (m, 2H), 7.97 (dd, J=2.4, 8.8 Hz, 1H), 8.02 (d, J=7.8 Hz, 1H), 8.16 (d, J=8.8 Hz, 1H), 8.45 (m, 2H), 9.13 (d, J=7.8 Hz, 1H), 10.78 (d, J=12.7 Hz, 1H), 12.29 (s, 1H).

FIA-MS, m/e: 616.0 (m+1)

Analysis for $C_{28}H_{30}ClN_5O_7S.1.0\ H_2O$:

| | |
|---|---|
| Calcd: | C, 53.04; H, 5.09; N, 11.04; |
| Found: | C, 52.77; H, 4.78; N, 11.32. |

D. (R)—N-(5-Chloropyridin-2-yl)-3-[4-methylsulfonyl-2-(3-pyrrolidinyloxy)benzoylamino]pyridine-2-carboxamide Hydrochloride Using a procedure analogous to Example 1-H, (R)—N-(5-chloropyridin-2-yl)-3-[4-methylsulfonyl-2-(3-pyrrolidinyloxy)benzoylamino]pyridine-2-carboxamide gave the title compound as a white solid (680 mg, 66% from B).

¹NMR (300 MHz, DMSO-d₆): δ 2.36 (m, 2H), 3.34 (m, 2H), 3.37 (s, 3H), 3.64 (m, 2H), 5.63 (m, 1H), 7.75 (m, 2H), 7.82 (dd, J=4.6, 8.8 Hz, 1H), 8.08 (m, 2H), 8.13 (d, J=8.0 Hz, 1H), 8.54 (m, 2H), 9.21 (dd, J=1.1, 8.8 Hz, 1H), 9.33 (br s, 1H), 11.08 (br s, 1H), 12.28 (s, 1H).

FIA-MS, m/e: 516.2 (m+1)

Analysis for $C_{23}H_{22}ClN_5O_5S.HCl.0.75\ H_2O$:

| | |
|---|---|
| Calcd: | C, 48.81; H, 4.36; N, 12.37; |
| Found: | C, 48.97; H, 4.09; N, 12.17. |

EXAMPLE 20

Preparation of N-(5-Chloropyridin-2-yl)-3-[4-methylsulfonyl-2-(3-piperidinyloxy)benzoylamino]pyridine-2-carboxamide

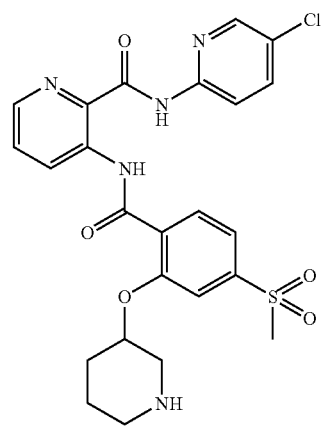

A. 1-t-Butoxycarbonyl-3-hydroxypiperidine

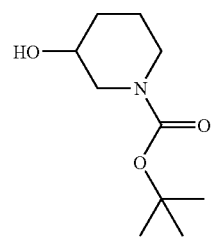

Using a procedure analogous to Example 1-C (K2CO3, acetone), 3-hydroxypiperidine gave the title compound as a solid (42 g, 84%).

¹NMR (300 MHz, DMSO-d₆): δ 1.25(m, 2H), 1.38(s, 9H), 1.59(m, 1H), 1.75(m, 1H), 2.55(br s, 1H), 2.71(m, 1H), 3.31 (m, 1H), 3.56(m, 1H), 3.68(m, 1H), 4.82(d, J=4.4 Hz, 1H).

FIA-MS, m/e: 202.2 (m+1).

B. 3-[2-(1-t-Butoxycarbonylpiperidin-3-yloxy)-4-methyl-thiobenzoylamino]-N-(5-chloropyridin-2-yl)pyridine-2-carboxamide

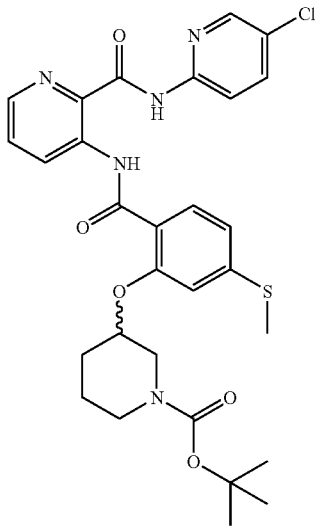

Using a procedure analogous to Example 1-D, 1-t-butoxycarbonyl-3-hydroxypiperidine gave the title compound as a white solid (600 mg, 20%).

$^1$NMR (250 MHz, DMSO-$d_6$): δ partial 1.13 (s, 9H), 2.53 (s, 3H), 4.85 (m, 1H).

FIA-MS, m/e: 598.3 (m+1)

Analysis for $C_{29}H_{32}ClN_5O_5S$:

| | |
|---|---|
| Calcd: | C, 58.26; H, 5.39; N, 11.71; |
| Found: | C, 57.62; H, 5.04; N, 12.71. |

C. 3-[2-(1-t-Butoxycarbonylpiperidin-3-yloxy)-4-methylsulfonylbenzoylamino]-N-(5-chloropyridin-2-yl)pyridine-2-carboxamide

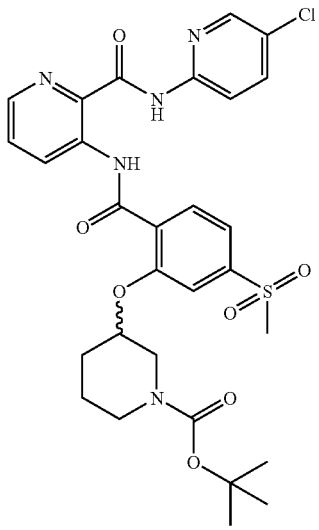

Using a procedure analogous to Example 3-A, 3-[2-(1-t-butoxycarbonylpiperidin-3-yloxy)-4-methylthiobenzoylamino]-N-(5-chloropyridin-2-yl)pyridine-2-carboxamide gave the title compound as a white solid (400 mg, 63%).

$^1$NMR (250 MHz, DMSO-$d_6$): δ partial 1.06 (s, 9H), 3.30 (s, 3H), 4.90 (m, 1H).

FIA-MS, m/e: 630 (m+1)

Analysis for $C_{29}H_{32}ClN_5O_7S$:

| | |
|---|---|
| Calcd: | C, 55.28; H, 5.12; N, 11.11; |
| Found: | C, 55.66; H, 5.18; N, 11.37. |

D. N-(5-Chloropyridin-2-yl)-3-[4-methylsulfonyl-2-(3-piperidinyloxy)benzoylamino]pyridine-2-carboxamide Using a procedure analogous to Example 1-H, 3-[2-(1-t-butoxycarbonylpiperidin-3-yloxy)-4-methylsulfonylbenzoyl-amino]-N-(5-chloropyridin-2-yl)pyridine-2-carboxamide gave the title compound as a white solid.

$^1$NMR (300 MHz, DMSO-$d_6$): δ 1.46 (m, 1H), 1.62 (m, 1H), 1.80 (m, 1H), 2.10 (m, 1H), 2.38 (m, 1H), 2.75 (m, 2H), 3.17 (m, 1H), 3.35 (s, 3H), 4.69 (m, 1H), 7.65 (dd, J=1.5, 8.1 Hz, 1H), 7.74 (d, J=1.5 Hz, 1H), 7.80 (dd, J=4.4, 8.4 Hz, 1H), 8.06 (m, 2H), 8.26 (dd, J=0.7, 8.4 Hz, 1H), 8.51 (m, 2H), 9.19 (dd, J=1.5, 8.8 Hz, 1H).

FIA-MS, m/e: 530.0 (m+1)

Analysis for $C_{24}H_{24}ClN_5O_5S \cdot 0.5\ H_2O$:

| | |
|---|---|
| Calcd: | C, 53.48; H, 4.68; N, 12.99; |
| Found: | C, 53.43; H, 4.27; N, 12.90. |

EXAMPLES 21-22

Preparation of Chiral Isomers of N-(5-Chloropyridin-2-yl)-3-[4-methylsulfonyl-2-(3-piperidinyloxy)benzoylamino]pyridine-2-carboxamide A racemic mixture of N-(5-chloropyridin-2-yl)-3-[4-methylsulfonyl-2-(3-piperidinyloxy)benzoylamino]pyridine-2-carboxamide (150 mg) was subjected to HPLC (Chiralcel AD, 50% IPA/heptane/0.2% DMEA) to give chiral isomer I (57 mg, 38%, 98% ee) and isomer II (60 mg, 40%, 97% ee) of the title compound.

EXAMPLE 21

Chiral isomer I of N-(5-chloropyridin-2-yl)-3-[4-methylsulfonyl-2-(3-piperidinyloxy)benzoylamino]-pyridine-2-carboxamide Rt: 14.7 min.

FIA-MS, m/e: 530.0 (m+1); HRMS for ($C_{24}H_{24}ClN_5O_5S$): 530.1265; found: 530.1262.

EXAMPLE 22

Chiral isomer II of N-(5-chloropyridin-2-yl)-3-[4-methylsulfonyl-2-(3-piperidinyloxy)benzoylamino]-pyridine-2-carboxamide Rt: 18.7 min.

FIA-MS, m/e: 530.0 (m+1); HRMS for ($C_{24}H_{24}ClN_5O_5S$): 530.1265; found: 530.1263.

EXAMPLE 23

Preparation of 3-[2-(3-Amino-2,2-dimethylpropoxy)-4-methyl-thiobenzoylamino]-N-(5-chloropyridin-2-yl)pyridine-2-carboxamide

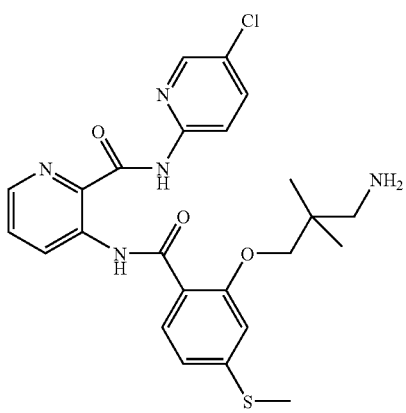

A. 3-t-Butoxycarbonylamino-2,2-dimethylpropanol

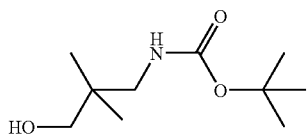

Using a procedure analogous to Example 1-C (except with acetone, K₂CO₃, water), 3-amino-2,2-dimethylpropanol gave the title compound as a solid (27.03 g, 94%).

¹NMR (300 MHz, DMSO-d₆): 0.84(s, 6H), 1.46(s, 9H), 2.96(d, 6.8 Hz, 2H), 3.19(s, 2H), 5.81(br s, 1H).

FIA-MS, m/e: 204.0 (m+1).

B. Methyl 2-(3-t-butoxycarbonylamino-2,2-dimethylpropoxy)-4-methylthiobenzoate

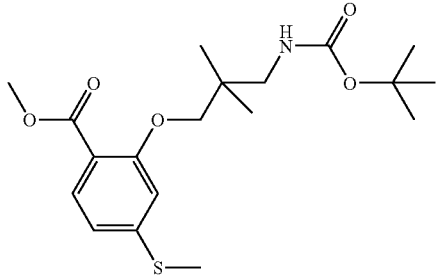

Using a procedure analogous to Example 1-D, 3-t-butoxycarbonylamino-2,2-dimethylpropanol gave the title compound as a solid (20 g, 69%).

¹NMR (300 MHz, DMSO-d₆): δ 0.94 (s, 6H), 1.37 (s, 9H), 2.52 (s, 3H), 2.99 (d, J=6.6 Hz, 2H), 3.74 (s, 2H), 3.78 (s, 3H), 6.84 (m, 3H), 7.66 (d, J=8.4 Hz, 1H).

FIA-MS, m/e: 384.2 (m+1).

Analysis for C₁₉H₂₉NO₅S:

| | |
|---|---|
| Calcd: | C, 59.51; H, 7.62; N, 3.65; |
| Found: | C, 59.34; H, 7.60; N, 4.14. |

C. 2-(3-t-Butoxycarbonylamino-2,2-dimethylpropoxy)-4-methylthiobenzoic acid

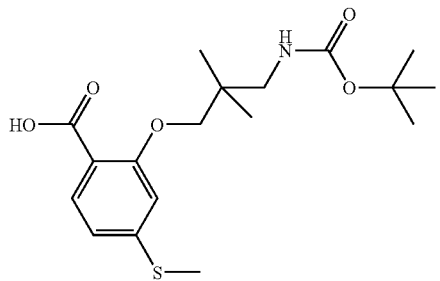

Using a procedure analogous to Example 1-E, except using KOH, H₂O and EtOH, heat, methyl 2-(3-t-butoxycarbonylamino-2,2-dimethylpropoxy)-4-methylthiobenzoate gave the title compound as a white solid (17.5 g, 82%).

¹NMR (300 MHz, DMSO-d₆): δ 0.94 (s, 6H), 1.36 (s, 9H), 2.51 (s, 3H), 2.97 (d, J=6.2 Hz, 2H), 3.72 (s, 2H), 6.82 (m, 3H), 7.63 (d, J=8.1 Hz, 1H), 12.33 (s, 1H).

FIA-MS, m/e: 370.1 (m+1).

D. 3-[2-(3-t-Butoxycarbonylamino-2,2-dimethylpropoxy)-4-methylthiobenzoylamino]-N-(5-chloropyridin-2-yl)pyridine-2-carboxamide

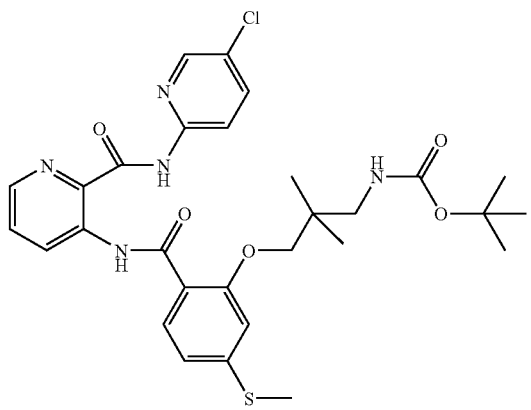

Using a procedure analogous to Example 1-G, 2-(3-t-butoxycarbonylamino-2,2-dimethylpropoxy)-4-methylthiobenzoic acid and 2-amino-N-(5-chloropyridin-2-yl)pyridine-2-carboxamide gave the title compound as a solid (2.2 g, 54%).

1NMR (300 MHz, DMSO-d₆) δ 0.81(s, 6H), 1.27(s, 9H), 2.56(s, 3H), 2.88(d, J=6.2 Hz, 1H), 3.92(s, 2H), 6.74(t, J=5.9 Hz, 1H), 6.97(dd, J=1.1, 8.1 Hz, 1H), 7.05(s, 1H), 7.65(d, J=8.1 Hz, 1H), 7.76(dd, J=4.4, 8.8 Hz, 1H), 7.98(dd, J=2.6, 8.8 Hz, 1H), 8.19(d, J=8.8 Hz, 1H), 8.44(m, 2H), 9.11(d, J=8.1 Hz, 1H), 10.79(s, 1H), 11.87(s, 1H).

FIA-MS, m/e: 600.2 (m+1)

Analysis for C₂₂H₂₂ClN₅O₅S.0.25 H₂O:

| | |
|---|---|
| Calcd: | C, 57.61; H, 5.75; N, 11.58; |
| Found: | C, 57.49; H, 5.44; N, 11.96. |

E. 3-[2-(3-Amino-2,2-dimethylpropoxy)-4-methylthiobenzoyl-amino]-N-(5-chloropyridin-2-yl)pyridine-2-carboxamide

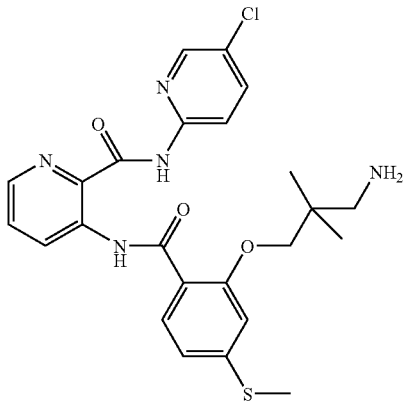

Using a procedure analogous to Example 1-H, 3-[2-(3-t-butoxycarbonylamino-2,2-dimethylpropoxy)-4-methylthiobenzoylamino]-N-(5-chloropyridin-2-yl)pyridine-2-carboxamide gave the title compound as a solid (300 mg, 80%).

$^1$NMR (300 MHz, DMSO-$d_6$): δ 0.80(s, 6H), 2.36(s, 2H), 2.57(s, 3H), 3.99(s, 2H), 6.96(dd, J=1.5, 8.1, 1H), 7.12(s, 1H), 7.65(d, J=8.4 Hz, 1H), 7.77(dd, J=4.4, 8.4 Hz, 1H), 8.01(dd, J=2.6, 8.8 Hz, 1H), 8.20(d, J=9.1 Hz, 1H), 8.46(m, 2H), 9.12(dd, J=1.1, 8.8 Hz, 1H).

FIA-MS, m/e: 500.1 (m+1)

Analysis for $C_{24}H_{26}ClN_5O_3S$:

| | |
|---|---|
| Calcd: | C, 57.65; H, 5.24; N, 14.01; |
| Found: | C, 57.41; H, 5.04; N, 13.73. |

EXAMPLE 24

Preparation of 3-[2-(3-Amino-2,2-dimethylpropoxy)-4-methyl-sulfinylbenzoylamino]-N-(5-chloropyridin-2-yl)pyridine-2-carboxamide

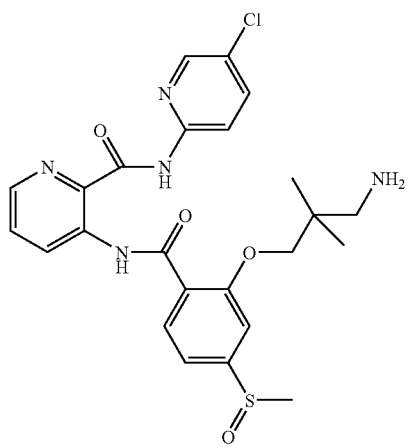

A. 3-[2-(3-t-Butoxycarbonylamino-2,2-dimethylpropoxy)-4-methylsulfinylbenzoylamino]-N-(5-chloropyridin-2-yl)-pyridine-2-carboxamide

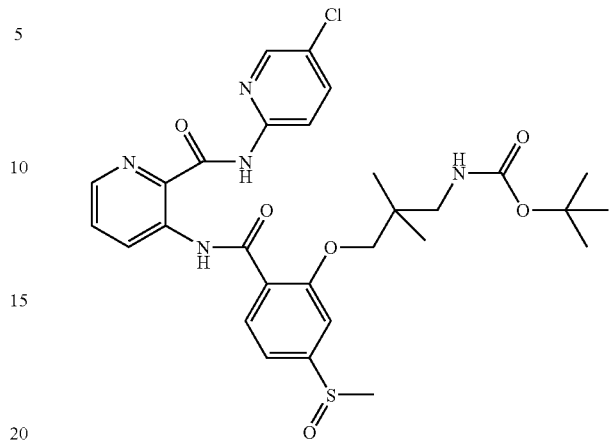

Using a procedure analogous to Example 2-A, 3-[2-(3-t-butoxycarbonylamino-2,2-dimethylpropoxy)-4-methylthiobenzoylamino]-N-(5-chloropyridin-2-yl)pyridine-2-carboxamide gave the title compound as a solid (800 mg, 92%).

$^1$NMR (300 MHz, DMSO-$d_6$): δ 0.82(s, 6H), 1.26(s, 3H), 2.88(d, J=6.2 Hz, 1H), 3.94(s, 2H), 6.77(m, 1 h), 7.39(dd, J=1.1, 8.1 Hz, 1H), 7.52(s, 1H), 7.79(dd, J=4.4, 8.4 Hz, 1H), 7.85(d, J=8.1 Hz, 1H), 7.97(dd, J=2.6, 8.8 Hz, 1H), 8.18(d, J=8.8 Hz, 1H), 8.46(m, 2H), 9.13(d, J=8.4 Hz, 1H), 10.80(s, 1H), 11.95(s, 1H).

FIA-MS, m/e: 616.2 (m+1)

Analysis for $C_{29}H_{34}ClN_5O_6S$:

| | |
|---|---|
| Calcd: | C, 56.53; H, 5.56; N, 11.37; |
| Found: | C, 56.45; H, 5.45; N, 11.28. |

B. 3-[2-(3-Amino-2,2-dimethylpropoxy)-4-methyl-sulfinylbenzoylamino]-N-(5-chloropyridin-2-yl)pyridine-2-carboxamide

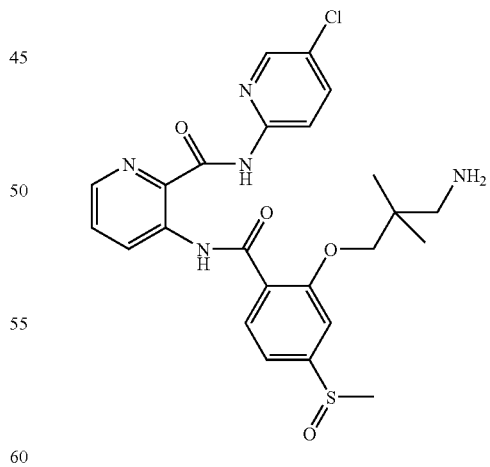

Using a procedure analogous to Example 1-H, 3-[2-(3-t-butoxycarbonylamino-2,2-dimethylpropoxy)-4-methylsulfinyl-benzoylamino]-N-(5-chloropyridin-2-yl)pyridine-2-carboxamide gave the title compound as a solid (510 mg, 81%).

$^1$NMR (300 MHz, DMSO-$d_6$): δ 0.81(s, 6H), 2.37(s, 2H), 2.84(s, 3H), 4.00(s, 2H), 7.39(dd, J=1.1, 8.1 Hz, 1H), 7.56(d,

J=1.1 Hz, 1H), 7.84(m, 2H), 7.99(dd, J=2.6, 8.8 Hz, 1H), 8.18(d, J=8.8 Hz, 1H), 8.47(m, 2H), 9.15(dd, J=1.1, 8.4 Hz, 1H).

FIA-MS, m/e: 516.2 (m+1)

Analysis for $C_{24}H_{26}ClN_5O_4S$:

| Calcd: | C, 55.86; H, 5.08; N, 13.57; |
|---|---|
| Found: | C, 55.47; H, 5.03; N, 13.17. |

EXAMPLE 25

Preparation of 3-[2-(3-Amino-2,2-dimethylpropoxy)-4-methyl-sulfonylbenzoylamino]-N-(5-chloropyridin-2-yl)pyridine-2-carboxamide

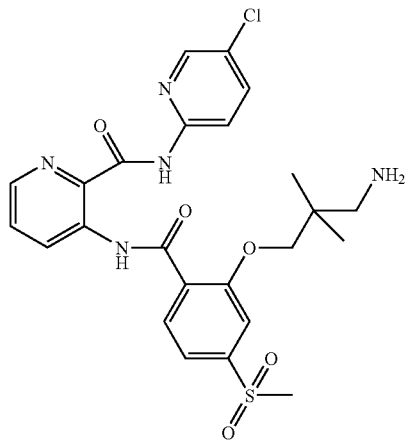

A. 3-[2-(3-t-Butoxycarbonylamino-2,2-dimethylpropoxy)-4-methylsulfonylbenzoylamino]-N-(5-chloropyridin-2-yl)-pyridine-2-carboxamide Using a procedure analogous to Example 3-A, 3-[2-(3-t-butoxycarbonylamino-2,2-dimethylpropoxy)-4-methylthiobenzoylamino]-N-(5-chloropyridin-2-yl)pyridine-2-carboxamide gave the title compound as a solid (710 mg, 79%).

$^1$NMR (300 MHz, DMSO-$d_6$): δ 0.82(s, 6H), 1.27(s, 9H), 2.88(d, J=6.6 Hz, 2H), 3.32(s, 3H), 3.95(s, 2H), 6.79(t, J=6.6 Hz, 1H), 7.64(dd, J=1.1, 8.1 Hz, 1H), 7.69(s, 1H), 7.79(dd, J=4.4, 8.4 Hz, 1H), 7.89(d, J=8.1 Hz, 1H), 7.97(dd, J=2.6, 8.8 Hz, 1H), 8.17(d, J=8.8 Hz, 1H), 8.45(d, J=2.2 Hz, 1H), 8.50 (dd, J=1.1, 4.4 Hz, 1H), 9.13(d, J=8.4 Hz, 1H), 10.80(s, 1H), 11.97(s, 1H).

FIA-MS, m/e: 630.3 (m−1)

Analysis for $C_{29}H_{34}ClN_5O_7S$:

| Calcd: | C, 55.10; H, 5.42; N, 11.08; |
|---|---|
| Found: | C, 54.89; H, 5.22; N, 11.51. |

B. 3-[2-(3-Amino-2,2-dimethylpropoxy)-4-methylsulfonyl-benzoylamino]-N-(5-chloropyridin-2-yl)pyridine-2-carboxamide Using a procedure analogous to Example 1-H, 3-[2-(3-t-butoxycarbonylamino-2,2-dimethylpropoxy)-4-methylsulfonyl-benzoylamino]-N-(5-chloropyridin-2-yl)pyridine-2-carboxamide gave the title compound as a solid (490 mg, 90%).

$^1$NMR (300 MHz, DMSO-$d_6$): δ 0.82(s, 6H), 2.37(s, 2H), 3.33(s, 3H), 4.02(s, 2H), 7.63(dd, J=1.1, 8.1 Hz, 1H), 7.75(d, J=1.1 Hz, 1H), 7.81(dd, J=4.4, 8.4 Hz, 1H), 7.89(d, J=8.1 Hz, 1H), 7.99(dd, J=2.6, 9.1 Hz, 1H), 8.17(d, J=9.1 Hz, 1H), 8.46(d, J=2.6 Hz, 1H), 8.51(dd, J=1.5, 4.4 Hz, 1H), 9.14(dd, J=1.1, 8.4 Hz, 1H).

FIA-MS, m/e: 532.1 (m+1)

Analysis for $C_{24}H_{26}ClN_5O_4S \cdot 0.25\ H_2O$:

| Calcd: | C, 53.73; H, 4.98; N, 13.05; |
|---|---|
| Found: | C, 53.89; H, 4.84; N, 12.73. |

EXAMPLE 26

Preparation of 3-[2-(cis-4-Aminocyclohexyloxy)-4-methyl-sulfinylbenzoylamino]-N-(5-chloropyridin-2-yl)pyridine-2-carboxamide

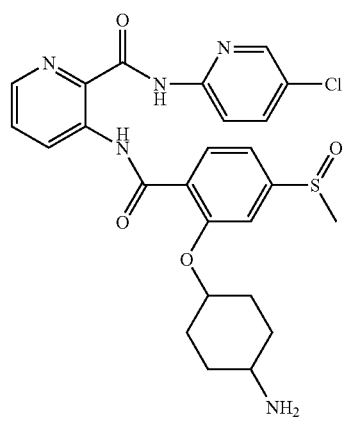

A. trans-4-(t-Butoxycarbonylamino)cyclohexanol

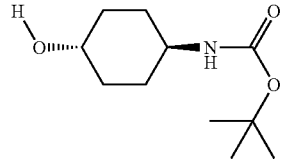

Using a procedure analogous to Example 1-C, trans-4-aminocyclohexanol gave the desired product as a white solid (70.1 g, 98.7%).

$^1$NMR (300 MHz, CDCl$_3$): δ 1.17(m, 2H) 1.39(s, 9H), 1.30-1.53(m, 2H), 1.99(m, 4H), 3.44(br s, 1H), 3.64(m, 1H), 4.33(br s, 1H).

IS-MS, m/e: 215.1 (m+1).

Analysis for $C_{11}H_{21}NO_3$:

| Calcd: | C, 61.37; H, 9.83; N, 6.51; |
|---|---|
| Found: | C, 61.33; H, 9.74; N, 6.54. |

B. Methyl 2-(cis-4-t-butoxycarbonylaminocyclohexyloxy)-4-methylthiobenzoate

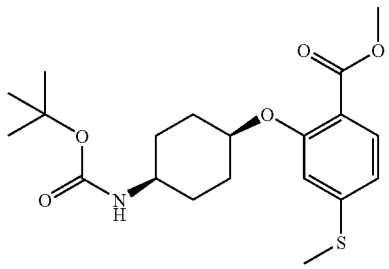

Using a procedure analogous to Example 1-D, trans-4-(t-butoxycarbonylamino)cyclohexanol and methyl 2-hydroxy-4-methylthiobenzoate gave the title compound as a white solid (16.0 g, 16%).

$^1$NMR (300 MHz, DMSO-$d_6$): δ 1.38(s, 9H), 1.56(m, 6H), 1.87(m, 2H), 2.50(s, 3H), 3.28(m, 1H), 3.80(s, 3H), 4.66(br m, 1H), 6.78(m, 1H), 6.83(d, J=8.1 Hz, 1H), 6.91(s, 1H), 7.60(d, J=8.1 Hz, 1H).

FIA-MS, m/e: 396.1 (m+1).

Analysis for $C_{20}H_{29}NO_5S$:

| Calcd: | C, 60.74; H, 7.39; N, 3.54; |
| Found: | C, 60.54; H, 7.11; N, 3.60. |

C. 2-(cis-4-t-Butoxycarbonylaminocyclohexyloxy)-4-methylthiobenzoic acid

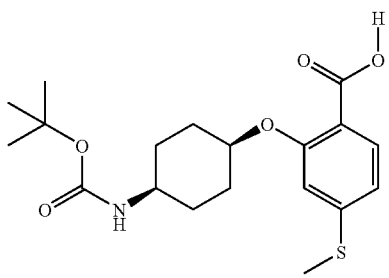

Using a procedure analogous to Example 1-E, methyl 2-(cis-4-t-butoxycarbonylaminocyclohexyloxy)-4-methylthio-benzoate gave the title compound as a white solid (2.03 g, 96%).

$^1$NMR (300 MHz, DMSO-$d_6$): δ 1.38(s, 9H), 1.56(m, 6H), 1.87(m, 2H), 2.50(s, 3H), 3.28(m, 1H), 4.60(br m, 1H), 6.62 (m, 1H), 6.83(d, J=8.1 Hz, 1H), 6.91(s, 1H), 7.60(d, J=8.1 Hz, 1H), 12.26(s, 1H).

FIA-MS, m/e: 382.4 (m+1).

Analysis for $C_{19}H_{27}NO_5S$:

| Calcd: | C, 59.82; H, 7.13; N, 3.67; |
| Found: | C, 60.11; H, 6.99; N, 3.95. |

D. 3-[2-(cis-4-t-Butoxycarbonylaminocyclohexyloxy)-4-methylthiobenzoylamino]-N-(5-chloropyridin-2-yl)pyridine-2-carboxamide

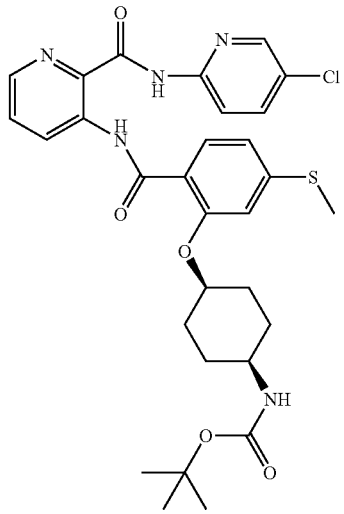

Using a procedure analogous to Example 1-G, 2-(cis-4-t-butoxycarbonylaminocyclohexyloxy)-4-methylthiobenzoic acid and 3-amino-N-(5-chloropyridin-2-yl)pyridine-2-carboxamide gave the title compound as a white solid (2.68 g, 85%).

E. 3-[2-(cis-4-t-Butoxycarbonylaminocyclohexyloxy)-4-methylsulfinylbenzoylamino]-N-(5-chloropyridin-2-yl)-pyridine-2-carboxamide

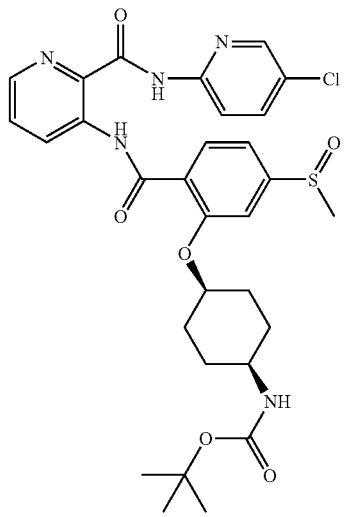

Using a procedure analogous to Example 2-A, 3-[2-(cis-4-t-butoxycarbonylaminocyclohexyloxy)-4-methylthiobenzoyl-amino]-N-(5-chloropyridin-2-yl)pyridine-2-carboxamide-gave the title compound as a white solid (1.04 g, 78%).

$^1$NMR (400 MHz, DMSO-$d_6$) δ 1.22(s, 9H), 1.40(m, 4H), 1.62(m, 2H), 2.01(m, 2H), 2.79(s, 3H), 3.24(m, 1H), 4.84(m, 1H), 6.56(d, J=7.3 Hz, 1H), 7.34(dd, J=1.5, 8.3 Hz, 1H), 7.48(d, J=1.5 Hz, 1H), 7.75(dd, J=4.4, 8.8 Hz, 1H), 7.92(d, J=8.3 Hz, 1H), 7.98(dd, J=2.4, 8.8 Hz, 1H), 8.14(d, J=8.3 Hz, 1H), 8.42(d, J=2.0 Hz, 1H), 8.45(dd, J=1.5, 4.4 Hz, 1H), 9.20(dd, J=1.5, 8.8 Hz, 1H), 10.78(s, 1H), 12.15(s, 1H).

FIA-MS, m/e: 628.4 (m+1).

Analysis for $C_{30}H_{34}ClN_5O_6S$:

| Calcd: | C, 57.36; H, 5.46; N, 11.15; |
| --- | --- |
| Found: | C, 57.43; H, 5.22; N, 11.43. |

F. 3-[2-(cis-4-Aminocyclohexyloxy)-4-methylsulfinyl-benzoylamino]-N-(5-chloropyridin-2-yl)pyridine-2-carboxamide Using a procedure analogous to Example 1-H, 3-[2-(cis-4-t-butoxycarbonylaminocyclohexyloxy)-4-methylsulfinyl-benzoylamino]-N-(5-chloropyridin-2-yl)pyridine-2-carboxamide gave the title compound as a white solid (860 mg, quantitative).

$^1$NMR (400 MHz, DMSO-$d_6$) δ 1.24(m, 2H), 1.41(m, 2H), 1.60(m, 2H), 2.01(m, 2H), 2.64(m, 1H), 2.80(s, 3H), 4.78(m, 1H), 7.34(dd, J=1.5, 7.8 Hz, 1H), 7.49(d, J=1.0 Hz, 1H), 7.75(dd, J=4.4, 8.8 Hz, 1H), 7.94(d, J=7.8 Hz, 1H), 8.00(dd, J=2.4, 8.0 Hz, 1H), 8.22(d, J=8.8 Hz, 1H), 8.42(d, J=2.0 Hz, 1H), 8.45(dd, J=1.5, 4.4 Hz, 1H), 9.18(dd, J=1.0, 8.8 Hz, 1H), 12.20(s, 1H).

FIA-MS, m/e: 528.1 (m+1)

Analysis for $C_{25}H_{26}ClN_5O_4S$:

| Calcd: | C, 56.87; H, 4.96; N, 13.26; |
| --- | --- |
| Found: | C, 56.84; H, 5.00; N, 13.46. |

EXAMPLE 27

Preparation of 3-[2-(cis-4-Aminocyclohexyloxy)-4-methyl-sulfonylbenzoylamino]-N-(5-chloropyridin-2-yl)pyridine-2-carboxamide

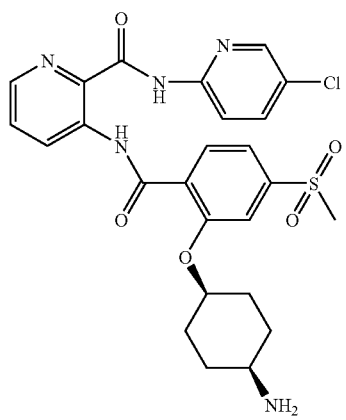

A. 3-[2-(cis-4-t-Butoxycarbonylaminocyclohexyloxy)-4-methylsulfonylbenzoylamino]-N-(5-chloropyridin-2-yl)-pyridine-2-carboxamide

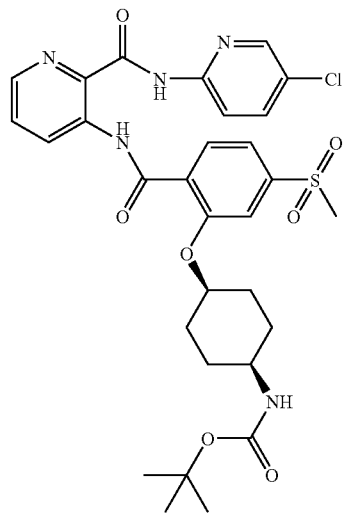

Using a procedure analogous to Example 3-A, 3-[2-(cis-4-t-butoxycarbonylaminocyclohexyloxy)-4-methylthiobenzoyl-amino]-N-(5-chloropyridin-2-yl)pyridine-2-carboxamide gave the title compound as a white solid (763 mg, 95%).

$^1$NMR (300 MHz, DMSO-$d_6$) δ 1.27(s, 9H), 1.43(m, 4H), 1.62(m, 2H), 1.99(m, 2H), 2.50(m, 1H), 3.31(s, 3H), 4.92(m, 1H), 6.53(m, 1H), 7.61(d, J=8.1 Hz, 1H), 7.70(s, 1H), 7.81(d, d, J=4.4, 8.4 Hz, 1H), 7.99(d, J=8.1 Hz, 1H), 8.02(dd, J=2.6, 8.8 Hz, 1H), 8.17(d, J=8.8 Hz, 1H), 8.46(d, J=2.6 Hz, 1H), 8.51(d, J=4.4 Hz, 1H), 9.23(d, J=8.4 Hz, 1H), 10.82(s, 1H), 12.20(s, 1H).

FIA-MS, m/e: 644.3 (m+1).

Analysis for $C_{30}H_{34}ClN_5O_7S \cdot 0.60 \, (CH_3CO_2CH_2CH_3)$:

| Calcd: | C, 55.84; H, 5.61; N, 10.05; |
| --- | --- |
| Found: | C, 55.67; H, 5.76; N, 10.18. |

B. 3-[2-(cis-4-aminocyclohexyloxy)-4-methylsulfonyl-benzoylamino]-N-(5-chloropyridin-2-yl)pyridine-2-carboxamide Using a procedure analogous to Example 1-H, 3-[2-(cis-4-t-butoxycarbonylaminocyclohexyloxy)-4-methylsulfonyl-benzoylamino]-N-(5-chloropyridin-2-yl)pyridine-2-carboxamide gave the title compound as a white solid (581 mg, 94%).

$^1$NMR (300 MHz, DMSO-$d_6$) δ 1.23(m, 2H), 1.43(m, 2H), 1.63(m, 2H), 1.98(m, 2H), 2.65(m, 1H), 3.32(s, 3H), 4.87(m, 1H), 7.61(d, J=4.4 Hz, 1H), 7.70(s, 1H), 7.79(dd, J=2.2, 4.4 Hz, 1H), 8.00(d, J=8.1 Hz, 1H), 8.03(dd, J=2.6, 9.1 Hz, 1H), 8.23(d, J=9.1 Hz, 1H), 8.46(d, J=2.6 Hz, 1H), 8.51(d, j=0.7 Hz, 1H), 9.22(d, J=8.4 Hz, 1 h), 12.25(br s, 1H).

FIA-MS, m/e: 544.2 (m+1)

Analysis for $C_{25}H_{26}ClN_5O_5S$:

| Calcd: | C, 55.19; H, 4.82; N, 12.87; |
| --- | --- |
| Found: | C, 55.26; H, 4.90; N, 12.84. |

An alternative preparation of the compound of this example is as follows:

C. N-Hydroxycarbamic Acid tert-Butyl Ester

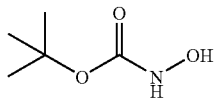

Sodium bicarbonate (12.20 g, 145.2 mmol) was added to a solution of hydroxylamine hydrochloride (5.06 g, 72.8 mmol) and 20% aqueous THF (65 mL) at room temperature. After stirring for 10 min, di-tert-butyl dicarbonate [(Boc)$_2$O] (3.95 g, 18.1 mmol) was added. After 4.5 h, the mixture was filtered through diatomaceous earth. The aqueous layer was concentrated in vacuo, and EtOAc (20 mL) was added. The organic layer was extracted with saturated NaCl (25 mL), and the combined aqueous layers were extracted with EtOAc (5×10 mL) until TLC analysis (50% EtOAc/hexanes) indicated no product remained in the aqueous layer. The combined organic layers were dried (Na$_2$SO$_4$), filtered and concentrated to an oil. Toluene (100 mL) was added and the mixture was concentrated again. The resulting oil began to crystallize, and hexanes (50 mL) was added with vigorous stirring. The slurry was filtered, rinsed with hexanes, and dried in a 40° C. vacuum oven (which caused partial melting) to provide 1.84 g (76%) of product as a white crystalline solid.

$^1$H NMR (300 MHz, CDCl$_3$) δ 1.46(s, 9H).

D. tert-Butyl 2-Aza-3-oxabicyclo[2.2.2]oct-5-ene-2-carboxylate

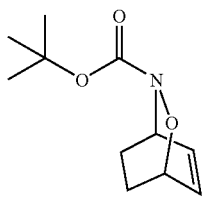

Solid N-hydroxycarbamic acid tert-butyl ester (100.19 g, 752.3 mmol) was added to a slurry of NaIO$_4$ (168.68 g, 788.6 mmol), 1,3-cyclohexadiene (86.0 mL, 902 mmol) and 50% MeOH/CH$_2$Cl$_2$ (3 L) cooled in an ice bath. The ice bath was removed after the addition. After 2 h, a warm (37° C.) water bath was installed for 5 min to raise the temperature from 17° C. to 24° C., at which point the bath was removed. The mixture thickened from a turbid solution to a white slurry, and the temperature climbed over 50 minutes to a peak of 40° C. before dropping slowly. Analysis by TLC (50% EtOAc/hexanes) at the temperature peak indicated the reaction was all but complete, and when it had cooled to room temperature the mixture was filtered and rinsed with EtOAc (3×175 mL). The filtrate was concentrated in vacuo to a cloudy oil which was partitioned between EtOAc (700 mL) and satd NaHSO$_3$ (400 mL). Organic layer was extracted with satd NaHSO$_3$ (200 mL), and the combined aqueous layers were extracted with EtOAc (100 mL). The combined organic layers were washed with H$_2$O (100 mL) and satd NaCl (100 mL), and were then dried (Na$_2$SO$_4$) and concentrated to provide 146.80 g (92%) of amber oil.

E. 3-Aza-2-oxabicyclo[2.2.2]oct-5-ene Trifluoroacetic Acid Salt

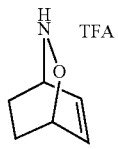

Trifluoroacetic acid (305 mL, 3.96 mol) was added to a solution of tert-butyl 2-aza-3-oxabicyclo[2.2.2]oct-5-ene-2-carboxylate (170.64 g, 807.7 mmol) and CH$_2$Cl$_2$ cooled in an ice bath. After 1 h the bath was removed and the dark solution was allowed to warm to room temperature. After 3.25 h the solution was concentrated on a rotary evaporator to a dark liquid. This liquid was concentrated from CH$_2$Cl$_2$ (5×1 L) to removed excess TFA, and then Et$_2$O (1.6 L) was added to triturate the product. The ether slurry was cooled in ice, filtered and dried in a 40° C. vacuum oven to provide 134.42 g (76%) of tan solid.

$^1$H NMR (300 MHz, DMSO-d$_6$) δ 6.86 (m, 1H), 6.84 (m, 1H), 4.96 (m, 1H), 4.56 (m, 1H), 2.20-1.95 (m, 2H), 1.50-1.35 (m, 2H); $^{13}$C (75 MHz, DMSO-d$_6$) 135.5, 129.2, 69.9, 47.7, 21.8, 16.9 ppm; IR (KBr) 1136, 1167, 1199, 1664 cm$^{-1}$;

MS (ESI+), m/e: 112.

F. cis-4-Aminocyclohexanol Trifluoroacetic Acid Salt

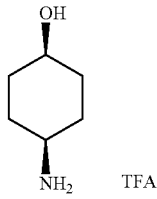

A pressure vessel was charged with 3-aza-2-oxa-bicyclo [2.2.2]oct-5-ene trifluoroacetic acid salt (5.00 g, 22.2 mmol), 10% Pd/C (500 mg), and anhydrous EtOH (50 mL). This mixture was pressurized to 3.4-4.1 bar (50-60 psig) with H$_2$ gas on a shaken hydrogenation apparatus, and was agitated for 6.5 h at ambient temperature (initially, the temperature of the reaction mixture rose from 22° C. to 33° C.). The mixture was filtered through diatomaceous earth and the filtrate concentrated to 4.83 g (95%) of solid product.

$^1$H NMR (300 MHz, DMSO-d$_6$) δ 3.75 (s, 1H), 2.96 (m, 1H), 1.75-1.29 (m, 8H); $^{13}$C (75 MHz, DMSO-d$_6$) 62.6, 48.8, 30.2, 24.6 ppm; IR (KBr) 11.37, 1180, 1203, 1540, 1677, 1692, 2950 cm$^{-1}$; MS (ESI+) m/z 116.

G. 2-(cis-4-tert-Butoxycarbonylaminocyclohexyloxy)-4-methylthiobenzoic Acid

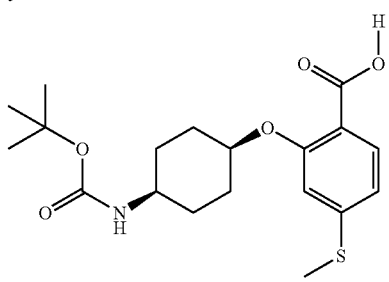

A mixture of 2,4-difluorobenzoic acid (36.08 g, 228.4 mmol), cis-4-aminocyclohexanol trifluoroacetic acid salt (53.87 g, 235.24 mmol) and DMSO (500 mL) was cooled to 15° C.; and NaH (60% dispersion in oil, 27.95 g, 700 mmol)

was added in 8 portions over 1.5 h. The resulting reaction mixture was stirred at ambient temperature for 12 h. HPLC showed a 9:1 ratio of intermediate product [2-(cis-4-aminocyclohexyl-oxy)-4-fluorobenzoic acid] to starting materials. Another 0.2 equiv of NaH was added, and the reaction stirred an additional 9 h.

Sodium methylthiolate (NaSMe) (25.92 g, 369.81 mmol) was added in one portion, and the reaction mixture was heated to 75° C. for 30 h. The reaction mixture was cooled to 23° C., 140 mL of 1 N aqueous HCl was added, and the reaction was placed under vacuum for 1 h.

The reaction mixture containing 2-(cis-4-aminocyclohexyloxy)-4-methylthiobenzoic acid was diluted with 1000 mL of MeOH, and triethyl amine (31.83 mL, 228.39 mmol) was added. A solution of $Boc_2O$ (49.85 g, 228.39 mmol) in 150 mL MeOH was added over 30 min, and the resulting solution stirred at 23° C. for 16 h. The reaction mixture was diluted with 1000 mL of $H_2O$ and the MeOH was evaporated in vacuo. The resulting mixture was again diluted with 1000 mL of $H_2O$ and the aqueous layer was extracted with 2×800 mL of 1:1 methyl tert-butyl ether (MTBE):hexane. Acetic acid (27.13 mL, 473.93 mmol) was added to the aqueous layer, and it was extracted with 2×1000 mL EtOAc. The combined organic layers were washed with 4×2000 mL of $H_2O$, dried over $Na_2SO_4$, filtered and concentrated in vacuo to give a white solid. The crude product was slurried in 600 mL of MTBE at reflux, cooled to 0° C. over 2 h, and filtered to give 53.97 g (62%) of the title compound. The mother liquor was concentrated in vacuo, and the resulting solid purified by silica gel chromatography using a gradient of 4/96 to 7/93 $IPA/CHCl_3$ to give another 21.2 g of the title acid. Total combined yield was 75.17 g (86%).

H. 3-[2-(cis-4-tert-Butoxycarbonylaminocyclohexyloxy)-4-methylthiobenzoylamino]-N-(5-chloropyridin-2-yl)pyridine-2-carboxamide

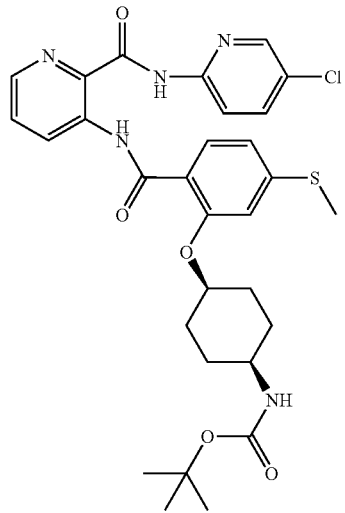

A solution of oxalyl chloride (1.6 mL, 18 mmol) and $CH_2Cl_2$ (12 mL) was added over 7 min to a solution of 2-(cis-4-tert-butoxycarbonylaminocyclohexyloxy)-4-methylthiobenzoic acid (7.00 g, 18.3 mmol), DMF (71 μL, 0.92 mmol), pyridine (1.5 mL, 18.9 mmol) and $CH_2Cl_2$ (62 mL) cooled in an ice bath. The bath was removed after the addition was complete. After 1 h the resulting yellow solution was added dropwise over 35 min to a slurry of 3-amino-N-(5-chloropyridin-2-yl)-pyridine-2-carboxamide (4.48 g, 18.0 mmol), pyridine (2.2 mL, 28 mmol), and $CH_2Cl_2$ (52 mL) cooled in an ice bath. At the end of the addition the bath was removed, and the mixture became homogeneous over 10-12 min, but became opaque again within 2 h. After 4 h the mixture was poured into satd citric acid (100 mL) and water (50 mL). The organic layer was extracted with a 1:1.5 solution of satd citric acid/water (125 mL), and the combined aqueous layers were back-extracted with $CH_2Cl_2$ (50 mL). The combined organic layers were rinsed with 25% NaCl (50 mL), heated to reflux on a steam bath to dissolve residual solids, dried ($Na_2SO_4$) and concentrated to a bright yellow solid (12.30 g) which was purified by flash chromatography (5% $EtOAc/CH_2Cl_2$, followed by 10% $EtOAc/CH_2Cl_2$) to provide 8.98 g (80%) of white foam.

Alternatively, the crude material may be purified in the following fashion: The crude solid from a 91.2 mmol-scale reaction was refluxed in MTBE (290 mL) for 45 min. The slurry was cooled in the refrigerator, filtered and rinsed with cold MTBE. The solid was dried in a 50° C. vacuum oven to provide 42.83 g (77%) of tan solid.

$^1$H NMR (500 MHz, $CDCl_3$) δ 12.19 (s, 1H), 10.86 (s, 1H), 9.29 (dd, J=8.7, 1.4 Hz, 1H), 8.32 (m, 2H), 8.28 (d, J=8.9 Hz, 1H) 7.87 (d, J=8.2 Hz, 1H), 7.70 (dd, J=8.7, 2.5 Hz, 1H), 7.55 (dd, J=8.5, 4.3 Hz, 1H), 6.87 (m, 2H), 4.67 (s, 1H), 4.33 (m, 1H), 2.52 (s, 3H), 2.17 (m, 2H), 1.70 (m, 4H), 1.57 (m, 4H), 1.31 (s, 9H).

I. 3-[2-(cis-4-tert-Butoxycarbonylaminocyclohexyloxy)-4-methylsulfonylbenzoylamino]-N-(5-chloropyridin-2-yl)-pyridine-2-carboxamide

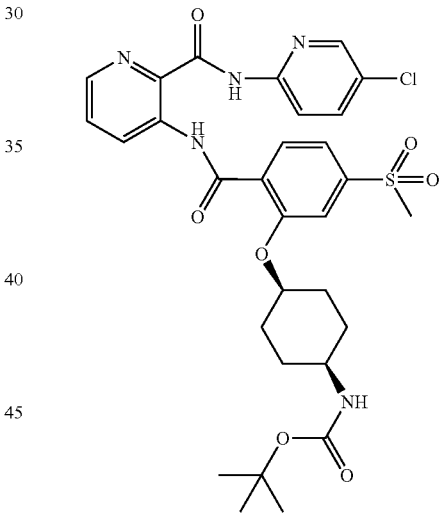

Solid 3-chloroperbenzoic acid (mCPBA, 2.69 g of 73 wt % potency, 11.4 mmol) was added in one portion to a slurry of 3-[2-(cis-4-tert-butoxycarbonylaminocyclohexyloxy)-4-methylthiobenzoylamino]-N-(5-chloropyridin-2-yl)pyridine-2-carboxamide (6.80 g, 11.1 mmol) and $CH_2Cl_2$ (135 mL) cooled in an ice bath. After 10 min another aliquot of mCPBA (2.60 g of 73 wt % potency, 11.0 mmol) was added, the slurry was stirred for 15 min, and the ice bath was then replaced with a warm water bath. When the temp was 21° C. the bath was removed. After 1 h the mixture was poured into 5% $NaHSO_3$ (100 mL), and a thick emulsion resulted. The layers were separated as well as possible; and the organic layer was concentrated to a paste which was dissolved in EtOAc (200 mL), and extracted with satd $NaHCO_3$ (3×75 mL) and 5% $NaHSO_3$ (50 mL). The combined aqueous layers then were back-extracted with EtOAc (25 mL), and the combined organic layers were rinsed with satd $NaHCO_3$ until HPLC analysis indicated no 3-chlorobenzoic acid remained. The organic solution was dried (Na$_2$SO$_4$) and concentrated to a yellow foam (7.57 g), which was purified by flash chromatography (10% EtOAc/CH$_2$Cl$_2$, followed by 20% EtOAc/CH$_2$Cl$_2$, followed by 30% EtOAc/CH$_2$Cl$_2$) to obtain 5.45 g (76%) of a white foam.

$^1$H NMR (300 MHz, CDCl$_3$) δ 12.38 (s, 1H), 10.88 (s, 1H), 9.34 (dd, J=8.5, 1.5 Hz, 1H), 8.40 (dd, J=4.4, 1.5 Hz, 1H), 8.34 (dd, J=2.6, 0.6 Hz, 1H), 8.24 (dd, J=8.8, 0.6 Hz, 1H), 8.03 (d, J=7.9 Hz, 1H), 7.71 (dd, J=8.8, 2.3 Hz, 1H), 7.60 (m, 3H), 4.78 (s, 1H), 4.30 (m, 1H), 3.10 (s, 3H), 2.17 (m, 2H), 1.81-1.70 (m, 4H), 1.60-1.45 (m, 2H), 1.33 (s, 9H).

J. 3-[2-(cis-4-Aminocyclohexyloxy)-4-methylsulfonyl-benzoylamino]-N-(5-chloropyridin-2-yl)carboxamide

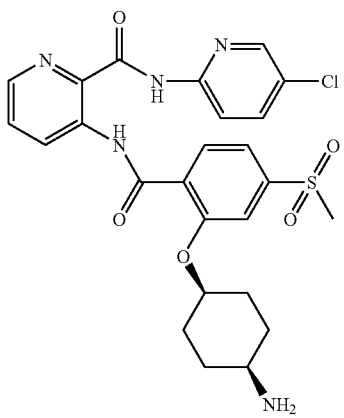

Trifluoroacetic acid (33 mL, 426 mmol) was added to a solution of 3-[2-(cis-4-tert-butoxycarbonylaminocyclohexyl-oxy)-4-methylsulfonylbenzoylamino]-N-(5-chloropyridin-2-yl)-pyridine-2-carboxamide and CH$_2$Cl$_2$ (220 mL) cooled in an ice bath. The bath was removed at the end of the addition and the mixture allowed to warm to 23° C. After 1.5 h the solution was carefully concentrated to an oil on a rotary evaporator, keeping the bath temperature at 25° C. and refraining from removing the last traces of solvent. The oil was redissolved in CH$_2$Cl$_2$ (200 mL) and again was concentrated as above. This was repeated an additional two times to remove all the excess TFA possible. The resulting liquid was dissolved in 20% MeOH/CH$_2$Cl$_2$ (200 mL) and was poured into 5% (w/w) NaHCO$_3$ (100 mL). The layers were separated; and the organic layer was extracted with 5% (w/w) NaHCO$_3$ (100 mL), which caused the entire mixture to solidify. The solids were dissolved upon addition of 20% MeOH/CH$_2$Cl$_2$ (100 mL), and the layers were then separated. The organic layer was extracted with 5% (w/w) NaHCO$_3$ (2×50 mL), and the combined aqueous layers were extracted with 20% MeOH/CH$_2$Cl$_2$ (2×70 mL), dried (Na$_2$SO$_4$) and concentrated to a foam (9.34 g, 101%) which contained an unknown amount of water.

$^1$H NMR (500 MHz, DMSO-d$_6$) δ 12.24 (s, 1H), 9.25 (dd, J=8.5, 1.1 Hz, 1H), 8.50 (dd, J=4.4, 1.4 Hz, 1H), 8.47 (m, 1H), 8.18 (d, J=8.9 Hz), 8.30 (dd, J=8.9, 2.7 Hz, 1H), 8.00 (d, J=8.0, 1H), 7.81 (dd, J=8.7, 4.3 Hz, 1H), 7.71 (m, 1H), 7.62 (dd, J=8.0, 1.6 Hz, 1H), 5.00 (s, 1H), 2.92 (m, 1H), 2.49 (m, 3H), 2.11 (m, 2H), 1.68 (m, 2H), 1.58 (m, 2H), 1.39 (m, 2H); $^{13}$C (63 MHz, DMSO-d$_6$) 164.5, 163.9, 154.4, 148.7, 146.9, 144.6, 143.0, 138.4, 137.6, 132.5, 132.1, 129.5, 128.9, 128.6, 126.4, 118.9, 114.5, 112.6, 72.7, 47.9, 43.1, 26.6, 26.3 ppm; IR (KBr) 1150, 1181, 1381, 1500, 1522, 1669, 1682, 3276 cm$^{-1}$;

MS (ESI+), m/e: 544, 293, 273.

EXAMPLE 28

Preparation of 3-[2-(cis-4-Aminocyclohexyloxy)-4-methyl-sulfonylbenzoylamino]-N-(5-chloropyridin-2-yl)pyridine-2-carboxamide hydrochloride

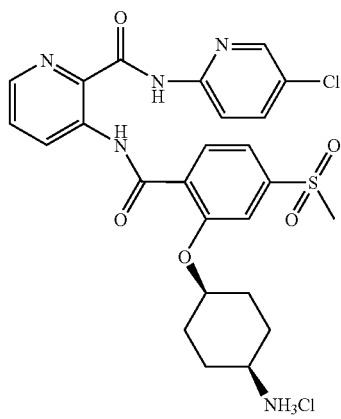

Using a procedure analogous to Example 4-F, 3-[2-(cis-4-aminocyclohexyloxy)-4-methylsulfonylbenzoylamino]-N-(5-chloropyridin-2-yl)pyridine-2-carboxamide gave the title compound as a white solid (210 mg, 82%).

$^1$NMR (300 MHz, DMSO-d$_6$) δ 1.53(m, 2H), 1.73(m, 4H), 2.18(m, 2H), 3.08(m, 1H), 3.36(s, 3H), 5.08(m, 1H), 7.66(dd, J=1.5, 8.4 Hz, 1H), 7.74(d, J=1.1 Hz, 1H), 7.84(dd, J=4.4, 8.8 Hz, 1H), 7.91(br s, 3H), 8.04(m, 2H), 8.18(d, J=9.2 Hz, 1H), 8.52(m, 2H), 9.29(dd, J=1.1, 8.8 Hz, 1H), 10.87(s, 1H), 12.25 (s, 1H).

FIA-MS, m/e: 544.3 (m+1).

Analysis for C$_{25}$H$_{26}$ClN$_5$O$_5$S.HCl.1.0 H$_2$O:

| Calcd: | C, 50.17; | H, 4.88; | N, 11.70; | Cl, 11.85; |
| --- | --- | --- | --- | --- |
| Found: | C, 50.13; | H, 4.67; | N, 11.70; | Cl, 11.85. |

EXAMPLE 29

Preparation of 3-[2-(trans-4-Aminocyclohexyloxy)-4-methyl-thiobenzoylamino]-N-(5-chloropyridin-2-yl)pyridine-2-carboxamide

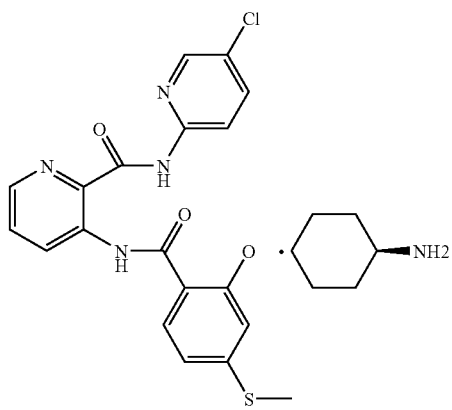

A. cis-4-(t-Butoxycarbonylamino)cyclohexyl 4-chloro-benzoate

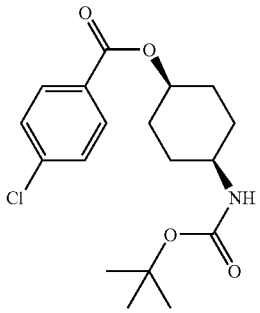

Using a procedure analogous to Example 1-D, trans-4-aminocyclohexanol and 4-chlorobenzoic acid gave the title compound as a solid (6.2 g, 17%).

$^1$NMR (300 MHz, DMSO-$d_6$): δ 1.38(s, 9H), 1.62(m, 6H), 1.87(m, 2H), 3.35(m, 1H), 5.06(m, 1H), 6.78(m, 1H), 6.79(m, 1H), 7.61(d, J=8.4 Hz, 1H), 7.99(d, J=8.8 Hz, 1H).

FIA-MS, m/e: 354 (m+1).

Analysis for $C_{18}H_{24}ClNO_4$:

| Calcd: | C, 61.10; H, 6.84; N, 3.96; |
| --- | --- |
| Found: | C, 61.59; H, 6.40; N, 3.97. |

B. cis-4-(t-Butoxycarbonylamino)cyclohexanol

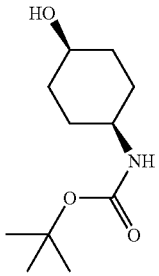

Using a procedure analogous to Example 4-C, cis-4-(t-butoxy-carbonylamino)cyclohexyl 4-chlorobenzoate gave the title compound as a white solid (3.3 g, 91%).

$^1$NMR (300 MHz, DMSO-$d_6$): δ 1.37(s, (H), 1.43(m, 4H), 1.55(m, 4H), 3.22(m, 1H), 3.65(m, 1H), 4.26(m, 1H), 6.66(m, 1H).

FIA-MS, m/e: 216.3 (m+1).

Analysis for $C_{11}H_{21}NO_3$:

| Calcd: | C, 61.37; H, 9.83; N, 6.51; |
| --- | --- |
| Found: | C, 61.29; H, 10.27; N, 6.55. |

C. Methyl 2-(trans-4-t-butoxycarbonylaminocyclohexyloxy)-4-methylthiobenzoate

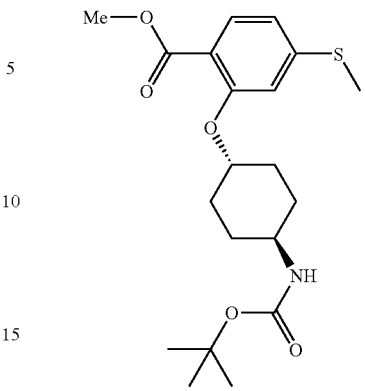

Using a procedure analogous to Example 1-D, cis-4-(butoxycarbonylamino)cyclohexanol and methyl 4-methylthio-2-hydroxybenzoate gave the title compound as a white solid (3.5 g, 65%).

$^1$NMR (300 MHz, DMSO-$d_6$): δ 1.38(m, 13H), 1.81(m, 2H), 1.99(m, 2H), 2.50(s, 3H), 3.28(m, 1H), 3.75(s, 3H), 4.39(m, 1H), 6.84(m, 2H), 6.98(d, J=1.5 Hz, 1H), 7.59(d, J=8.1 Hz, 1H).

FIA-MS, m/e: 396.0 (m+1).

Analysis for $C_{20}H_{29}NO_5S$:

| Calcd: | C, 60.74; H, 7.39; N, 3.54; |
| --- | --- |
| Found: | C, 60.47; H, 7.14; N, 3.71. |

D. 2-(trans-4-t-Butoxycarbonylaminocyclohexyloxy)-4-methylthiobenzoic acid

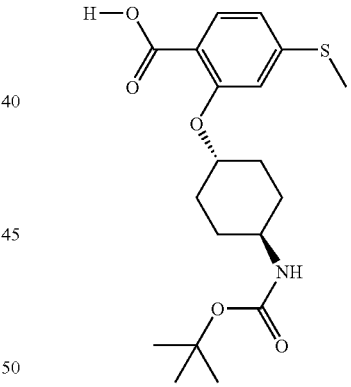

Using a procedure analogous to Example 4-C, methyl 2-(trans-4-t-butoxycarbonylaminocyclohexyloxy)-4-methylthio-benzoate gave the title compound as a white solid (3.13 g, 94%).

$^1$NMR (300 MHz, DMSO-$d_6$): δ 1.38(m, 3H), 1.82(m, 2H), 2.00(m, 2H), 2.50(s, 3H), 3.28(m, 1H), 4.37(m, 1H), 6.79(m, 1H), 6.85(dd, J=1.5, 8.1 Hz, 1H), 6.95(s, 1H), 7.58(d, J=8.1 Hz, 1H), 12.32(s, 1H).

FIA-MS, m/e: 382.4 (m+1).

Analysis for $C_{19}H_{27}NO_5S$:

| Calcd: | C, 59.82; H, 7.13; N, 3.67; |
| --- | --- |
| Found: | C, 59.35; H, 7.04; N, 3.47. |

E. 3-[2-(trans-4-t-Butoxycarbonylaminocyclohexyloxy)-4-methylthiobenzoylamino]-N-(5-chloropyridin-2-yl)pyridine-2-carboxamide

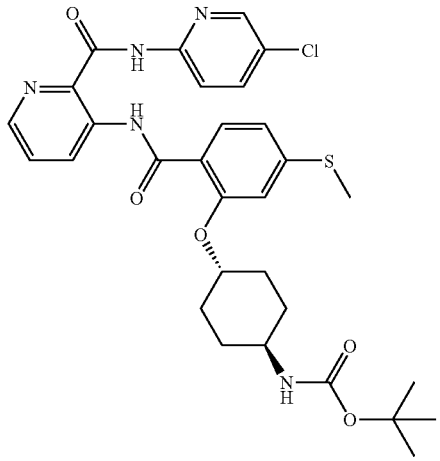

Using a procedure analogous to Example 1-F, 2-(trans-4-t-butoxycarbonylaminocyclohexyloxy)-4-methylthiobenzoic acid gave the title compound as a white solid (2.77 g, 58%).

1NMR (300 MHz, DMSO-$d_6$): δ 1.41(m, 1H), 1.86(m, 4H), 2.11(m, 2H), 2.56(s, 3H), 3.37(m, 1H), 4.68(m, 1H), 6.89(m, 1H), 6.95(dd, J=1.1, 8.8 Hz, 1H), 7.10(s, 1H), 7.74 (dd, J=4.4, 8.8 Hz, 1H), 7.88(d, J=8.4 Hz, 1H), 8.35(d, J=8.8 Hz, 1H), 8.45(m, 2H), 9.21(dd, J=1.1, 8.8 Hz, 1H), 10.84(s, 1H), 12.22(s, 1H).

FIA-MS, m/e: 612.1 (m+1).

Analysis for $C_{19}H_{27}NO_5S$:

| Calcd: | C, 58.86; H, 5.60; N, 11.44; |
| Found: | C, 58.39; H, 5.35; N, 11.94 |

F. 3-[2-(trans-4-Aminocyclohexyloxy)-4-methylthio-benzoylamino]-N-(5-chloropyridin-2-yl)pyridine-2-carboxamide

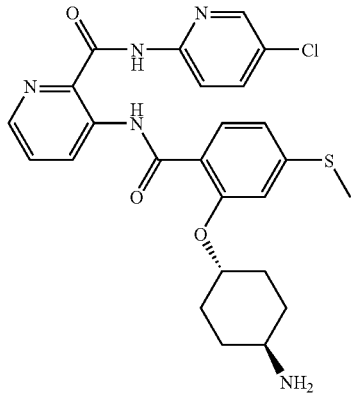

Using a procedure analogous to Example 1-H, 3-[2-(trans-4-t-butoxycarbonylaminocyclohexyloxy)-4-methylthio-benzoylamino]-N-(5-chloropyridin-2-yl)pyridine-2-carboxamide gave the title compound as a white solid (170 mg, quantitative).

$^1$NMR (300 MHz, DMSO-$d_6$): δ 1.21(m, 2H), 1.77(m, 4H), 2.07(m, 2H), 2.56(s, 3H), 3.36(m, 1H), 4.63(m, 1H), 6.95(dd, J=1.1, 8.1 Hz, 1H), 7.07(s, 1H), 7.74(dd, J=4.4, 8.8 Hz, 1H), 7.84(d, J=8.4 Hz, 1H), 8.07(dd, J=2.2, 8.8 Hz, 1H), 8.26(d, J=8.4 Hz, 1H), 8.48(m, 2H), 9.18(d, J=8.8 Hz, 1H), 12.18(s, 1H).

FIA-MS, m/e: 512.4 (m+1).

Analysis for $C_{25}H_{26}ClN_5O_3S \cdot 0.25\ H_2O$:

| Calcd: | C, 58.13; H, 5.17; N, 13.56; |
| Found: | C, 57.88; H, 4.99; N, 13.93. |

EXAMPLE 30

Preparation of 3-[2-(trans-4-Aminocyclohexyloxy)-4-methyl-sulfinylbenzoylamino]-N-(5-chloropyridin-2-yl)pyridine-2-carboxamide

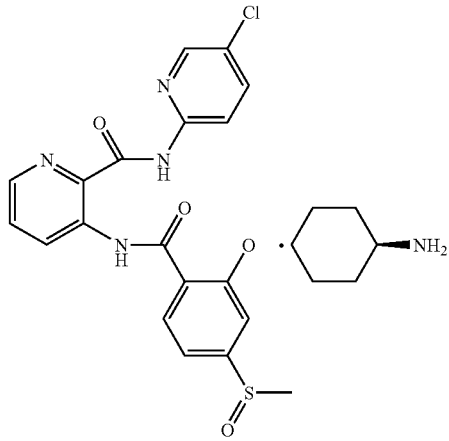

A. 3-[2-(trans-4-t-Butoxycarbonylaminocyclohexyloxy)-4-methylsulfinylbenzoylamino]-N-(5-chloropyridin-2-yl)-pyridine-2-carboxamide

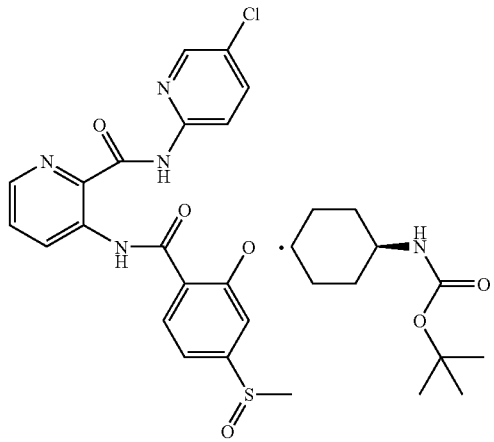

Using a procedure analogous to Example 2-A, 3-[2-(trans-4-t-butoxycarbonylaminocyclohexyloxy)-4-methylthio-benzoylamino]-N-(5-chloropyridin-2-yl)pyridine-2-carboxamide gave the title compound as a white solid (300 mg, 58%).

$^1$NMR (300 MHz, DMSO-$d_6$): δ 1.41(m, 11H), 1.87(m, 4H), 2.11(m, 2H), 2.84(s, 3H), 3.37(m, 1H), 4.63(m, 1H), 6.94(m, 1H), 7.38(d, J=8.0 Hz, 1H), 7.57(s, 1H), 7.77(dd, J=4.5, 8.5 Hz, 1H), 8.08(d, J=8.0 Hz, 1H), 8.25(m, 1H), 8.33(d, J=9.0 Hz, 1H), 8.47(m, 2H), 9.25(d, J=8.5 Hz, 1H), 10.86(s, 1H), 12.34(s, 1H).

FIA-MS, m/e: 628.3 (m+1).

Analysis for $C_{30}H_{34}ClN_5O_6S$:

| Calcd: | C, 57.36; H, 5.46; N, 11.15; |
| Found: | C, 57.46; H, 5.26; N, 10.99. |

B. 3-[2-(trans-4-Aminocyclohexyloxy)-4-methylsulfinyl-benzoylamino]-N-(5-chloropyridin-2-yl)pyridine-2-carboxamide Using a procedure analogous to Example 1-H, 3-[2-(trans-4-t-butoxycarbonylaminocyclohexyloxy)-4-methyl-sulfinyl-benzoylamino]-N-(5-chloropyridin-2-yl)pyridine-2-carboxamide gave the title compound as a white solid (210 mg, 86%).

$^1$NMR (300 MHz, DMSO-d$_6$): δ 1.20(m, 2H), 1.73(m, 4H), 2.08(m, 2H), 2.55(m, 1H), 2.83(s, 3H), 4.64(m, 1H), 7.38(dd, J=0.7, 8.1 Hz, 1H), 7.54(s, 1H), 7.77(dd, J=4.4, 8.4 Hz, 1H), 8.05(m, 2H), 8.24(d, J=8.8 Hz, 1H), 8.48(m, 2H), 9.21(d, J=8.8 Hz, 1H), 12.28(s, 1H).

FIA-MS, m/e: 528.1 (m+1).

Analysis for C$_{25}$H$_{36}$ClN$_5$O$_4$S:

| Calcd: | C, 56.87; H, 4.96; N, 13.26; |
| Found: | C, 56.62; H, 4.88; N, 12.96. |

EXAMPLE 31

Preparation of 3-[2-(trans-4-Aminocyclohexyloxy)-4-methylsulfonylbenzoylamino]-N-(5-chloropyridin-2-yl)-pyridine-2-carboxamide

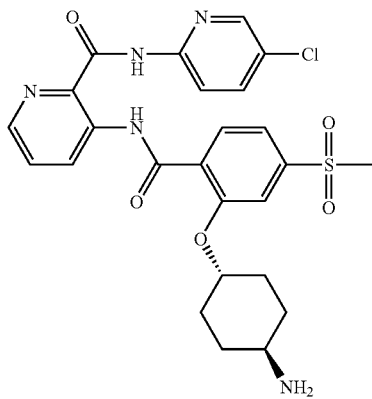

A. 3-[2-(trans-4-t-Butoxycarbonylaminocyclohexyloxy)-4-methylsulfonylbenzoylamino]-N-(5-chloropyridin-2-yl)-pyridine-2-carboxamide

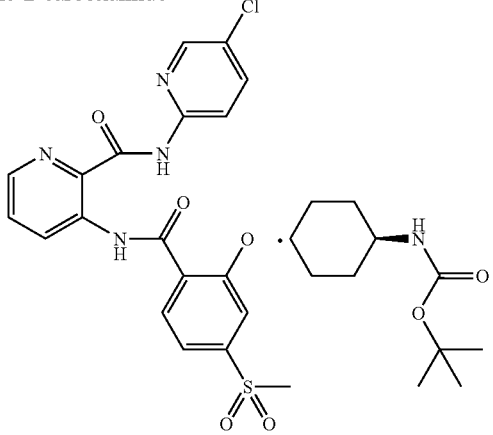

Using a procedure analogous to Example 3-A, 3-[2-(trans-4-t-butoxycarbonylaminocyclohexyloxy)-4-methylthio-benzoylamino]-N-(5-chloropyridin-2-yl)pyridine-2-carboxamide gave the title compound as a white solid (550 mg, quantitative).

$^1$NMR (300 MHz, DMSO-d$_6$): δ 1.40(s, 11H), 1.87(s, 4H), 2.12(s, 2H), 3.28(m, 1H), 3.34(s, 3H), 4.77(m, 1H), 6.91(m, 1H), 7.61(d, J=8.1 Hz, 1H), 7.74(s, 1H), 7.78(dd, J=4.4, 8.8 Hz, 1H), 8.11(d, J=8.1 Hz, 1H), 8.21(d, J=8.1 Hz, 1H), 8.30 (d, J=8.8 Hz, 1H), 8.48(m, 2H), 9.23(d, J=8.4 Hz, 1H), 10.85 (s, 1H), 12.34(s, 1H).

FIA-MS, m/e: 644.5 (m+1).

Analysis for C$_{30}$H$_{34}$ClN$_5$O$_7$S.0.25 H$_2$O:

| Calcd: | C, 55.55; H, 5.36; N, 10.80; |
| Found: | C, 55.19; H, 4.84; N, 11.20. |

B. 3-[2-(trans-4-Aminocyclohexyloxy)-4-methylsulfonyl-benzoylamino]-N-(5-chloropyridin-2-yl)pyridine-2-carboxamide Using a procedure analogous to Example 1-H, 3-[2-(trans-4-t-butoxycarbonylaminocyclohexyloxy)-4-methyl-sulfonylbenzoylamino]-N-(5-chloropyridin-2-yl)pyridine-2-carboxamide gave the title compound as a white solid (300 mg, 68%).

$^1$NMR (300 MHz, DMSO-d$_6$): δ 1.22(m, 2H), 1.75(m, 4H), 2.09(m, 2H), 2.56(m, 1H), 3.34(s, 3H), 4.71(m, 1H), 7.61(dd, J=1.1, 8.1 Hz, 1H), 7.72(s, 1H), 7.78(dd, J=4.4, 8.4 Hz, 1H), 8.05(m, 2H), 8.23(d, J=8.8 Hz, 1H), 8.48(m, 2H), 9.20(dd, J=1.1, 8.8 Hz, 1H), 12.30(s, 1H).

FIA-MS, m/e: 544.2 (m+1).

Analysis for C$_{25}$H$_{36}$ClN$_5$O$_5$S:

| Calcd: | C, 55.19; H, 4.82; N, 12.87; |
| Found: | C, 55.07; H, 4.90; N, 12.61. |

EXAMPLE 32

Preparation of 3-[2-(3-Aminopropoxy)-4-methylthiobenzoyl-amino]-N-(5-chloropyridin-2-yl)-6-methylpyridine-2-carboxamide

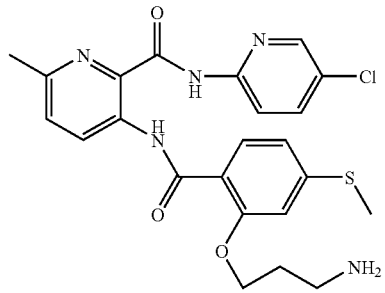

A. 3-Amino-N-(5-chloropyridin-2-yl)-6-methylpyridine-2-carboxamide

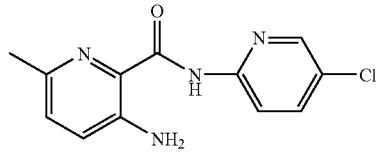

Using a procedure analogous to Example 1-F, 3-amino-2-chloro-6-methylpyridine and 2-amino-5-chloropyridine gave the title compound as a white solid (16 g, 46%).

¹NMR (300 MHz, DMSO-d₆) δ 2.39(s, 3H), 6.81(br s, 2H), 7.23(m, 2H), 7.97(dd, J=2.6, 8.8 Hz, 1H), 8.26(d, J=8.8 Hz, 1H), 8.39(d, J=2.6 Hz, 1H), 10.56(s, 1H).

FIA-MS, m/e: 263.1 (m+1).

Analysis for C₁₂H₁₁ClN₄O:

| Calcd: | C, 54.87; H, 4.22; N, 21.33; |
| Found: | C, 52.04; H, 3.97; N, 20.94. |

B. 3-[2-(3-t-Butoxycarbonylaminopropoxy)-4-methylthiobenzoylamino]-N-(5-chloropyridin-2-yl)-6-methylpyridine-2-carboxamide

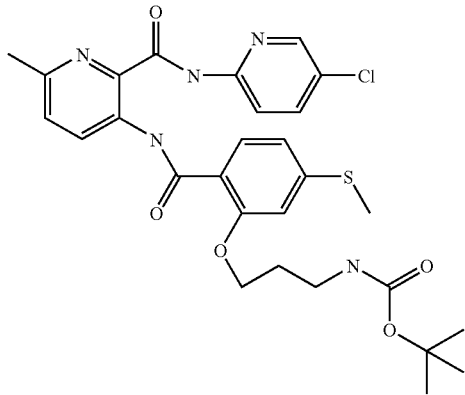

Using a procedure analogous to Example 1-G, 2-(3-aminopropoxy)-4-methylthiobenzoic acid and 3-amino-N-(5-chloro-pyridin-2-yl)-6-methylpyridine-2-carboxamide gave the title compound as a white solid (4 g, 61%).

¹NMR (300 MHz, DMSO-d₆) δ 1.27(s, 9H), 1.98(m, 2H), 2.56(s, 6H), 3.04(m, 2H), 4.36 (t, J=6.2 Hz, 2H), 6.78 (t, J=5.1 Hz, 1H), 6.96(d, J=0.7, 8.4 Hz, 1H), 7.04(s, 1H), 7.59(d, J=8.8 Hz, 1H), 7.88(d, J=8.4 Hz, 1H), 8.02(dd, J=2.6, 8.8 Hz, 1H), 8.27(d, J=8.8 Hz, 1H), 8.45(d, J=2.6 Hz, 1H), 9.10(d, J=8.4 Hz, 1H), 10.82(s, 1H), 12.30(s, 1H).

FIA-MS, m/e: 586.3 (m+1).

Analysis for C₂₈H₃₂ClN₅O₅S:

| Calcd: | C, 57.38; H, 5.50; N, 11.95; |
| Found: | C, 57.56; H, 5.62; N, 12.19. |

C. 3-[2-(3-Aminopropoxy)-4-methylthiobenzoylamino]-N-(5-chloropyridin-2-yl)-6-methylpyridine-2-carboxamide Using a procedure analogous to Example 1-H, 3-[2-(3-t-butoxycarbonylaminopropoxy)-4-methylthiobenzoylamino]-N-(5-chloropyridin-2-yl)-6-methylpyridine-2-carboxamide gave the title compound as a white solid (790 mg, quantitative).

1NMR (300 MHz, DMSO-d₆) δ 1.89(m, 2H), 2.62(m, 8H), 4.44 (t, J=6.6 Hz, 2H), 6.97(dd, J=1.5, 8.4 Hz, 1H), 7.09(d, J=1.5 Hz, 1H), 7.61(d, J=8.8 Hz, 1H), 7.88(d, J=8.4 Hz, 1H), 8.04(dd, J=2.9, 8.8 Hz, 1H), 8.28(d, J=8.8 Hz, 1H), 8.46(d, J=2.9 Hz, 1H), 9.11(d, J=8.4 Hz, 1H).

FIA-MS, m/e: 486.4 (m+1)

Analysis for C₂₃H₂₄ClN₅O₃S:

| Calcd: | C, 56.84; H, 4.98; N, 14.41; |
| Found: | C, 56.76; H, 4.89; N, 14.53. |

EXAMPLE 33

Preparation of 3-[2-(3-Aminopropoxy)-4-methylsulfinyl-benzoylamino]-N-(5-chloropyridin-2-yl)-6-methylpyridine-2-carboxamide

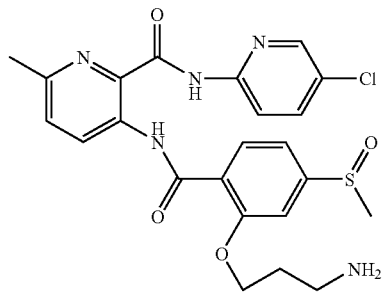

A. 3-[2-(3-t-butoxycarbonylaminopropoxy)-4-methylsulfinyl-benzoylamino]-N-(5-chloropyridin-2-yl)-6-methylpyridine-2-carboxamide

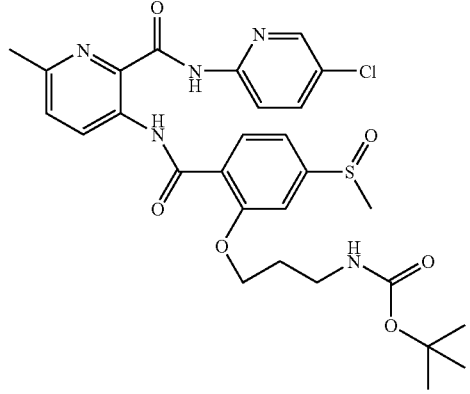

Using a procedure analogous to Example 2-A, 3-[2-(3-t-butoxycarbonylaminopropoxy)-4-methylthiobenzoylamino]-N-(5-chloropyridin-2-yl)-6-methylpyridine-2-carboxamide gave the title compound as a white solid (1.35 g, 88%).

1NMR (300 MHz, DMSO-d₆) δ 1.26(s, 9H), 1.98(m, 2H), 2.58(s, 3H), 2.83(s, 3H), 3.04(m, 2H), 4.37 (t, J=6.2 Hz, 2H), 6.78(m, 1H), 7.40(d, J=8.4 Hz, 1H), 7.53(s, 1H), 7.63(d, J=8.8 Hz, 1H), 8.02(dd, J=2.6, 8.8 Hz, 1H), 8.08(d, J=8.1 Hz, 1H), 8.26(d, J=8.8 Hz, 1H), 8.45(d, J=2.6 Hz, 1H), 9.11(d, J=8.4 Hz, 1H), 10.84(s, 1H), 12.36(s, 1H).

FIA-MS, m/e: 602.3 (m+1).

Analysis for C₂₈H₃₂ClN₅O₆S:

| Calcd: | C, 55.86; H, 5.36; N, 11.63; |
| Found: | C, 56.12; H, 5.38; N, 11.65. |

B. 3-[2-(3-Aminopropoxy)-4-methylsulfinylbenzoylamino]-N-(5-chloropyridin-2-yl)-6-methylpyridine-2-carboxamide Using a procedure analogous to Example 1-H, 3-[2-(3-t-butoxycarbonylaminopropoxy)-4-methylsulfinylbenzoylamino]-N-(5-chloropyridin-2-yl)-6-methylpyridine-2-carboxamide gave the title compound as a white solid (940 mg, 85%).

¹NMR (300 MHz, DMSO-d₆) δ 1.90(m, 2H), 2.58(s, 3H), 2.63 (t, J=6.6 Hz, 2H), 2.84(s, 3H), 4.45 (t, J=6.6 Hz, 2H), 7.39(dd, J=1.1, 8.1 Hz, 1H), 7.56(s, 1H), 7.63(d, J=8.8 Hz, 1H), 8.05(m, 2H), 8.27(d, J=9.1 Hz, 1H), 8.46(d, J=2.6 Hz, 1H), 9.11(d, J=8.8 Hz, 1H).

FIA-MS, m/e: 502.0 (m+1)

Analysis for $C_{23}H_{24}ClN_5O_4S$:

| | |
|---|---|
| Calcd: | C, 55.03; H, 4.82; N, 13.95; |
| Found: | C, 54.79; H, 4.84; N, 13.77. |

EXAMPLE 34

Preparation of 3-[2-(3-Aminopropoxy)-4-methylsulfonyl-benzoylamino]-N-(5-chloropyridin-2-yl)-6-methylpyridine-2-carboxamide

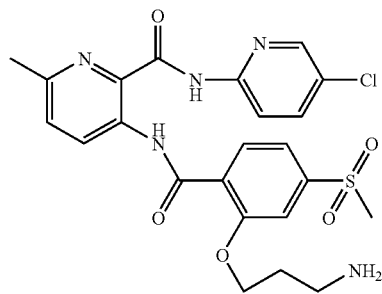

A. 3-[2-(3-t-Butoxycarbonylaminopropoxy)-4-methylsulfonyl-benzoylamino]-N-(5-chloropyridin-2-yl)-6-methylpyridine-2-carboxamide

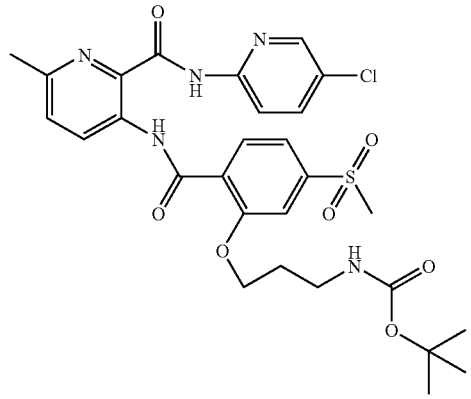

Using a procedure analogous to Example 3-A, 3-[2-(3-t-butoxycarbonylaminopropoxy)-4-methylthiobenzoylamino]-N-(5-chloropyridin-2-yl)-6-methylpyridine-2-carboxamide gave the title compound as a white solid (1.3 g, 82%).

$^1$NMR (300 MHz, DMSO-$d_6$) δ 1.26(s, 9H), 1.98(m, 2H), 2.58(s, 3H), 3.04(m, 2H), 3.32(s, 3H), 4.39 (t, J=6.2 Hz, 2H), 6.79(m, 1H), 7.65(d, J=8.8 Hz, 1H), 7.71(s, 1H), 8.01(dd, J=2.6 Hz, 1H), 8.11(d, J=8.1 Hz, 1H), 8.25(d, J=8.8 Hz, 1H), 8.46(d, J=2.6 Hz, 1H), 9.10(d, J=8.8 Hz, 1H), 10.84(s, 1H), 12.37(s, 1H).

FIA-MS, m/e: 618.4 (m+1).

Analysis for $C_{28}H_{32}ClN_5O_7S$:

| | |
|---|---|
| Calcd: | C, 54.41; H, 5.22; N, 11.33; |
| Found: | C, 55.36; H, 5.47; N, 11.49. |

B. 3-[2-(3-Aminopropoxy)-4-methylsulfonylbenzoylamino]-N-(5-chloropyridin-2-yl)-6-methylpyridine-2-carboxamide Using a procedure analogous to Example 1-H, 3-[2-(3-t-butoxycarbonylaminopropoxy)-4-methylsulfonylbenzoylamino]-N-(5-chloropyridin-2-yl)-6-methylpyridine-2-carboxamide gave the title compound as a white solid (940 mg, 86%).

$^1$NMR (300 MHz, DMSO-$d_6$) δ 1.89(m, 2H), 2.59(s, 3H), 2.63 (t, J=6.6 Hz, 2H), 3.33(s, 3H), 4.47 (t, J=6.6 Hz, 2H), 7.64(m, 2H), 7.75(s, 1H), 8.03(dd, J=2.6, 8.8 Hz, 1H), 8.10(d, J=8.1 Hz, 1H), 8.26(d, J=8.8 Hz, 1H), 8.46(d, J=2.6 Hz, 1H), 9.10(d, J=8.8 Hz, 1H).

FIA-MS, m/e: 518.2 (m+1)

Analysis for $C_{23}H_{24}ClN_5O_5S$:

| | |
|---|---|
| Calcd: | C, 53.33; H, 4.67; N, 13.52; |
| Found: | C, 53.16; H, 4.67; N, 13.40. |

EXAMPLE 35

Preparation of N-(5-Chloropyridin-2-yl)-6-methyl-3-[4-methylthio-2-(4-piperidinyloxy)benzoylamino]pyridine-2-carboxamide

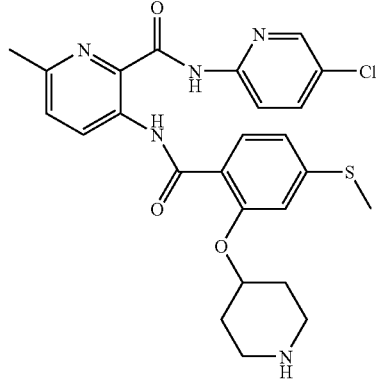

A. 3-[2-(1-t-Butoxycarbonylpiperidin-4-yloxy)-4-methylthiobenzoylamino]-N-(5-chloropyridin-2-yl)-6-methylpyridine-2-carboxamide

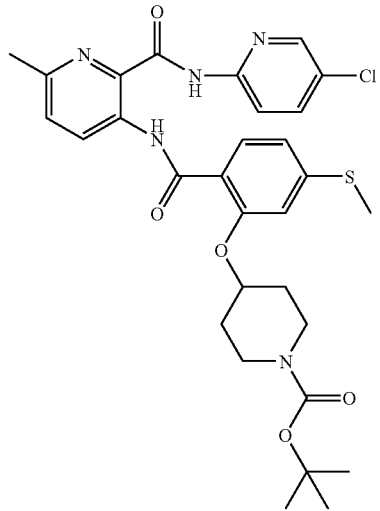

Using a procedure analogous to Example 1-G, 2-(1-t-butoxycarbonylpiperidin-4-yloxy)-4-methylthiobenzoic acid and 3-amino-6-methyl-N-(5-chloropyridin-2-yl)pyridine-2-carboxamide gave the title compound as a white solid (7.4 g, 93%).

¹NMR (300 MHz, DMSO-d₆) δ 1.27(s, 9H), 1.85(m, 2H), 1.98(m, 2H), 2.56(s, 3H), 2.57(s, 3H), 3.08(m, 2H), 3.73(m, 2H), 4.89(m, 1H), 6.98(dd, J=1.5, 8.1 Hz, 1H), 7.13(s, 1H), 7.61(d, J=8.8 Hz, 1H), 7.83(d, J=8.1 Hz, 1H), 7.96(dd, J=2.6, 8.8 Hz, 1H), 8.22(d, J=8.8 Hz, 1H), 8.45(d, J=2.6 Hz, 1H), 9.08(d, J=8.8 Hz, 1H), 10.81(s, 1H), 12.14(s, 1H).

FIA-MS, m/e: 612.2 (m+1).

Analysis for C₃₀H₃₄ClN₅O₅S:

| Calcd: | C, 58.86; H, 5.60; N, 11.44; |
|---|---|
| Found: | C, 58.94; H, 5.74; N, 11.49. |

B. N-(5-Chloropyridin-2-yl)-6-methyl-3-[4-methylthio-2-(4-piperidinyloxy)benzoylamino]pyridine-2-carboxamide Using a procedure analogous to Example 1-H, 3-[2-(1-t-butoxycarbonylpiperidin-4-yloxy)-4-methylthiobenzoylamino]-N-(5-chloropyridin-2-yl)-6-methylpyridine-2-carboxamide gave the title compound as a white solid (1.01 g, quant.).

¹NMR (300 MHz, DMSO-d₆) δ 1.94(m, 2H), 2.07(m, 2H), 2.56(s, 3H), 2.58(s, 3H), 2.92(m, 2H), 3.07(m, 2H), 4.94(m, 1H), 7.01(dd, J=1.1, 8.4 Hz, 1H), 7.13(d, J=1.1 Hz, 1H), 7.63(d, J=8.8 Hz, 1H), 7.79(d, J=8.4 Hz, 1H), 8.03(dd, J=2.6, 8.8 Hz, 1H), 8.25(d, J=8.8 Hz, 1H), 8.47(d, J=2.6 Hz, 1H), 9.07(d, J=8.8 Hz, 1H), 10.83(s, 1H), 12.08(s, 1H).

FIA-MS, m/e: 512.4 (m+1)

Analysis for C₂₅H₂₆ClN₅O₃S.1.1 H₂O:

| Calcd: | C, 56.46; H, 5.34; N, 13.17; |
|---|---|
| Found: | C, 56.10; H, 5.02; N, 12.98. |

EXAMPLE 36

Preparation of N-(5-Chloropyridin-2-yl)-6-methyl-3-[4-methylsulfinyl-2-(4-piperidinyloxy)benzoylamino]pyridine-2-carboxamide

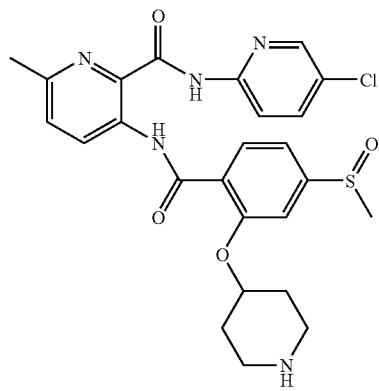

A. 3-[2-(1-t-Butoxycarbonylpiperidin-4-yloxy)-4-methylsulfinylbenzoylamino]-N-(5-chloropyridin-2-yl)-6-methylpyridine-2-carboxamide

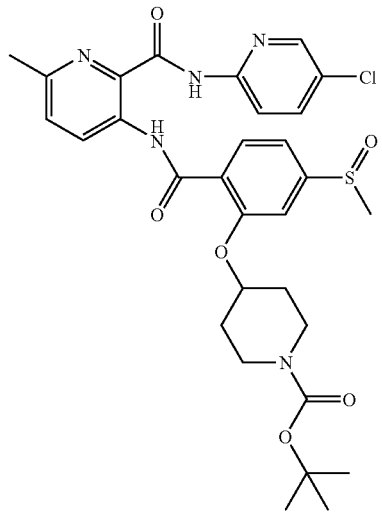

Using a procedure analogous to Example 2-A, 3-[2-(1-t-butoxycarbonylpiperidin-4-yloxy)-4-methylthiobenzoylamino]-N-(5-chloropyridin-2-yl)-6-methylpyridine-2-carboxamide gave the title compound as a white solid (6.6 g, 91%).

¹NMR (300 MHz, DMSO-d₆) δ 1.27(s, 9H), 1.85(m, 2H), 1.98(m, 2H), 2.58(s, 3H), 2.84(s, 3H), 3.11(m, 2H), 3.70(m, 2H), 4.91(m, 1H), 7.40(dd, J=0.7, 8.1 Hz, 1H), 7.58(s, 1H), 7.64(d, J=8.4 Hz, 1H), 7.96(dd, J=2.6, 8.8 Hz, 1H), 8.02(d, J=8.1 Hz, 1H), 8.20(d, J=8.8 Hz, 1H), 8.46(d, J=2.6 Hz, 1H), 9.10(d, J=8.8 Hz, 1H), 10.83(s, 1H), 12.22(s, 1H).

FIA-MS, m/e: 628.3 (m+1).

Analysis for C₃₀H₃₄ClN₅O₆S:

| Calcd: | C, 57.36; H, 5.46; N, 11.15; |
|---|---|
| Found: | C, 54.25; H, 4.89; N, 12.61. |

B. N-(5-Chloropyridin-2-yl)-6-methyl-3-[4-methylsulfinyl-2-(4-piperidinyloxy)benzoylamino]pyridine-2-carboxamide Using a procedure analogous to Example 1H, 3-[2-(1-t-butoxycarbonylpiperidin-4-yloxy)-4-methylsulfinylbenzoyl-amino]-N-(5-chloropyridin-2-yl)-6-methylpyridine-2-carboxamide gave the title compound as a white solid (800 mg, 95%).

¹NMR (300 MHz, DMSO-d₆) δ 1.78(m, 2H), 1.94(m, 2H), 2.57(m, 2H), 2.58(s, 3H), 2.83(s, 3H), 2.87(m, 2H), 4.79(m, 1H), 7.38(dd, J=1.1, 8.1 Hz, 1H), 7.55(d, J=1.1 Hz, 1H), 7.46(d, J=8.8 Hz, 1H), 8.03(m, 2H), 8.34(d, J=8.8 Hz, 1H), 8.46(d, J=2.6 Hz, 1H), 9.10(d, J=8.8 Hz, 1H), 10.81(br s, 1H), 12.24(s, 1H).

FIA-MS, m/e: 528.1 (m+1)

Analysis for C₂₅H₂₆ClN₅O₄S:

| Calcd: | C, 56.87; H, 4.96; N, 13.26; |
|---|---|
| Found: | C, 56.57; H, 5.11; N, 13.25. |

EXAMPLE 37

Preparation of N-(5-Chloropyridin-2-yl)-6-methyl-3-[4-methylsulfonyl-2-(4-piperidinyloxy)benzoylamino]pyridine-2-carboxamide

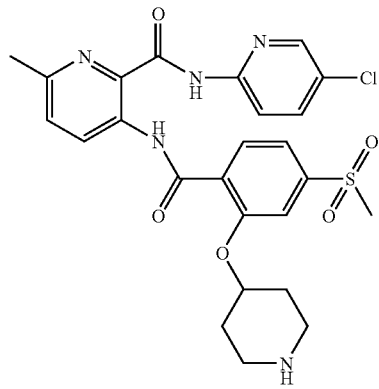

A. 3-[2-(1-t-Butoxycarbonylpiperidin-4-yloxy)-4-methylsulfonylbenzoylamino]-N-(5-chloropyridin-2-yl)-6-methylpyridine-2-carboxamide

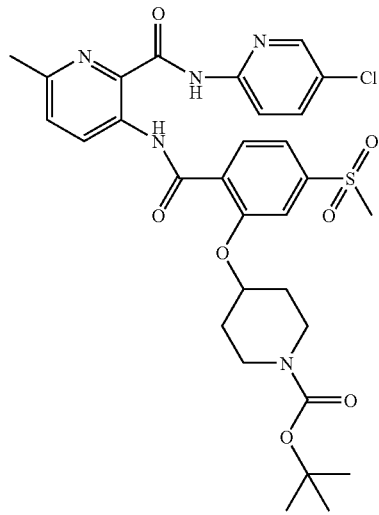

Using a procedure analogous to Example 3-A, 3-[2-(1-t-butoxycarbonylpiperidin-4-yloxy)-4-methylthiobenzoylamino]-N-(5-chloropyridin-2-yl)-6-methylpyridine-2-carboxamide gave the title compound as a white solid (5.6 g, 82%).

$^1$NMR (300 MHz, DMSO-$d_6$) δ 1.27(s, 9H), 1.83(m, 2H), 1.98(m, 2H), 2.58(s, 3H), 3.15(m, 2H), 3.33(s, 3H), 3.67(m, 2H), 4.99(m, 1H), 7.64(m, 2H), 7.77(s, 1H), 7.97(dd, J=2.6, 8.8 Hz, 1H), 8.05(d, J=8.1 Hz, 1H), 8.20(d, J=8.8 Hz, 1H), 8.46(d, J=2.6 Hz, 1H), 9.09(d, J=8.8 Hz, 1H), 10.83(s, 1H), 12.23(s, 1H).

FIA-MS, m/e: 643 (m+).

Analysis for $C_{30}H_{34}ClN_5O_7S$:

| Calcd: | C, 55.94; H, 5.32; N, 10.87; |
|---|---|
| Found: | C, 56.22; H, 5.56; N, 10.84. |

B. N-(5-Chloropyridin-2-yl)-6-methyl-3-[4-methylsulfonyl-2-(4-piperidinyloxy)benzoylamino]pyridine-2-carboxamide Using a procedure analogous to Example 1-H, 3-[2-(1-t-butoxycarbonylpiperidin-4-yloxy)-4-methylsulfonylbenzoyl-amino]-N-(5-chloropyridin-2-yl)-6-methylpyridine-2-carboxamide gave the title compound as a white solid (790 mg, 94%).

$^1$NMR (300 MHz, DMSO-$d_6$) δ 1.74(m, 2H), 1.94(m, 2H), 2.55(m, 2H), 2.59(s, 3H), 2.88(m, 2H), 3.33(s, 3H), 4.87(m, 1H), 7.64(m, 2H), 7.73(s, 1H), 8.03(m, 2H), 8.31(d, J=8.8 Hz, 1H), 8.46(d, J=2.6 Hz, 1H), 9.10(d, J=8.8 Hz, 1H), 10.80(br s, 1H), 12.25(s, 1H).

FIA-MS, m/e: 544.3 (m+1)

Analysis for $C_{25}H_{26}ClN_5O_5S \cdot 0.5\ H_2O$:

| Calcd: | C, 54.30; H, 4.92; N, 12.66; |
|---|---|
| Found: | C, 54.25; H, 4.89; N, 12.61. |

EXAMPLE 38

Preparation of N-(5-Chloropyridin-2-yl)-3-[4-methylsulfonyl-2-(4-piperidinylmethoxy)benzoylamino]pyridine-2-carboxamide

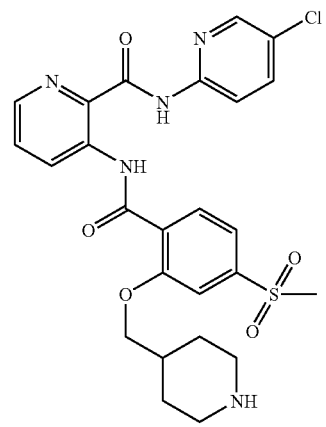

A. 4-Methylthio-2-acetoxybenzoic acid

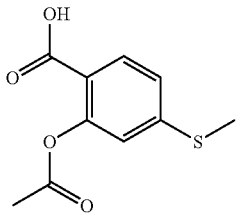

To a mixture of 4-methylthio-2-hydroxybenzoic acid (50.0 g, 272 mmol) and acetic anhydride (77.0 mL, 815 mmol) was added 36 N sulfuric acid (0.45 mL, 8.16 mmol) and the mixture was heated to 75° C. for 1 h. To the reaction mixture was added $H_2O$ (200 mL), and it was stirred for 18 h. A white precipitate was collected, triturated with dichloromethane, (100 mL), diluted with 20% $Et_2O$/hexanes (300 mL), and filtered to give the title compound as a white solid (49 g, 80%).

$^1$NMR (300 MHz, DMSO-$d_6$): δ 2.23(s, 3H), 2.52(s, 3H), 7.05(d, J=1.5 Hz, 1H), 7.22(dd, J=1.5, 8.1 Hz, 1H), 7.84(d, J=8.1 Hz, 1H), 12.91(s, 1H).

MS (EI), m/e: 226.0 (m+).

B. 3-[2-Acetoxy-4-methylthiobenzoylamino]-N-(5-chloropyridin-2-yl)pyridine-2-carboxamide

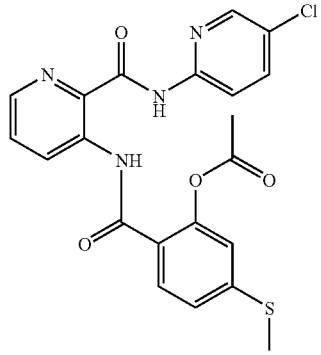

To a 0° C. mixture of 2-acetoxy-4-methylthiobenzoic acid (5 g, 22.1 mmol), dichloromethane (75 mL), NEt₃ (3.1 mL, 22.1 mmol) and DMF (17 μL, 0.221 mmol) was added oxalyl chloride (1.92 mL, 22.1 mL) at a rate to give gentle bubbling. The mixture was stirred for 1 h and then was concentrated in vacuo. The resulting residue was dissolved in dichloromethane (75 mL). To this solution was added 3-amino-N-(5-chloropyridin-2-yl)pyridine-2-carboxamide (5.5 g, 22.1 mmol) followed by NEt₃ (3.1 mL, 22.1 mmol). The reaction mixture was stirred for 18 h, concentrated to a slurry in dichloromethane and chromatographed (75 g silica gel; 100% dichloromethane to 100% EtOAc) to give the title compound as an impure solid (8.5 g).

FIA-MS, m/e: 456.8 (m+1)

C. N-(5-Chloropyridin-2-yl)-3-[2-hydroxy-4-methylthiobenzoylamino]pyridine-2-carboxamide

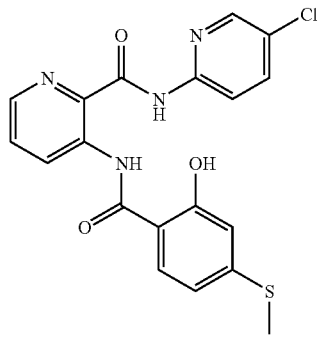

To a mixture of 3-[2-acetoxy-4-methylthiobenzoylamino]-N-(5-chloropyridin-2-yl)pyridine-2-carboxamide (13 g, 28.4 mmol), THF (100 mL) and MeOH (50 mL) was added Na2CO3 (5.75 g, 54.3 mmol), and the mixture was stirred for 18 h. The resulting yellow suspension was diluted with dichloro-methane (100 mL), and 1 N HCl (about 55 mL) was slowly added. The mixture was partitioned and the white organic suspension was concentrated. The residue was triturated with dichloromethane (200 mL) and filtered to give the title compound as a white solid (9.5 g, 22.9 mmol, 80%).

¹NMR (400 MHz, DMSO-d₆): δ 2.46(s, 3H), 6.83(m, 2H), 7.70(dd, J=1.5, 6.6 Hz, 1H), 7.82(d, J=8.3 Hz, 1H), 8.03(dd, J=2.4, 8.8 Hz, 1H), 8.22(d, J=8.3, 1H), 8.42(m, 2H), 9.15(dd, J=1.5, 8.8 Hz, 1H), 10.81(s, 1H), 11.67(s, 1H), 12.55(s, 1H).

FIA-MS, m/e: 413.1 (m−1)

D. 3-[2-[1-(t-Butoxycarbonyl)piperidin-4-ylmethoxy]-4-methylthiobenzoylamino]-N-(5-chloropyridin-2-yl)pyridine-2-carboxamide

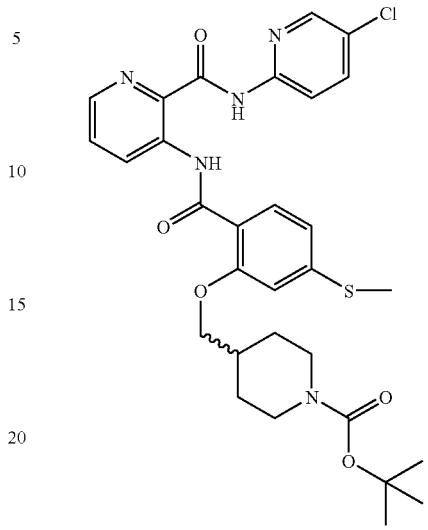

To a 0° C. mixture of N-(5-chloropyridin-2-yl)-3-[2-hydroxy-4-methylthiobenzoylamino]pyridine-2-carboxamide (750 mg, 1.8 mmol), 1-t-butoxycarbonyl-4-hydroxymethylpiperidine (387 mg, 1.8 mmol), triphenylphosphine (568 mg, 2.26 mmol) and DMF (9 mL) was added DEAD (0.36 mL, 2.26 mmol), and the mixture was stirred for 18 h. The reaction mixture was concentrated and chromatographed (CH₂Cl₂; 10% EtOAc/CH₂Cl₂) to give the desired product as a white solid (950 mg, 86%).

¹NMR (300 MHz, DMSO-d₆): δ 1.21(m, 4H), 1.30(s, 9H), 1.67(m, 2H), 2.17(m, 1H), 2.58(s, 3H), 3.80(m, 2H), 4.20(m, 2H), 7.01(dd, J=1.5, 8.5 Hz, 1H), 7.08(d, J=1.5 Hz, 1H), 7.76(dd, J=4.3, 8.5 Hz, 1H), 7.87(d, J=8.2 Hz, 1H), 8.07(dd, J=2.7, 8.8 Hz, 1H), 8.28(d, J=8.8 Hz, 1H), 8.48(m, 2H), 9.24(dd, J=1.5, 8.5 Hz, 1H), 10.86(s, 1H), 12.27(s, 1H).

FIA-MS, m/e: 612.3 (m+1).

E. 3-[2-[1-(t-Butoxycarbonyl)piperidin-4-ylmethoxy]-4-methylsulfonylbenzoylamino]-N-(5-chloropyridin-2-yl)-pyridine-2-carboxamide

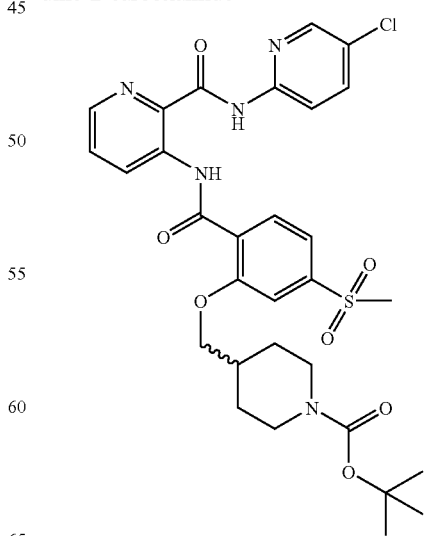

Using a procedure analogous to Example 3-A, 3-[2-[1-(t-butoxycarbonyl)piperidin-4-ylmethoxy]-4-methylthio-benzoylamino]-N-(5-chloropyridin-2-yl)pyridine-2-carboxamide gave the desired product as a white solid (800 mg, 89%).

$^1$NMR (300 MHz, DMSO-d$_6$) δ ppm: 1.12 (m, 4H), 1.30 (s, 9H), 1.72 (m, 2H), 2.15 (m, 1H), 3.34 (s, 3H), 3.78 (m, 2H), 4.24 (m, 2H), 7.66 (dd, J=1.5, 7.9 Hz, 1H), 7.75 (d, J=1.2 Hz, 1H), 7.81 (dd, J=4.6, 8.5 Hz, 1H), 8.06 (m, 2H), 8.24 (d, 8.8 Hz, 1H), 8.49 (m, 2H), 9.23 (dd, J=1.5 Hz, 8.8 Hz, 1H), 10.87 (s, 1H), 12.31 (s, 1H).

FIA-MS, m/e: 644.2 (m+1).

Analysis for C$_{30}$H$_{34}$ClN$_5$O$_7$S:

| Calcd: | C, 55.94; H, 5.32; N, 10.87; |
|---|---|
| Found: | C, 55.94; H, 5.17; N, 11.11. |

F. N-(5-Chloropyridin-2-yl)-3-[4-methylsulfonyl-2-(4-piperidinylmethoxy)benzoylamino]pyridine-2-carboxamide Using a procedure analogous to Example 1-H, 3-[2-[1-(t-butoxycarbonyl)piperidin-4-ylmethoxy]-4-methylsulfonylbenzoylamino]-N-(5-chloropyridin-2-yl)pyridine-2-carboxamide gave the desired product as a white solid (600 mg, 89%).

$^1$NMR (300 MHz, DMSO-d$_6$): δ 1.12(m, 2H), 1.64(m, 2H), 2.06(m, 1H), 2.22(m, 2H), 2.65(m, 2H), 3.35(s, 3H), 4.19(d, J=6.7 Hz, 2H), 7.66(dd, J=1.2, 8.2 Hz, 1H), 7.74(d, J=1.5 Hz, 1H), 7.81(dd, J=4.3, 8.8 Hz, 1H), 8.07(m, 2H), 8.26(d, J=8.8 Hz, 1H), 8.50(m, 2H), 9.24(dd, J=1.2, 8.8 Hz, 1H), 12.36(s, 1H).

FIA-MS, m/e: 544.2 (m+1).

Analysis for C$_{28}$H$_{32}$NClN$_5$O$_7$S:

| Calcd: | C, 55.19; H, 4.82; N, 12.87; |
|---|---|
| Found: | C, 51.46; H, 3.96; N, 11.94. |

EXAMPLE 39

Preparation of N-(5-Chloropyridin-2-yl)-3-[4-methyl-sulfonyl-2-(3-pyrrolidinylmethoxy)benzoylamino]pyridine-2-carboxamide Hydrochloride

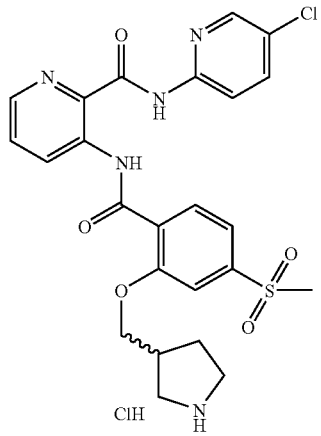

A. 3-[2-[1-(t-Butoxycarbonyl)pyrrolidin-3-ylmethoxy]-4-methylthiobenzoylamino]-N-(5-chloropyridin-2-yl)pyridine-2-carboxamide

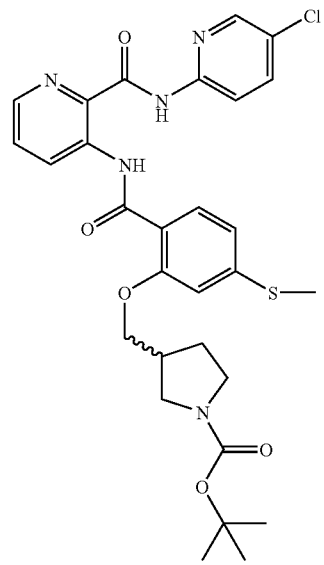

Using a procedure analogous to Example 38-D, N-(5-chloropyridin-2-yl)-3-[2-hydroxy-4-methylthiobenzoylamino]-pyridine-2-carboxamide gave the title compound as a solid (950 mg, 88%).

$^1$NMR (300 MHz, DMSO-d$_6$): δ 1.20 (s, 9H), 1.80 (m, 1H), 2.02 (m, 1H), 2.58 (s, 3H), 2.92 (m, 1H), 3.09 (m, 2H), 3.25 (m, 2H), 4.37 (m, 2H), 7.01 (dd, J=1.5, 8.5 Hz, 1H), 7.12 (d, J=1.5 Hz, 1H), 7.77 (dd, J=4.3, 8.5 Hz, 1H), 7.90 (d, J=8.2 Hz, 1H), 8.03 (dd, J=2.4, 8.8 Hz, 1H), 8.22 (m, 1H), 8.47 (m, 2H), 9.23 (dd, J=0.9, 8.5 Hz, 1H), 10.83 (s, 1H), 12.30 (s, 1H).

FIA-MS, m/e: 598.3 (m+1)

Analysis for C$_{29}$H$_{32}$ClN$_5$O$_5$S:

| Calcd: | C, 58.24; H, 5.39; N, 11.71; |
|---|---|
| Found: | C, 56.05; H, 5.48; N, 11.92. |

B. 3-[2-[1-(t-Butoxycarbonyl)pyrrolidin-3-ylmethoxy]-4-methylsulfonylbenzoylamino]-N-(5-chloropyridin-2-yl)-pyridine-2-carboxamide

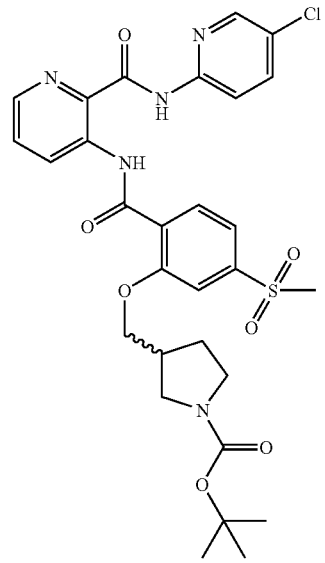

Using a procedure analogous to Example 3-A, 3-[2-[1-(t-butoxycarbonyl)pyrrolidin-3-ylmethoxy]-4-methylthio-benzoylamino]-N-(5-chloropyridin-2-yl)pyridine-2-carboxamide gave the title compound as a white solid (800 mg, 89%).

$^1$NMR (300 MHz, DMSO-d$_6$): δ 1.20 (s, 9H), 1.80 (m, 1H), 2.02 (m, 1H), 2.92 (m, 1H), 3.09 (m, 2H), 3.25 (m, 2H), 3.35 (s, 3H), 4.37 (m, 2H), 7.68 (dd, J=1.2, 8.2 Hz, 1H), 7.79 (m, 2H), 8.02 (dd, J=2.5, 9.1 Hz/1H), 8.10 (d, J=8.2 Hz, 1H), 8.21 (d, J=9.1 Hz, 1H), 8.47 (d, J=2.1 Hz, 1H), 8.51 (dd, J=1.2, 4.6 Hz, 1H), 9.21 (dd, 0.9, 8.5 Hz, 1H), 10.84 (s, 1H), 12.35 (s, 1H).

FIA-MS, m/e: 630.3 (m+1)

C. N-(5-Chloropyridin-2-yl)-3-[4-methylsulfonyl-2-(3-pyrrolidinylmethoxy)benzoylamino]pyridine-2-carboxamide hydrochloride Using a procedure analogous to Examples 1-H and 4-F, 3-[2-[1-(t-butoxycarbonyl)pyrrolidin-3-ylmethoxy]-4-methylsulfonylbenzoylamino]-N-(5-chloropyridin-2-yl)-pyridine-2-carboxamide gave the title compound as a white solid (340 mg, 46%).

$^1$NMR (300 MHz, DMSO-d$_6$): δ 1.80 (m, 1H), 2.02 (m, 1H), 2.92 (m, 1H), 3.08 (m, 2H), 3.23 (m, 2H), 3.36 (s, 3H), 4.43 (m, 2H), 7.70 (dd, J=1.5, 8.2 Hz, 1H), 7.80 (m, 2H), 8.08 (m, 2H), 8.21 (dd, J=0.6, 8.8 Hz, 1H), 8.50 (m, 2H), 8.96 (br s, 1H), 9.08 (br s, 1H), 9.20 (dd, J=1.2, 8.5 Hz, 1H), 10.88 (s, 1H), 12.32 (s, 1H).

FIA-MS, m/e: 530.0 (m+1)

Analysis for C$_{24}$H$_{25}$Cl$_2$N$_5$O$_5$S:

| | |
|---|---|
| Calcd: | C, 50.89; H, 4.45; N, 12.36; |
| Found: | C, 51.14; H, 4.39; N, 12.06. |

EXAMPLE 40

Preparation of 3-[2-[(2R)-3-Amino-2-methylpropoxy]-4-methyl-sulfonylbenzoylamino]-N-(5-chloropyridin-2-yl)pyridine-2-carboxamide Hydrochloride

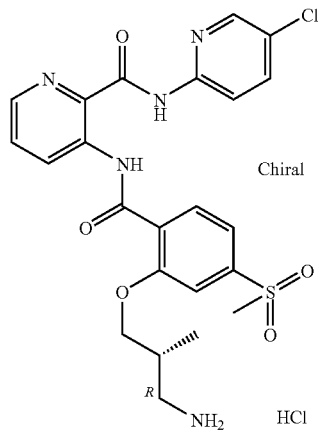

A. (R)-(+)-α-Methylbenzylammonium salt of (2R)-3-t-Butoxy-carbonylamino-2-methylpropionic acid

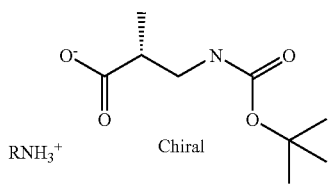

To a vigorously mechanically stirred solution of 3-[tert-butoxycarbonyl)amino]-2-methylpropionic acid (202.4 g, 0.99 mol) in ethyl acetate (0.7 L) was added (R)-(+)-α-methylbenzylamine (127.0 mL) all at once. The exothermic reaction was allowed to cool to room temperature. The precipitate was filtered and dried. The solid was dissolved in hot ethyl acetate (0.8 L) and allowed to equilibrate 34° C. The precipitate was filtered and subjected to recrystallization for three more times with hot ethyl acetate (0.5 L, 0.35 L and 0.3 L) to afford the title compound (49.79 g, 15.4%).

Analysis of chiral acid:

A sample of this salt was subjected to a 1 N HCl acid wash in CH$_2$Cl$_2$. The organic layer was separated, dried with anhydrous MgSO$_4$, filtered and concentrated to an oil in vacuo. Analysis of oil gave the following results:

% ee=96.0%; optical rotation=−17.90; % wt yield based on theory=62.34%).

$^1$H NMR (CDCl$_3$, 300 MHz) δ 1.15 (d, J=7.1 Hz, 3H), 1.4 (s, 9H), 2.6 (m, 1H), 3.2 (m, 2H), 5.09 (bs, 0.73H) 6.19 (bs, 0.27H), 9.2 (bs, 1H).

$^{13}$C NMR (CDCl$_3$, 300 MHz) δ 180.55, 155.93, 79.60, 42.75, 40.08, 28.41, 14.70.

IR(CHCl$_3$) 3457, 2982, 1709, 1508, 1368, 1243, 1168 cm$^{-1}$.

MS {FD$^+$} m/z (relative intensity) 204.0.

Analysis for C$_9$H$_{17}$NO$_4$:

| | |
|---|---|
| Calcd: | C, 53.19; H, 8.43; N, 6.89; |
| Found: | C, 53.14; H, 8.40; N, 6.73. |

B. (2R)-3-(t-Butoxycarbonylamino)-2-methylpropionic acid

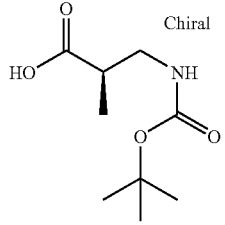

A mixture of (2R)-3-t-butoxycarbonylamino-2-methylpropionic acid/(1S)-phenethylamine salt (9.0 g, 27.7 mmol) and EtOAc was treated with sufficient 50% saturated citric acid to obtain an acidic aqueous solution. The organic layer was partitioned, washed with water (3×), dried (Na$_2$SO$_4$), concentrated, and vacuum dried. To the resulting solid was added 20% Et$_2$O/hexanes (3 mL); the mixture was sonicated and filtered; and the filtered solid dried to give the title compound as a solid (5.0 g, 90%).

$^1$NMR (300 MHz, DMSO-d$_6$) δ ppm: 1.00 (d, J=7.3 Hz, 3H), 1.37 (s, 9H), 2.49 (m, 1H), 2.91 (m, 1H), 3.15 (m, 1H), 6.82 (s, 1H), 12.17 (s, 1H).

FIA-MS, m/e: 204.2 (m+1)

C. (2R)-3-(t-Butoxycarbonylamino)-2-methylpropanol

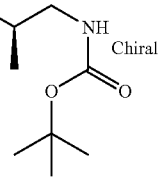

To a 0° C. mixture of (2R)-3-t-butoxycarbonylamino-2-methylpropionic acid (4.6 g, 21.0 mmol) in THF (100 mL) was added 2 M Me₂S.BH₃/THF (16 mL, 31.5 mmol, 1.5 equivalents). After stirring for 2 h, water was added and the mixture stirred for 18 h. The mixture was diluted with CH₂Cl₂ and washed with satd Na₂CO₃. The organic layer was dried (Na₂SO₄), concentrated, and chromatographed (CH₂Cl₂; EtOAc) to give the title compound as an oil (2.4 g, 61%).

¹NMR (300 MHz, DMSO-$d_6$): δ 0.79 (d, J=6.7 Hz, 3H), 1.38 (s, 9H), 1.62(m, 1H), 2.77(m, 1H), 2.92 (m, 1H), 3.23(m, 2H), 4.40(t, J=5.2 Hz, 1H), 6.75(m, 1H).

FIA-MS, m/e: 190.5 (m+1)

Analysis for $C_9H_{19}NO_3$:

| Calcd:  | C, 57.12; H, 10.12; N, 7.40; |
| Found:  | C, 56.78; H, 10.14; N, 7.12. |

D. 3-[2-[(2R)-3-(t-Butoxycarbonylamino)-2-methylpropoxy]-4-methylthiobenzoylamino]-N-(5-chloropyridin-2-yl)pyridine-2-carboxamide

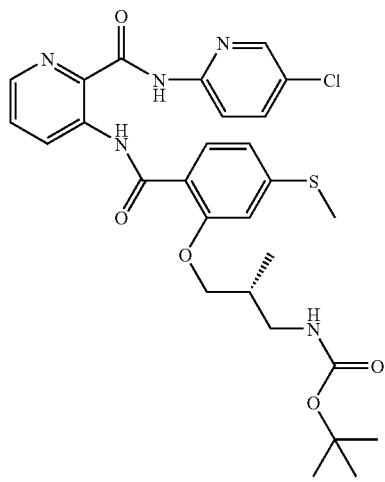

Using a procedure analogous to Example 38-D, N-(5-chloropyridin-2-yl)-3-[2-hydroxy-4-methylthiobenzoyl-amino]pyridine-2-carboxamide and (2R)-3-(t-butoxycarbonylamino)-2-methylpropanol gave the desired product as a solid (850 mg, 81%).

¹NMR (300 MHz, DMSO-$d_6$) δ ppm: 0.84 (d, J=6.8 Hz, 3H), 1.29 (s, 9H), 2.24 (m, 1H), 2.55 (s, 3H), 2.82 (m, 1H), 3.02 (m, 1H), 4.08 (m, 1H), 4.22 (m, 1H), 6.98 (m, 1H), 7.01 (m, 2H), 7.76 (dd, J=4.4, 8.8 Hz, 1H), 7.87 (d, J=8.2 Hz, 1H), 8.04 (dd, J=2.4, 8.8 Hz, 1H), 8.26 (d, J=8.8 Hz, 1H), 8.46 (m, 2H), 9.21 (dd, J=1.5, 8.5 Hz, 1H), 10.82 (s, 1H), 12.28 (s, 1H).

FIA-MS, m/e: 586.2 (m+1).

E. 3-[2-[(2R)-3-(t-Butoxycarbonylamino)-2-methylpropoxy]-4-methylsulfonylbenzoylamino]-N-(5-chloropyridin-2-yl)-pyridine-2-carboxamide

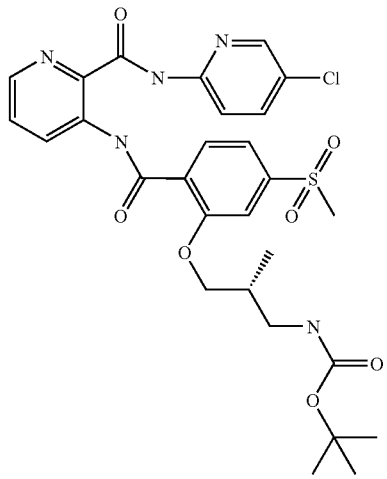

Using a procedure analogous to Example 3-A, 3-[2-[(2R)-3-(t-butoxycarbonylamino)-2-methylpropoxy]-4-methylthio-benzoylamino]-N-(5-chloropyridin-2-yl)pyridine-2-carboxamide gave the desired product as a solid (650 mg, 73%).

¹NMR (300 MHz, DMSO-$d_6$): δ 0.87 (d, J=7.0 Hz, 2H), 1.28 (s, 9H), 2.80 (m, 1H), 3.02 (m, 1H), 3.30 (s, 3H), 4.11 (m, 1H), 4.19 (m, 1H), 6.81 (m, 1H), 7.67 (dd, J=1.5, 7.9 Hz, 1H), 7.72 (s, 1H), 7.98 (dd, J=2.4, 8.8 Hz, 1H), 8.04 (m, 2H), 8.23 (d, J=8.8 Hz, 1H), 8.50 (m, 2H), 9.20 (dd, J=1.5, 8.8 Hz, 1H), 10.83 (s, 1H), 12.32 (s, 1H).

FIA-MS, m/e: 616.3 (m−1)

Analysis for $C_{28}H_{32}ClN_5O_7S$:

| Calcd:  | C, 54.41; H, 5.22; N, 11.33; |
| Found:  | C, 53.73; H, 5.03; N, 11.40. |

F. N-(5-Chloropyridin-2-yl)-3-[2-[(2R)-2-methyl-3-(2-propylimino)propoxy]-4-methylsulfonylbenzoylamino]-pyridine-2-carboxamide

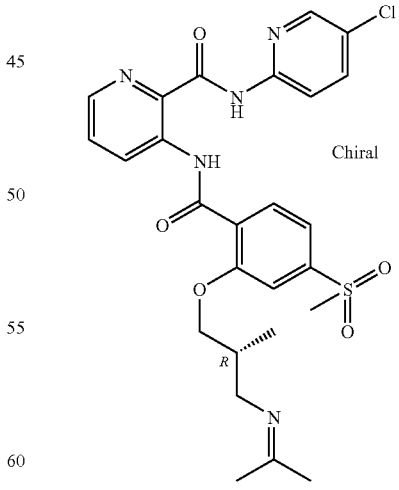

Using a procedure analogous to Example 1-H, 3-[2-[(2R)-3-(t-butoxycarbonylamino)-2-methylpropoxy]-4-methylsulfonyl-benzoylamino]-N-(5-chloropyridin-2-yl)pyridine-2-carboxamide gave, after crystallization from acetone, the title compound as a white solid (400 mg, 73%).

¹NMR (250 MHz, DMSO-d₆): δ 0.96 (d, J=5.5 Hz, 3H), 1.57 (s, 3H), 1.82 (s, 3H), 2.32 (m, 1H), 3.10 (m, 2H), 3.35 (s, 3H), 4.32 (m, 2H), 7.66 (dd, J=1.5, 7.9 Hz, 1H), 7.82 (m, 2H), 8.05 (m, 2H), 8.21 (d, J=8.5 Hz, 1H), 8.50 (m, 2H), 9.21 (dd, J=1.5, 8.5 Hz, 1H), 12.33 (s, 1H).

FIA-MS, m/e: 558.0 (m+1)

Analysis for $C_{26}H_{28}ClN_5O_5S$:

| Calcd: | C, 55.96; H, 5.06; N, 12.55; |
|---|---|
| Found: | C, 54.89; H, 4.56; N, 12.43. |

G. 3-[2-[(2R)-3-Amino-2-methylpropoxy]-4-methylsulfonyl-benzoylamino]-N-(5-chloropyridin-2-yl)pyridine-2-carboxamide Hydrochloride N-(5-Chloropyridin-2-yl)-3-[2-[(2R)-2-methyl-3-(2-propylimino)propoxy]-4-methylsulfonylbenzoylamino]-pyridine-2-carboxamide was treated with 1 N HCl and purified by HPLC (Vydac C18, 5-70% 0.1% TFA/CH₃CN in 0.1% TFA/H₂O; Rt: 27.6 m) to give the title compound as a solid (205 mg, 69%).

¹NMR (250 MHz, DMSO-d₆) δ ppm: 1.00 (d, J=7.0 Hz, 3H), 2.40 (m, 1H), 2.76 (dd, J=7.0, 12.8 Hz, 1H), 2.94 (dd, J=6.6, 12.8 Hz, 1H), 3.35 (s, 3H), 4.31 (m, 2H), 7.69 (dd, J=1.1, 8.1 Hz, 1H), 7.75 (s, 1H), 7.81 (dd, J=4.4, 8.8 Hz, 1H), 7.87 (br s, 1H), 8.03 (m, 2H), 8.19 (d, J=8.8 Hz, 1H), 8.48 (d, J=2.6 Hz, 1H), 8.52 (dd, J=1.1, 4.4 Hz, 1H), 9.17 (dd, J=1.1, 8.4 Hz, 1H), 10.70 (br s, 1H), 12.55 (br s, 1H).

FIA-MS, m/e: 518.2 (m+1)

Analysis for $C_{23}H_{24}ClN_5O_5S$:

| Calcd: | C, 49.82; H, 4.54; N, 12.63; |
|---|---|
| Found: | C, 49.93; H, 4.60; N, 12.21. |

EXAMPLE 41

Preparation of N-(5-Chloropyridin-2-yl)-3-[4-methylsulfonyl-2-(3-pyrrolidinylmethoxy)benzoylamino]pyridine-2-carboxamide Isomer I A. 1-t-Butoxycarbonylpyrrolidine-3-methanol Isomer I and Isomer II

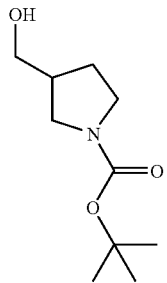

Isomer I  Isomer II

Racemic 1-t-butoxycarbonylpyrrolidine-3-methanol (15 g, 74.53 mmol) was chromatographed on a chiral column [ChiralPak AD 8×25 cm; 2.5% of (6% MeOH/94% EtOH); 400 mL/min; UV: 210 nm] to give 1-t-butoxycarbonylpyrrolidine-3-methanol:

Isomer I (Rt: 8.81 min, ChiralPak AD 4.6×250 mm; 1.0 mL/min; UV: 210 nm) (6.35 g, 42%, 94% ee) and Isomer II (Rt: 9.68 min) (6.43 g, 43%, 90% ee).

Isomer I: FIA-MS, m/e: 202.2 (m+1).

Isomer II: FIA-MS, m/e: 202.2 (m+1).

B. 3-[2-(1-t-Butoxycarbonylpyrrolidin-3-ylmethoxy)-4-methylthiobenzoylamino]-N-(5-chloropyridin-2-yl)pyridine-2-carboxamide (Isomer I)

Using a procedure analogous to Example 38-D, 1-t-butoxycarbonylpyrrolidine-3-methanol (Isomer I) and N-(5-chloropyridin-2-yl)-3-[2-hydroxy-4-methylthiobenzoylamino]pyridine-2-carboxamide gave the title compound as a solid (1.7 g).

FIA-MS, m/e: 586.5 (m−1).

C. 3-[2-(1-t-Butoxycarbonylpyrrolidin-3-ylmethoxy)-4-methylsulfonylbenzoylamino]-N-(5-chloropyridin-2-yl)-pyridine-2-carboxamide (Isomer I)

Using a procedure analogous to Example 3-A, 3-[2-(1-t-butoxycarbonylpyrrolidin-3-ylmethoxy)-4-methylthiobenzoyl-amino]-N-(5-chloropyridin-2-yl)pyridine-2-carboxamide (Isomer I) gave the title compound as a white solid (1.1 g).

FIA-MS, m/e: 630.2 (m+1).

D. N-(5-Chloropyridin-2-yl)-3-[4-methylsulfonyl-2-(3-pyrrolidinylmethoxy)benzoylamino]pyridine-2-carboxamide (Isomer I)

Using a procedure analogous to Example 1-H, 3-[2-(1-t-butoxycarbonylpyrrolidin-3-ylmethoxy)-4-methylsulfonylbenzoylamino]-N-(5-chloropyridin-2-yl)pyridine-2-carboxamide (Isomer I) gave the title compound as a white solid (400 mg, 42% from B, 98% ee).

FIA-MS, m/e: 530.0 (m+1).

Rt: 27.5 min, Chiralcel OD 4.6×250 mm; 1.0 mL/min; 0.25% DMEA in 49% IPA/heptane; UV: 300 nm)

Analysis for $C_{24}H_{24}ClN_5O_5S$:

| Calcd: | C, 54.39; H, 4.56; N, 13.21; |
|---|---|
| Found: | C, 54.08; H, 4.64; N, 12.96. |

EXAMPLE 42

Preparation of N-(5-Chloropyridin-2-yl)-3-[4-methylsulfonyl-2-(3-pyrrolidinylmethoxy)benzoylamino]pyridine-2-carboxamide (Isomer II)

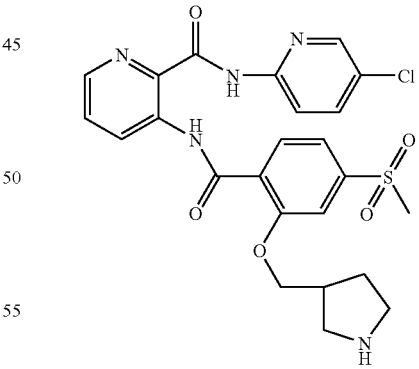

A. 3-[2-(1-t-Butoxycarbonylpyrrolidin-3-ylmethoxy)-4-methylthiobenzoylamino]-N-(5-chloropyridin-2-yl)pyridine-2-carboxamide (Isomer II)

Using a procedure analogous to Example 38-D, 1-t-butoxycarbonylpyrrolidin-3-ylmethanol (Isomer II), from the prior example, and N-(5-chloropyridin-2-yl)-3-[2-hydroxy-4-methylthiobenzoylamino]pyridine-2-carboxamide gave the title compound as a white solid (1.0 g).

93

FIA-MS, m/e: 598.3 (m–1).
Analysis for $C_7H_{15}NO_2 \cdot 0.25\ H_2O$:

| | |
|---|---|
| Calcd: | C, 56.16; H, 10.44; N, 9.36; |
| Found: | C, 56.28; H, 10.43; N, 9.45. |

B. 3-[2-(1-t-Butoxycarbonylpyrrolidin-3-ylmethoxy)-4-methylsulfonylbenzoylamino]-N-(5-chloropyridin-2-yl)-pyridine-2-carboxamide (Isomer II)

Using a procedure analogous to Example 3-A, 3-[2-(1-t-butoxycarbonylpyrrolidin-3-ylmethoxy)-4-methylthiobenzoyl-amino]-N-(5-chloropyridin-2-yl)pyridine-2-carboxamide (Isomer II) gave the title compound as a white solid (650 mg).

FIA-MS, m/e: 630.0 (m+1).

C. N-(5-Chloropyridin-2-yl)-3-[4-methylsulfonyl-2-(3-pyrrolidinylmethoxy)benzoylamino]pyridine-2-carboxamide (Isomer II)

Using a procedure analogous to Example 1-H, 3-[2-(1-t-butoxycarbonyl-3-pyrrolidinylmethoxy)-4-methylsulfonylbenzoylamino]-N-(5-chloropyridin-2-yl)pyridine-2-carboxamide (Isomer II) gave the title compound as a white solid (400 mg, 73% from step A, 89% ee).

FIA-MS, m/e: 530.0 (m+1).

Rt: 31 min, Chiralcel OD 4.6×250 mm; 1.0 mL/min; 0.25% DMEA in 49% IPA/heptane; UV: 300 nm).

EXAMPLE 43

Preparation of N-(5-Chloropyridin-2-yl)-3-[4-methylsulfonyl-2-[3-(4-morpholinyl)propoxy]benzoylamino]pyridine-2-carboxamide hydrochloride A. 3-(4-Morpholinyl)propanol

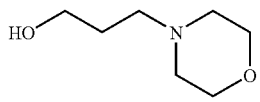

To a mixture of morpholine (33 mL, 371 mmol) and $CH_2Cl_2$ (650 mL) was added 3-bromopropanol (25.8 g, 186 mmol), and the mixture was heated at 50° C. for 18 h. The reaction was cooled, diluted with $CH_2Cl_2$, and filtered. The filtrate was chromatographed (150 g $SiO_2$, $CH_2Cl_2$ to 5% 2 M $NH_3$/MeOH in $CH_2Cl_2$) to give the title compound as a liquid (27.0 g, 50%).

1NMR (250 MHz, DMSO-$d_6$): δ 1.50(m, 2H), 2.24(m, 6H), 3.36(t, J=6.5 Hz, 1H), 3.49(m, 2H), 4.36(s, 1H).

FIA-MS, m/e: 146.1 (m+1).

B. N-(5-Chloropyridin-2-yl)-3-[4-methylthio-2-[3-(4-morpholinyl)propoxy]benzoylamino]pyridine-2-carboxamide Using a procedure analogous to Example 38-D, 3-(4-morpholinyl)propanol and N-(5-chloropyridin-2-yl)-3-[2-hydroxy-4-methylthiobenzoylamino]pyridine-2-carboxamide gave the title compound as a white solid (320 mg, 48%).

$^1$NMR (300 MHz, DMSO-$d_6$): δ 2.33(m, 2H), 2.59(s, 3H), 2.94(m, 2H), 3.21(m, 4H), 3.76(m, 4H), 4.50 (t, J=6.6 Hz, 2H), 7.01(dd, J=1.5, 8.4 Hz, 1H), 7.11(d, J=1.5 Hz, 1H), 7.76(dd, J=4.4, 8.4 Hz, 1H), 7.89(d, J=8.1 Hz, 1H), 8.09(dd, J=2.6, 8.8 Hz, 1H), 8.24(d, J=8.8 Hz, 1H), 8.47(m, 2H), 9.22(dd, J=1.5, 8.8 Hz, 1H), 10.86(s, 1H), 11.03(br s, 1H), 12.32(s, 1H).

FIA-MS, m/e: 542.2 (m+1); HRMS for $C_{26}H_{29}ClN_5O_4S$: 542.1629; found: 542.1627.

C. 3-[4-Methylsulfonyl-2-(3-(4-oxomorpholin-4-yl)-propoxy)benzoylamino]-N-(5-chloropyridin-2-yl)pyridine-2-carboxamide Using a procedure analogous to Example 3-A, 3-[4-methylsulfonyl-2-(3-morpholin-4-ylpropoxy)benzoylamino]-N-(5-chloropyridin-2-yl)pyridine-2-carboxamide and 3-chloroperbenzoic acid (mCPBA) (4.5 equivalents) gave the title compound as a white solid (150 mg, 52%).

1NMR (300 MHz, DMSO-$d_6$): δ 2.63(m, 2H), 3.12(s, 3H), 3.54(m, 2H), 3.77(m, 2H), 3.94(m, 4H), 4.05 (t, J=6.9 Hz, 2H), 4.45 (t, J=6.9 Hz, 2H), 6.98(dd, J=1.5, 8.1 Hz, 1H), 7.19(d, J=1.5, 1H), 7.66(dd, J=4.4, 8.4 Hz, 1H), 7.95(dd, J=2.6, 8.8 Hz, 1H), 8.01(d, J=8.1 Hz, 1H), 8.25(d, J=8.8 Hz, 1H), 8.38(dd, J=1.5, 4.4 Hz, 1H), 8.41(d, J=2.6 Hz, 1H), 9.11(d, J=1.5, 8.8 Hz, 1H), 10.76(s, 1H).

FIA-MS, m/e: 590.3 (m+1).

D. 3-[4-methylsulfonyl-2-[3-(morpholin-4-yl)propoxy]-benzoylamino]-N-(5-chloropyridin-2-yl)pyridine-2-carboxamide hydrochloride Using a procedure analogous to Example 62 (using Pd/$H_2$), 3-[4-methylsulfonyl-2-[3-(4-oxomorpholin-4-yl)-propoxy]benzoylamino]-N-(5-chloropyridin-2-yl)pyridine-2-carboxamide gave, after HPLC (Vydac C18; 5-70% (0.1% TFA/$CH_3CN$) in 0.1% TFA/$H_2O$; 1.0 mL/min; UV: 214 nm; Rt: 28.07 min), the title compound as a white solid (37 mg, 32%).

$^1$NMR (300 MHz, DMSO-$d_6$): δ 2.29(m, 2H), 2.94(m, 2H), 3.22(m, 2H), 3.67(m, 2H), 3.83(m, 2H), 3.35(m, 5H), 4.52(m, 2H), 7.69(dd, J=1.5, 8.1 Hz, 1H), 7.76(d, J=1.5 Hz, 1H), 7.81(dd, J=4.4, 8.8 Hz, 1H), 8.05(dd, J=2.6, 8.8 Hz, 1H), 8.11(d, J=8.1 Hz, 1H), 8.20(d, J=8.8 Hz, 1H), 8.51(m, 2H), 9.21(dd, J=1.5, 8.8 Hz, 1H), 10.35(br s, 1H), 10.89(s, 1H), 12.38(s, 1H).

FIA-MS, m/e: 574.0 (m+1); HRMS for $C_{26}H_{29}ClN_5O_6S$: 574.1527; found: 574.1533.

EXAMPLE 44

Preparation of 3-[4-Methylthio-2-(piperidin-3-ylmethoxy)-benzoylamino]-N-(5-chloropyridin-2-yl)pyridine-2-carboxamide

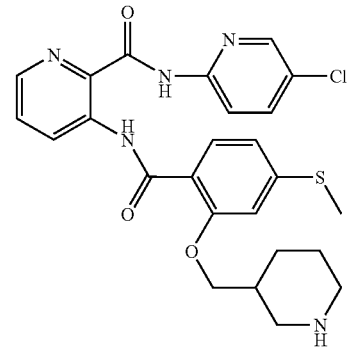

A. 1-t-Butoxycarbonyl-3-hydroxymethylpiperidine

Using a procedure analogous to Example 1-C ($K_2CO_3$, acetone), 3-hydroxymethylpiperidine gave the title compound as a solid (34.2 g, 88%).

$^1$NMR (300 MHz, DMSO-$d_6$): δ 1.04(m, 1H), 1.17-1.42 (m, 2H), 1.36(s, 9H), 1.48-1.65(m, 2H), 2.35(br s, 1H), 2.65 (m, 1H), 3.17(m, 1H), 3.21(m, 1H), 3.73(m, 1H), 3.85(br m, 1H), 4.49(s, 1H).

FIA-MS, m/e: 216.3 (m+1).

B. 3-[4-Methylthio-2-(1-t-butoxycarbonylpiperidin-3-yl-methoxy)benzoylamino]-N-(5-chloropyridin-2-yl)pyridine-2-carboxamide Using a procedure analogous to Example 38-D, 1-t-butoxycarbonyl-3-hydroxymethylpiperidine and 3-[4-methylthio-2-(hydroxy)benzoylamino]-N-(5-chloropyridin-2-yl)-pyridine-2-carboxamide gave the title compound as a white solid (2.5 g, 84%).

FIA-MS, m/e: 612.2 (m+1).

Analysis for $C_{30}H_{34}ClN_5O_5S$:

| Calcd: | C, 58.86; H, 5.60; N, 11.44; |
| Found: | C, 58.26; H, 5.47; N, 11.55. |

C. 3-[4-Methylthio-2-(piperidin-3-ylmethoxy)benzoylamino]-N-(5-chloropyridin-2-yl)pyridine-2-carboxamide Using a procedure analogous to Example 1-H, 3-[4-methylthio-2-(1-t-butoxycarbonylpiperidin-3-ylmethoxy)-benzoylamino]-N-(5-chloropyridin-2-yl)pyridine-2-carboxamide gave the title compound as a white solid (300 mg, 90%).

$^1$NMR (250 MHz, DMSO-$d_6$): δ 1.12(m, 2H), 1.42(m, 1H), 1.70(m, 1H), 2.04(m, 1H), 2.31(m, 2H), 2.51(s, 3H), 2.69(m, 1H), 2.92(m, 1H), 4.16(d, J=7.0 Hz, 1H), 6.92(dd, J=1.5, 8.2 Hz, 1H), 7.02(d, J=1.5 Hz, 1H), 7.70(dd, J=4.6, 8.5 Hz, 1H), 7.80(d, J=8.2 Hz, 1H), 7.99(dd, J=2.4, 8.8 Hz, 1H), 8.21(d, J=9.4 Hz, 1H), 8.41(m, 2H), 9.16(dd, J=1.5, 8.8 Hz, 1H), 12.26(br s, 1H).

FIA-MS, m/e: 512.4 (m+1).

Analysis for $C_{25}H_{26}ClN_5O_3S$:

| Calcd: | C, 58.64; H, 5.12; N, 13.68; |
| Found: | C, 58.26; H, 5.06; N, 13.48. |

EXAMPLE 45

Preparation of 3-[4-Methylsulfinyl-2-(piperidin-3-yl-methoxy)benzoylamino]-N-(5-chloropyridin-2-yl)pyridine-2-carboxamide

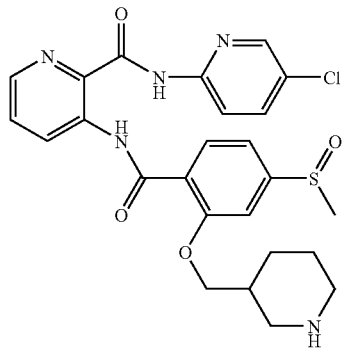

A. 3-[4-Methylsulfinyl-2-(1-t-butoxycarbonylpiperidin-3-ylmethoxy)benzoylamino]-N-(5-chloropyridin-2-yl)pyridine-2-carboxamide Using a procedure analogous to Example 2-A, 3-[4-methylthio-2-(1-t-butoxycarbonylpiperidin-3-ylmethoxy)-benzoylamino]-N-(5-chloropyridin-2-yl)pyridine-2-carboxamide gave the title compound as a white solid (900 mg, 88%).

FIA-MS, m/e: 628.3 (m+1).

Analysis for $C_{30}H_{34}ClN_5O_6S$:

| Calcd: | C, 57.36; H, 5.46; N, 11.15; |
| Found: | C, 57.19; H, 5.28; N, 11.62. |

B. 3-[4-Methylsulfinyl-2-(piperidin-3-ylmethoxy)]-benzoylamino]-N-(5-chloropyridin-2-yl)pyridine-2-carboxamide Using a procedure analogous to Example 1-H, 3-[4-methylsulfinyl-2-(1-t-butoxycarbonylpiperidin-3-ylmethoxy)-benzoylamino]-N-(5-chloropyridin-2-yl)pyridine-2-carboxamide gave the title compound as a white solid (680 mg, 95%).

$^1$NMR (250 MHz, DMSO-$d_6$): δ 1.17(m, 2H), 1.44(m, 1H), 1.72(m, 1H), 2.04(m, 1H), 2.30(m, 2H), 2.69(m, 1H), 2.85(s, 3H), 2.94(m, 1H), 4.21(d, J=6.7 Hz, 1H), 7.42(dd, J=1.5, 8.2 Hz, 1H), 7.56(d, J=1.2 Hz, 1H), 7.80(dd, J=4.6, 8.8 Hz, 1H), 8.05(m, 2H), 8.26(d, J=8.8 Hz, 1H), 8.48(m, 2H), 9.24(dd, J=1.5, 8.5 Hz, 1H).

FIA-MS, m/e: 528.1 (m+1).

Analysis for $C_{25}H_{26}ClN_5O_3S$:

| Calcd: | C, 56.87; H, 4.96; N, 13.26; |
| Found: | C, 57.15; H, 4.98; N, 13.17. |

EXAMPLE 46

Preparation of 3-[4-Methylsulfonyl-2-(piperidin-3-yl-methoxy)benzoylamino]-N-(5-chloropyridin-2-yl)pyridine-2-carboxamide

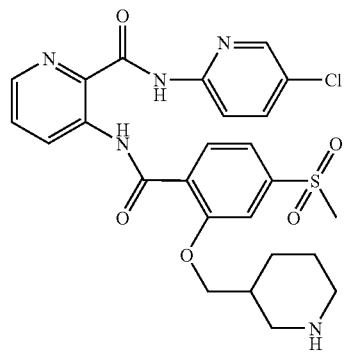

A. 3-[4-Methylsulfinyl-2-(1-t-butoxycarbonylpiperidin-3-ylmethoxy)benzoylamino]-N-(5-chloropyridin-2-yl)pyridine-2-carboxamide Using a procedure analogous to Example 3-A, 3-[4-methylthio-2-(1-t-butoxycarbonylpiperidin-3-ylmethoxy)-benzoylamino]-N-(5-chloropyridin-2-yl)pyridine-2-carboxamide gave the title compound as a white solid (950 mg, 91%).

FIA-MS, m/e: 644.3 (m+1).

Analysis for $C_{30}H_{34}ClN_5O_7S$:

| Calcd: | C, 54.42; H, 5.48; N, 10.58; |
| Found: | C, 54.75; H, 5.13; N, 10.87. |

B. 3-[4-Methylsulfonyl-2-(piperidin-3-ylmethoxy)-benzoylamino]-N-(5-chloropyridin-2-yl)pyridine-2-carboxamide Using a procedure analogous to Example 1-H, 3-[4-methylsulfonyl-2-(1-t-butoxycarbonylpiperidin-3-ylmethoxy)-benzoylamino]-N-(5-chloropyridin-2-yl)pyridine-2-carboxamide gave the title compound as a white solid (720 mg, 95%).

$^1$NMR (250 MHz, DMSO-$d_6$): δ 1.19(m, 2H), 1.46(m, 1H), 1.74(m, 1H), 2.05(m, 1H), 2.33(m, 2H), 2.72(m, 1H), 2.96(m, 1H), 3.35(s, 3H), 4.25(d, J=6.7 Hz, 1H), 7.66(dd, J=1.5, 8.2 Hz, 1H), 7.75(d, J=1.5 Hz, 1H), 7.81(dd, J=4.6, 8.5 Hz, 1H), 8.06(m, 2H), 8.25(dd, J=0.6, 8.8 Hz, 1H), 8.50(m, 2H), 9.22(dd, J=1.5, 8.8 Hz, 1H).

FIA-MS, m/e: 544.3 (m+1).

Analysis for $C_{25}H_{26}ClN_5O_5S$:

| Calcd: | C, 55.19; H, 4.82; N, 12.87; |
|---|---|
| Found: | C, 55.42; H, 4.87; N, 12.77. |

EXAMPLES 47-48

Preparation of chiral isomers of 3-[4-Methylsulfonyl-2-(piperidin-3-ylmethoxy)benzoylamino]-N-(5-chloropyridin-2-yl)pyridine-2-carboxamide

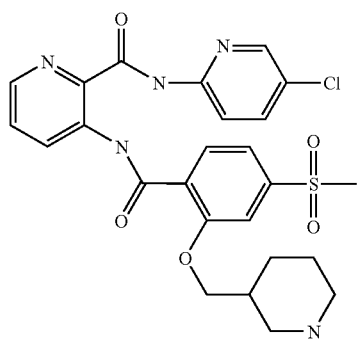

Racemic 3-[4-methylsulfonyl-2-(piperidin-3-ylmethoxy)-benzoylamino]-N-(5-chloropyridin-2-yl)pyridine-2-carboxamide was chromatographed (Chiralcel OD 8×32 cm, 40% IPA in (0.2% DMEA in heptane)) to give isomer I (14 mg, 56%, 95% ee, Chiralcel OD 4.6×250 mm, Rt: 16.9 min) and isomer II (12 mg, 48%, 95% ee, Chiralcel OD 4.6×250 mm, Rt: 19.00 min) as solids.

Example 47: Isomer I:

FIA-MS, m/e: 544.3 (m+1).

Example 48: Isomer II:

FIA-MS, m/e: 544.2 (m+1).

EXAMPLE 49

Preparation of 3-[4-Methylsulfonyl-2-(piperidin-4-yloxy)-benzoylamino]-N-(5-methylpyridin-2-yl)pyridine-2-carboxamide

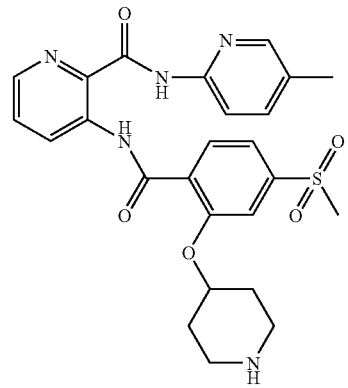

A. 3-[4-Methylsulfonyl-2-(1-t-butoxycarbonylpiperidin-4-yloxy)benzoylamino]-N-(5-methylpyridin-2-yl)pyridine-2-carboxamide Using a procedure analogous to Example 1-G, 4-methylsulfonyl-2-(1-t-butoxycarbonylpiperidin-4-yloxy)benzoic acid and 3-amino-N-(5-methylpyridin-2-yl)pyridine-2-carboxamide gave the title compound as a white solid (2.53 g, 71%).

$^1$NMR (300 MHz, DMSO-$d_6$): δ 1.23(s, 9H), 1.79(m, 2H), 1.97(m, 2H), 2.24(s, 3H), 3.12(m, 2H), 3.30(s, 3H), 3.63(m, 2H), 4.96(m, 1H), 7.63(m, 2H), 7.75(m, 2H), 8.02(m, 2H), 8.20(s, 1H), 8.45(d, J=4.3 Hz, 1H), 9.17(d, J=8.8 Hz, 1H), 10.62(s, 1H), 12.39(s, 1H).

FIA-MS, m/e: 610.2 (m+1).

Analysis for $C_{30}H_{35}N_5O_7S$:

| Calcd: | C, 59.10; H, 5.79; N, 11.49; |
|---|---|
| Found: | C, 58.81; H, 5.75; N, 11.42. |

B. 3-[4-Methylsulfonyl-2-(piperidin-4-yloxy)benzoylamino]-N-(5-methylpyridin-2-yl)pyridine-2-carboxamide Using a procedure analogous to Example 1-H, 3-[4-methylsulfonyl-2-(1-t-butoxycarbonylpiperidin-4-yloxy)-benzoylamino]-N-(5-methylpyridin-2-yl)pyridine-2-carboxamide gave the title compound as a white solid (1.7 g, 81%).

$^1$NMR (250 MHz, DMSO-$d_6$): δ 1.75(m, 2H), 1.94(m, 2H), 2.29(s, 3H), 2.56(m, 2H), 2.87(m, 2H), 3.34(s, 3H), 4.87(m, 1H), 7.62(dd, J=1.3, 8.3 Hz, 1H), 7.74(m, 2H), 7.79(dd, J=4.3, 8.8 Hz, 1H), 8.04(d, J=7.8 Hz, 1H), 8.17(d, J=8.3 Hz, 1H), 8.24(d, J=1.3 Hz, 1H), 8.49(dd, J=1.3, 4.3 Hz, 1H), 9.23(dd, J=1.3, 8.5 Hz, 1H), 10.68(br s, 1H), 12.44(s, 1H).

FIA-MS, m/e: 510.3 (m+1).

Analysis for $C_{25}H_{27}N_5O_5S$:

| Calcd: | C, 58.93; H, 5.34; N, 13.74; |
|---|---|
| Found: | C, 58.50; H, 4.99; N, 13.53. |

EXAMPLE 50

Preparation of 3-[4-Methylsulfonyl-2-(piperidin-4-yloxy)-benzoylamino]-N-(5-chloropyridin-2-yl)pyridine-2-carboxamide Hydrochloride

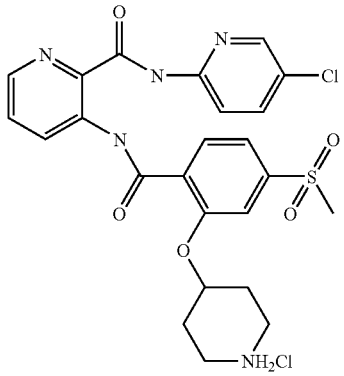

Using a procedure analogous to Example 4-F, 3-[4-methylsulfonyl-2-(piperidin-4-yloxy)benzoylamino]-N-(5-chloropyridin-2-yl)pyridine-2-carboxamide gave the title compound as a white solid (640 mg, quantitative).

$^1$NMR (300 MHz, DMSO-d$_6$): δ 2.01(m, 2H), 2.16(m, 2H), 3.19(m, 4H), 3.34(s, 3H), 5.10(m, 1H), 7.69(dd, J=1.1, 8.1 Hz, 1H), 7.80(m, 2H), 8.01(m, 2H), 8.17(d, J=9.1 Hz, 1H), 8.48(d, J=2.6 Hz, 1H), 8.52(dd, J=1.1, 4.4 Hz, 1H), 8.82(br s, 1H), 9.17(d, J=8.8 Hz, 1H), 10.85(s, 1H), 12.19(s, 1H).

FIA-MS, m/e: 530.0 (m+1).

Analysis for C$_{24}$H$_{24}$ClN$_5$O$_5$S—HCl:

| | |
|---|---|
| Calcd: | C, 50.89; H, 4.45; N, 12.36; |
| Found: | C, 50.60; H, 4.31; N, 12.12. |

EXAMPLE 51

Preparation of 3-[4-Isopropylthio-2-(piperidin-4-yloxy)-benzoylamino]-N-(5-chloropyridin-2-yl)pyridine-2-carboxamide

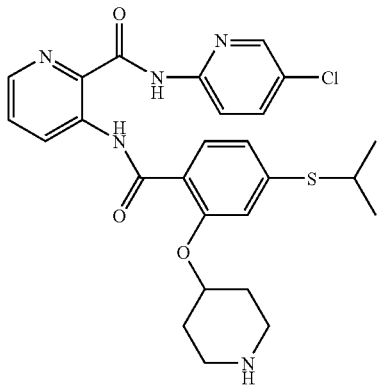

A. Methyl 4-isopropylthio-2-hydroxybenzoate

Using a procedure analogous to Example 66-A, methyl 4-fluoro-2-(methoxymethoxy)benzoate and potassium 2-propanethiolate gave the title compound.

B. Methyl 4-isopropylthio-2-(1-t-butoxycarbonylpiperidin-4-yloxy)benzoate

Using a procedure analogous to Example 1-D, 1-t-butoxycarbonyl-4-hydroxypiperidine and methyl 4-isopropylthio-2-hydroxybenzoate gave the title compound as an oil (6.6 g, 73%).

$^1$NMR (300 MHz, DMSO-d$_6$): δ 1.28(d, J=6.6 Hz, 1H), 1.40(s, 9H), 1.63(m, 2H), 1.78(m, 2H), 2.49(m, 1H), 3.42(m, 4H), 3.76(s, 3H), 4.78(m, 1H), 6.95(dd, J=1.1, 8.4 Hz, 1H), 7.07(s, 1H), 7.62(d, J=8.1 Hz, 1H).

FIA-MS, m/e: 410.3 (m+1).

Analysis for C$_{21}$H$_{31}$NO$_5$S.HCl:

| | |
|---|---|
| Calcd: | C, 61.59; H, 7.63; N, 3.42; |
| Found: | C, 60.78; H, 7.37; N, 3.49. |

C. 4-Isopropylthio-2-(1-t-butoxycarbonylpiperidin-4-yloxy)benzoic acid

Using a procedure analogous to Example 1-E, methyl 4-isopropylthio-2-(piperidin-4-yloxy)benzoate gave the title compound as a glass (4.7 g, 77%).

$^1$NMR (300 MHz, DMSO-d$_6$): δ 1.27(d, J=6.6 Hz, 6H), 1.40(s, 9H), 1.63(m, 2H), 1.78(m, 2H), 2.50(m, 1H), 3.48(m, 2H), 3.68(m, 2H), 4.76(m, 1H), 6.94(dd, J=0.7, 8.1 Hz, 1H), 7.05(s, 1H), 7.60(d, J=8.1 Hz, 1H), 12.52(br s, 1H).

FIA-MS, m/e: 396.1 (m+1).

Analysis for C$_{20}$H$_{29}$NO$_5$S:

| | |
|---|---|
| Calcd: | C, 60.74; H, 7.39; N, 3.54; |
| Found: | C, 61.89; H, 7.38; N, 3.71. |

D. 3-[4-Isopropylthio-2-(1-t-butoxycarbonylpiperidin-4-yloxy)benzoylamino]-N-(5-chloropyridin-2-yl)pyridine-2-carboxamide Using a procedure analogous to Example 1-G, 4-iso-propylthio-2-(1-t-butoxycarbonylpiperidin-4-yloxy)benzoic acid and 3-amino-N-(5-chloropyridin-2-yl)pyridine-2-carboxamide gave the title compound as a glass (350 mg, 28%).

$^1$NMR (300 MHz, DMSO-d$_6$): δ 1.27(s, 9H), 1.32(d, J=6.6 Hz, 6H), 1.85(m, 2H), 1.97(m, 2H), 3.08(m, 2H), 3.76(m, 3H), 4.89(m, 1H), 7.06(d, J=8.1 Hz, 1H), 7.20(s, 1H), 7.75 (dd, J=4.4, 8.4 Hz, 1H), 7.83(d, J=8.1 Hz, 1H), 7.97(d, J=2.6, 8.8 Hz, 1H), 8.21(d, J=8.8 Hz, 1H), 8.47(m, 2H), 9.19(d, J=8.1 Hz, 1H), 10.80(s, 1H), 12.22(s, 1H).

FIA-MS, m/e: 626.2 (m+1).

Analysis for C$_{31}$H$_{36}$ClN$_5$O$_5$S:

| | |
|---|---|
| Calcd: | C, 59.46; H, 5.79; N, 11.18; |
| Found: | C, 58.82; H, 5.47; N, 11.40. |

E. 3-[4-Isopropylthio-2-(piperidin-4-yloxy)benzoylamino]-N-(5-chloropyridin-2-yl)pyridine-2-carboxamide Using a procedure analogous to Example 1-H, 3-[4-isopropylthio-2-(1-t-butoxycarbonylpiperidin-4-yloxy)-benzoylamino]-N-(5-chloropyridin-2-yl)pyridine-2-carboxamide gave the title compound as a solid (60 mg, 20%).

$^1$NMR (300 MHz, DMSO-d$_6$): δ 1.32(d, J=6.6 Hz, 1H), 1.83(m, 2H), 1.96(m, 2H), 2.67(m, 2H), 2.92(m, 2H), 3.76(m, 1H), 4.82(m, 1H), 7.05(d, J=8.4 Hz, 1H), 7.18(s, 1H), 7.76 (dd, J=4.4, 8.4 Hz, 1H), 7.81(d, J=8.1 Hz, 1H), 8.02(dd, J=2.6, 8.8 Hz, 1H), 8.32(d, J=8.8 Hz, 1H), 8.46(m, 2H), 9.20(d, J=8.4 Hz, 1H), 10.80(br s, 1H), 12.20(s, 1H).

FIA-MS, m/e: 526.2 (m+1).

Analysis for C$_{26}$H$_{28}$ClN$_5$O$_3$S.0.5H$_2$O:

| Calcd: | C, 58.36; H, 5.46; N, 13.09; |
| --- | --- |
| Found: | C, 58.04; H, 5.08; N, 13.13. |

EXAMPLE 52

Preparation of 3-[4-Methylsulfonyl-2-(3-aminopropoxy)-benzoylamino]-N-(5-methylpyridin-2-yl)pyridine-2-carboxamide

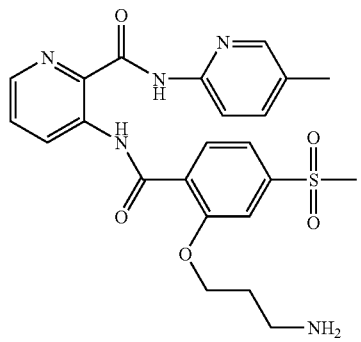

A. 3-[4-Methylsulfonyl-2-[3-(t-butoxycarbonylamino)-propoxy]benzoylamino]-N-(5-methylpyridin-2-yl)pyridine-2-carboxamide Using a procedure analogous to Example 1-G, 4-methylsulfonyl-2-[3-(t-butoxycarbonylamino)propoxy]benzoic acid and 3-amino-N-(5-methylpyridin-2-yl)pyridine-2-carboxamide gave the title compound as a white solid (4.6 g, 61%).

$^1$NMR (250 MHz, DMSO-d$_6$): δ 1.30(s, 9H), 1.97(m, 2H), 2.30(s, 3H), 2.50(s, 3H), 3.05(m, 2H), 4.22(t, J=6.6 Hz, 2H), 6.82(m, 1H), 7.71(m, 4H), 8.09(s, 1H), 8.12(s, 1H), 8.24(s, 1H), 8.49(d, J=4.4 Hz, 1H), 9.22(d, J=8.8 Hz, 1H), 10.67(s, 1H), 12.56(s, 1H).

FIA-MS, m/e: 584.1 (m+1).

B. 3-[4-Methylsulfonyl-2-(3-aminopropoxy)benzoylamino]-N-(5-methylpyridin-2-yl)pyridine-2-carboxamide Using a procedure analogous to Example 1-H, 3-[4-methylsulfonyl-2-[3-(t-butoxycarbonylamino)propoxy]-benzoylamino]-N-(5-methylpyridin-2-yl)pyridine-2-carboxamide gave the title compound as a solid (2.0 g, 54%).

$^1$NMR (300 MHz, DMSO-d$_6$): δ 1.90(m, 2H), 2.29(s, 3H), 2.63(t, J=6.6 Hz, 2H), 3.32(s, 3H), 4.47(t, J=6.6 Hz, 2H), 7.64(dd, J=1.5, 8.1 Hz, 1H), 7.76(m, 3H), 8.11(m, 2H), 8.25 (s, 1H), 8.49(dd, J=1.5, 4.4 Hz, 1H), 9.21(d, J=8.8 Hz, 1H).

FIA-MS, m/e: 484.5 (m+1).

Analysis for C$_{23}$H$_{25}$N$_5$O$_5$S:

| Calcd: | C, 57.13; H, 5.21; N, 14.48; |
| --- | --- |
| Found: | C, 56.46; H, 4.95; N, 14.06. |

EXAMPLE 53

Preparation of 3-[4-Methylsulfonyl-2-(1-methylpiperidin-4-yloxy)benzoylamino]-N-(5-chloropyridin-2-yl)pyridine-2-carboxamide.

3-[4-Methylsulfonyl-2-(piperidin-4-yloxy)benzoylamino]-N-(5-chloropyridin-2-yl)pyridine-2-carboxamide was converted into the title compound by using a procedure analogous to that of Example 5, except the crude product residue was chromatographed over silica gel (dichloromethane to 5% [2 M NH$_3$ in methanol] in dichoromethane), partially evaporated, and precipitated with ether to give the title compound as a solid (1.9 g, 69%).

$^1$NMR (300 MHz, DMSO-d$_6$): δ 1.97(m, 4H), 2.08(s, 3H), 2.17(m, 2H), 2.51(m, 2H), 3.33(s, 3H), 4.84(m, 1H), 7.63(dd, J=1.5, 8.1 Hz, 1H), 7.75(d, J=1.5 Hz, 1H), 7.80(dd, J=4.4, 8.4 Hz, 1H), 7.97(dd, J=2.6, 8.8 Hz, 1H), 8.04(d, J=8.1 Hz, 1H), 8.29(d, J=8.8 Hz, 1H), 8.47(d, J=2.6 Hz, 1H), 8.50(dd, J=1.1, 4.4 Hz, 1H), 9.22(dd, J=1.1, 8.4 Hz, 1H), 10.82(s, 1H), 12.30 (s, 1H).

FIA-MS, m/e: 544.3 (m+1).

Analysis for C$_{25}$H$_{26}$ClN$_5$O$_5$S:

| Calcd: | C, 55.19; H, 4.82; N, 12.87; |
| --- | --- |
| Found: | C, 54.95; H, 4.80; N, 12.73. |

EXAMPLE 54

Preparation of 3-[4-Methylsulfonyl-2-[3-(dimethylamino)-propoxy]benzoylamino]-N-(5-chloropyridin-2-yl)pyridine-2-carboxamide Using a procedure analogous to Example 53, 3-[4-methylsulfonyl-2-(3-aminopropoxy)benzoylamino]-N-(5-chloropyridin-2-yl)pyridine-2-carboxamide gave the title compound as a solid (920 mg, 36%).

$^1$NMR (300 MHz, CDCl$_3$): δ 2.35(m, 2H), 2.75(s, 6H), 3.17(s, 3H), 3.24(t, J=6.6 Hz, 2H), 4.51(t, J=5.9 Hz, 2H), 7.61(dd, J=4.4, 8.8 Hz, 1H), 7.65(d, J=1.5 Hz, 1H), 7.70(dd, J=1.5, 8.1 Hz, 1H), 7.76(dd, J=2.6, 8.8 Hz, 1H), 8.08(d, J=8.1 Hz, 1H), 8.26(d, J=8.8 Hz, 1H), 8.34(d, J=2.2 Hz, 1H), 8.40 (dd, J=1.5, 4.4 Hz, 1H), 9.24(dd, J=1.1, 8.8 Hz, 1H), 10.88(s, 1H), 12.64(s, 1H).

FIA-MS, m/e: 532.1 (m+1).

EXAMPLE 55

Preparation of 3-[4-Methylthio-2-[3-(formylamino) propoxy]-benzoylamino]-N-(5-chloropyridin-2-yl) pyridine-2-carboxamide

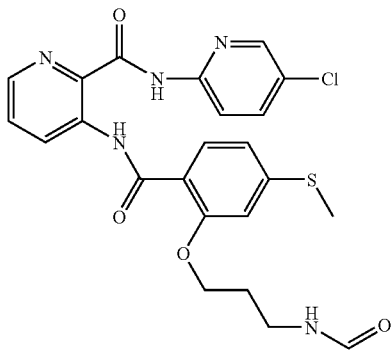

A. 3-[4-Methylthio-2-[3-(N-t-butoxycarbonyl-N-formylamino)propoxy]benzoylamino]-N-(5-chloropyridin-2-yl)-pyridine-2-carboxamide Using a procedure analogous to Example 1-G but with 0.18 equivalent of DMF, 4-methylthio-2-[3-(t-butoxycarbonylamino)propoxy]benzoic acid and 3-amino-N-(5-chloropyridin-2-yl)pyridine-2-carboxamide gave the title compound as a solid after HPLC (1.2 g, 16%).

FAB-MS, m/e: 600.4 (m+).

B. 3-[4-Methylthio-2-[3-(formylamino)propoxy]benzoylamino]-N-(5-chloropyridin-2-yl)pyridine-2-carboxamide Using a procedure analogous to Example 1-H, 3-[4-methylthio-2-[3-(N-t-butoxycarbonyl-N-formylamino)propoxy]-benzoylamino]-N-(5-chloropyridin-2-yl)pyridine-2-carboxamide gave the title compound as a solid (920 mg, 92%).

$^1$NMR (300 MHz, CDCl$_3$): δ 2.01(m, 2H), 2.57(s, 3H), 3.20(m, 2H), 4.38(t, J=6.6 Hz, 2H), 7.99(dd, J=1.1, 8.4 Hz, 1H), 7.06(s, 1H), 7.74(dd, J=4.4, 8.8 Hz, 1H) 7.89(d, J=8.4 Hz, 1H), 7.99(br s, 1H), 8.03(dd, J=2.6, 8.8 Hz, 1H), 8.24(d, J=8.8 Hz, 1H), 8.46(m, 2H), 9.21(d, J=8.8 Hz, 1H), 10.81(s, 1H), 12.35(s, 1H).

FIA-MS, m/e: 500.1 (m+1).

Analysis for C$_{23}$H$_{22}$ClN$_5$O$_6$S:

| Calcd: | C, 55.25; H, 4.44; N, 14.01; |
| Found: | C, 54.99; H, 4.44; N, 14.09. |

EXAMPLE 56

Preparation of 3-[4-Methylsulfonyl-2-[3-(formylamino)-propoxy]benzoylamino]-N-(5-chloropyridin-2-yl)pyridine-2-carboxamide Using a procedure analogous to Example 3-A, 3-[4-methylthio-2-[3-(formylamino)propoxy]benzoylamino]-N-(5-chloropyridin-2-yl)pyridine-2-carboxamide gave the title compound as a solid (1 g, quantitative).

$^1$NMR (300 MHz, CDCl$_3$): δ 2.01(m, 2H), 3.21(m, 2H), 3.33(s, 3H), 4.42(t, J=6.2 Hz, 2H), 7.66(d, J=8.1 Hz, 1H), 7.72(s, 1H), 7.78(dd, J=4.4, 8.8 Hz, 1H), 7.90(s, 1H), 8.02(dd, J=2.6, 8.8 Hz, 1H), 8.11(d, J=8.1 Hz, 1H), 8.21(d, J=8.8 Hz, 1H), 8.46(d, J=2.6 Hz, 1H), 8.49(dd, J=1.1, 4.4 Hz, 1H), 9.21(d, J=8.4 Hz, 1H), 10.82(s, 1H), 12.42(s, 1H).

FIA-MS, m/e: 532.1 (m+1).

Analysis for C$_{23}$H$_{22}$ClN$_5$O$_6$S:

| Calcd: | C, 51.93; H, 4.17; N, 13.16; |
| Found: | C, 52.19; H, 4.02; N, 13.14. |

EXAMPLE 57

Preparation of N-(5-Chloropyridin-2-yl)-3-[4-methylsulfonyl-2-[(2S)-3-amino-2-hydroxypropoxy]benzoylamino]pyridine-2-carboxamide

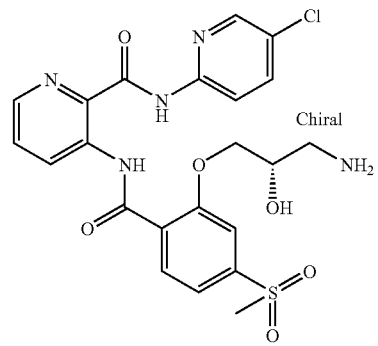

A. 3,4-Dimethoxybenzyl Bromide

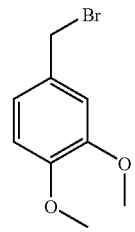

To a solution of 3,4-dimethoxybenzyl alcohol (10 g, 59.5 mmol), carbon tetrabromide (22 g, 65.4 mmol), and THF (250 mL) was added triphenylphosphine (17 g, 65.4 mmol) in THF (75 mL). The reaction was heated at 60° C. for 1 h and concentrated to an oil. To the residue was added 1:1 CH$_2$Cl$_2$:Et$_2$O and the resulting solid was filtered. The filtrate was concentrated and chromatographed on florisil with CH$_2$Cl$_2$ to give the title compound (8.05 g, 59%).

$^1$NMR (300 MHz, DMSO-d$_6$): δ 3.79 (m, 3H), 3.80 (m, 3H), 5.35 (s, 2H), 7.04 (m, 3H).

B. (2S)-3-(t-Butoxycarbonylamino)-2-(3,4-dimethoxybenzyl-oxy)propyl Triisopropylsilyl Ether

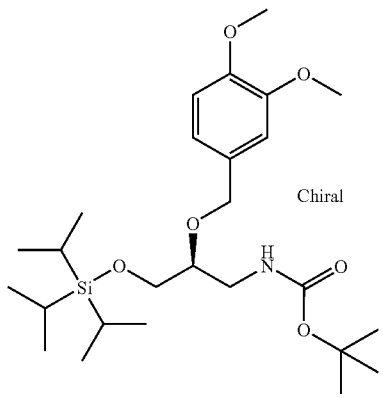

To a 0° C. mixture of (2S)-3-(t-butoxycarbonylamino)-2-hydroxypropyl triisopropylsilyl ether (6 g, 17.2 mmol) and THF (35 mL) was added NaH (60% dispersion in oil, hexane washed). The reaction was stirred for 1 h, 3,4-dimethoxybenzyl bromide (4.3 g, 18.9 mmol) in THF (20 mL) was added, and then stirred at ambient temperature for 18 h. The mixture was concentrated and chromatographed on SiO$_2$ (gradient CH$_2$Cl$_2$ to EtOAc) to give the title compound (1.1 g, 12.8%).

1NMR (300 MHz, DMSO-d$_6$): δ 1.03 (s, 0.21), 1.35 (s, 9H), 3.05 (m, 2H), 3.45 (m, 1H), 3.65 (m, 2H), 3.72 (s, 3H), 3.74 (s, 3H), 4.51 (s, 2H), 6.77 (m, 1H), 6.86 (m, 3H).

ES-MS, exact m/e: calc. 520.3070 (C$_{26}$H$_{47}$NO$_6$Si+Na); found 520.3060.

C. (2S)-3-(t-Butoxycarbonylamino)-2-(3,4-dimethoxy-benzyloxy)propanol

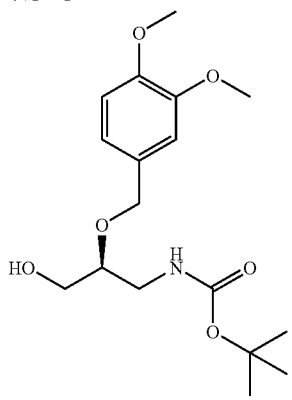

To a 0° C. mixture of (2S)-3-(t-butoxycarbonylamino)-2-(3,4-dimethoxybenzyloxy)propyl triisopropylsilyl ether (1 g, 2.01 mmol) and THF (5 mL) was added 1 M TBAF/THF (2.11 mL, 2.11 mmol). The reaction was stirred for 1 h and satd citric acid (5 mL) and CH$_2$Cl$_2$ were added. The organic layer was partitioned, concentrated, and chromatographed (CH$_2$Cl$_2$ to 50% EtOAc/CH$_2$Cl$_2$) to give the title compound (545 mg, 80%).

$^1$NMR (300 MHz, DMSO-d$_6$): δ 1.36 (s, 9H), 3.02 (m, 2H), 3.40 (m, 3H), 3.73 (s, 3H), 4.48 (s, 2H), 4.58 (m, 1H), 6.72 (m, 1H), 6.86 (m, 2H), 6.97 (s, 1H).

ES-MS, exact m/e: calc. 364.1736 (C$_{17}$H$_{27}$NO$_6$+Na). found 364.1739.

D. N-(5-Chloropyridin-2-yl)-3-[4-methylthio-2-[(2S)-3-(t-butoxycarbonylamino)-2-(3,4-dimethoxybenzyloxy)propoxy]-benzoylamino]pyridine-2-carboxamide Using a procedure analogous to Example 38-D, (2S)-3-(t-butoxycarbonylamino)-2-(3,4-dimethoxybenzyloxy)propanol and 3-[4-methylthio-2-(hydroxy)benzoylamino]-N-(5-chloro-pyridin-2-yl)pyridine-2-carboxamide gave the title compound as a solid (800 mg, 71%).

ES-MS: 738 (m+1).

E. N-(5-Chloropyridin-2-yl)-3-[4-methylsulfonyl-2-[(2S)-3-(t-butoxycarbonylamino)-2-(3,4-dimethoxybenzyloxy)-propoxy]benzoylamino]pyridine-2-carboxamide Using a procedure analogous to Example 3-A, N-(5-chloropyridin-2-yl)-3-[4-methylthio-2-[(2S)-3-(t-butoxycarbonylamino)-2-(3,4-dimethoxybenzyloxy)propoxy]-benzoylamino]pyridine-2-carboxamide gave the title compound as a solid (600 mg, 71%).

ES-MS, exact m/e: calc. 770.2263 (C$_{36}$H$_{40}$ClN$_5$O$_{10}$S); found 770.2255.

F. N-(5-Chloropyridin-2-yl)-3-[4-methylsulfonyl-2-[(2S)-3-amino-2-hydroxypropoxy]benzoylamino]pyridine-2-carboxamide Using a procedure analogous to Example 1-H, N-(5-chloropyridin-2-yl)-3-[4-methylsulfonyl-2-[(2S)-3-(t-butoxycarbonylamino)-2-(3,4-dimethoxybenzyloxy)propoxy]-benzoylamino]pyridine-2-carboxamide gave the title compound as a solid (300 mg, 69%).

$^1$NMR (300 MHz, DMSO-d$_6$): δ 2.56 (dd, J=5.9, 12.8 Hz, 1H), 2.65 (dd, J=5.1, 12.8 Hz, 1H), 3.32 (s 3H), 3.91 (m, 1H), 4.30 (m, 1H), 4.42 (m, 1H), 7.65 (dd, J=1.8, 8.1 Hz, 1H), 7.82 (m, 2H), 8.01 (dd, J=2.6, 8.8 Hz, 1H), 8.10 (d, 8.1 Hz, 1H), 8.24 (d, J=8.4 Hz, 1H), 8.47 (dd, J=0.7, 2.6 Hz, 1H), 8.50 (dd, J=1.5, 4.4 Hz, 1H), 8.20 (dd, J=1.5, 8.8 Hz, 1H).

ES-MS, exact m/e: calc. 520.1088 (C$_{22}$H$_{23}$ClN$_5$O$_6$S). found 520.1058.

Analysis for C$_{22}$H$_{22}$ClN$_5$O$_{56}$S.0.5 H$_2$O:

| Calcd: | C, 49.95; H, 4.38; N, 13.24; |
| Found: | C, 49.98; H, 4.11; N, 13.07. |

EXAMPLE 58

Preparation of N-(5-Chloropyridin-2-yl)-3-[4-methylsulfonyl-2-(3-amino-2-methoxypropyloxy)benzoylamino]pyridine-2-carboxamide

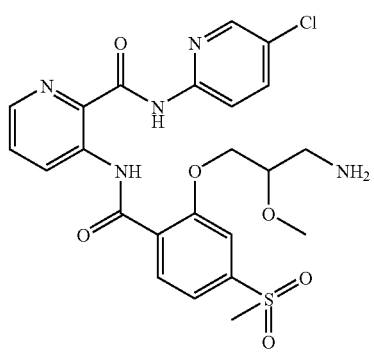

A. 3-t-Butoxycarbonylamino-2-hydroxypropanol

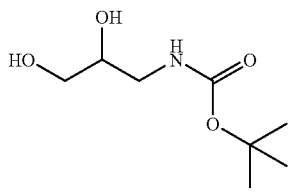

Using a procedure analogous to Example 1-C, 3-amino-2-hydroxypropanol gave the title compound as a white solid (97 g, quantitative).

$^1$NMR (300 MHz, DMSO-d$_6$): δ 1.37 (s, 9H), 2.86 (m, 1H), 3.00 (m, 1H), 3.27 (m, 2H), 3.43 (m, 1H), 4.44 (t, J=5.9 Hz, 1H), 4.59 (d, J=4.8 Hz, 1H), 6.56 (br m, 1H).

FIA-MS, m/e: 192.3 (m+1).

Analysis for C$_8$H$_{17}$NO$_4$·0.25 H$_2$O:

| | |
|---|---|
| Calcd: | C, 49.09; H, 9.01; N, 7.16; |
| Found: | C, 49.34; H, 9.05; N, 7.20. |

B. 3-(t-Butoxycarbonylamino)-2-hydroxypropyl Triisopropylsilyl Ether

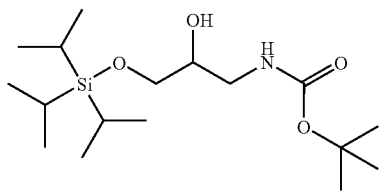

To a 0° C. mixture of 3-(t-butoxycarbonylamino)-2-hydroxypropanol (22.5 g, 118 mmol), imidazole (8.8 g, 130 mmol) and DMF (450 ml) was added triisopropylsilyl chloride (25 mL, 118 mmol). The reaction was warmed to room temperature and stirred for 3 h. The reaction was concentrated to a slurry, CH$_2$Cl$_2$ was added, and the mixture filtered. The filtrate was washed with water (2×) and concentrated. The reaction was repeated. The combined crude product was chromatographed with SiO$_2$ (hexanes to 30% EtOAc/hexanes) to give the title compound (62.2 g, 76%).

$^1$NMR (300 MHz, DMSO-d$_6$): δ 1.03 (m, 21H), 1.34 (s, 9H), 2.87 (m, 1H), 3.08 (m, 1H), 3.50 (m, 2H), 4.67 (m, 1H), 6.56 (m, 1H).

ES-MS, exact m/e: calc. 370.2390 (C$_{17}$H$_{37}$NO$_4$Si). found 370.2372.

C. 3-(t-Butoxycarbonylamino)-2-methoxypropyl Triisopropylsilyl Ether

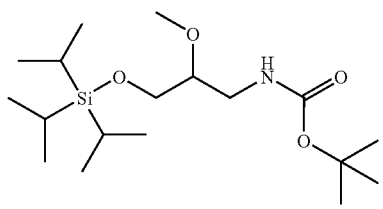

Using a procedure analogous to Example 57-B, 3-(t-butoxycarbonylamino)-2-hydroxypropyl triisopropylsilyl ether and methyl iodide gave the title compound (13 g, 62%).

$^1$NMR (300 MHz, DMSO-d$_6$): δ 1.02 (m, 21H), 1.37 (s, 9H), 2.50 (m, 2H), 3.23 (m, 1H), 3.33 (s, 3H), 3.59 (m, 1H), 3.70 (m, 1H), 6.74 (m, 1H).

FIA-MS, m/e: 362.4 (m+1).

D. 3-(t-Butoxycarbonylamino)-2-methoxypropanol

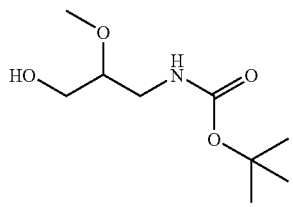

Using a procedure analogous to Example 57-C, 3-(t-butoxycarbonylamino)-2-methoxypropyl triisopropylsilyl ether gave the title compound (4.1 g, 73%).

$^1$NMR (300 MHz, DMSO-d$_6$): δ 1.37 (s, 9H), 2.98 (m, 2H), 3.15 (m, 1H), 3.31 (s, 3H), 3.34 (m, 2H), 4.52 (t, J=5.9 Hz, 1H), 6.70 (m, 1H).

ES-MS, exact m/e: calc. 228.1212 (C$_9$H$_{19}$NO$_4$Na); found 228.1208.

E. N-(5-Chloropyridin-2-yl)-3-[4-methylthio-2-[3-(t-butoxycarbonylamino)-2-methoxypropoxy])benzoylamino]-pyridine-2-carboxamide

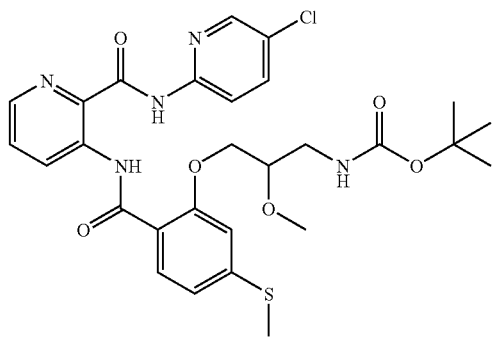

Using a procedure analogous to Example 38-D, 3-(t-butoxycarbonylamino)-2-methoxypropanol gave the title compound as a solid (2.0 g, 46%).

$^1$NMR (300 MHz, DMSO-d$_6$): δ 1.27 (s, 9H), 2.57 (s, 3H), 3.06 (m, 1H), 3.14 (m, 1H), 3.21 (s, 3H), 3.78 (m, 1H), 4.32 (m, 2H), 6.83 (m, 1H), 7.00 (dd, J=1.5, 8.1 Hz, 1H), 7.08 (s, 1H), 7.75 (dd, J=4.4, 8.8 Hz, 1H), 7.85 (d, J=8.4 Hz, 1H), 8.02 (dd, J=2.6, 9.1 Hz, 1H), 8.28 (d, J=9.1 Hz, 1H), 8.46 (m, 2H), 9.19 (dd, J=1.1, 8.8 Hz, 1H), 10.83 (s, 1H), 12.29 (s, 1H).

ES-MS, m/e: 602.2 (m+1).

F. N-(5-Chloropyridin-2-yl)-3-[4-methylsulfonyl-2-[3-(t-butoxycarbonylamino)-2-methoxypropoxy]benzoylamino]-pyridine-2-carboxamide

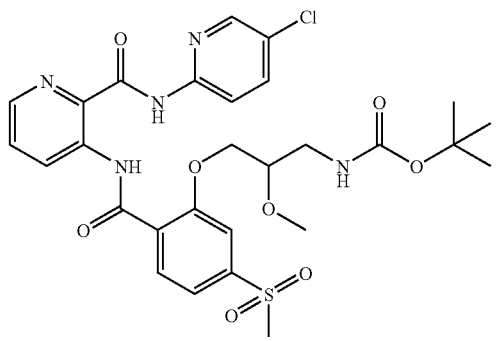

Using a procedure analogous to Example 3-A, N-(5-chloropyridin-2-yl)-3-[4-methylthio-2-[3-(t-butoxy-carbonylamino)-2-methoxypropoxy]benzoylamino]pyridine-2-carboxamide gave the title compound as a solid (1.4 g, 70%).

$^1$NMR (300 MHz, DMSO-d$_6$): δ 1.26 (s, 9H), 3.06 (m, 1H), 3.15 (m, 1H), 3.22 (s, 3H), 3.74 (m, 1H), 4.35 (m, 2H), 6.84 (m, 1H), 7.67 (dd, J=1.1, 8.1 Hz, 1H), 7.77 (m, 2H), 8.00 (dd, J=2.6, 8.8 Hz, 1H), 8.07 (d, J=8.1 Hz, 1H), 8.24 (d, J=8.8 Hz, 1H), 8.46 (d, J=2.6 Hz, 1H), 8.50 (dd, J=1.1 Hz, 4.4 Hz, 1H), 9.18 (d, J=8.4 Hz, 1H), 10.83 (s, 1H), 12.35 (s, 1H).

ES-MS, exact m/e: calc. 634.1738 (C$_{28}$H$_{32}$ClN$_5$O$_8$S); found 634.1715.

G. N-(5-Chloropyridin-2-yl)-3-[4-methylsulfonyl-2-(3-amino-2-methoxypropoxy)benzoylamino]pyridine-2-carboxamide

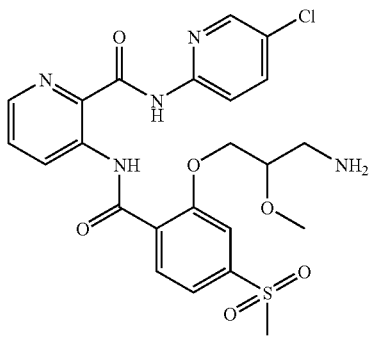

Using a procedure analogous to Example 1-H, N-(5-chloropyridin-2-yl)-3-[4-methylsulfonyl-2-[3-(t-butoxy-carbonylamino)-2-methoxypropoxy]benzoylamino]pyridine-2-carboxamide gave the title compound as a solid (1.2 g, quantitative).

$^1$NMR (300 MHz, DMSO-d$_6$): δ 2.66 (t, J=5.9 Hz, 2H), 3.21 (s, 3H), 3.33 (s, 3H), 3.60 (m, 1H), 4.37 (m, 1H), 4.50 (m, 1H), 7.66 (dd, J=1.1, 8.4 Hz, 1H), 7.81 (m, 2H), 8.05 (m, 2H), 8.25 (d, J=9.1 Hz, 1H), 8.47 (d, J=2.6 Hz, 1H), 8.50 (dd, J=1.1, 4.4 Hz, 1H), 9.19 (dd, J=1.1, 8.4 Hz, 1H).

ES-MS, m/e: 534.1 (m+1).

Analysis for C$_{23}$H$_{24}$ClN$_5$O$_6$S:

| | |
|---|---|
| Calcd: | C, 51.73; H, 4.53; N, 13.12; |
| Found: | C, 51.64; H, 4.32; N, 12.80. |

EXAMPLE 59

Preparation of N-(5-Chloropyridin-2-yl)-3-[4-methylsulfonyl-2-[(2S)-3-amino-2-methoxypropoxy]benzoylamino]pyridine-2-carboxamide

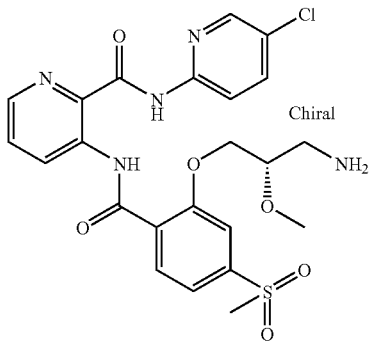

A. (2S)-3-(t-Butoxycarbonylamino)-2-hydroxypropanol

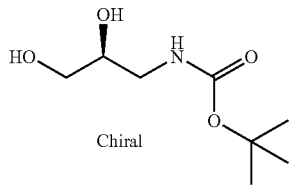

Using a procedure analogous to Example 1-C, (2S)-3-amino-2-hydroxypropanol gave the title compound as a viscous yellow oil (54.2 g, quantitative).

$^1$NMR

ES-MS, m/e: 190.1 (m–1).

B. (2S)-3-(t-Butoxycarbonylamino)-2-hydroxypropyl Triisopropylsilyl Ether

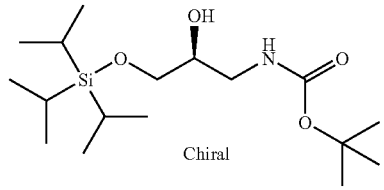

Using a procedure analogous to Example 58-B, (2S)-3-(t-butoxycarbonylamino)-2-hydroxypropanol gave the title compound (60 g, 61%).

$^1$NMR

ES-MS, m/e: calc. 346.3 (m–1).

C. (2S)-3-(t-Butoxycarbonylamino)-2-methoxypropyl Triisopropylsilyl Ether

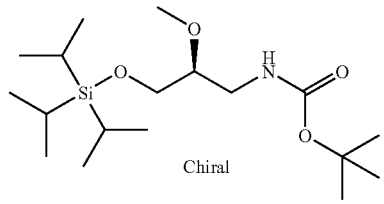

Using a procedure analogous to Example 57-B, (2S)-3-(t-butoxycarbonylamino)-2-hydroxypropyl triisopropylsilyl ether and methyl iodide gave the title compound (4.2 g, 81%).

$^1$NMR

ES-MS, exact m/e: calc. 384.2546 (C$_{18}$H$_{39}$NO$_4$NaSi). found 384.2550.

D. (2S)-3-(t-Butoxycarbonylamino)-2-methoxypropanol

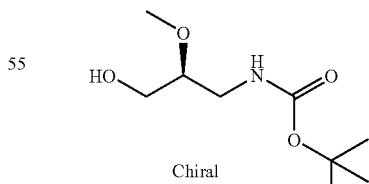

Using a procedure analogous to Example 57-C, (2S)-3-(t-butoxycarbonylamino)-2-methoxypropyl triisopropylsilyl ether gave the title compound (2.1 g, 72%).

$^1$NMR

ES-MS, m/e: 228.1 (m+Na).

E. N-(5-Chloropyridin-2-yl)-3-[4-methylthio-2-[(2S)-3-(t-butoxycarbonylamino)-2-methoxypropoxy]benzoylamino]-pyridine-2-carboxamide

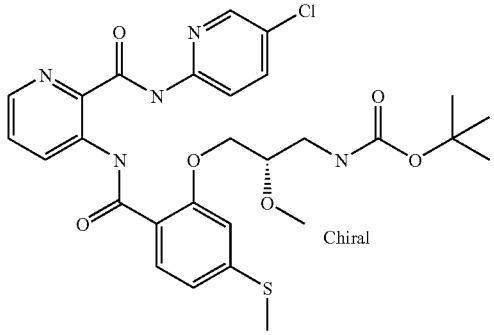

Using a procedure analogous to Example 38-D, (2S)-3-(t-butoxycarbonylamino)-2-methoxypropanol gave the title compound as a solid (1.1 mg, 76%).
$^1$NMR
ES-MS, m/e: 600.2 (m−1).

F. N-(5-Chloropyridin-2-yl)-3-[4-methylsulfonyl-2-[(2S)-3-(t-butoxycarbonylamino)-2-methoxypropoxy)benzoylamino]-pyridine-2-carboxamide

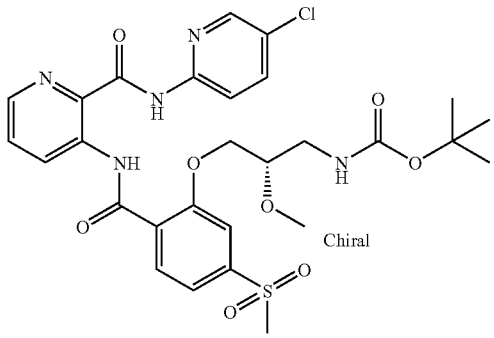

Using a procedure analogous to Example 3-A, N-(5-chloropyridin-2-yl)-3-[4-methylthio-2-[(2S)-3-(t-butoxy-carbonylamino)-2-methoxypropoxy]benzoylamino]pyridine-2-carboxamide gave the title compound as a solid (800 mg, 76%).
$^1$NMR
ES-MS, m/e: 632.2 (m−1).

G. N-(5-Chloropyridin-2-yl)-3-[4-methylsulfonyl-2-[(2S)-3-amino-2-methoxypropoxy]benzoylamino]pyridine-2-carboxamide

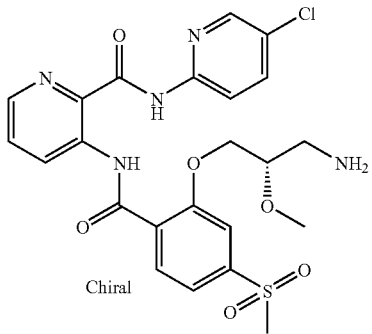

Using a procedure analogous to Example 1-H, N-(5-chloropyridin-2-yl)-3-[4-methylsulfonyl-2-[(2S)-3-(t-butoxycarbonylamino)-2-methoxypropoxy)benzoylamino]pyridine-2-carboxamide gave the title compound as a white solid (250 mg, 40%).
$^1$NMR
ES-MS, m/e: 534.1 (m+1).
Analysis for $C_{23}H_{24}ClN_5O_6S$:

| Calcd: | C, 51.73; H, 4.53; N, 13.12; |
| Found: | C, 51.79; H, 4.47; N, 13.06. |

EXAMPLE 60

Preparation of N-(5-Chloropyridin-2-yl)-3-[4-methylsulfonyl-2-[(2S)-3-amino-2-methylpropoxy]benzoylamino]pyridine-2-carboxamide Hydrochloride

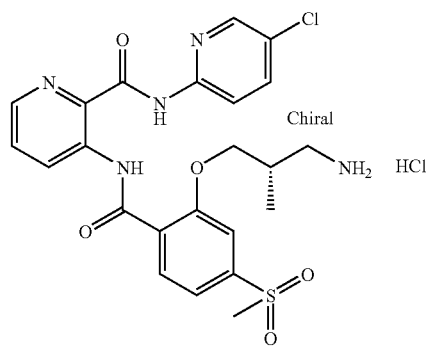

A. 3:1 S:R Isomers of (S)-(−)-α-Methylbenzylammonium Salt of 3-(t-Butoxycarbonylamino)-2-methylpropionic Acid

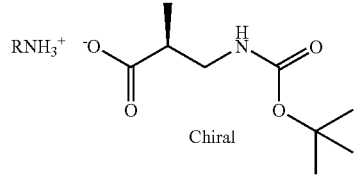

Using a procedure analogous to Example 40-A, 3-(t-butoxycarbonylamino)-2-methylpropionic acid and (S)-(−)-α-methylbenzylamine gave a mixture of 3:1 S:R isomers of (S)-(−)-α-methylbenzylammonium salt of 3-(t-butoxycarbonylamino)-2-methylpropionic acid (60%).

B. 3:1 Ratio of S:R Enantiomers of 3-(t-Butoxycarbonylamino)-2-methylpropionic Acid

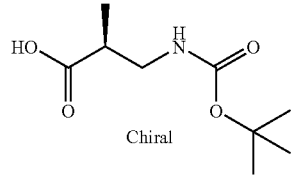

Using a procedure analogous to Example 40-B, a 3:1 ratio of S:R diastereomers of (S)-(−)-α-methylbenzyl ammonium salt of 3-t-butoxycarbonylamino-2-methylpropionic acid gave the title compound as a white solid (50 g, quantitative).
$^1$NMR
ES-MS, m/e: 204.2 (m+1).

C. 3:1 Ratio of S:R Enantiomers of (2S)-3-(t-butoxy-carbonylamino)-2-methylpropanol

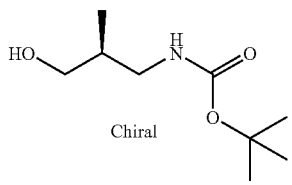

Using a procedure analogous to Example 40-C, a 3:1 ratio of S:R enantiomers of 3-(t-butoxycarbonylamino)-2-methylpropionic acid gave the title compound (3.0 g, 54%).
¹NMR
ES-MS, exact m/e: calc. 212.1443 ($C_9H_{19}NO_3N$); found 212.1438.

D. 3:1 Ratio of S:R Enantiomers of N-(5-Chloropyridin-2-yl)-3-[4-methylthio-2-[3-(t-butoxycarbonylamino)-2-methyl-propoxy]benzoylamino]pyridine-2-carboxamide

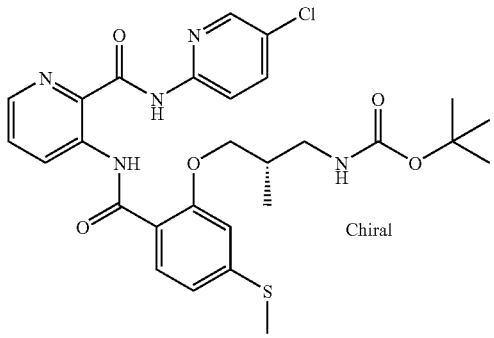

Using a procedure analogous to Example 38-D, a 3:1 ratio of S:R enantiomers of 3-(t-butoxycarbonylamino)-2-methylpropanol gave the title compound as a solid (2.9 g, 69%).
¹NMR
ES-MS, m/e: 587.1 (m+1).

E. 3:1 Ratio of S:R Enantiomers of N-(5-Chloropyridin-2-yl)-3-[4-methylsulfonyl-2-[3-(t-butoxycarbonylamino)-2-methylpropoxy]benzoylamino]pyridine-2-carboxamide

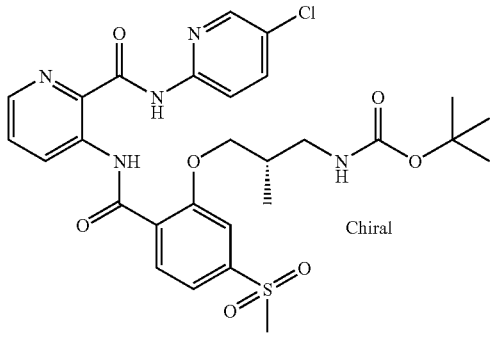

Using a procedure analogous to Example 3-A, the 3:1 ratio of S:R enantiomers of N-(5-chloropyridin-2-yl)-3-[4-methylthio-2-[3-(t-butoxycarbonylamino)-2-methylproloxy]-benzoylamino]pyridine-2-carboxamide gave the title compound as a solid (2.25 g, 74%).
¹NMR
ES-MS, exact m/e: calc. 618.1758 ($C_{28}H_{33}ClN_5O_7S$, m+1).
found 618.1789.

F. N-(5-Chloropyridin-2-yl)-3-[4-methylsulfonyl-2-[(2S)-(3-amino-2-methylpropoxy]benzoylamino]pyridine-2-carboxamide

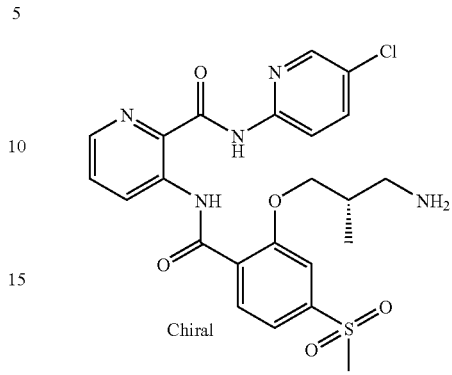

Using a procedure analogous to Example 1-H, a 3:1 ratio of S:R enantiomers of N-(5-chloropyridin-2-yl)-3-[4-methylsulfonyl-2-[3-(t-butoxycarbonylamino)-2-methylpropoxy]-benzoylamino]pyridine-2-carboxamide gave the title compound as a white solid (1.05 g, 56%, 95.8% ee) after HPLC purification on a ChiralPak AD column (4.6×250 mm, 70:30: 0.2 EtOH:heptane:DMEA, 1.0 mL/min, rt=16.17 min).
¹NMR
ES-MS, m/e: 518.1 (m+1).

G. N-(5-Chloropyridin-2-yl)-3-[4-methylsulfonyl-2-[(2S)-3-amino-2-methylpropoxy]benzoylamino]pyridine-2-carboxamide Hydrochloride

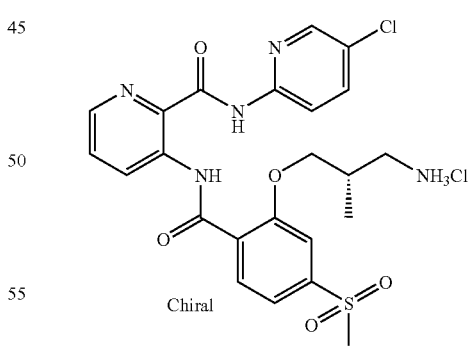

Using a procedure analogous to Example 4-F, N-(5-chloropyridin-2-yl)-3-[4-methylsulfonyl-2-[(2S)-3-amino-2-methylpropoxy]benzoylamino]pyridine-2-carboxamide gave the title compound as a white solid (740 mg, 87%).
¹NMR
ES-MS, m/e: 518.1 (m+1).

EXAMPLE 61

Preparation of N-(5-Chloropyridin-2-yl)-3-[2-(2S-3-amino-2-benzyloxypropoxy)-4-(methylsulfonyl)benzoylamino]pyridine-2-carboxamide

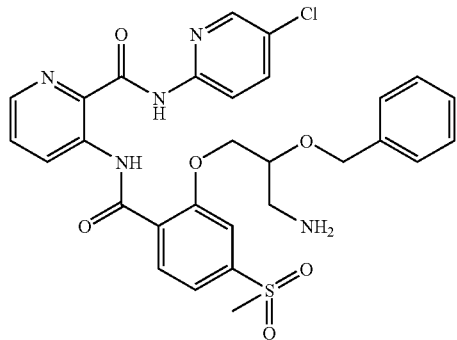

A. 2-Benzyloxy-3-(t-butoxycarbonylamino)propyl Triisopropylsilyl Ether

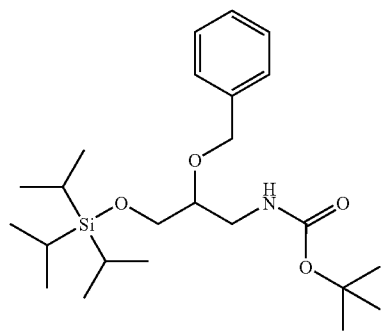

Using an analogous procedure described in Example 57-B, benzyl bromide gave the title compound (59%).

$^1$NMR (300 MHz, DMSO-d$_6$): δ 1.03 (m, 21H), 1.36 (s, 9H), 3.06 (m, 2H), 3.49 (m, 1H), 3.65 (m, 1H), 3.73 (m, 1H), 4.31 (s, 2H), 6.81 (m, 1H), 7.33 (m, 5H).

ES-MS: 438.2 (m+H).

ES-MS, exact m/e: calc. 460.2859 (C$_{24}$H$_{43}$NO$_4$Si+Na); found 460.2865.

Analysis for C$_{24}$H$_{43}$NO$_4$Si:

| Calcd: | C, 65.86; H, 9.90; N, 3.20; |
|---|---|
| Found: | C, 65.63; H, 9.33; N, 3.50. |

B. 2-Benzyloxy-3-(t-butoxycarbonylamino)propanol

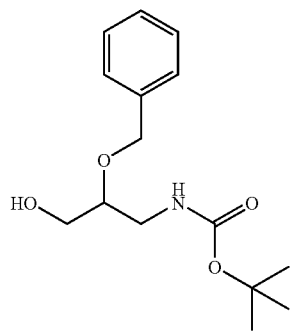

Using an analogous procedure described in Example 57-C, 2-benzyloxy-3-(t-butoxycarbonylamino)propyl triisopropylsilyl ether gave the title compound (67%).

$^1$NMR (300 MHz, DMSO-d$_6$): δ 1.37 (s, 9H), 3.06 (m, 2H), 3.42 (m, 3H), 4.56 (s, 2H), 4.60 (m, 1H), 6.76 (m, 1H), 7.34 (m, 5H).

ES-MS: 282.2 (m+H).

ES-MS, exact m/e: calc. 304.1525 (C$_{15}$H$_{23}$NO$_4$Na); found 304.1530.

C. Preparation of R and S isomers of 2-benzyloxy-3-(t-butoxycarbonylamino)propanol Chiral isomers of 2-benzyloxy-3-(t-butoxycarbonylamino)propanol were separated on a Chiralpak AD column, eluting with 0.2% DMEA in 10% EtOH/heptane to give 2S-2-benzyloxy-3-(t-butoxycarbonylamino)propanol (Isomer I, 1.48 g, 93%; analytical HPLC: 0.2% DMEA in 10% EtOH/heptane (1 mL/min), rt=7.48 min) and 2R-2-benzyloxy-3-(t-butoxy-carbonylamino)propanol (Isomer II, 1.23 g, 77%, rt=8.83 min).

Isomer I:

2S-2-Benzyloxy-3-t-butoxycarbonylaminopropanol:
NMR
ES-MS: 304.1 (m+Na).
Analysis for C$_{15}$H$_{23}$NO$_4$.0.1 H$_2$O:

| Calcd: | C, 63.63; H, 8.26; N, 4.95; |
|---|---|
| Found: | C, 63.52; H, 8.03; N, 4.80. |

Correlation with 2S-2-benzyloxy-3-(t-butoxycarbonylamino)-propanol derived from 2S-3-amino-2-hydroxypropanol (Synthon)

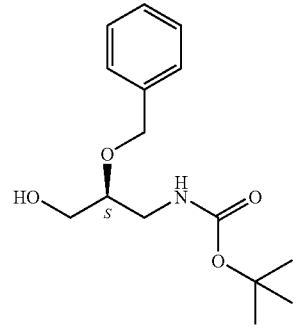

i) 2S-3-(t-Butoxycarbonylamino)-2-hydroxypropanol

Using a procedure analogous to Example 58-A, 2S-3-amino-2-hydroxypropanol gave the title compound as a yellow oil (54.2 g, quant.).

ii) 2S-3-(t-Butoxycarbonylamino)-2-hydroxypropyl Triisopropylsilyl Ether

Using a procedure analogous to Example 58-B, 2S-3-(t-butoxycarbonylamino)-2-hydroxypropanol gave the title compound as a yellow oil (60 g, 61%).

iii) 2S-2-Benzyloxy-3-(t-butoxycarbonylamino)propyl Triisopropylsilyl Ether

Using a procedure analogous to Example 61-A, 2S-3-(t-butoxycarbonylamino)-2-hydroxypropyl triisopropylsilyl ether gave the title compound (2.2 g, 76%).

iv) 2S-2-Benzyloxy-3-t-butoxycarbonylaminopropanol

Using a procedure analogous to Example 61-B, 2S-2-benzyloxy-3-(t-butoxycarbonylamino)propyl triisopropylsilyl ether gave the title compound (52%).

ES-MS, exact m/e: calc. 304.1525 ($C_{15}H_{23}NO_4Na$); found 304.1559.

HPLC on a Chiracel OD (0.2% DMEA in 10% IPA/heptane, 1.0 mL/min correlated, rt=7.04 min) correlated with isomer I.

Isomer II:

2R-2-Benzyloxy-3-(t-butoxycarbonylamino)propanol:
NMR
ES-MS: 304.1 (m+Na).
Analysis for $C_{15}H_{23}NO_4$:

| Calcd: | C, 64.04; H, 8.24; N, 4.98; |
| Found: | C, 64.80; H, 8.42; N, 4.90. |

D. N-(5-Chloropyridin-2-yl)-3-[2-(2S-2-benzyloxy-3-t-butoxycarbonylaminopropoxy)-4-(methylthio)benzoylamino]-pyridine-2-carboxamide Using a procedure analogous to Example 38-D, 2S-2-benzyloxy-3-(t-butoxycarbonylamino)propanol and N-(5-chloro-pyridin-2-yl)-3-(2-hydroxy-4-methylthiobenzoylamino)-pyridine-2-carboxamide gave the title compound as a solid (73%).

ES-MS: 678.2 (m+1).

$^1$NMR (300 MHz, DMSO-$d_6$): δ 1.30 (s, 9H), 2.55 (s, 3H), 3.24 (m, 1H), 3.29 (m, 1H), 4.04 (m, 1H), 4.44 (m, 3H), 4.51 (m, 1H), 6.93 (m, 1H), 7.00 (dd, J=1.5, 8.4 Hz, 1H), 7.08 (m, 2H), 7.73 (dd, J=4.4, 8.4 Hz, 1H), 7.87 (d, J=8.4 Hz, 1H), 7.96 (dd, J=2.6, 9.1 Hz, 1H), 8.24 (d, J=8.8 Hz, 1H), 8.44 (m, 2H), 9.18 (d, J=8.8 Hz, 1H), 10.75 (s, 1H), 12.34 (s, 1H).

E. N-(5-Chloropyridin-2-yl)-3-[2-(2S-2-benzyloxy-3-t-butoxycarbonylaminopropoxy)-4-(methylsulfonyl)benzoylamino]-pyridine-2-carboxamide Using a procedure analogous to that of Example 3-A, N-(5-chloropyridin-2-yl)-3-[2-(2S-2-benzyloxy-3-t-butoxy-carbonylaminopropoxy)-4-(methylthio)benzoylamino]pyridine-2-carboxamide gave the title compound as a solid (63%).

$^1$NMR (300 MHz, DMSO-$d_6$): δ 1.28 (s, 9H), 3.17 (m, 1H), 3.25 (m, 1H), 3.28 (s, 3H), 4.02 (m, 1H), 4.46 (m, 4H), 6.94 (m, 1H), 7.08 (m, 5H), 7.67 (dd, J=1.1, 8.1 Hz, 1H), 7.77 (m, 2 h), 7.95 (dd, J=2.6, 8.8 Hz, 1H), 8.08 (d, J=8.1 Hz, 1H), 8.20 (d, J=8.8 Hz, 1H), 8.46 (m, 2H), 9.18 (d, J=8.1 Hz, 1H), 10.77 (s, 1H), 12.38 (s, 1H).

ES-MS, exact m/e: calc. 710.2051 ($C_{34}H_{36}ClN_5O_8S$); found 710.2072.

F. N-(5-Chloropyridin-2-yl)-3-[2-(2S-3-amino-2-benzyloxy-propoxy)-4-(methylsulfonyl)benzoylamino]pyridine-2-carboxamide Using a procedure analogous to that of Example 1-H, N-(5-chloropyridin-2-yl)-3-[2-(2S-2-benzyloxy-3-t-butoxy-carbonylaminopropoxy)-4-(methylsulfonyl)benzoylamino]-pyridine-2-carboxamide gave the title compound as a solid (90%).

$^1$NMR (300 MHz, DMSO-$d_6$): δ 2.74 (m, 2H), 3.30 (s, 3H), 3.87 (m, 1H), 4.47 (m, 3H), 4.58 (m, 1H), 7.07 (m, 5H), 7.66 (dd, J=1.5, 8.1 Hz, 1H), 7.78 (dd, J=4.4, 8.8 Hz, 1H), 7.82 (d, J=1.1 Hz, 1H), 7.97 (dd, J=2.6, 8.8 Hz, 1H), 8.07 (d, J=8.1 Hz, 1H), 8.21 (d, J=9.1 Hz, 1H), 8.47 (m, 2H), 9.19 (dd, J=1.1, 8.8 Hz, 1H).

ES-MS, exact m/e: calc. 610.1527 ($C_{29}H_{28}ClN_5O_6S$); found 610.1500.

Analysis for $C_{29}H_{28}ClN_5O_6S$:

| Calcd: | C, 57.09; H, 4.63; N, 11.48; |
| Found: | C, 56.88; H, 4.57; N, 11.44. |

EXAMPLE 62

Preparation of N-(5-Chloropyridin-2-yl)-3-[2-(2S-3-amino-2-benzyloxypropoxy)-4-(methylsulfonyl)benzoylamino]pyridine-2-carboxamide Hydrochloride (Isomer 1)

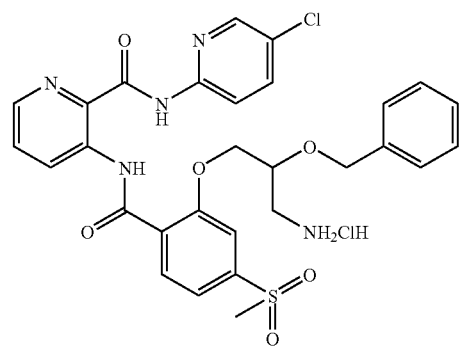

A mixture of N-(5-chloropyridin-2-yl)-3-[2-(2S-3-amino-2-benzyloxypropoxy)-4-(methylsulfonyl)benzoylamino]pyridine-2-carboxamide (1.0 g, 1.64 mmol), 10% Pd/C (100 mg) and 20% EtOH/EtOAc was subjected to hydrogenolysis conditions under hydrogen at atmospheric pressure for 16 h. The reaction mixture was diluted with dichloromethane, filtered through diatomaceous earth and concentrated. The resulting residue was chromatographed on a HPLC (Vydac C18), the eluent diluted with 1 N HCl and concentrated to give the title compound (the salt of recovered starting material) as a solid (526 mg, 50%; analytical HPLC: 0.46×25 cm, gradient 5-70% (0.1% TFA/$CH_3CN$) in 0.1% TFA/$H_2O$; rt=35.0 min).

$^1$NMR (300 MHz, DMSO-$d_6$): δ 3.04 (m, 1H), 3.16 (m, 1H), 3.32 (s, 3H), 4.20 (m, 4H), 4.58 (m, 5H), 7.70 (dd, J=1.5, 8.1 Hz, 1H), 7.80 (m, 2H), 7.96 (dd, J=2.9, 9.1 Hz, 1H), 8.00 (br s, 1H), 8.05 (d, J=8.1 Hz, 1H), 8.18 (d, J=8.8 Hz, 1H), 8.49 (m, 2H), 9.16 (dd, J=1.1, 8.8 Hz, 1H), 10.64 (br s, 1H), 12.30 (s, 1H).

ES-MS: 610.1 (m+1);

Analysis for $C_{29}H_{28}ClN_5O_6S \cdot HCl$:

| Calcd: | C, 53.87; H, 4.52; N, 10.83; |
| Found: | C, 53.53; H, 4.36; N, 10.68. |

EXAMPLE 63

Preparation of N-(5-Chloropyridin-2-yl)-3-[2-(2R-3-amino-2-benzyloxypropoxy)-4-(methylsulfonyl)benzoylamino]pyridine-2-carboxamide

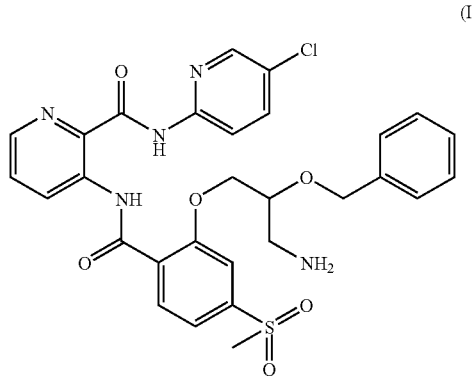
(Isomer 2)

A. N-(5-Chloropyridin-2-yl)-3-[2-(2R-2-benzyloxy-3-t-butoxycarbonylaminopropoxy)-4-(methylthio)benzoylamino]-pyridine-2-carboxamide Using a procedure analogous to Example 38-D, 2R-2-benzyloxy-3-t-butoxycarbonylaminopropanol and N-(5-chloro-pyridin-2-yl)-3-[2-hydroxy-4-(methylthio)benzoylamino]-pyridine-2-carboxamide gave the title compound as a solid (98%).

ES-MS: 678.2 (m+1).

B. N-(5-Chloropyridin-2-yl)-3-[2-(2R-2-benzyloxy-3-t-butoxycarbonylaminopropoxy)-4-(methylsulfonyl)-benzoylamino]pyridine-2-carboxamide Using a procedure analogous to Example 3-A, N-(5-chloropyridin-2-yl)-3-[2-(2R-2-benzyloxy-3-t-butoxycarbonylaminopropoxy)-4-(methylthio)benzoylamino]pyridine-2-carboxamide gave the title compound as a solid (38%).

ES-MS, exact m/e: calc. 710.2051 ($C_{34}H_{36}ClN_5O_8S$); found 710.2020.

C. N-(5-Chloropyridin-2-yl)-3-[2-(2S-3-amino-2-benzyloxy-propoxy)-4-(methylsulfonyl)benzoylamino]pyridine-2-carboxamide Using a procedure analogous to Example 1-H, N-(5-chloropyridin-2-yl)-3-[2-(2R-2-benzyloxy-3-(t-butoxy-carbonylamino)propoxy)-4-(methylsulfonyl)benzoylamino]-pyridine-2-carboxamide gave the title compound as a solid (83%).

ES-MS, exact m/e: calc. 610.1527 ($C_{29}H_{28}ClN_5O_6S$); found 610.1524.

Analysis for $C_{29}H_{28}ClN_5O_6S$:

| | |
|---|---|
| Calcd: | C, 57.09; H, 4.63; N, 11.48; |
| Found: | C, 57.21; H, 4.59; N, 11.35. |

EXAMPLE 64

Preparation of N-(5-Chloropyridin-2-yl)-3-[2-(2R-3-amino-2-benzyloxypropoxy)-4-(methylsulfonyl)benzoylamino]pyridine-2-carboxamide Hydrochloride

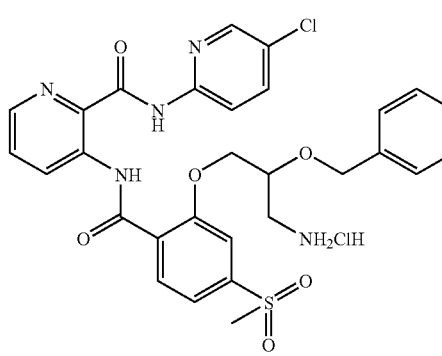
(Isomer 2)

Using a procedure analogous to Example 62, N-(5-chloropyridin-2-yl)-3-[2-(2R-3-amino-2-benzyloxy-propoxy)-4-(methylsulfonyl)benzoylamino]pyridine-2-carboxamide gave the title compound (49%, Vydac C18: rt=31.1 min).

ES-MS: 610.1 (m+1);

Analysis for $C_{29}H_{28}ClN_5O_6S \cdot HCl$:

| | |
|---|---|
| Calcd: | C, 53.87; H, 4.52; N, 10.83; |
| Found: | C, 53.92; H, 4.45; N, 10.74. |

EXAMPLE 65

Preparation of N-(5-Chloropyridin-2-yl)-3-[2-(azetidin-3-yl-methoxy)-4-(methylsulfonyl)benzoylamino]pyridine-2-carboxamide

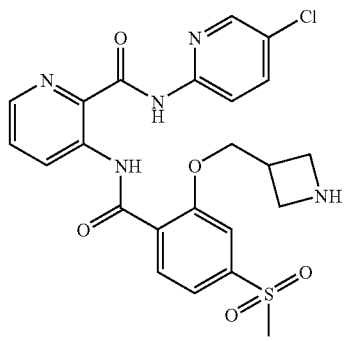

A. 1-t-Butoxycarbonylazetidine-3-carboxylic acid

Using a procedure analogous to Example 1-C ($K_2CO_3$, acetone), azetidine-3-carboxylic acid gave the title compound as a solid (3.61 g, 91%).

[1]NMR (300 MHz, DMSO-$d_6$) δ 1.37 (s, 9H), 3.35 (m, 1H), 3.85 (m, 2H), 3.99 (m, 2H).

ESI-MS, m/e: 202 (m+1).

Analysis for $C_9H_{15}NO_4 \cdot 0.1\ H_2O$:

| | |
|---|---|
| Calcd: | C, 53.24; H, 7.55; N, 6.90; |
| Found: | C, 53.38; H, 7.39; N, 6.87. |

B. 1-t-Butoxycarbonyl-3-hydroxymethylazetidine

Using a procedure analogous to Example 40-B (using $Me_2S \cdot BH_3$), 1-t-butoxycarbonylazetidine-3-carboxylic acid gave the title compound (3.0 g, quantitative).

ES-MS, exact m/e: calc. 188.1287 ($C_9H_{17}NO_3+1$); found 188.1293.

C. N-(5-Chloropyridin-2-yl)-3-[2-(1-t-butoxycarbonyl-azetidin-3-ylmethoxy)-4-(methylthio)benzoylamino]pyridine-2-carboxamide Using a procedure analogous to Example 38-D, 1-t-butoxycarbonyl-3-hydroxymethylazetidine and N-(5-chloropyridin-2-yl)-3-[2-hydroxy-4-(methylthio)benzoylamino]-pyridine-2-carboxamide gave the title compound as a white solid (1.1 g, 78%).

FIA-MS, m/e: 584.2 (m+1).

D. N-(5-Chloropyridin-2-yl)-3-[2-(1-t-butoxycarbonyl-azetidin-3-ylmethoxy)-4-(methylsulfonyl)benzoylamino]-pyridine-2-carboxamide Using a procedure analogous to Example 3-A, N-(5-chloropyridin-2-yl)-3-[2-(1-t-butoxycarbonylazetidin-3-ylmethoxy)-4-(methylthio)benzoylamino]pyridine-2-carboxamide gave the title compound as a solid (1.1 g, 80%).

ES-MS, m/e: 614.2 (m−1).

E. N-(5-Chloropyridin-2-yl)-3-[2-(azetidin-3-ylmethoxy)-4-(methylsulfonyl)benzoylamino]pyridine-2-carboxamide Using a procedure analogous to Example 1-H, N-(5-chloropyridin-2-yl)-3-[2-(1-t-butoxycarbonylazetidin-3-ylmethoxy)-4-(methylsulfonyl)benzoylamino]pyridine-2-carboxamide gave the title compound as a solid (640 mg, 76%).

$^1$NMR (250 MHz, DMSO-$d_6$): δ 3.13 (m, 1H), 3.35 (m, 5H), 3.48 (m, 2H), 4.57 (d, J=6.9 Hz, 2H), 7.67 (dd, J=1.5, 8.0 Hz, 1H), 7.79 (m, 2H), 8.04 (dd, J=2.7, 8.8 Hz, 1H), 8.11 (d, J=8.0 Hz, 1H), 8.26 (d, J=8.8 Hz, 1H), 8.48 (d, J=2.7 Hz, 1H), 8.51 (dd, J=1.5, 4.6 Hz, 1H), 9.16 (dd, J=1.5, 8.8 Hz, 1H).

ES-MS, m/e: 516.1 (m+1).

Analysis for $C_{23}H_{22}ClN_5O_5S \cdot 0.5\ H_2O$:

| | |
|---|---|
| Calcd: | C, 52.62; H, 4.42; N, 13.34; |
| Found: | C, 52.99; H, 4.04; N, 13.14. |

EXAMPLE 66

Preparation of 3-[2-(3-Aminopropoxy)-4-(ethylthio)-benzoylamino]-N-(5-chloropyridin-2-yl)pyridine-2-carboxamide

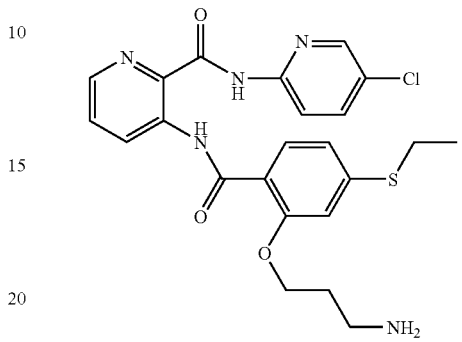

A. Methyl 2-Hydroxy-4-(ethylthio)benzoate

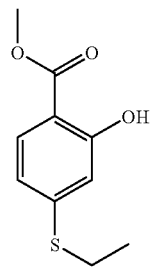

To a solution of methyl 4-fluoro-2-(methoxymethoxy)-benzoate (10.6 g, 50 mmol) and DMSO (20 mL), under nitrogen, was added sodium ethanethiolate (5.8 g, 55 mmol) in portions. The exothermic reaction was stirred for 19 h, diluted with water, and extracted with ethyl acetate. The organic layer was concentrated; and the residue was dissolved in ether, filtered through diatomaceus earth, and concentrated to give intermediate methyl 4-(ethylthio)-2-(methoxymethoxy)benzoate.

To this intermediate was added methylene chloride (75 mL), TFA (377 mL), and water (377 mL); and the mixture was stirred for 0.5 h. The reaction was concentrated and chromatographed (silica gel, 5% ethyl acetate/hexane) to give the title compound (5.8 g, 55%).

$^1$NMR (250 MHz, CDCl$_3$): δ 10.87 (s, 1H); 7.71 (d, J=8.5 Hz, 1H); 6.84 (d, J=1.8 Hz, 1H); 6.76 (dd, J=1.8, 8.5 Hz, 1H); 3.96 (s, 3H); 3.02 (q, J=7.3 Hz, 2H); 1.40 (t, J=7.3 Hz, 3H).

IS-MS, m/e 213.1 (m+1).

B. Methyl 2-(3-t-Butoxycarbonylaminopropoxy)-4-(ethylthio)benzoate

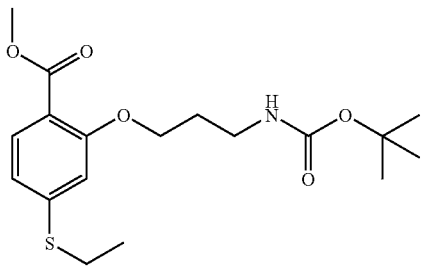

Using a procedure analogous to Example 1-D, methyl 2-hydroxy-4-(ethylthio)benzoate and 3-t-butoxycarbonylamino-propanol gave the title compound as a solid (10.41 g, 85%).

$^1$NMR (250 MHz, CHCl$_3$): δ 7.85 (d, J=8.2 Hz, 1H), 6.80 (m, 2H), 6.12 (br s, 1H), 4.14 (t, 5.8 Hz, 2H), 3.91 (s, 3H), 3.43 (m, 2H), 3.03 (q, J=7.3 Hz, 2H), 2.09 (m, 2H), 1.48 (s, 9H), 1.39 (t, J=7.3 Hz, 3H).

IS-MS, m/e: 370.1 (m+1).

C. 2-(3-t-Butoxycarbonylaminopropoxy)-4-(ethylthio)benzoic Acid

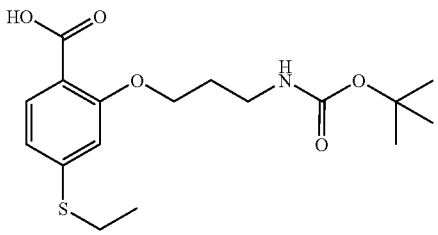

Using a procedure analogous to Example 4-C, methyl 2-(3-t-butoxycarbonylaminopropoxy)-4-(ethylthio)benzoate gave the title compound as a solid (8.28 g, 96%).

$^1$NMR (250 MHz, CDCl$_3$): δ 8.04 (d, J=8.5 Hz, 1H), 6.97 (dd, J=1.5, 8.5 Hz, 1H), 6.88 (d, J=1.5 Hz, 1H), 4.94 (br s, 1H), 4.27 (t, J=6.4 Hz, 2H), 3.05 (q, J=7.3 Hz, 2H), 2.11 (m, 2H), 1.44 (s, 9H), 1.40 (t, J=7.3 Hz, 3H).

IS-MS, m/e: 356.3 (m+1).

Analysis for C$_{17}$H$_{25}$NO$_5$S:

| Calcd: | C, 57.44; H, 7.09; N, 3.94; |
| Found: | C, 57.60; H, 7.05; N, 4.02. |

D. 3-[2-(3-t-Butoxycarbonylaminopropoxy)-4-(ethylthio)-benzoylamino]-N-(5-chloropyridin-2-yl)pyridine-2-carboxamide Using a procedure analogous to Example 1-G, 2-(3-t-butoxycarbonylaminopropoxy)-4-(ethylthio)benzoic acid and 3-amino-N-(5-chloropyridin-2-yl)pyridine-2-carboxamide gave the title compound as a solid (2.04 g, 67%).

$^1$NMR (300 MHz, CDCl$_3$): δ 12.45 (s, 1H), 10.91 (s, 1H), 9.36 (dd, J=1.1, 8.8 Hz, 1H), 8.34 (m, 2H), 8.30 (d, J=8.8 Hz, 1H), 8.00 (d, J=8.4 Hz, 1H), 7.75 (dd, J=2.6, 8.4 Hz, 1H), 7.53 (dd, J=4.4, 8.4 Hz, 1H), 7.05 (s, 1H), 6.97 (dd, J=1.5, 8.1 Hz, 1H), 6.93 (s, 1H), 4.97 (br s, 1H), 4.39 (t, J=6.2 Hz, 2H), 3.28 (m, J=5.9 Hz), 3.06 (q, J=7.3 Hz, 2H), 2.11 (m, J=6.2 Hz, 2H), 1.40 (t, J=7.3 Hz, 3H), 1.34 (s, 9H).

IS-MS, m/e: 585.8 (m+1).

Analysis for C$_{28}$H$_{32}$ClN$_5$O$_5$S:

| Calcd: | C, 57.38; H, 5.50; N, 11.95; |
| Found: | C, 57.26; H, 5.54; N, 11.89. |

E. 3-[2-(3-Aminopropoxy)-4-(ethylthio)benzoylamino]-N-(5-chloropyridin-2-yl)pyridine-2-carboxamide Using a procedure analogous to Example 1-H, 3-[2-(3-t-butoxycarbonylaminopropoxy)-4-(ethylthio)benzoylamino]-N-(5-chloropyridin-2-yl)pyridine-2-carboxamide gave the title compound as a solid (323 mg, 94%).

$^1$NMR (300 MHz, CDCl$_3$): δ 12.43 (s, 1H) 10.81 (s 1H), 9.28 (d, J=, 8.4 Hz, 1H), 8.24 (m, 3H), 7.93 (d, J=8.8 Hz, 1H), 7.64 (dd, J=2.6, 8.8 Hz, 1H), 7.44 (dd, J=2.6, 8.8 Hz, 1H), 6.89 (m, 2H), 4.35 (t, J=6.2 Hz, 2H), 2.96 (q, J=7.3 Hz, 2H), 2.77 (m, 2H), 1.97 (m, 2H) 1.43 (br s, 2H), 1.31 (t, J=7.3 Hz, 3H).

IS-MS, m/e: 486.4 (m+1).

Analysis for C$_{23}$H$_{24}$ClN$_5$O$_3$S.H$_2$O:

| Calcd: | C, 54.81; H, 5.20; N, 13.90; |
| Found: | C, 55.11; H, 4.76; N, 13.84. |

EXAMPLE 67

Preparation of 3-[2-(3-Aminopropoxy)-4-ethylsulfonylbenzoyl-amino]-N-(5-chloropyridin-2-yl)pyridine-2-carboxamide Using a procedures analogous to Example 3-A followed by Example 1-H, 3-[2-(3-t-butoxycarbonylaminopropoxy)-4-ethyl-sulfonylbenzoylamino]-N-(5-chloropyridin-2-yl)pyridine-2-carboxamide gave the title compound as a solid (1.0 g, 88%).

$^1$NMR (300 MHz, CDCl$_3$): δ 12.57 (s, 1H), 10.81 (s, 1H), 9.28 (dd, J=1.1, 8.8 Hz, 1H), 8.27 (m, 2H), 8.10 (d, J=8.1 Hz, 1H), 7.65 (dd, J=2.6, 8.8 Hz, 1H), 7.52 (m, 3H), 4.40 (t, J=6.2 Hz, 2H), 3.09 (q, J=7.3 Hz, 2H), 2.78 (t, J=6.6 Hz, 2H), 1.98 (m, 2H), 1.26 (t, J=7.3 Hz, 3H), 1.26 (br s, 2H).

IS-MS, m/e: 518.2 (m+1).

Analysis for C$_{23}$H$_{24}$ClN$_5$O$_5$S:

| Calcd: | C, 53.33; H, 4.67; N, 13.52; |
| Found: | C, 52.88; H, 4.54; N, 13.29. |

EXAMPLE 68

Preparation of 3-[2-(3-Aminopropoxy)-4-(ethylthio)benzoyl-amino]-N-(5-chloropyridin-2-yl)-6-methylpyridine-2-carboxamide

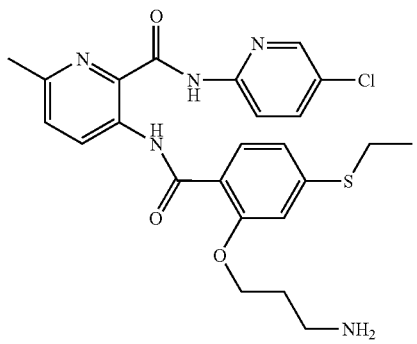

A. 3-[2-(3-tert-Butoxycarbonylaminopropoxy)-4-(ethylthio)benzoylamino]-N-(5-chloropyridin-2-yl)-6-methylpyridine-2-carboxamide Using a procedure analogous to Example 1-G, 2-(3-t-butoxycarbonylaminopropoxy)-4-(ethylthio)benzoic acid and 3-amino-N-(5-chloropyridin-2-yl)-6-methylpyridine-2-carboxamide gave the title compound as a solid (2.2 g, 67%).

$^1$NMR (250 MHz, CDCl$_3$): δ 12.40 (s, 1H), 10.96 (s, 1H), 9.26 (d, J=8.8 Hz, 1H), 8.37 (d, J=2.4 Hz, 1H), 8.35 (d, J=8.8 Hz, 1H), 8.03 (d, J=8.2 Hz, 1H), 7.78 (dd, J=2.4, 8.8 Hz, 1H), 7.41 (d, J=8.5 Hz, 1H), 7.00 (dd, J=1.5, 8.2 Hz, 1H), 6.95 (d, J=1.5 Hz, 1H), 5.03 (br s, 1H), 4.41 (t, J=6.4 Hz, 2H), 3.30 (m, J=6.4 Hz), 3.06 (q, J=7.3 Hz, 2H), 2.61 (s, 3H), 2.13 (m, J=6.4 Hz, 2H), 1.42 (t, J=7.3 Hz, 3H), 1.37 (s, 9H).

IS-MS, m/e: 600 (m+1).

Analysis for C$_{29}$H$_{34}$ClN$_5$O$_5$S:

| Calcd: | C, 58.04; H, 5.71; N, 11.67; |
| Found: | C, 57.74; H, 5.65; N, 11.62. |

B. 3-[2-(3-Aminopropoxy)-4-(ethylthio)benzoylamino]-N-(5-chloropyridin-2-yl)-6-methylpyridine-2-carboxamide Using a procedure analogous to Example 1-H, 3-[2-(3-t-butoxycarbonylaminopropoxy)-4-(ethylthio)benzoylamino]-N-(5-chloropyridin-2-yl)-6-methylpyridine-2-carboxamide gave the title compound as a solid (290 mg, 87%).

$^1$NMR (300 MHz, CDCl$_3$): δ 12.34 (s, 1H), 10.83 (s 1H), 9.15 (d, J=, 8.4 Hz, 1H), 8.26 (m, 2H), 7.91 (d, J=8.8 Hz, 1H), 7.65 (dd, J=2.6, 8.8 Hz, 1H), 7.29 (d, J=8.8 Hz, 1H), 6.88 (m, 2H), 4.33 (t, J=6.6 Hz, 2H), 2.96 (q, J=7.3 Hz, 2H), 2.80 (m, 2H), 2.48 (s, 3H), 2.00 (m, 2H), 1.67 (br s, 2H), 1.31 (t, J=7.3 Hz, 3H).

IS-MS, m/e: 500.0 (m+).

Analysis for C$_{24}$H$_{26}$ClN$_5$O$_3$S:

| Calcd: | C, 57.65; H, 5.24; N, 14.01; |
| Found: | C, 56.91; H, 5.05; N, 13.71. |

EXAMPLE 69

Preparation of 3-[2-(3-Aminopropoxy)-4-ethylsulfonylbenzoyl-amino]-N-(5-chloropyridin-2-yl)-6-methylpyridine-2-carboxamide

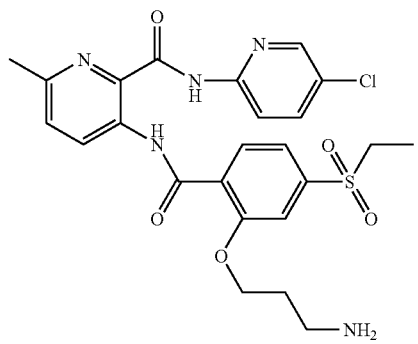

Using procedures analogous to Example 3-A followed by Example 1-H, 3-[2-(3-t-butoxycarbonylaminopropoxy)-4-(ethylthio)benzoylamino]-N-(5-chloropyridin-2-yl)-6-methylpyridine-2-carboxamide gave the title compound as a solid (507 mg, 30%).

$^1$NMR (250 MHz, CDCl$_3$): δ 12.46 (s, 1H), 10.81 (s, 1H), 9.08 (d, J=8.8 Hz, 1H), 8.26 (d, J=2.7 Hz, 2H), 8.18 (d, J=8.8 Hz, 1H), 8.04 (d, J=8.0 Hz, 1H), 7.64 (dd, J=2.3, 8.8 Hz, 1H), 7.52 (m, 2H), 7.32 (d, J=8.8 Hz, 1H), 4.38 (t, J=6.1 Hz, 2H), 3.11 (q, J=7.3 Hz, 2H), 2.95 (t, J=6.1 Hz, 2H), 2.95 (br s, 2H), 2.47 (s, 1H), 2.10 (m, 2H), 1.26 (t, J=7.3 Hz, 3H).

IS-MS, m/e: 532.1 (m+1).

Analysis for C$_{24}$H$_{26}$ClN$_5$O$_5$S.2 H$_2$O:

| Calcd: | C, 50.75; H, 5.32; N, 12.33; |
| Found: | C, 50.43; H, 4.47; N, 11.84. |

Isolation of N-(1-oxo-5-chloropyridin-2-yl)-3-[4-methylsulfonyl-2-(piperidin-4-yloxy)benzoylamino]-6-methyl-pyridine-2-carboxamide.

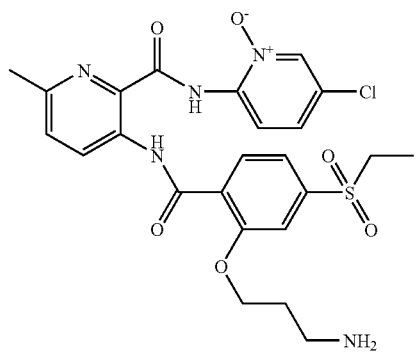

Chromatography of the crude product of the above example yielded the title pyridine N-oxide as a solid (417 mg, 21%).

$^1$NMR (300 MHz, CDCl$_3$): δ 12.26 (s, 1H), 9.14 (d, J=8.8 Hz, 1H), 8.42 (d, J=8.8 Hz, 1H), 8.28 (d, J=1.8 Hz, 1H), 8.12

(d, J=8.1 Hz, 1H), 7.55 (d, J=1.5 Hz, 1H), 7.52 (dd, J=1.5, 8.1, Hz, 1H), 7.36 (d, J=8.8 Hz, 1H), 7.27 (dd, J=2.2, 9.1 Hz, 1H), 4.40 (t, J=6.6 2H), 3.10 (q, J=7.3 Hz, 2H), 2.79 (t, J=6.6 Hz, 2H), 2.56 (s, 3H), 1.98 (m, 2H), 1.50 (br s, 3H), 1.26 (t, J=7.3 Hz, 3H).

IS-MS, m/e 548.2 (m+1).

Analysis for $C_{24}H_{26}ClN_5O_6S \cdot H_2O$:

| | |
|---|---|
| Calcd: | C, 50.93; H, 4.99; N, 12.37; |
| Found: | C, 50.97; H, 4.58; N, 12.31. |

EXAMPLE 70

Preparation of N-(5-Chloropyridin-2-yl)-3-[4-(ethylsulfonyl)-2-(piperidin-4-yloxy)benzoylamino]pyridine-2-carboxamide

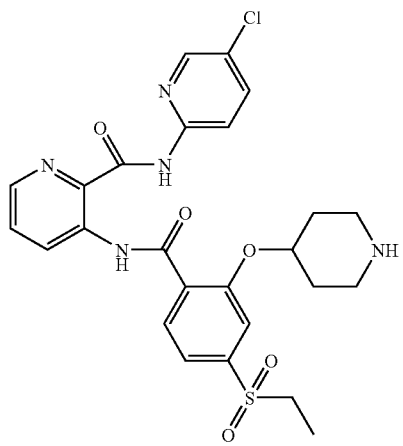

A. Methyl 2-(1-t-Butoxycarbonylpiperidin-4-yloxy)-4-(ethylthio)benzoate

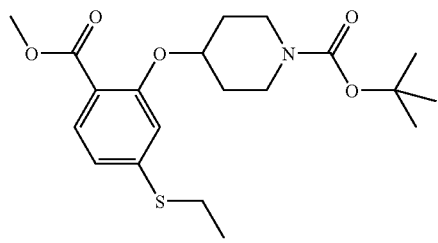

Using a method similar to Example 1-D, methyl 2-hydroxy-4-(ethylthio)benzoate and 1-Boc-4-hydroxy-piperidine gave the title compound (5.0 g, 12.64 mmol 46%).

IS-MS, m/e 396.1 (m+1).

B. 2-(1-t-Butoxycarbonylpiperidin-4-yloxy)-4-(ethylsulfonyl)benzoic Acid

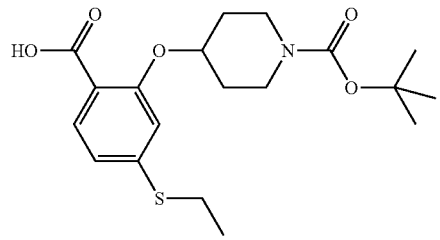

Using a procedure analogous to Example 4-C, methyl 2-(1-t-butoxycarbonylpiperidin-4-yloxy)-4-(ethylsulfonyl)-benzoate gave the title compound as a solid (4.76 g, 12.55 mmol, 99%).

$^1$NMR (300 MHz, CDCl$_3$): δ 8.09 (d, J=8.1 Hz, 1H), 6.98 (dd, J=1.8, 8.4 Hz, 1H), 6.88 (d, J=1.5 Hz, 1H), 4.71 (m, 1H), 3.79 (m, 2H), 3.27 (m, 2H), 3.03 (q, J=7.3 Hz, 2H), 2.07 (m, 2H), 1.84 (m, 2H), 1.47 (s, 9H), 1.39 (t, J=7.3 Hz, 3H).

IS-MS, m/e 382.4 (m+1).

Analysis for $C_{19}H_{27}NO_5S$:

| | |
|---|---|
| Calcd: | C, 59.82; H, 7.13; N, 3.67; |
| Found: | C, 59.58; H, 7.06; N, 3.72. |

C. 3-[2-(1-t-Butoxycarbonylpiperidin-4-yloxy)-4-ethyl-sulfonylbenzoylamino]-N-(5-chloropyridin-2-yl)pyridine-2-carboxamide

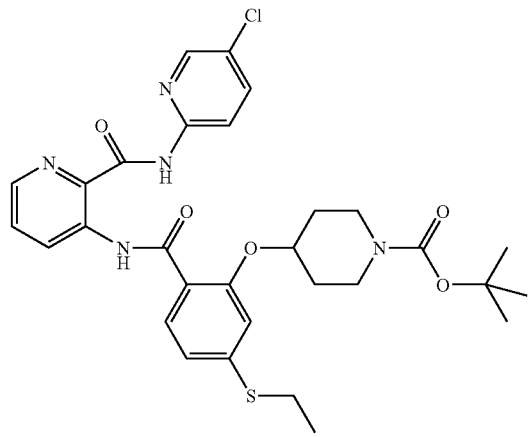

Using a procedure analogous to Example 1-G, 2-(1-t-butoxycarbonylpiperidin-4-yloxy)-4-(ethylthio)benzoic acid and 3-amino-N-(5-chloropyridin-2-yl)pyridine-2-carboxamide gave the title compound as a solid (1.67 g, 2.73 mmol, 53%).

IS-MS, m/e 612 (m+1).

D. N-(5-Chloropyridin-2-yl)-3-[4-ethylsulfonyl-2-(piperidin-4-yloxy)benzoylamino]pyridine-2-carboxamide Using procedures analogous to Example 3-A followed by Example 1-H, 3-[2-(1-t-butoxycarbonylpiperidin-4-yloxy)-4-(ethylthio)benzoylamino]-N-(5-chloropyridin-2-yl)pyridine-2-carboxamide gave the title compound as a solid (920 mg, 1.66 mmol, 68%).

¹NMR (300 MHz, CDCl₃): δ 12.54 (s, 1H), 10.87 (s, 1H), 9.35 (d, J=8.4 Hz, 1H), 8.37 (d, J=4.0 Hz, 1H), 8.34 (m, 1H), 8.12 (d, J=8.1 Hz, 1H), 7.71 (dd, J=2.2, 8.4 Hz, 1H), 7.56 (m, 3H), 4.73 (m, 1H), 3.17 (q, J=7.3 Hz, 2H), 3.11 (m, 2H), 2.77 (m, 2H), 2.11 (m, 2H), 1.98 (m, 2H), 1.34 (t, J=7.3 Hz, 3H).
IS-MS, m/e 542 (m−1).
Analysis for C₂₅H₂₆ClN₅O₅S.0.5 H₂O:

| Calcd: | C, 54.29; H, 4.92; N, 12.66; |
| Found: | C, 54.07; H, 4.79; N, 12.54. |

Isolation of N-(1-oxo-5-chloropyridin-2-yl)-3-[4-ethyl-sulfonyl-2-(piperidin-4-yloxy)benzoylamino]pyridine-2-carboxamide.

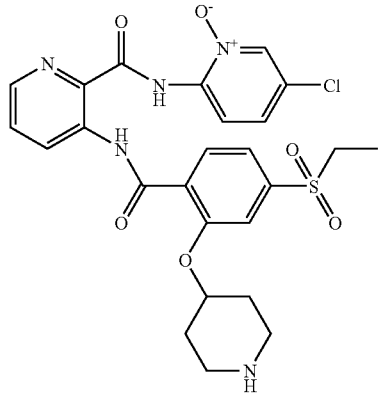

Chromatography of the crude product of the above example yielded the title pyridine N-oxide as a solid (110 mg, 8%).
¹NMR (300 MHz, CDCl₃): δ 12.36 (s, 1H), 12.35 (br s, 1H), 9.35 (d, J=8.8 Hz, 1H), 8.57 (d, J=8.8 Hz, 1H), 8.46 (dd, J=0.7, 4.4 Hz, 1H), 8.37 (d, J=2.2 Hz, 1H), 8.16 (d, J=8.4 Hz, 1H), 7.59 (m, 3H), 7.34 (dd, J=2.2, 9.1 Hz, 1H), 4.71 (m, 1H), 3.17 (q, J=7.3 Hz, 2H), 3.10 (m, 2H), 2.73 (m, 2H), 2.08 (m, 2H), 1.95 (m, 2H), 1.34 (t, J=7.3 Hz, 3H).
IS-MS, m/e 560.2 (m+1).
Analysis for C₂₅H₂₆ClN₅O₆S.0.5H₂O:

| Calcd: | C, 52.76; H, 4.78; N, 12.31; |
| Found: | C, 52.44; H, 4.59; N, 12.04. |

EXAMPLE 71

Preparation of 3-[2-(3-Aminopropoxy)-4-(propylsulfonyl)-benzoylamino]-N-(5-chloropyridin-2-yl)pyridine-2-carboxamide

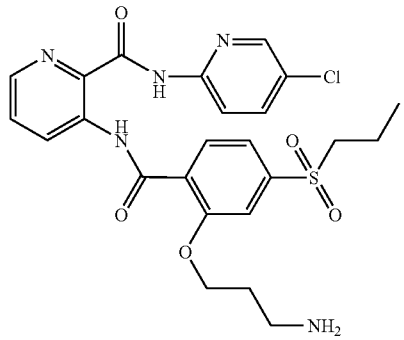

A. Methyl 2-hydroxy-4-(propylthio)benzoate

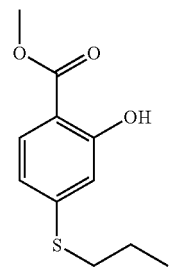

Using a procedure analogous to Example 66-A, methyl 4-fluoro-2-(methoxymethoxy)benzoate and potassium propanethiolate gave the title compound (6.1 g, 55%).
¹NMR (300 MHz, CDCl₃): δ 10.83 (s, 1H), 7.67 (d, J=8.4 Hz, 1H), 6.80 (d, J=1.8 Hz, 1H), 6.73 (dd, J=1.8, 8.4 Hz, 1H), 3.92 (s, 3H), 2.94 (t, J=7.3 Hz, 2H), 1.74 (m, 2H), 1.05 (t, J=7.3 Hz, 3H).
IS-MS, m/e 227.1 (m+1).

B. Methyl 2-(3-t-Butoxycarbonylaminopropoxy)-4-(propylthio)benzoate

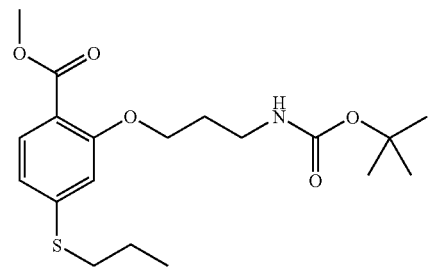

Using a procedure analogous to Example 1-D, methyl 2-hydroxy-4-(propylthio)benzoate and 3-t-butoxycarbonylaminopropanol gave the title compound (5.57 g, 54%).
¹NMR (300 MHz, CHCl₃): δ 7.80 (d, J=8.1 Hz, 1H), 6.85 (dd, J=1.5, 8.1 Hz, 1H), 6.82 (d, J=1.5 Hz, 1H), 5.86 (br s, 1H), 4.11 (t, J=5.5 Hz, 2H), 3.88 (s, 3H), 3.46 (m, 2H), 2.95 (t, J=7.3 Hz, 2H), 2.04 (m, 2H), 1.73 (m, 2H), 1.45 (s, 9H), 1.05 (t, J=7.3 Hz, 3H).
IS-MS, m/e: 384.2 (m+1).

C. 2-(3-t-Butoxycarbonylaminopropoxy)-4-(propylthio)-benzoic Acid

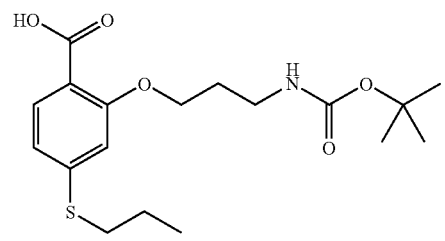

Using a procedure analogous to Example 4-C, methyl 2-(3-t-butoxycarbonylaminopropoxy)-4-(propylthio)benzoate gave the title compound as a solid (5.12 g, 95%).
¹NMR (300 MHz, CDCl₃): δ 8.01 (d, J=8.4 Hz, 1H), 6.95 (dd, J=1.5, 8.4 Hz, 1H), 6.86 (d, J=1.5 Hz, 1H), 4.87 (br s, 1H), 4.25 (t, J=6.2 Hz, 2H), 3.35 (m, 2H), 2.97 (t, J=7.3 Hz, 2H), 2.09 (m, 2H), 1.74 (m, 2H), 1.42 (s, 9H), 1.06 (t, J=7.3 Hz, 3H).
IS-MS, m/e: 370.1 (m+1).

Analysis for $C_{18}H_{27}NO_5S$:

| | |
|---|---|
| Calcd: | C, 58.51; H, 7.37; N, 3.79; |
| Found: | C, 57.91; H, 7.20; N, 3.86. |

D. 3-[2-(3-t-Butoxycarbonylaminopropoxy)-4-(propylthio)-benzoylamino]-N-(5-chloropyridin-2-yl)pyridine-2-carboxamide Using a procedure analogous to Example 1-G, 2-(3-t-butoxycarbonylaminopropoxy)-4-(propylthio)benzoic acid and 3-amino-N-(5-chloropyridin-2-yl)pyridine-2-carboxamide gave the title compound as a solid product (2.82 g, 90%).

$^1$NMR (300 MHz, CDCl$_3$): δ 12.39 (s, 1H), 11.18 (br s, 1H), 9.36 (dd, J=1.1, 8.4 Hz, 1H), 8.36 (m, 3H), 8.00 (d, J=8.4 Hz, 1H), 7.82 (dd, J=2.6, 8.8 Hz, 1H), 7.54 (dd, J=4.4, 8.4 Hz, 1H), 6.96 (dd, J=1.5, 8.4 Hz, 1H), 6.93 (d, J=1.5 1H), 4.90 (br s, 1H), 4.38 (t, J=6.2 Hz, 2H), 3.27 (m, 2H), 2.99 (t, J=7.3 Hz, 2H), 2.11 (m, J=6.2 Hz, 2H), 1.75 (m, J=7.3 Hz, 2H), 1.34 (s, 9H), 1.08 (t, J=7.3 Hz, 3H).

IS-MS, m/e: 600.2 (m+1).

Analysis for $C_{29}H_{34}ClN_5O_5S$:

| | |
|---|---|
| Calcd: | C, 58.04; H, 5.71; N, 11.67; |
| Found: | C, 57.64; H, 5.58; N, 11.56. |

E. 3-[2-(3-Aminopropoxy)-4-(propylsulfonyl)benzoylamino]-N-(5-chloropyridin-2-yl)pyridine-2-carboxamide Using procedures analogous to Example 3-A followed by Example 1-H, 3-[2-(3-t-butoxycarbonylaminopropoxy)-4-(propylthio)benzoylamino]-N-(5-chloropyridin-2-yl)pyridine-2-carboxamide gave the title compound as a solid (1.17 g, 82%).

$^1$NMR (300 MHz, DMSO-d$_6$): δ 9.20 (dd, J=1.1, 8.8 Hz, 1H), 8.49 (dd, J=1.1, 4.4 Hz, 1H), 8.47 (m, 1H), 8.25 (d, J=8.8 Hz, 1H), 8.09 (d, J=8.1 Hz, 1H), 8.03 (dd, J=2.6, 8.8 Hz, 1H), 7.79 (dd, J=4.4, 8.8 Hz, 1H), 7.71 (d, J=1.1 Hz, 1H), 7.61 (dd, J=1.1, 8.1 Hz, 1H), 6.68 (br s, 1H), 4.47 (t, J=6.2 Hz, 2H), 3.41 (m, 2H), 3.30 (br s, 1H), 2.65 (t, J=6.2 Hz, 2H), 1.91 (m, 2H), 1.60 (m, 2H), 0.96 (t, J=7.3 Hz, 3H).

IS-MS, m/e: 532.1 (m+1).

Analysis for $C_{24}H_{26}ClN_5O_5S$:

| | |
|---|---|
| Calcd: | C, 54.18; H, 4.93; N, 13.16; |
| Found: | C, 53.85; H, 4.90; N, 13.21. |

EXAMPLE 72

Preparation of N-(5-Chloropyridin-2-yl)-2-[4-(ethylsulfonyl)-2-(3S-pyrrolidin-3-yloxy)benzoylamino]pyridin-2-carboxamide

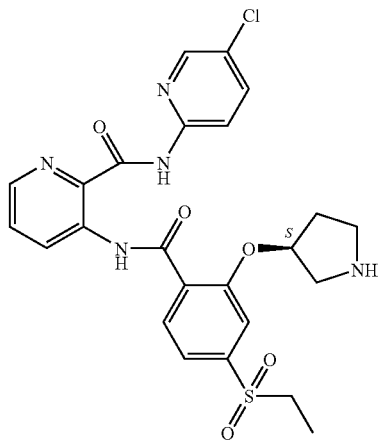

A. Methyl 4-(Ethylthio)-2-(3S-1-t-butoxycarbonyl-pyrrolidin-3-yloxy)benzoate

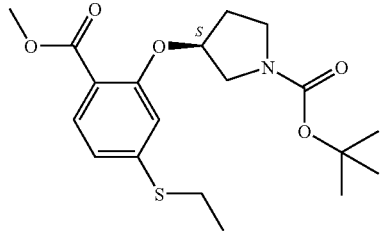

Using a procedure analogous to Example 1-D, methyl 4-(ethylthio)-2-hydroxybenzoate and 3R-1-t-butoxycarbonyl-3-hydroxypyrrolidine gave the title compound as a solid (2.91 g, 85%).

$^1$NMR (300 MHz, CDCl$_3$)

ES-MS, m/e 404.1 (m+Na).

B. 4-(Ethylthio)-2-(3S-1-t-butoxycarbonylpyrrolidin-3-yloxy)benzoic Acid

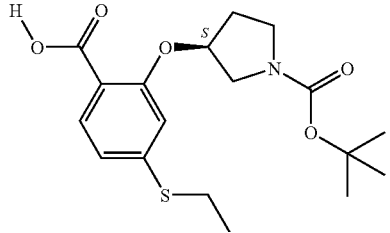

Using a procedure analogous to Example 4-C, methyl 4-(ethylthio)-2-(3S-1-t-butoxycarbonylpyrrolidin-3-yl-oxy)benzoate gave the title compound (2.47 g, 88%).

$^1$NMR (300 MHz, CDCl$_3$)

ES-MS, m/e: 390.1 (m+1).

Analysis for $C_{18}H_{25}NO_5S$:

| | |
|---|---|
| Calcd: | C, 58.84; H, 6.86; N, 3.81; |
| Found: | C, 58.42; H, 6.84; N, 3.54. |

C. N-(5-Chloropyridin-2-yl)-2-[4-(ethylthio)-2-(3S-1-t-butoxycarbonylpyrrolidin-3-yloxy)benzoylamino]pyridin-2-carboxamide Using a procedure analogous to Example 1-G, N-(5-chloropyridin-2-yl)-3-aminopyridin-2-carboxamide and 4-(ethylthio)-2-(3S-1-t-butoxycarbonylpyrrolidin-3-yl-oxy)benzoic acid gave the title compound as a solid (1.07 g, 51%).

$^1$NMR (300 MHz, CDCl$_3$)
ES-MS, m/e: 598.2 (m+1).
Analysis for $C_{29}H_{32}ClN_5O_5S$:

| | |
|---|---|
| Calcd: | C, 58.24; H, 5.39; N, 11.71; |
| Found: | C, 57.83; H, 5.36; N, 11.65. |

D. N-(5-chloropyridin-2-yl)-2-[4-(ethylsulfonyl)-2-(3S-pyrrolidin-3-yloxy)benzoylamino]pyridin-2-carboxamide Using a sequential procedures analogous to Examples 3-A and 1-H, N-(5-chloropyridin-2-yl)-2-[4-(ethylthio)-2-(3S-1-t-butoxycarbonylpyrrolidin-3-yloxy)benzoylamino]pyridin-2-carboxamide gave the title compound as a foam (0.77 g, 80%).

$^1$NMR (300 MHz, DMSO-d$_6$)
ES-MS, m/e: 529.9 (m+1).
Analysis for $C_{24}H_{24}ClN_5O_5S \cdot 0.5H_2O$:

| | |
|---|---|
| Calcd: | C, 53.48; H, 4.68; N, 12.99; |
| Found: | C, 53.60; H, 4.50; N, 13.05. |

EXAMPLE 73

Preparation of 3-[4-(Methylsulfonylmethyl)-2-(4-piperidinyl-oxy)benzoylamino]-N-(5-chloropyridin-2-yl)pyridine-2-carboxamide

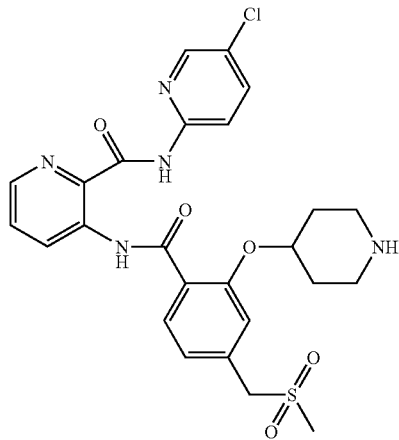

A. Methyl 2-Methoxy-4-methylbenzoate

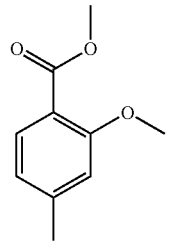

To a mixture of 2-hydroxy-4-methylbenzoic acid (30.43 g, 200 mmol), K$_2$CO$_3$ (62.19 g, 450 mmol) and DMF (600 mL) was added methyl iodide (28.01 mL, 450 mmol). The reaction was stirred for 18 h, poured into ice/water (1.2 L), and extracted with EtOAc (2×300 mL). The combined organic layer was washed with brine, satd NaHCO$_3$ and dried (MgSO$_4$). The resulting solution was concentrated and distilled to give the title compound as a pale yellow liquid (32.73 g, 91%, bp 120-4° C./1333 Pa, 10 mm).

1NMR (400 MHz, CDCl$_3$) δ 2.40 (s, 3H), 3.90 (s, 3H), 3.93 (s, 3H), 6.80 (m, 2H), 7.75 (d, J=7.6 Hz, 1H).
FIA-MS, m/e: 180.9 (m+1).

B. Methyl 2-Methoxy-4-(bromomethyl)benzoate

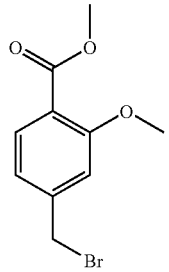

To a refluxing mixture of methyl 2-methoxy-4-methylbenzoate (21.625 g, 120 mmol) in CCl$_4$ (240 mL) was added dropwise a solution of bromine (6.19 mL, 120 mmol) in CCl$_4$ (75 mL) over 1.5 h. During the bromine addition the reaction was irradiated with a 250 W tungsten lamp. After the addition, the reaction was refluxed for 15 min and concentrated, and vacuum pumped to give methyl 2-methoxy-4-(bromomethyl)benzoate as an oil (29.864 g, 96%).

$^1$NMR (400 MHz, CDCl$_3$): δ partial 2.40 (s, 3H), 3.87 (s, 3H), 3.91 (s, 3H), 4.44 (s, 2H).
FIA-MS, m/e: 259 (m+1).

C. Methyl 2-Methoxy-4-(methylthiomethyl)benzoate

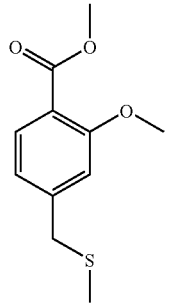

To a mixture of methyl 2-methoxy-4-(bromomethyl)-benzoate (10.36 g, 40 mmol) and DMF (80 mL) was added solid sodium methylthiolate (4.21 g, 60 mmol), and the mixture was stirred for 18 h. The reaction was poured into EtOAc (300 mL) and water (400 mL), and partitioned. The aqueous layer was extracted with EtOAc (2×200 mL). The combined organic layer was washed with water (3×100 mL), dried (MgSO$_4$) and concentrated. The resulting residue was chromatographed (400 g SiO$_2$, hexanes to 10% EtOAc/hexanes) to give the title compound as colorless oil (3.8 g, 36%).

$^1$NMR (400 MHz, CDCl$_3$): δ 2.00 (s, 3H), 3.68 (s, 2H), 3.88 (s, 3H), 3.92 (s, 3 h), 6.90 (d, J=7.7 Hz, 1H), 6.95 (s, 1H), 7.75 (d, J=7.7 Hz, 1H).
FIA-MS, m/e: 226.9 (m+1).
Analysis for $C_{11}H_{14}O_3S$:

|   |   |
|---|---|
| Calcd: | C, 58.38; H, 6.24; |
| Found: | C, 56.57; H, 5.98. |

D. 2-Hydroxy-4-(methylthiomethyl)benzoic Acid

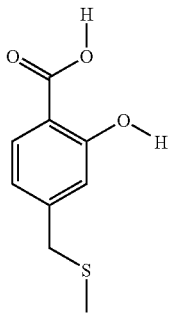

To a −78° C. mixture of methyl 2-methoxy-4-(methylthiomethyl)benzoate (5.29 (g, 23.36 mmol) and $CH_2Cl_2$ (80 mL) was added $BBr_3$ (2.4 mL, 24.52 mmol) dropwise. The reaction was stirred for 15 min, warmed to room temperature and stirred for 6 h. The reaction mixture was added to ice/water (100 mL). The suspension was added 2 M NaOH to dissolve the precipitate. After partitioning, the organic layer was extracted with 2 M NaOH. The combined aqueous layer was washed with EtOAc, acidified with 12 N HCl and cooled to room temperature. The solid was filtered with water wash and vacuum dried to give the title compound as a light yellow solid (2.96 g, 64%).

$^1$NMR (300 MHz, DMSO-$d_6$): δ 1.91 (s, 3H), 3.67 (s, 2H), 6.86 (d, J=1.5 Hz, 1H), 6.88 (s, 1H), 7.74 (d, J=8.8 Hz, 1H), 11.25 (br s, 1H).

FIA-MS, m/e: 199 (m+1).

E. Methyl 2-Hydroxy-4-(methylthiomethyl)benzoate

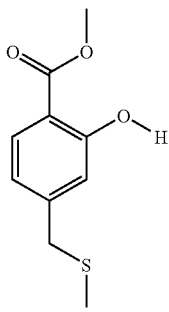

To a mixture of 2-hydroxy-4-(methylthiomethyl)benzoic acid (3.96 g, 20 mmol), $CH_2Cl_2$ (75 mL), and MeOH (15 mL) was added a solution of 2 M trimethylsilyldiazomethane ($TMSCHN_2$) in hexane (10.5 mL, 21 mmol) over 30 min. After stirring for 10 min, the reaction was concentrated and vacuum dried. The residue was chromatographed (250 g $SiO_2$, hexanes to 5% EtOAc/hexanes) to give the title compound as a colorless oil (3.96 g, 93%).

$^1$NMR (300 MHz, $CDCl_3$): δ 2.02 (s, 3H), 3.64 (s, 2 h), 3.96 (s, 3H), 6.87 (dd, J=1.5, 8.1 Hz, 1H), 6.93 (d, J=1.5 Hz, 1H), 7.80 (d, J=8.1 Hz, 1H), 1078 (s, 1H).

FIA-MS, m/e: 213.1 (m+1).

F. Methyl 2-[4-(methylthiomethyl)-2-(1-t-butoxycarbonyl-piperidin-4-yloxy)benzoate

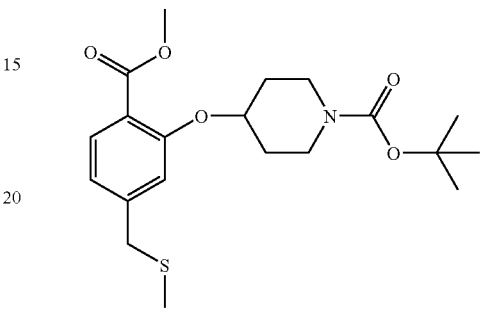

Using a procedure analogous to Example 1-D, methyl 2-hydroxy-4-(methylthiomethyl)benzoate and 1-t-butoxycarbonyl-4-hydroxypiperidine gave the title as a colorless oil (3.4 g, 98%).

$^1$NMR (250 MHz, $CDCl_3$): δ 1.50 (s, 9H), 1.80 (m, 4H), 2.02 (s, 3H), 3.55 (m, 4H), 3.68 (s, 2H), 3.90 (s, 3H), 4.64 (m, 1H), 6.94 (dd, J=1.1, 7.6 Hz, 1H), 6.98 (s, 1H), 7.78 (d, J=7.6 Hz, 1H).

FIA-MS, m/e: 396.1 (m+1).

G. 2-[4-(Methylthiomethyl)-2-(1-t-butoxycarbonylpiperidin-4-yloxy)benzoic Acid

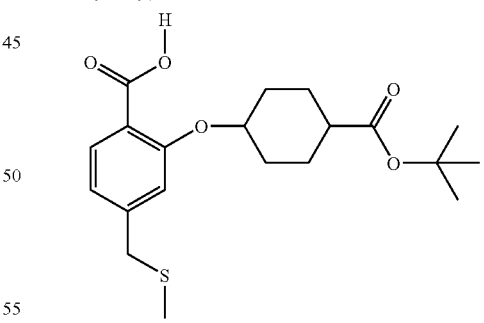

Using a procedure analogous to Example 1-E, methyl 2-[4-(methylthiomethyl)-2-(1-t-butoxycarbonylpiperidin-4-yloxy)benzoate gave the title compound as a pale yellow oil (2.57 g, 81%).

$^1$NMR (300 MHz, $CDCl_3$): δ 1.40 (s, 9H), 1.57 (m, 2H), 1.77 (m, 2H), 1.96 (s, 3H), 3.33 (m, 2 h), 3.41 (m, 2 h), 3.69 (s, 2H), 4.66 (m, 1 h), 6.93 (dd, J=1.1, 8.0 Hz, 1H), 7.11 (s, 1 h), 7.59 (d, J=7.7 Hz, 1H).

FIA-MS, m/e: 382.4 (m+1).

H. 3-[4-(Methylthiomethyl)-2-(1-t-butoxycarbonylpiperidin-4-yloxy)benzoylamino]-N-(5-chloropyridin-2-yl)pyridine-2-carboxamide

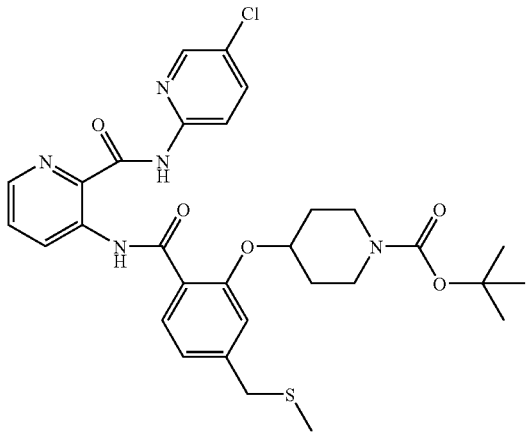

Using a procedure analogous to Example 1-G, 3-[4-(methylthiomethyl)-2-(1-t-butoxycarbonylpiperidin-4-yloxy)-benzoic acid and 3-amino-N-(5-chloropyridin-2-yl)pyridine-2-carboxamide gave the title compound as a white solid (751 mg, 43%).

$^{1}$NMR (300 MHz, DMSO-$d_6$): δ 1.28 (s, 9H), 1.77 (m, 2H), 1.97 (m, 2H), 2.00 (s, 3H), 3.04 (m, 2H), 3.70 (m, 2H), 3.76 (s, 2H), 4.76 (m, 1H), 7.05 (d, J=8.4 Hz, 1H), 7.28 (s, 1H), 7.72 (dd, J=4.4, 8.8 Hz, 1H), 7.83 (d, 8.1 Hz, 1H), 7.96 (dd, J=2.6, 9.1 Hz, 1H), 8.21 (d, J=8.8 Hz, 1H), 8.46 (m, 2H), 9.20 (d, J=8.4 Hz, 1H), 10.80 (s, 1H), 12.24 (s, 1H).

FIA-MS, m/e: 612.1 (m+1).

Analysis for $C_{30}H_{34}ClN_5O_5S$:

| | |
|---|---|
| Calcd: | C, 58.86; H, 5.60; N, 11.44; |
| Found: | C, 58.76; H, 5.56; N, 11.39. |

I. 3-[4-(Methylsulfonylmethyl)-2-(1-t-butoxycarbonyl-piperidin-4-yloxy)benzoylamino]-N-(5-chloropyridin-2-yl)-pyridine-2-carboxamide

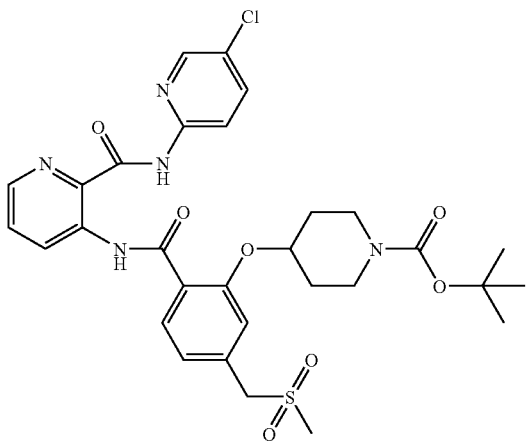

Using a procedure analogous to Example 3-A, 3-[4-(methylthiomethyl)-2-(1-t-butoxycarbonylpiperidin-4-yloxy)-benzoylamino]-N-(5-chloropyridin-2-yl)pyridine-2-carboxamide gave the title compound as a white solid (551 mg, 75%).

$^{1}$NMR (250 MHz, DMSO-$d_6$): δ 1.29 (s, 9H), 1.79 (br m, 2H), 1.96 (br m, 2H), 2.98 (s, 3H), 3.06 (m, 2H), 3.68 (m, 2H), 4.60 (s, 2H), 4.72 (br m, 1H), 7.18 (dd, J=0.8, 8.0 Hz, 1H), 7.40 (s, 1H), 7.80 (dd, J=4.6, 8.8 Hz, 1H), 7.89 (d, J=8.0 Hz, 1H), 7.99 (dd, J=2.7, 8.8 Hz, 1H), 8.23 (d, 8.4 Hz, 1H), 8.47 (m, 2H), 9.22 (dd, J=1.1, 8.8 Hz, 1H), 10.83 (s, 1H), 12.30 (s, 1H).

FIA-MS, m/e: 644.3 (m+1).

Analysis for $C_{30}H_{34}ClN_5O_7S$:

| | |
|---|---|
| Calcd: | C, 55.94; H, 5.32; N, 10.87; |
| Found: | C, 55.39; H, 5.23; N, 10.85. |

J. 2-[4-(Methylsulfonylmethyl)-2-(4-piperidinyloxy)-benzoylamino]-N-(5-chloropyridin-2-yl)pyridine-2-carboxamide

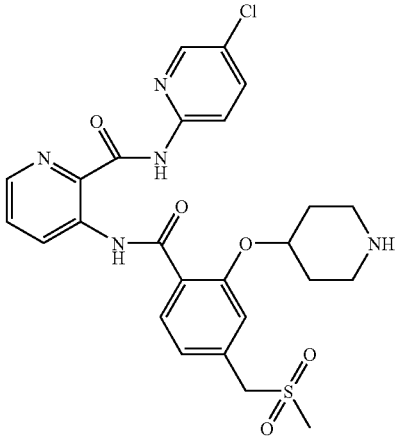

Using a procedure analogous to Example 1-H, 3-[4-(methylsulfonylmethyl)-2-(1-t-butoxycarbonylpiperidin-4-yloxy)benzoylamino]-N-(5-chloropyridin-2-yl)pyridine-2-carboxamide gave the title compound as a white solid (377 mg, 89%).

$^{1}$NMR (250 MHz, DMSO-$d_6$) δ 1.78 (m, 2H), 1.95 (m, 2H), 2.52 (m, 2H), 2.88 9 m, 2H), 2.96 (s, 3H), 4.58 (s, 2H), 4.64 (m, 1H), 7.14 (d, J=8.1 Hz, 1H), 7.36 (s, 1H), 7.77 (dd, J=4.4, 8.8 Hz, 1H), 7.87 (d, J=8.1 Hz, 1H), 8.00 (dd, J=2.6, 8.8 Hz, 1H), 8.35 (d, J=8.8 Hz, 1H), 8.47 (m, 2H), 9.22 (dd, J=1.1, 8.8 Hz, 1H), 12.28 (s, 1H).

FIA-MS, m/e: 544.3 (m+1).

Analysis for $C_{25}H_{26}ClN_5O_5S$:

| | |
|---|---|
| Calcd: | C, 54.30; H, 4.92; N, 12.66; |
| Found: | C, 54.55; H, 4.81; N, 12.32. |

EXAMPLE 74

Preparation of 3-[4-Methylsulfonylmethyl-2-(3-aminopropoxy)-benzoylamino]-N-(5-chloropyridin-2-yl)pyridine-2-carboxamide

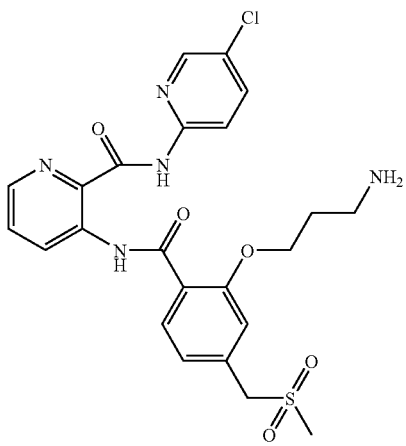

A. Methyl 4-(Methylthiomethyl)-2-[3-(t-butoxycarbonylamino)propoxy]benzoate

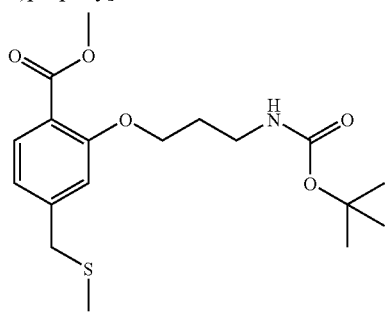

Using a procedure analogous to Example 1-D, methyl 4-(methylthiomethyl)-2-hydroxybenzoate and 3-(t-butoxycarbonylamino)propanol gave the title compound as a white solid (2.70 g, 76%).

$^1$NMR (400 MHz, CDCl$_3$): δ 1.45 (s, 9H), 2.00 (s, 3H), 2.04 (m, 2H), 3.40 (m, 2H), 3.67 (s, 2H), 3.92 (s, 3H), 4.15 (m, 2H), 6.02 (br m, 1H), 6.92 (d, J=7.6 Hz, 1H), 6.95 (s, 1H), 7.83 (d, J=7.6 Hz, 1H).

FIA-MS, m/e: 370.0 (m+1).

B. 4-(Methylthiomethyl)-2-[3-(t-butoxycarbonylamino)propoxy]benzoic Acid

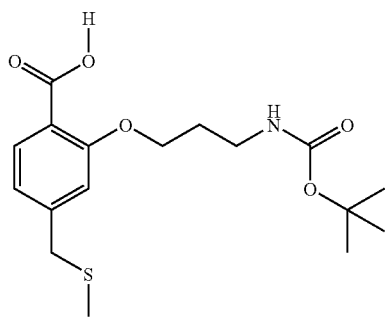

Using a procedure analogous to Example 1-E, methyl 4-(methylthiomethyl)-2-[3-(t-butoxycarbonylamino)propoxy]-benzoate gave the title compound as an oil (2.44 g, 98%).

$^1$NMR (250 MHz, DMSO-d$_6$): δ 1.37 (s, 9H), 1.84 (t, J=6.4 Hz, 2H), 1.97 (s, 3H), 3.12 (m, 2H), 3.71 (s, 2H), 4.04 (t, J=6.1 Hz, 2H), 6.90 (m, 1H), 6.93 (d, J=7.9 Hz, 1H), 7.04 (s, 1H), 7.61 (d, J=7.6 Hz, 1H), 12.50 (br s, 1H).

FIA-MS, m/e: 356.3 (m+1);

HRMS (C$_{17}$H$_{25}$NO$_5$SNa) theoretical 378.1351, found 378.1342.

C. 3-[4-(Methylthiomethyl-2-[3-(t-butoxycarbonylamino)-propoxy]benzoylamino]-N-(5-chloropyridin-2-yl)pyridine-2-carboxamide

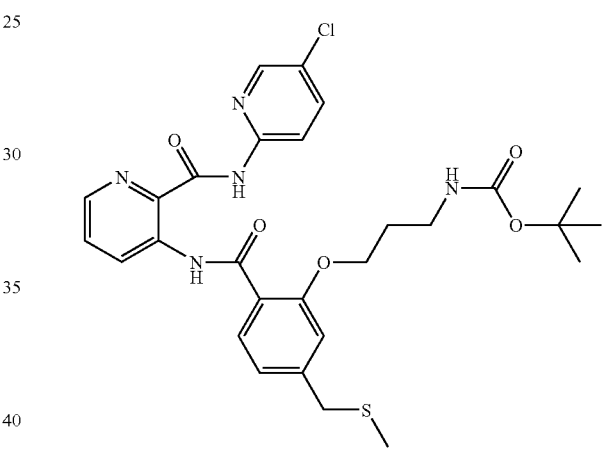

Using a procedure analogous to Example 1-G, 4-(methylthiomethyl)-2-[3-(t-butoxycarbonylamino)propoxy]-benzoic acid and 3-amino-N-(5-chloropyridin-2-yl)pyridine-2-carboxamide gave the title compound as a white solid (891 mg, 46%).

$^1$NMR (250 MHz, DMSO-d$_6$): δ 1.98 (m, 2H), 2.00 (s, 3H), 3.05 (m, 2H), 3.76 (s, 2H), 4.33 (t, J=6.6 Hz, 2H), 6.78 (m, 1H), 7.05 (dd, J=0.7, 8.0, 1H), 7.21 (s, 1H), 7.75 (dd, J=4.4, 8.8 Hz, 1H), 7.90 (d, J=8.0 Hz, 1H), 8.02 (dd, 2.6, 8.8 Hz, 1H), 8.27 (d, J=8.8 Hz, 1H), 8.45 (m, 2H), 9.23 (dd, J=0.7, 8.8 Hz, 1H), 10.82 (s, 1H), 12.40 (s, 1H).

FIA-MS, m/e: 586.2 (m+1).

Analysis for C$_{28}$H$_{32}$ClN$_5$O$_5$S:

| | |
|---|---|
| Calcd: | C, 57.38; H, 5.50; N, 11.95; |
| Found: | C, 57.48; H, 5.48; N, 12.12. |

D. 3-[4-(Methylsulfonylmethyl)-2-[3-(t-butoxycarbonylamino)propoxy]benzoylamino]-N-(5-chloropyridin-2-yl)-pyridine-2-carboxamide

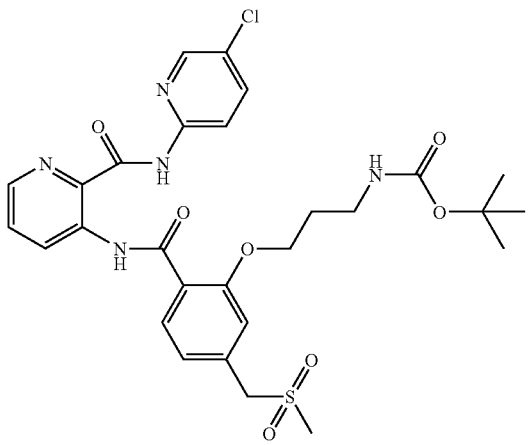

Using a procedure analogous to Example 3-A, 3-[4-methylthiomethyl-2-[3-(t-butoxycarbonylamino)propoxy]-benzoylamino]-N-(5-chloropyridin-2-yl)pyridine-2-carboxamide gave the title compound as a white solid (681 mg, 93%).

$^1$NMR (300 MHz, DMSO-$d_6$): δ 1.26 (s, 9H), 1.96 (m, 2H), 2.97 (s, 3H), 3.05 (m, 2H), 4.32 (t, J=5.9 Hz, 2H), 4.59 (s, 2H), 6.79 (m, 1H), 7.17 (d, J=8.1 Hz, 1H), 7.33 (s, 1H), 7.77 (dd, J=4.4, 8.4 Hz, 1H), 7.95 (d, J=8.1 Hz, 1H), 8.02 (dd, J=2.6, 8.4 Hz, 1H), 8.27 (d, J=4.4 Hz, 1H), 8.46 (m, 2H), 9.24 (d, J=8.8 Hz, 1H), 10.81 (s, 1H), 12.45 (s, 1H).

FIA-MS, m/e: 618.4 (m+1).

Analysis for $C_{28}H_{32}ClN_5O_7S \cdot 0.5\ H_2O$:

| | |
|---|---|
| Calcd: | C, 53.63; H, 5.30; N, 11.17; |
| Found: | C, 53.82; H, 5.20; N, 11.26. |

E. 3-[4-(Methylsulfonylmethyl)-2-(3-aminopropoxy)benzoyl-amino]-N-(5-chloropyridin-2-yl)pyridine-2-carboxamide

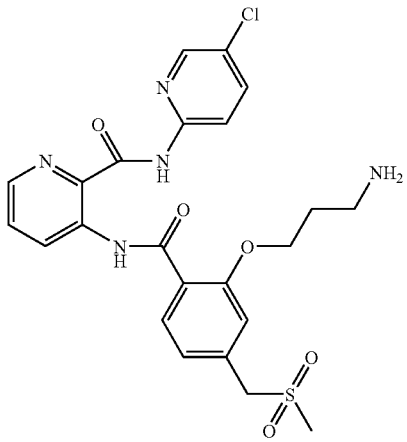

Using a procedure analogous to 1-H, 3-[4-(methyl-sulfonylmethyl)-2-[3-(t-butoxycarbonylamino)propoxy]benzoylamino]-N-(5-chloropyridin-2-yl)pyridine-2-carboxamide gave the title compound as a white solid (244 mg, 46%).

$^1$NMR (300 MHz, DMSO-$d_6$): δ 2.09 (m, 2H), 2.91 (t, J=7.0 Hz, 2H), 2.99 (s, 3H), 4.40 (t, J=5.9 Hz, 2H), 4.60 (s, 2 h), 7.19 (d, J=8.1 Hz, 1H), 7.35 (s, 1H), 7.79 (dd, J=4.4, 8.4 Hz, 1H), 7.92 (d, J=8.1 Hz, 1H), 8.02 (dd, J=2.6, 8.4 Hz, 1H), 8.25 (d, J=4.4 Hz, 1H), 8.48 (m, 2H), 9.24 (d, J=8.8 Hz, 1H).

FIA-MS, m/e: 518.2 (m+1);

HRMS ($C_{28}H_{32}ClN_5O_5S$) theoretical 518.1265, found 518.1282.

EXAMPLE 75

Preparation of 3-[4-Methylsulfonylmethyl-2-(3-aminopropoxy)-benzoylamino]-6-methyl-N-(5-chloropyridin-2-yl)pyridine-2-carboxamide

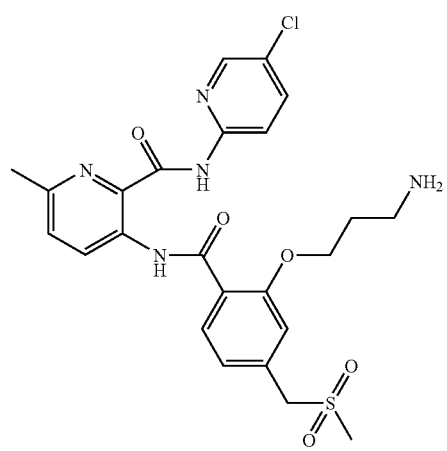

A. 3-[4-Methylthiomethyl-2-[3-(t-butoxycarbonylamino)-propoxy]benzoylamino]-6-methyl-N-(5-chloropyridin-2-yl)-pyridine-2-carboxamide

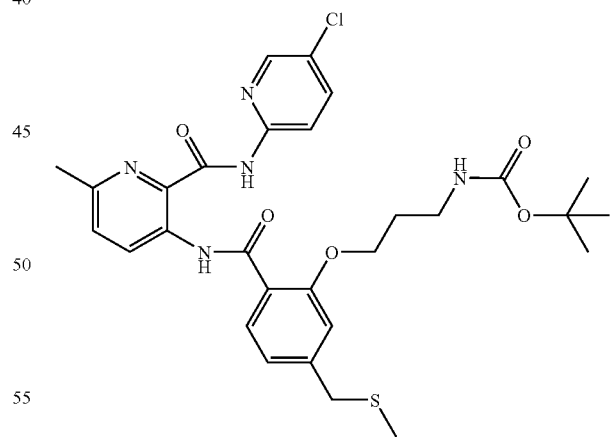

Using a procedure analogous to Example 1-G, 2-[4-methylthiomethyl-2-[3-(t-butoxycarbonylamino)propoxy]benzoic acid and 3-amino-6-methyl-N-(5-chloropyridin-2-yl) pyridine-2-carboxamide gave the title compound as a white glassy solid (1.41 g, 71%).

$^1$NMR (250 MHz, DMSO-$d_6$)

High Res. ES-MS: 622.1848; calc. for $C_{29}H_{34}ClN_5O_5S$+ Na: 622.1867.

B.   3-[4-Methylsulfonylmethyl-2-[3-(t-butoxycarbonylamino)-propoxy]benzoylamino]-6-methyl-N-(5-chloropyridin-2-yl)-pyridine-2-carboxamide

EXAMPLE 76
Preparation of 3-[4-Methylsulfonyl-2-[cis-4-(methylamino)-cyclohexyloxy]benzoylamino]-N-(5-chloropyridin-2-yl)-pyridine-2-carboxamide

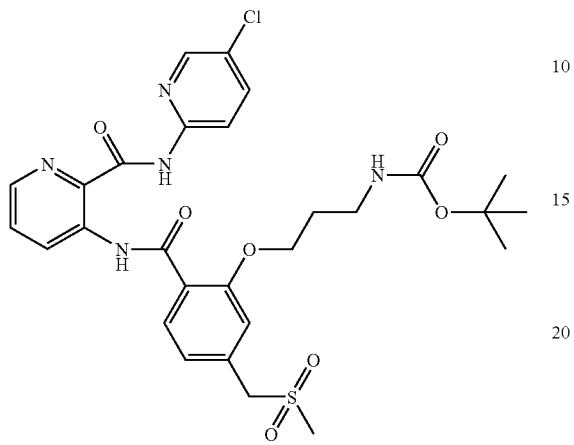

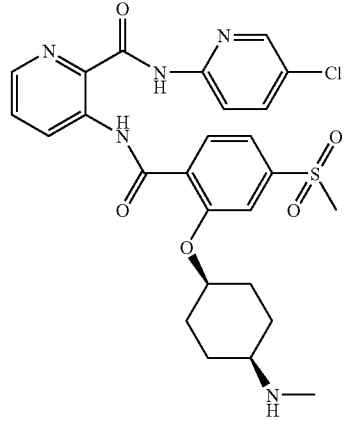

Using a procedure analogous to Example 3-A, 3-[4-methylthiomethyl-2-[3-(t-butoxycarbonylamino)propoxy]-benzoylamino]-6-methyl-N-(5-chloropyridin-2-yl)pyridine-2-carboxamide gave the title compound as a white solid (1.1 g, 80%).

$^1$NMR (300 MHz, DMSO-d$_6$): δ 1.26 (s, 9H), 1.99 (m, 2H), 2.57 (s, 3H), 2.96 (s, 3H), 3.05 (m, 2H), 4.31 (t, J=6.2 Hz, 2H), 4.58 (s, 2H), 6.76 (m, 1H), 7.16 (dd, J=0.7, 8.1 Hz, 1H), 7.32 (s, 1H), 7.62 (d, J=8.8 Hz, 1H), 7.94 (d, J=8.1 Hz, 1H), 8.01 (dd, J=2.6, 8.8 Hz, 1H), 8.29 (d, J=8.8 Hz, 1H), 8.46 (d, J=2.6 Hz, 1H), 9.12 (d, J=8.4 Hz, 1H), 10.84 (s, 1H), 12.36 (s, 1H).

FIA-MS, m/e: 632.3 (m+1).

C. 3-[4-Methylsulfonylmethyl-2-(3-aminopropoxy)benzoylamino]-6-methyl-N-(5-chloropyridin-2-yl)pyridine-2-carboxamide Using a procedure analogous to 1-H, 3-[4-methyl-sulfonylmethyl-2-[3-(t-butoxycarbonylamino)propoxy]-benzoylamino]-6-methyl-N-(5-chloropyridin-2-yl)pyridine-2-carboxamide gave the title compound as a white solid (819 mg, 93%).

$^1$NMR (300 MHz, DMSO-d$_6$): δ 1.89 (m, 2H), 2.56 (s, 1H), 2.58 (s, 2H), 2.63 (t, J=6.6 Hz, 2H), 2.96 (s, 3H), 4.37 (m, 2H), 4.56 (s, 0.7H), 4.58 (s, 1.3H), 7.10 (d, J=7.7 Hz, 0.3H), 7.15 (d, J=7.7 Hz, 0.7H), 7.30 (s, 0.3H), 7.35 (s, 0.7H), 7.57 (d, J=8.8 Hz, 0.3H), 7.64 (d, J=8.8 Hz, 0.7H), 7.92 (d, J=8.1 Hz, 1H), 8.03 (m, 0.7H), 8.12 (m, 0.3H), 8.28 (m, 1H), 8.38 (d, J=2.2 Hz, 0.3H), 8.46 (d, J=2.2 Hz, 0.7H), 9.11 (m, 1H).

FIA-MS, m/e: 532.1 (m+1).

A.   Methyl 4-Methylthio-2-[cis-4-(N-t-butoxycarbonyl-N-methylamino)cyclohexyloxy]benzoate

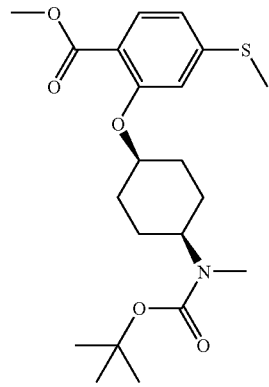

To a mixture of methyl 4-methylthio-2-[cis-4-(t-butoxycarbonylamino)cyclohexyloxy]benzoate (3.0 g, 7.59 mmol) in THF (15 mL) at −20° C. was added 1 M lithium hexamethyl-disilazide (LiHMDS)/hexane (8.0 ml, 7.97 mmol, 1.05 eq), and the mixture was warmed to 0° C. for 10 min. To the reaction mixture was added methyl iodide (0.5 mL, 7.97 mmol, 1.05 equivalent), the mixture was warmed to room temperature and stirred for 7 h, and the reaction was quenched with satd citric acid. The mixture was diluted with CH$_2$Cl$_2$ and partitioned. The organic layer was dried (Na$_2$SO$_4$) and concentrated. This material was combined with the crude product from a small scaled reaction (500 mg, 1.27 mmol), chromatographed (400 g, SiO$_2$, hexanes to 20% EtOAc/hexanes) and triturated with Et$_2$O to give the title compound as a white solid (1.3 g, 36%).

$^1$NMR (300 MHz, DMSO-d$_6$): δ 1.40 (m, 11H), 1.58 (m, 2H), 1.85 (m, 2H), 1.99 (m, 2H), 2.51 (s, 3H), 2.70 (s, 3H), 3.77 (s, 3H), 3.93 (m, 1H), 4.81 (m, 1H), 6.85 (dd, J=1.1, 8.4 Hz, 1H), 6.96 (d, J=1.1 Hz, 1H), 7.63 (d, J=8.4 Hz, 1H).

FIA-MS, m/e: 410 (m+1).

Analysis for C$_{21}$H$_{31}$NO$_5$S:

| Calcd: | C, 61.59; H, 7.63; N, 3.42; |
| --- | --- |
| Found: | C, 61.87; H, 7.61; N, 3.58. |

B. 4-Methylthio-2-[cis-4-(N-t-butoxycarbonyl-N-methyl-amino)cyclohexyloxy]benzoic Acid

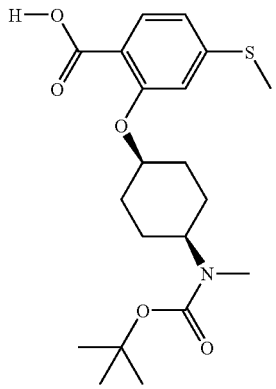

Using a procedure analogous to Example 1-E, methyl 4-methylthio-2-[cis-4-(N-t-butoxycarbonyl-N-methy-lamino)-cyclohexyloxy]benzoate gave the title as a white solid (1.14 g, 99%).

$^1$NMR (300 MHz, DMSO-d$_6$): δ 1.31 (m, 2H), 1.39 (s, 9H), 1.56 (m, 2H), 1.95 (m, 4H), 2.50 (s, 3H), 2.68 (s, 3H), 3.96 (br s, 1H), 4.81 (br s, 1H), 6.83 (dd, J=1.5, 8.1 Hz, 1H), 6.95 (d, J=1.5 Hz, 1H), 7.63 (d, J=8.1 Hz, 1H), 12.62 (s, 1H).

ES-MS, m/e: 394.3 (m−1).

ES-MS, exact m/e: calc. 418.1664 (C$_{20}$H$_{29}$NO$_5$SNa); found 418.1665.

Analysis for C$_{20}$H$_{29}$NO$_5$S:

| Calcd: | C, 60.05; H, 7.43; N, 3.50; |
| --- | --- |
| Found: | C, 60.28; H, 7.45; N, 3.84. |

C. 3-[4-Methylthio-2-[cis-4-(N-t-butoxycarbonyl-N-methyl-amino)cyclohexyloxy]benzoylamino]-N-(5-chloropyridin-2-yl)-pyridine-2-carboxamide

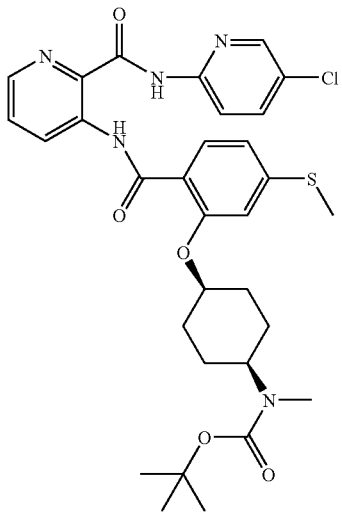

Using a procedure analogous to Example 1-G, 4-methyl-thio-2-[cis-4-(N-t-butoxycarbonyl-N-methylamino)cyclo-hexyl-oxy]benzoic acid gave the title as a white solid (1.0 g, 57%).

$^1$NMR (300 MHz, DMSO-d$_6$): δ 1.20 (m, 2H), 1.29 (s, 9H), 1.53 (m, 4H), 2.04 (m, 2H), 2.08 (s, 3H), 2.55 (s, 3H), 3.79 (br s, 1H), 4.99 (br s, 1H), 6.98 (dd, J=1.5, 8.1 Hz, 1H), 7.12 (s, 1H), 7.72 (d, J=8.4 Hz, 1H), 7.78 (m, 1H), 8.03 (dd, J=2.6, 8.8 Hz, 1H), 8.19 (d, J=8.8 Hz, 1H), 8.46 (m, 2H), 9.18 (dd, J=1.1, 8.4 Hz, 1H), 10.82 (s, 1H), 12.18 (s, 1H).

ES-MS, m/e: 626.2 (m+1).

ES-MS, exact m/e: calc. 626.2204 (C$_{31}$H$_{36}$ClN$_5$O$_5$S+H); found 626.2227.

D. 3-[4-Methylsulfonyl-2-[cis-4-(N-t-butoxycarbonyl-N-methylamino)cyclohexyloxy]benzoylamino]-N-(5-chloro-pyridin-2-yl)pyridine-2-carboxamide

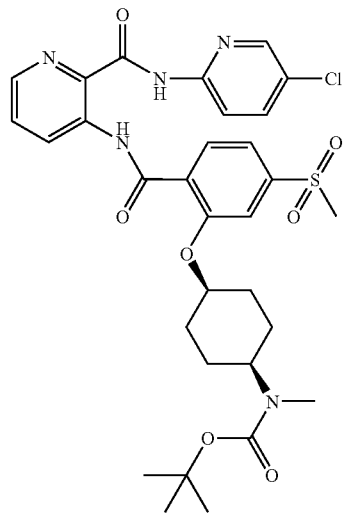

Using a procedure analogous to Example 3-A, 3-[4-methylthio-2-[cis-4-(N-t-butoxycarbonyl-N-methylamino)-cyclohexyloxy]benzoylamino]-N-(5-chloropyridin-2-yl)-pyridine-2-carboxamide gave the title as a white solid (810 mg, 81%).

$^1$NMR (300 MHz, DMSO-d$_6$): δ 1.25 (m, 2H), 1.30 (s, 9H), 1.59 (m, 4H), 2.06 (m, 2H), 2.15 (s, 3H), 3.34 (s, 3H), 3.80 (br s, 1H), 5.04 (br s, 1H), 7.64 (dd, J=1.1, 8.1 Hz, 1H), 7.77 (s, 1H), 7.82 (dd, J=4.4, 8.8 Hz, 1H), 7.96 (d, J=8.1 Hz, 1H), 8.01 (dd, J=2.6, 8.8 Hz, 1H), 8.16 (d, J=8.8 Hz, 1H), 8.47 (d, J=2.6 Hz, 1H), 8.51 (dd, J=1.1, 4.4 Hz, 1H), 9.20 (d, J=8.4 Hz, 1H), 10.85 (s, 1H), 12.25 (s, 1H).

ES-MS, exact m/e: calc. 658.2102 (C$_{31}$H$_{36}$ClN$_5$O$_7$S+H); found 658.2082.

E. 3-[4-Methylsulfonyl-2-[cis-4-(methylamino)cyclohexyloxy]benzoylamino]-N-(5-chloropyridin-2-yl)pyridine-2-carboxamide

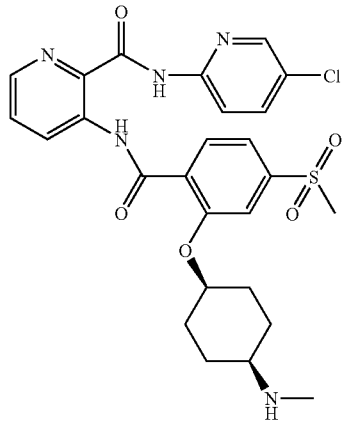

Using a procedure analogous to Example 1-H, 3-[4-methylsulfonyl-2-[cis-4-(N-t-butoxycarbonyl-N-methylamino)-cyclohexyloxy]benzoylamino]-N-(5-chloropyridin-2-yl)-pyridine-2-carboxamide gave the title as a white solid (400 mg, 63%).

$^1$NMR (300 MHz, DMSO-d$_6$): δ 1.37 (m, 2H), 1.53 (m, 2H), 1.65 (m, 2H), 2.03 (m, 2H), 2.09 (s, 3H), 2.44 (m, 1H), 3.33 (s, 3H), 4.92 (br s, 1H), 7.62 (dd, J=1.1, 8.1 Hz, 1H), 7.71 (s, 1H), 8.80 (dd, J=4.4, 8.8 Hz, 1H), 8.00 (d, J=8.1 Hz, 1H), 8.04 (dd, J=2.6, 8.8 Hz, 1H), 8.21 (d, J=8.8 Hz, 1H), 8.47 (d, J=2.2 Hz, 1H), 8.50 (dd, J=1.1, 4.4 Hz, 1H), 9.21 (d, J=8.8 Hz, 1H), 12.25 (s, 1H).

ES-MS, exact m/e: calc. 558.1578 ($C_{26}H_{28}ClN_5O_5S$+H); found 558.1607.

Analysis for $C_{26}H_{28}ClN_5O_5S \cdot 0.5\ H_2O$:

| Calcd: | C, 55.07; H, 5.15; N, 12.35; |
|---|---|
| Found: | C, 55.04; H, 5.06; N, 12.12. |

What is claimed is:

1. A compound of formula I,

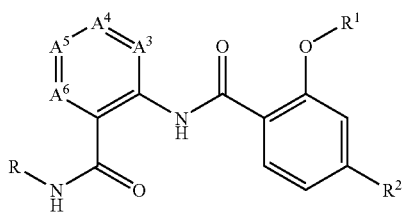

or a pharmaceutically acceptable salt thereof, wherein:
$A^3$, $A^4$, $A^5$ and $A^6$, together with the two carbons to which they are attached, complete a substituted pyridine ring in which
(a) $A^3$ is N, and each of the others is $CR^4$, $CR^5$ or $CR^6$, respectively; wherein $R^4$ is hydrogen, carboxy, aminocarbonyl or methylaminocarbonyl; $R^5$ is hydrogen, fluoro, chloro, or methyl; and $R^6$ is hydrogen; or wherein each of $R^3$, $R^4$ and $R^6$ is hydrogen and $R^5$ is acetyl or cyano;
(b) $A^4$ is N, and each of the others is $CR^3$, $CR^5$ or $CR^6$, respectively; wherein each of $R^3$ and $R^6$ is hydrogen and $R^5$ is hydrogen, methyl, acetyl or cyano;
(c) $A^5$ is N, and each of the others is $CR^3$, $CR^4$ or $CR^6$, respectively; wherein each of $R^3$ and $R^6$ is hydrogen and $R^4$ is hydrogen, carboxy, aminocarbonyl or methylamino-carbonyl;
(d) $A^6$ is N, and each of the others is $CR^3$, $CR^4$ or $CR^5$, respectively; wherein $R^3$ is hydrogen; $R^4$ is hydrogen, carboxy, aminocarbonyl or methylaminocarbonyl; and $R^5$ is hydrogen or methyl;
R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);
$R^1$ is —$(CH_2)_i$-Q-$(CH_2)_j$—$NR^aR^b$ in which
a) Q is a single bond; the sum of i and j is 2 or 3; and each of $R^a$ and $R^b$ is hydrogen, or each of $R^a$ and $R^b$ is independently (1-3C) normal alkyl, or $R^a$ is hydrogen and $R^b$ is (1-3C)alkyl or formyl, or $NR^aR^b$ is 1-pyrrolidinyl or 4-morpholinyl;
b) Q is —$CH(CH_3)$—, —$C(CH_3)_2$—, or —$CH(OR^c)$—; each of i and j is 1; $R^a$ is hydrogen; and $R^b$ is hydrogen or methyl; and $R^c$ is hydrogen, methyl or benzyl;
c) Q is cis- or trans-cyclohexane-1,4-diyl; each of i and j is 0; $R^a$ is hydrogen; and $R^b$ is hydrogen or methyl;
d) Q is —$CHR^d$—; i is 0; j is 1; $R^a$ is hydrogen or methyl; and $R^b$ and $R^d$ together are —$(CH_2)_k$— wherein k is 2 or 3;
e) Q is —$CHR^d$—; i is 1; j is 1; $R^a$ is hydrogen or methyl; and $R^b$ and $R^d$ together are —$(CH_2)_k$— wherein k is 1, 2 or 3; or
f) Q is —$CHR^d$—; i is 0 or 1; j is 2; $R^a$ is hydrogen or methyl; and $R^b$ and $R^d$ together are —$(CH_2)_k$— wherein k is 2; and
$R^2$ is —$(CH_2)_m$—$S(O)_n$—$R^e$ in which m is 0 or 1, n is 0, 1 or 2, and $R^e$ is (1-3C)alkyl or 2-fluoroethyl; and
wherein (1-3C) normal alkyl is methyl, ethyl or propyl; and (1-3C)alkyl is methyl, ethyl, propyl, or isopropyl.

2. The compound or salt of claim 1 wherein
one of $A^3$, $A^4$, $A^5$ and $A^6$ is N, and each of the others is $CR^3$, $CR^4$, $CR^5$ or $CR^6$, respectively; wherein
each of $R^3$, $R^4$ and $R^6$ is hydrogen and $R^5$ is hydrogen or methyl;
R is 2-pyridinyl, which bears a methyl, fluoro or chloro substituent at the 5-position.

3. The compound or salt of claim 2 wherein
$A^6$ is N;
each of $R^3$ and $R^4$ is hydrogen; and
$R^5$ is hydrogen or methyl;
R is 5-chloropyridin-2-yl or 5-methylpyridin-2-yl;
$R^1$ is 2-aminoethyl, 2-(dimethylamino)ethyl, 3-amino-propyl, 3-(formylamino)propyl, 3-(1-pyrrolidinyl)propyl, 3-(4-morpholinyl)propyl, 3-amino-2-methylpropyl, 3-amino-2,2-dimethylpropyl, 3-amino-2-hydroxypropyl, 3-amino-2-methoxypropyl, 3-amino-2-benzyloxypropyl, cis-4-amino-cyclohexyl, cis-4-(methylamino) cyclohexyl, trans-4-amino-cyclohexyl, 3-pyrrolidinyl, 3-piperidinyl, 3-azetidinyl-methyl, 3-pyrrolidinylmethyl, 3-piperidinylmethyl, 4-piperidinyl, 4-piperidinylmethyl or 1-methyl-piperidin-4-yl; and $R^2$ is methylthio, methylsulfinyl, methylsulfonyl, ethylthio, ethylsulfinyl, ethylsulfonyl, isopropylthio, propylsulfonyl or methylsulfonylmethyl.

4. The compound or salt of claim 3 wherein

R is 5-chloropyridin-2-yl;

$R^1$ is 3-aminopropyl, 3-amino-2-methylpropyl, 3-amino-2,2-dimethylpropyl, 3-amino-2-methoxypropyl, 3-amino-2-benzyloxypropyl, cis-4-aminocyclohexyl, cis-4-(methylamino)-cyclohexyl, 3-pyrrolidinyl, 3-piperidinyl, 3-azetidinyl-methyl, 3-pyrrolidinylmethyl, 3-piperidinylmethyl, 4-piperidinyl, 4-piperidinylmethyl or 1-methyl-piperidin-4-yl; and $R^2$ is methylsulfinyl, ethylsulfinyl, methylsulfonyl, ethylsulfonyl or propylsulfonyl.

5. The compound or salt of claim 4 wherein $R^1$ is 3-aminopropyl, 3-amino-2-methylpropyl (as the racemate or as either isomer), 3-amino-2,2-dimethylpropyl; (2S)-3-amino-2-methoxypropyl; (2S)-3-amino-2-benzyloxy-propyl; cis-4-aminocyclohexyl, cis-4-(methylamino)-cyclohexyl, (3S)-3-pyrrolidinyl, 3-piperidinyl (as the racemate or as either isomer), 3-azetidinylmethyl, 3-pyrrolidinylmethyl (as the racemate or as either isomer), 4-piperidinyl, or 1-methylpiperidin-4-yl; and $R^2$ is methylsulfonyl, ethylsulfonyl or propylsulfonyl.

6. The compound of claim 1 which is 3-[2-(cis-4-aminocyclohexyloxy)-4-methylsulfonylbenzoyl-amino]-N-(5-chloropyridin-2-yl)pyridine-2-carboxamide, or a pharmaceutically acceptable salt thereof.

7. The pharmaceutically acceptable salt of claim 1 which is an acid-addition salt made from a basic compound of formula I and an acid which provides a pharmaceutically acceptable anion.

8. A pharmaceutical composition comprising in association with a pharmaceutically acceptable carrier, diluent or excipient, a compound of formula I, or a pharmaceutically acceptable salt thereof, as provided in any of claims 1-7.

9. A process for preparing a compound of formula I,

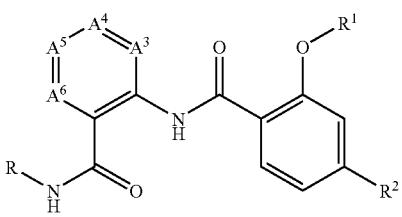

I or a pharmaceutically acceptable salt thereof, wherein, unless otherwise specified in this claim:

$A^3$, $A^4$, $A^5$ and $A^6$, together with the two carbons to which they are attached, complete a substituted pyridine ring in which (a) $A^3$ is N, and each of the others is $CR^4$, $CR^5$ or $CR^6$, respectively; wherein $R^4$ is hydrogen, carboxy, aminocarbonyl or methylaminocarbonyl; $R^5$ is hydrogen, fluoro, chloro, or methyl; and $R^6$ is hydrogen; or wherein each of $R^3$, $R^4$ and $R^6$ is hydrogen and $R^5$ is acetyl or cyano;

(b) $A^4$ is N, and each of the others is $CR^3$, $CR^5$ or $CR^6$, respectively; wherein each of $R^3$ and $R^6$ is hydrogen and $R^5$ is hydrogen, methyl, acetyl or cyano;

(c) $A^5$ is N, and each of the others is $CR^3$, $CR^4$ or $CR^6$, respectively; wherein each of $R^3$ and $R^6$ is hydrogen and $R^4$ is hydrogen, carboxy, aminocarbonyl or methylamino-carbonyl;

(d) $A^6$ is N, and each of the others is $CR^3$, $CR^4$ or $CR^5$, respectively; wherein $R^3$ is hydrogen; $R^4$ is hydrogen, carboxy, aminocarbonyl or methylaminocarbonyl; and $R^5$ is hydrogen or methyl;

R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);

$R^1$ is $-(CH_2)_i-Q-(CH_2)_j-NR^aR^b$ in which a) Q is a single bond; the sum of i and j is 2 or 3; and each of $R^a$ and $R^b$ is hydrogen, or each of $R^a$ and $R^b$ is independently (1-3C)normal alkyl, or $R^a$ is hydrogen and $R^b$ is (1-3C)alkyl or formyl, or $NR^aR^b$ is 1-pyrrolidinyl or 4-morpholinyl;

b) Q is $-CH(CH_3)-$, $-C(CH_3)_2-$, or $-CH(OR^c)-$; each of i and j is 1; $R^a$ is hydrogen; and $R^b$ is hydrogen or methyl; and $R^c$ is hydrogen, methyl or benzyl;

c) Q is cis- or trans-cyclohexane-1,4-diyl; each of i and j is 0; $R^a$ is hydrogen; and $R^b$ is hydrogen or methyl;

d) Q is $-CHR^d-$; j is 0; j is 1; $R^a$ is hydrogen or methyl; and $R^b$ and $R^d$ together are $-(CH_2)_k-$ wherein k is 2 or 3;

e) Q is $-CHR^d-$; i is 1; j is 1; $R^a$ is hydrogen or methyl; and $R^b$ and $R^d$ together are $-(CH_2)_k-$ wherein k is 1, 2 or 3; or f) Q is $-CHR^d-$; i is 0 or 1; j is 2; $R^a$ is hydrogen or methyl; and $R^b$ and $R^d$ together are $-(CH_2)_k-$ wherein k is 2; and $R^2$ is $-(CH_2)_m-S(O)_n-R^e$ in which m is 0 or 1, n is 0, 1 or 2, and $R^e$ is (1-3C)alkyl or 2-fluoroethyl; and wherein (1-3C) normal alkyl is methyl, ethyl or propyl; and (1-3C)alkyl is methyl, ethyl, propyl, or isopropyl, comprising the step selected from (A) acylating an amine of formula II,

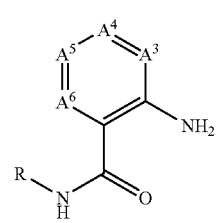

II using an acid of formula III (in which $R^a$ as hydrogen may be replaced by a nitrogen protecting group $R^p$);

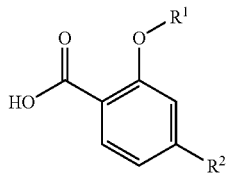

(B) for a compound of formula I in which n is 1, oxidizing the corresponding compound of formula I (in which $R^a$ as hydrogen may be replaced by a nitrogen protecting group $R^p$) in which n is 0;

(C) for a compound of formula I in which n is 2, oxidizing the corresponding compound of formula I (in which $R^a$ as hydrogen may be replaced by a nitrogen protecting group $R^p$) in which n is 1;

(D) for a compound of formula I in which each of $R^a$ and $R^b$ is (1-3C)normal alkyl, or $R^a$ is hydrogen and $R^b$ is methyl or (1-3C)alkyl, or $NR^aR^b$ is 1-pyrrolidinyl or 4-morpholinyl, alkylating a corresponding compound of formula I in which each of $R^a$ and $R^b$ is hydrogen;

(E) for a compound of formula I in which $R^a$ is methyl or (1-3C)normal alkyl, alkylating a corresponding compound of formula I in which $R^a$ is hydrogen;

(F) for a compound of formula I in which $R^b$ is formyl, formylating a corresponding compound of formula I in which $R^b$ is hydrogen;

(G) alkylating the phenolic oxygen of a compound of formula IV,

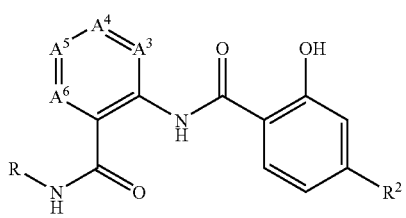

using a corresponding compound of formula V (in which $R^a$ as hydrogen may be replaced by a nitrogen protecting group $R^p$),

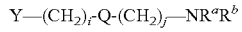

Y—(CH$_2$)$_i$-Q-(CH$_2$)$_j$—NR$^a$R$^b$  V wherein Y is a conventional leaving group for nucleophilic substitution and wherein, for a compound of formula I in which i is 0, the stereochemistry of the carbon to which Y is attached is inverted from that of the product; and (H) acylating an amine of formula R—NH$_2$ using an acid of formula VI (in which $R^a$ as hydrogen may be replaced by a nitrogen protecting group $R^p$);

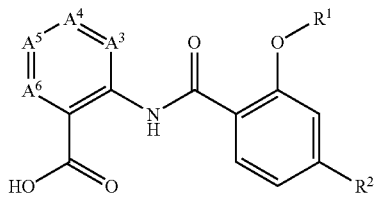

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure.

10. A process for preparing a compound of formula I,

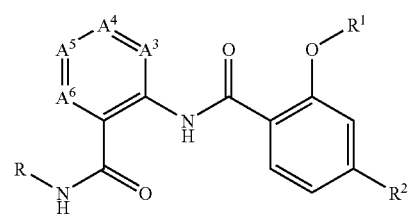

in which m is 0, or a pharmaceutically acceptable salt thereof, wherein:

$A^3$, $A^4$, $A^5$ and $A^6$, together with the two carbons to which they are attached, complete a substituted pyridine ring in which (a) $A^3$ is N, and each of the others is $CR^4$, $CR^5$ or $CR^6$, respectively; wherein $R^4$ is hydrogen, carboxy, aminocarbonyl or methylaminocarbonyl; $R^5$ is hydrogen, fluoro, chloro, or methyl; and $R^6$ is hydrogen; or wherein each of $R^3$, $R^4$ and $R^6$ is hydrogen and $R^5$ is acetyl or cyano;

(b) $A^4$ is N, and each of the others is $CR^3$, $CR^5$ or $CR^6$, respectively; wherein each of $R^3$ and $R^6$ is hydrogen and $R^5$ is hydrogen, methyl, acetyl or cyano;

(c) $A^5$ is N, and each of the others is $CR^3$, $CR^4$ or $CR^6$, respectively; wherein each of $R^3$ and $R^6$ is hydrogen and $R^4$ is hydrogen, carboxy, aminocarbonyl or methylamino-carbonyl;

(d) $A^6$ is N, and each of the others is $CR^3$, $CR^4$ or $CR^5$, respectively; wherein $R^3$ is hydrogen; $R^4$ is hydrogen, carboxy, aminocarbonyl or methylaminocarbonyl; and $R^5$ is hydrogen or methyl;

R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);

$R^1$ is —(CH$_2$)$_i$-Q-(CH$_2$)$_j$—NR$^a$R$^b$ in which a) Q is a single bond; the sum of i and j is 2 or 3; and each of $R^a$ and $R^b$ is hydrogen, or each of $R^a$ and $R^b$ is independently (1-3C)normal alkyl, or $R^a$ is hydrogen and $R^b$ is (1-3C)alkyl or formyl, or $NR^aR^b$ is 1-pyrrolidinyl or 4-morpholinyl;

b) Q is —CH(CH$_3$)—, —C(CH$_3$)$_2$—, or —CH(OR$^c$)—; each of i and j is 1; $R^a$ is hydrogen; and $R^b$ is hydrogen or methyl; and $R^c$ is hydrogen, methyl or benzyl;

c) Q is cis- or trans-cyclohexane-1,4-diyl; each of i and j is 0; $R^a$ is hydrogen; and $R^b$ is hydrogen or methyl;

d) Q is —CHR$^d$—; i is 0; j is 1; R$^a$ is hydrogen or methyl; and R$^b$ and R$^d$ together are —(CH$_2$)$_k$— wherein k is 2 or 3;

e) Q is —CHR$^d$—; i is 1; j is 1; R$^a$ is hydrogen or methyl; and R$^b$ and R$^d$ together are —(CH$_2$)$_k$— wherein k is 1, 2 or 3; or f) Q is —CHR$^d$—; i is 0 or 1; j is 2; R$^a$ is hydrogen or methyl; and R$^b$ and R$^d$ together are —(CH$_2$)$_k$— wherein k is 2; and R$^2$ is (CH$_2$)$_m$—S(O)$_n$—R$^e$ in which n is 0, 1 or 2, and R$^e$ is (1-3C)alkyl or 2-fluoroethyl; and wherein (1-3C) normal alkyl is methyl, ethyl or propyl; and (1-3C)alkyl is methyl, ethyl, propyl, or isopropyl, from 2,4-difluorobenzoic acid, or a salt thereof, comprising (a) treating 2,4-difluorobenzoic acid, or the salt thereof, with an alkoxide of an alcohol of formula HO—R$^1$ (in which R$^a$ as hydrogen may be replaced by a nitrogen protecting group R$^p$), to form a corresponding ether of formula VIII (in which R$^a$ as hydrogen may be replaced by a nitrogen protecting group R$^p$), or salt thereof;

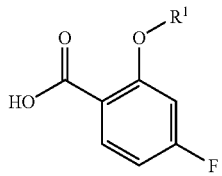

VIII (b) treating the ether of formula VIII (in which R$^a$ as hydrogen may be replaced by a nitrogen protecting group R$^p$), or salt thereof, with a thiolate of the thiol of formula HS—R$^e$ to form a compound of formula VII (in which R$^a$ as hydrogen may be replaced by a nitrogen protecting group R$^p$), or salt thereof;

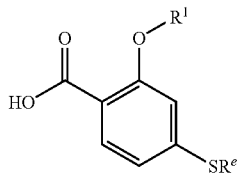

VII followed by converting the compound of formula VII (in which R$^a$ as hydrogen may be replaced by a nitrogen protecting group R$^p$), or salt thereof, into a compound of formula I in which m is 0; and whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure.

11. The process of claim 10, further comprising:

(c) for an acid of formula VII in which R$^a$ is hydrogen, converting the acid of formula VII into a corresponding acid of formula VII in which R$^a$ as hydrogen is replaced by a nitrogen protecting group R$^p$;

(d) acylating an amine of formula II,

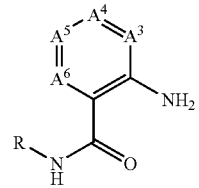

II using the acid of formula VII (in which R$^a$ is not hydrogen or R$^a$ as hydrogen is replaced by a nitrogen protecting group R$^p$), to form a compound of formula IX (in which R$^a$ is not hydrogen or R$^a$ as hydrogen is replaced by a nitrogen protecting group R$^p$),

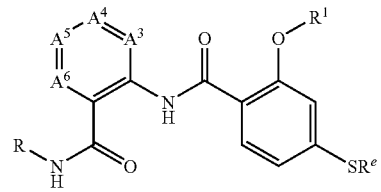

IX which is a compound of Formula I in which m is 0 and n is 0 in which R$^a$ is not hydrogen when R$^a$ is not hydrogen;

(e) for a compound of formula I in which n is 1, oxidizing the sulfur of the compound of formula IX (in which R$^a$ is not hydrogen or R$^a$ as hydrogen is replaced by a nitrogen protecting group R$^p$), followed by reducing any N-oxide formed for a compound in which R$^a$ is not hydrogen, to afford the corresponding sulfoxide of formula X (in which R$^a$ is not hydrogen or R$^a$ as hydrogen is replaced by a nitrogen protecting group R$^p$),

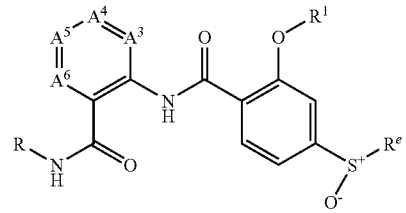

X which is a compound of Formula I in which m is 0 and n is 1 in which R$^a$ is not hydrogen when R$^a$ is not hydrogen;

(f) for a compound of formula I in which n is 2, oxidizing the corresponding sulfoxide of the compound of formula X (in which R$^a$ is not hydrogen or R$^a$ as hydrogen is replaced by a nitrogen protecting group R$^p$), followed by reducing any N-oxide formed for a compound in which R$^a$ is not hydrogen, to afford the corresponding sulfone of formula XI (in which R$^a$ is not hydrogen or R$^a$ as hydrogen is replaced by a nitrogen protecting group R$^p$),

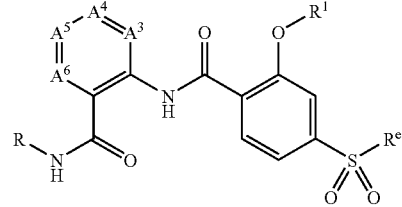

XI which is a compound of Formula I in which m is 0 and n is 2 in which $R^a$ is not hydrogen when $R^a$ is not hydrogen;

or, optionally, combining steps (e) and (f) to directly provide the compound of formula XI from the compound of formula IX; and (g) when $R^a$ as hydrogen is replaced by a nitrogen protecting group $R^p$, removing the nitrogen protecting group $R^p$ from the product of step (d), (e) or (f), respectively, to provide a compound of formula I in which $R^a$ is hydrogen, m is 0, and n is 0, 1 or 2, respectively;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above in this claim, $A^3$-$A^6$, R, $R^1$, Q, $R^a$-$R^e$, i, j, k, and n have any of the values defined in claim 10.

12. The process of claim 11 in which $R^1$ is 3-aminopropyl, 3-amino-2,2-dimethylpropyl; cis-4-aminocyclohexyl, 4-piperidinyl or 1-methylpiperidin-4-yl;

$R^e$ is methyl; and for steps (c) through (f), $R^p$ is t-butoxycarbonyl.

13. The process of any one of claims 10-12 in which $R^1$ is cis-4-aminocyclohexyl.

14. The process of claim 13 wherein the starting cis-4-aminocyclohexanol is prepared using a process comprising (i) dehydrogenating a substituted hydroxylamine derivative of formula $R^qNHOH$, in which $R^q$ is an electron withdrawing nitrogen protecting group, in the presence of 1,3-cyclohexadiene to afford a 2-substituted 2-aza-3-oxa-bicyclo[2.2.2]oct-5-ene compound of formula XII,

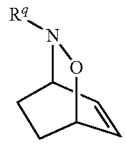

XII (ii) removing the protecting group $R^q$ to provide 3-aza-2-oxabicyclo[2.2.2]oct-5-ene, formula XIII;

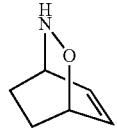

XIII optionally obtained as an acid addition salt; and (iii) hydrogenating and hydrogenolyzing the compound of formula XIII to provide cis-4-aminocyclohexanol, optionally obtained as an acid addition salt, and followed, when required, by formation of the free base by a conventional method.

15. The process of any one of claims 10-12 wherein a salt of 2,4-difluorobenzoic acid is the sodium or potassium salt, the alkoxide of an alcohol of formula HO—$R^1$ (in which $R^a$ as hydrogen may be replaced by a nitrogen protecting group $R^p$) is the sodium or potassium alkoxide; and the thiolate of the thiol of formula HS—$R^e$ is the sodium or potassium thiolate.

16. The process of claim 14 wherein $R^q$ is t-butoxycarbonyl, the dehydrogenation reagent of step (i) is $NaIO_4$, trifluoroacetic acid is the reagent of step (ii) for removing the protecting group $R^q$ and is the acid with which the optional acid addition salts of steps (ii) and (iii) are formed, and Pd/C is the catalyst for the hydrogenation and hydrogenolysis of step (iii).

* * * * *

UNITED STATES PATENT AND TRADEMARK OFFICE
CERTIFICATE OF CORRECTION

| | | |
|---|---|---|
| PATENT NO. | : 7,615,568 B2 | Page 1 of 1 |
| APPLICATION NO. | : 10/556313 | |
| DATED | : November 10, 2009 | |
| INVENTOR(S) | : Franciskovich et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 572 days Delete the phrase "by 572 days" and insert -- by 836 days --

Signed and Sealed this

Thirteenth Day of July, 2010

David J. Kappos
*Director of the United States Patent and Trademark Office*